(12) United States Patent
Ryu et al.

(10) Patent No.: US 11,563,179 B2
(45) Date of Patent: Jan. 24, 2023

(54) COMPOUND, ORGANIC OPTOELECTRONIC ELEMENT COMPRISING SAME AND DISPLAY DEVICE THEREOF

(71) Applicant: SAMSUNG SDI CO., LTD., Yongin-si (KR)

(72) Inventors: Dong-Wan Ryu, Suwon-si (KR); Young-Kyoung Jo, Suwon-si (KR); Sung-Hyun Jung, Suwon-si (KR); Chang-Ju Shin, Suwon-si (KR); Han-Ill Lee, Suwon-si (KR); Eui-Su Kang, Suwon-si (KR); Chang-Woo Kim, Suwon-si (KR); Min-Jee Park, Suwon-si (KR); Eun-Sun Yu, Suwon-si (KR); Pyeong-Seok Cho, Suwon-si (KR)

(73) Assignee: SAMSUNG SDI CO., LTD., Yongin-si (KR)

( * ) Notice: Subject to any disclaimer, the term of this patent is extended or adjusted under 35 U.S.C. 154(b) by 0 days.

(21) Appl. No.: 15/117,753

(22) PCT Filed: Apr. 13, 2015

(86) PCT No.: PCT/KR2015/003678
§ 371 (c)(1),
(2) Date: Aug. 10, 2016

(87) PCT Pub. No.: WO2015/174640
PCT Pub. Date: Nov. 19, 2015

(65) Prior Publication Data
US 2016/0372666 A1   Dec. 22, 2016

(30) Foreign Application Priority Data

May 13, 2014  (KR) .......................... 10-2014-0057324
Apr. 10, 2015  (KR) .......................... 10-2015-0051095

(51) Int. Cl.
*H01L 51/00*  (2006.01)
*C07D 307/91*  (2006.01)
(Continued)

(52) U.S. Cl.
CPC .......... *H01L 51/006* (2013.01); *C07D 209/86* (2013.01); *C07D 307/91* (2013.01);
(Continued)

(58) Field of Classification Search
CPC combination set(s) only.
See application file for complete search history.

(56) References Cited

U.S. PATENT DOCUMENTS

2010/0219404 A1* 9/2010 Endo ..................... H01L 51/006
   257/40
2010/0314612 A1* 12/2010 Lee ..................... H01L 51/5036
   257/40
(Continued)

FOREIGN PATENT DOCUMENTS

CN       1769269 A  *  5/2006
CN    101971384 A      2/2011
(Continued)

OTHER PUBLICATIONS

S. Ogawa, Organic Electronics Materials and Devices, 2015, 1-251. (Year: 2015).*
(Continued)

*Primary Examiner* — Sean M DeGuire
(74) *Attorney, Agent, or Firm* — Lee IP Law, P.C.

(57) ABSTRACT

The present invention relates to a compound represented by formula 1, an organic optoelectronic element comprising the same, and a display device comprising the organic optoeletric element.
Formula 1 and the description regarding the samen are as defined in the specification.

8 Claims, 2 Drawing Sheets

(51) Int. Cl.

| | | |
|---|---|---|
| *C07D 333/76* | (2006.01) | |
| *C07D 209/86* | (2006.01) | |
| *C07D 405/12* | (2006.01) | |
| *C07D 409/12* | (2006.01) | |
| *C09K 11/06* | (2006.01) | |
| *H01L 51/50* | (2006.01) | |

(52) U.S. Cl.
CPC ......... *C07D 333/76* (2013.01); *C07D 405/12* (2013.01); *C07D 409/12* (2013.01); *C09K 11/06* (2013.01); *H01L 51/0059* (2013.01); *H01L 51/0061* (2013.01); *H01L 51/0067* (2013.01); *H01L 51/0072* (2013.01); *H01L 51/0073* (2013.01); *H01L 51/0074* (2013.01); *C09K 2211/1022* (2013.01); *C09K 2211/1088* (2013.01); *C09K 2211/1092* (2013.01); *H01L 51/0081* (2013.01); *H01L 51/5056* (2013.01); *H01L 51/5064* (2013.01)

(56) References Cited

U.S. PATENT DOCUMENTS

| | | | |
|---|---|---|---|
| 2011/0248246 A1 | 10/2011 | Ogita et al. | |
| 2012/0043531 A1 | 2/2012 | Jung et al. | |
| 2013/0256645 A1* | 10/2013 | Min | C09K 11/06 257/40 |
| 2014/0042412 A1 | 2/2014 | Ryu et al. | |
| 2014/0131670 A1 | 5/2014 | Lin et al. | |
| 2015/0171356 A1* | 6/2015 | Nakamura | C09K 11/06 257/40 |
| 2015/0280136 A1* | 10/2015 | Ryu | C09K 11/06 257/40 |
| 2016/0172593 A1* | 6/2016 | Takada | H01L 51/0061 257/40 |

FOREIGN PATENT DOCUMENTS

| | | | |
|---|---|---|---|
| CN | 102372661 A | | 3/2012 |
| CN | 102911159 A | | 2/2013 |
| CN | 104903421 A | | 9/2015 |
| JP | 2005-085599 A | | 3/2005 |
| JP | 2005-120030 A | | 5/2005 |
| JP | 2005120030 A | * | 5/2005 |
| JP | 3983215 B2 | | 9/2007 |
| JP | 2009-170819 A | | 7/2009 |
| JP | WO2010/052932 A1 | | 5/2010 |
| JP | 2011-006405 A | | 1/2011 |
| JP | 4765589 B2 | | 9/2011 |
| JP | 2012-046478 A | | 3/2012 |
| JP | 2012-067093 A | | 4/2012 |
| JP | 2013-035839 A | | 2/2013 |
| JP | 5202759 B2 | | 6/2013 |
| JP | 2013-151537 A | | 8/2013 |
| JP | 5268207 B2 | | 8/2013 |
| JP | 6323815 B2 | | 5/2018 |
| KR | 10-2009-0028346 A | | 3/2009 |
| KR | 10-2009-0028357 A | | 3/2009 |
| KR | 10-1002733 B1 | | 12/2010 |
| KR | 10-2011-0029831 A | | 3/2011 |
| KR | 10-2011-0113593 A | | 10/2011 |
| KR | 10-1084287 B1 | | 11/2011 |
| KR | 10-1093122 B1 | | 12/2011 |
| KR | 10-2012-0017382 A | | 2/2012 |
| KR | 10-2012-0060611 A | | 6/2012 |
| KR | 10-2013-0016032 A | | 2/2013 |
| KR | 10-2013-0058086 A | | 6/2013 |
| KR | 10-2013-0078749 A | | 7/2013 |
| KR | 10-1297161 B1 | | 8/2013 |
| KR | 10-2014-0014956 A | | 2/2014 |
| KR | 10-2014-0014959 A | | 2/2014 |
| KR | 10-2014-0030297 A | | 3/2014 |
| KR | 10-2014-0039864 A | | 4/2014 |
| KR | 10-2014-0092962 A | | 7/2014 |
| KR | 10-2015-0083917 A | | 7/2015 |
| KR | 10-1684979 B1 | | 12/2016 |
| WO | WO 2008/126393 A1 | | 10/2008 |
| WO | WO 2009/041635 A1 | | 4/2009 |
| WO | WO 2010/052932 A1 | | 5/2010 |
| WO | WO 2013/120577 A | | 8/2013 |
| WO | WO-2014030921 A * | 2/2014 | ............. H05B 33/14 |
| WO | WO 2014/051244 A1 | | 4/2014 |
| WO | WO 2014/104514 A1 | | 7/2014 |
| WO | WO 2015/058826 A1 | | 4/2015 |

OTHER PUBLICATIONS

Extended European Search Report dated Sep. 26, 2017 for EP 15791911.9. Ryu, et al.

M. Nomura., "Synthesis of thermally stable and hole-transporting amorphous molecule having four carbazole moieties," Elsevier, Synthetic Metals (2005), 148, pp. 155-160.

Chinese Office action dated Oct. 19, 2020.

\* cited by examiner

[FIG. 1]
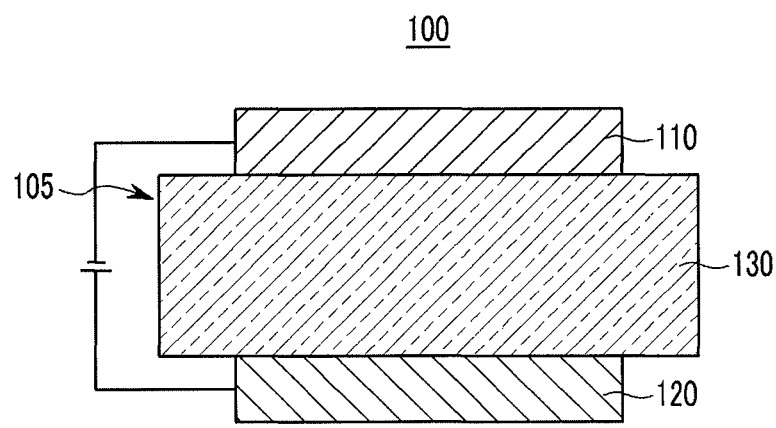
[FIG. 2]
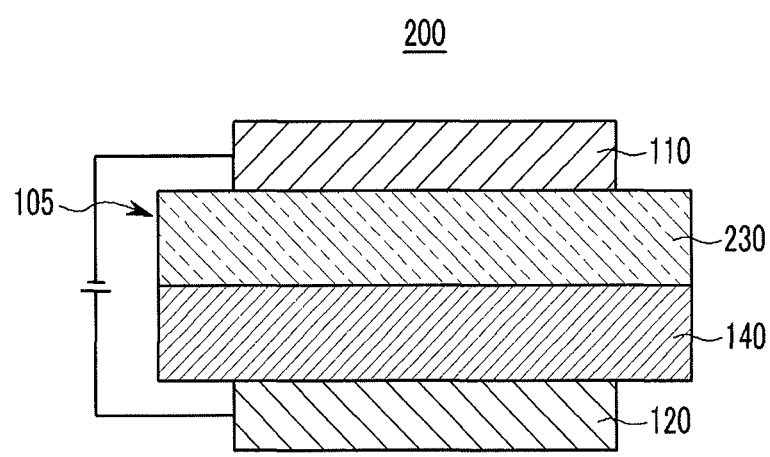

[FIG. 3]
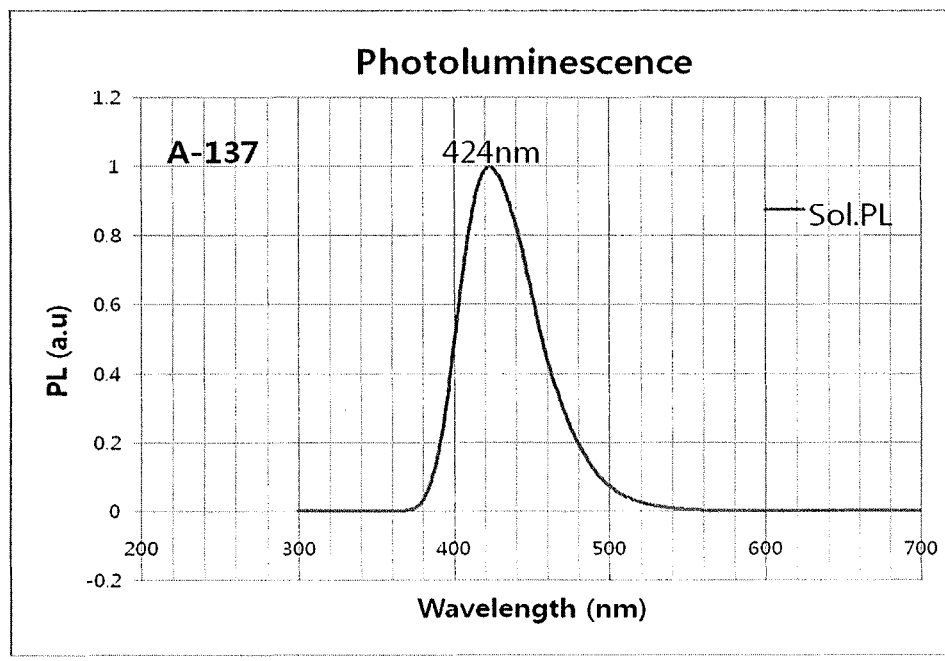

COMPOUND, ORGANIC OPTOELECTRONIC ELEMENT COMPRISING SAME AND DISPLAY DEVICE THEREOF

CROSS REFERENCE TO RELATED APPLICATIONS

This is the U.S. national phase application based on PCT Application No. PCT/KR2015/003678, filed Apr. 13, 2015, which is based on Korean Patent Application Nos. 10-2014-0057324, filed May 13, 2014, and 10-2015-0051095, filed Apr. 10, 2015, the entire contents of all of which are hereby incorporated by reference.

TECHNICAL FIELD

A compound, an organic optoelectric device, and a display device are disclosed.

BACKGROUND ART

An organic optoelectric device is a device that converts electrical energy into photoenergy, and vice versa.

An organic optoelectric device may be classified as follows in accordance with its driving principles. One is an optoelectric device where excitons are generated by photoenergy, separated into electrons and holes, and are transferred to different electrodes to generate electrical energy, and the other is a light emitting device where a voltage or a current is supplied to an electrode to generate photoenergy from electrical energy.

Examples of an organic optoelectric device may be an organic photoelectric device, an organic light emitting diode, an organic solar cell and an organic photo conductor drum.

Of these, an organic light emitting diode (OLED) has recently drawn attention due to an increase in demand for flat panel displays. Such an organic light emitting diode converts electrical energy into light by applying current to an organic light emitting material. It has a structure in which an organic layer is interposed between an anode and a cathode. Herein, an organic layer may include an emission layer and optionally an auxiliary layer, and the auxiliary layer may include, for example at least one selected from a hole injection layer, a hole transport layer, an electron blocking layer, an electron transport layer, an electron injection layer and a hole blocking layer in order increase efficiency and stability of an organic light emitting diode.

Performance of an organic light emitting diode may be affected by characteristics of the organic layer, and among them, may be mainly affected by characteristics of an organic material of the organic layer.

Particularly, development for an organic material being capable of increasing hole and electron mobility and simultaneously increasing electrochemical stability is needed so that the organic light emitting diode may be applied to a large-size flat panel display.

DISCLOSURE

Technical Problem

A compound being capable of realizing an organic optoelectric device having high efficiency and long life-span is provided.

An organic optoelectric device including the compound and a display device including the organic optoelectric device are provided.

Technical Solution

In one embodiment of the present invention, a compound represented by Chemical Formula 1 is provided.

[Chemical Formula 1]

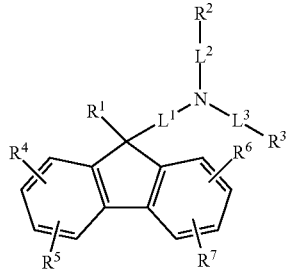

$L^1$ to $L^3$ are independently a single bond, a substituted or unsubstituted C1 to C30 alkylene group, a substituted or unsubstituted C3 to C30 cycloalkylene group, a substituted or unsubstituted C6 to C30 arylene group, a substituted or unsubstituted C2 to C30 heteroarylene group, a substituted or unsubstituted C6 to C30 aryleneamine group, a substituted or unsubstituted C1 to C30 alkoxylene group, a substituted or unsubstituted C1 to C30 aryloxylene group, a substituted or unsubstituted C2 to C30 alkenylene group, a substituted or unsubstituted C2 to C30 alkynylene group, or a combination thereof, and $R^1$ to $R^7$ are independently hydrogen, deuterium, a substituted or unsubstituted C1 to C30 alkyl group, a substituted or unsubstituted C3 to C30 cycloalkyl group, a substituted or unsubstituted C2 to C30 heterocyclic group, a substituted or unsubstituted C6 to C30 aryl group, a substituted or unsubstituted C6 to C30 arylamine group, a substituted or unsubstituted C1 to C30 alkoxy group, a substituted or unsubstituted C2 to C30 alkoxycarbonyl group, a substituted or unsubstituted C2 to C30 alkoxycarbonylamino group, a substituted or unsubstituted C7 to C30 aryloxycarbonylamino group, a substituted or unsubstituted C1 to C30 sulfamoylamino group, a substituted or unsubstituted C2 to C30 alkenyl group, a substituted or unsubstituted C2 to C30 alkynyl group, a substituted or unsubstituted C3 to C40 silyl group, a substituted or unsubstituted C3 to C40 silyloxy group, a substituted or unsubstituted C1 to C30 acyl group, a substituted or unsubstituted C1 to C20 acyloxy group, a substituted or unsubstituted C1 to C20 acylamino group, a substituted or unsubstituted C1 to C30 sulfonyl group, a substituted or unsubstituted C1 to C30 alkylthiol group, a substituted or unsubstituted C6 to C30 arylthiol group, a substituted or unsubstituted C1 to C30 ureide group, a halogen, a halogen-containing group, a cyano group, a hydroxyl group, an amino group, a nitro group, a carboxyl group, a ferrocenyl group, or a combination thereof, at least one of $R^2$ and $R^3$ is represented by Chemical Formula 2 or Chemical Formula 3:

[Chemical Formula 2]

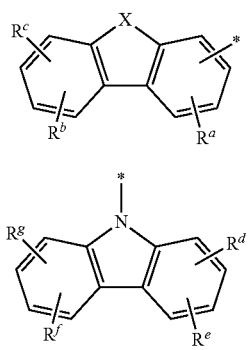

[Chemical Formula 3]

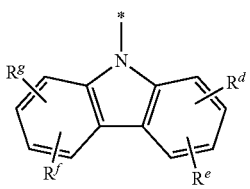

in Chemical Formulae 2 and 3,
* is a linking point,
X is O or S, and
$R^a$ to $R^g$ are each independently hydrogen, deuterium, a substituted or unsubstituted C1 to C30 alkyl group, a substituted or unsubstituted C3 to C30 cycloalkyl group, a substituted or unsubstituted C2 to C30 heterocyclic group, a substituted or unsubstituted C6 to C30 aryl group, a substituted or unsubstituted C6 to C30 arylamine group, a substituted or unsubstituted C1 to C30 alkoxy group, a substituted or unsubstituted C2 to C30 alkoxycarbonyl group, a substituted or unsubstituted C2 to C30 alkoxycarbonylamino group, a substituted or unsubstituted C7 to C30 aryloxycarbonylamino group, a substituted or unsubstituted C1 to C30 sulfamoylamino group, a substituted or unsubstituted C2 to C30 alkenyl group, a substituted or unsubstituted C2 to C30 alkynyl group, a substituted or unsubstituted C3 to C40 silyl group, a substituted or unsubstituted C3 to C40 silyloxy group, a substituted or unsubstituted C1 to C30 acyl group, a substituted or unsubstituted C1 to C20 acyloxy group, a substituted or unsubstituted C1 to C20 acylamino group, a substituted or unsubstituted C1 to C30 sulfonyl group, a substituted or unsubstituted C1 to C30 alkylthiol group, a substituted or unsubstituted C6 to C30 arylthiol group, a substituted or unsubstituted C1 to C30 ureide group, a halogen, a halogen-containing group, a cyano group, a hydroxyl group, an amino group, a nitro group, a carboxyl group, a ferrocenyl group, or a combination thereof.

The compound according to one embodiment of the present invention may be used for an organic optoelectric device.

In another embodiment of the present invention, an organic optoelectric device includes an anode and a cathode facing each other and at least one organic layer between the anode and the cathode, wherein the organic layer includes an emission layer and at least one auxiliary layer selected from a hole injection layer, a hole transport layer, an electron blocking layer, an electron transport layer, an electron injection layer, and a hole blocking layer, and the auxiliary layer includes the compound.

In yet another embodiment of the present invention, a display device including the organic optoelectric device is provided.

Advantageous Effect

An organic optoelectric device having high efficiency long life-span may be realized.

DESCRIPTION OF DRAWINGS

FIGS. 1 and 2 are cross-sectional views showing organic light emitting diodes according to one embodiment of the present invention.

FIG. 3 is a graph showing PL wavelength measurement results of the compound according to one embodiment of the present invention.

DESCRIPTION OF SYMBOLS

100: organic light emitting diode
105: organic layer
110: cathode
120: anode
130: emission layer
140: hole auxiliary layer
200: organic light emitting diode
230: emission layer

BEST MODE

Hereinafter, embodiments of the present invention are described in detail. However, these embodiments are exemplary, the present invention is not limited thereto and the present invention is defined by the scope of claims.

In the present specification, when a definition is not otherwise provided, the term "substituted" refers to one substituted with a substituent selected from deuterium, a halogen, a hydroxy group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C3 to C30 cycloalkyl group, a C6 to C30 aryl group, a C1 to C20 alkoxy group, a fluoro group, a C1 to C10 trifluoroalkyl group such as a trifluoromethyl group, or a cyano group, instead of at least one hydrogen of a substituent or a compound.

In the present specification, when specific definition is not otherwise provided, "hetero" refers to one including 1 to 3 hetero atoms selected from N, O, S, P, and Si, and remaining carbons in one functional group.

In the present specification, when a definition is not otherwise provided, "alkyl group" refers to an aliphatic hydrocarbon group. The alkyl group may be "a saturated alkyl group" without any double bond or triple bond.

The alkyl group may be a C1 to C20 alkyl group. More specifically, the alkyl group may be a C1 to 010 alkyl group or a C1 to C5 alkyl group. For example, a C1 to C4 alkyl group may have 1 to 4 carbon atoms in an alkyl chain which may be selected from methyl, ethyl, propyl, iso-propyl, n-butyl, iso-butyl, sec-butyl, and t-butyl.

Specific examples of the alkyl group may be a methyl group, an ethyl group, a propyl group, an isopropyl group, a butyl group, an isobutyl group, a t-butyl group, a pentyl group, a hexyl group, a cyclopropyl group, a cyclobutyl group, a cyclopentyl group, a cyclohexyl group, and the like.

In the present specification, the term "aryl group" refers to a substituent including all element of the cycle having p-orbitals which form conjugation, and may be monocyclic, polycyclic or fused ring polycyclic (i.e., rings sharing adjacent pairs of carbon atoms) functional group.

In the present specification, the term "heterocyclic group" refers to a cyclic compound such as an aryl group, a cycloalkyl group, a fused ring thereof, or a combination thereof including at least one heteroatoms selected from N, O, S, P, and Si, and remaining carbons. When the heterocyclic group is a fused ring, the entire ring or each ring of the heterocyclic group may include one or more heteroatoms. Accordingly, the heterocyclic group is a general term including a heteroaryl group.

More specifically, the substituted or unsubstituted C6 to C30 aryl group and/or the substituted or unsubstituted C2 to C30 heterocyclic group may be a substituted or unsubstituted phenyl group, a substituted or unsubstituted naphthyl group, a substituted or unsubstituted anthracenyl group, a substituted or unsubstituted phenanthrylene group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted chrysenyl group, a substituted or unsubstituted triphenylenyl group, a substituted or unsubstituted perylenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted fluorenyl group, a substituted or unsubstituted carbazolyl group, a substituted or unsubstituted dibenzofuranyl group, a substituted or unsubstituted dibenzothiophenyl group, a combination thereof, or a combined fused ring of the foregoing groups, but are not limited thereto.

In the specification, the single bond may refer to direct linkage without carbon a hetero atom except carbon, and specifically when L is a single bond, a substituent linked to L directly links to core directly. That is to say, in the present specification, a single bond excludes methylene including carbon, and the like.

In the specification, hole characteristics refer to characteristics capable of donating an electron when an electric field is applied and that a hole formed in the anode is easily injected into the emission layer and transported in the emission layer due to conductive characteristics according to highest occupied molecular orbital (HOMO) level.

In addition, electron characteristics refer to characteristics capable of accepting an electron when an electric field is applied and that an electron formed in the cathode is easily injected into the emission layer and transported in the emission layer due to conductive characteristics according to lowest unoccupied molecular orbital (LUMO) level.

Hereinafter, a compound according to one embodiment is described.

In one embodiment of the present invention, a compound represented by Chemical Formula 1 is provided.

[Chemical Formula 1]

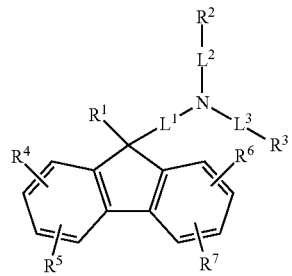

In Chemical Formula 1, $L^1$ to $L^3$ are independently a single bond, a substituted or unsubstituted C1 to C30 alkylene group, a substituted or unsubstituted C3 to C30 cycloalkylene group, a substituted or unsubstituted C6 to C30 arylene group, a substituted or unsubstituted C2 to C30 heteroarylene group, a substituted or unsubstituted C6 to C30 aryleneamine group, a substituted or unsubstituted C1 to C30 alkoxylene group, a substituted or unsubstituted C1 to C30 aryloxylene group, a substituted or unsubstituted C2 to C30 alkenylene group, a substituted or unsubstituted C2 to C30 alkynylene group, or a combination thereof, $R^1$ to $R^7$ are independently hydrogen, deuterium, a substituted or unsubstituted C1 to C30 alkyl group, a substituted or unsubstituted C3 to C30 cycloalkyl group, a substituted or unsubstituted C2 to C30 heterocyclic group, a substituted or unsubstituted C6 to C30 aryl group, a substituted or unsubstituted C6 to C30 arylamine group, a substituted or unsubstituted C1 to C30 alkoxy group, a substituted or unsubstituted C2 to C30 alkoxycarbonyl group, a substituted or unsubstituted C2 to C30 alkoxycarbonylamino group, a substituted or unsubstituted C7 to C30 aryloxycarbonylamino group, a substituted or unsubstituted C1 to C30 sulfamoylamino group, a substituted or unsubstituted C2 to C30 alkenyl group, a substituted or unsubstituted C2 to C30 alkynyl group, a substituted or unsubstituted C3 to C40 silyl group, a substituted or unsubstituted C3 to C40 silyloxy group, a substituted or unsubstituted C1 to C30 acyl group, a substituted or unsubstituted C1 to C20 acyloxy group, a substituted or unsubstituted C1 to 020 acylamino group, a substituted or unsubstituted C1 to C30 sulfonyl group, a substituted or unsubstituted C1 to C30 alkylthio group, a substituted or unsubstituted C6 to C30 arylthio group, a substituted or unsubstituted C1 to C30 ureide group, a halogen, a halogen-containing group, a cyano group, a hydroxyl group, an amino group, a nitro group, a carboxyl group, a ferrocenyl group, or a combination thereof, and at least one of $R^2$ and $R^3$ is represented by Chemical Formula 2 or Chemical Formula 3:

[Chemical Formula 2]

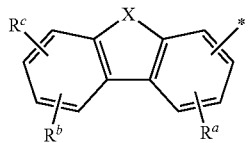

-continued

[Chemical Formula 3]

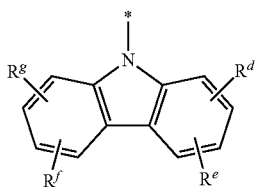

in Chemical Formulae 2 and 3,

* is a linking point,

X is O or S, $R^a$ to $R^g$ are each independently hydrogen, deuterium, a substituted or unsubstituted C1 to C30 alkyl group, a substituted or unsubstituted C3 to C30 cycloalkyl group, a substituted or unsubstituted C2 to C30 heterocyclic group, a substituted or unsubstituted C6 to C30 aryl group, a substituted or unsubstituted C6 to C30 arylamine group, a substituted or unsubstituted C1 to C30 alkoxy group, a substituted or unsubstituted C2 to C30 alkoxycarbonyl group, a substituted or unsubstituted C2 to C30 alkoxycarbonylamino group, a substituted or unsubstituted C7 to C30 aryloxycarbonylamino group, a substituted or unsubstituted C1 to C30 sulfamoylamino group, a substituted or unsubstituted C2 to C30 alkenyl group, a substituted or unsubstituted C2 to C30 alkynyl group, a substituted or unsubstituted C3 to C40 silyl group, a substituted or unsubstituted C3 to C40 silyloxy group, a substituted or unsubstituted C1 to C30 acyl group, a substituted or unsubstituted C1 to C20 acyloxy group, a substituted or unsubstituted C1 to C20 acylamino group, a substituted or unsubstituted C1 to C30 sulfonyl group, a substituted or unsubstituted C1 to C30 alkylthiol group, a substituted or unsubstituted C6 to C30 arylthiol group, a substituted or unsubstituted C1 to C30 ureide group, a halogen, a halogen-containing group, a cyano group, a hydroxyl group, an amino group, a nitro group, a carboxyl group, a ferrocenyl group, or a combination thereof.

The compound according to one embodiment of the present invention has at least either one of the $R^2$ and $R^3$ represented by Chemical Formula 2 or 3 and thus, may increase hole transporting properties of the molecule and thus, show excellent efficiency when applied to a hole transport layer and a hole transporting light emitting host for an organic optoelectric device.

Particularly, the compound may improve hole transporting properties and increase a glass transition temperature compared with a compound having an aryl group for the $R^2$ and the $R^3$ and thus, improve thermal stability and show long life-span and high efficiency characteristics when applied as a thin film for an organic optoelectric device, and has heat-resistant stability against a thermal decomposition compared with a compound having a fluorenyl group for at least either one of the $R^2$ and the $R^3$ and thus, may secure improved processability and device stability when formed into a thin film in a thermal evaporation method.

Accordingly, high efficiency, long life-span, and low voltage drive characteristics of an organic optoelectric device manufactured by using the compound may be adjusted.

The Chemical Formula 1 may be specifically represented by one of Chemical Formula 4 to Chemical Formula 12.

[Chemical Formula 4]

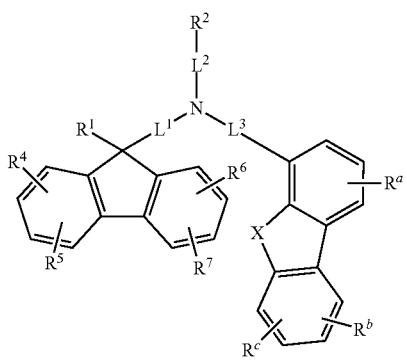

[Chemical Formula 5]

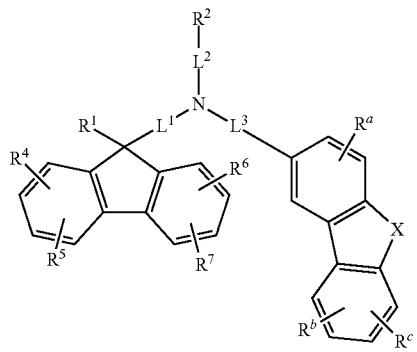

[Chemical Formula 6]

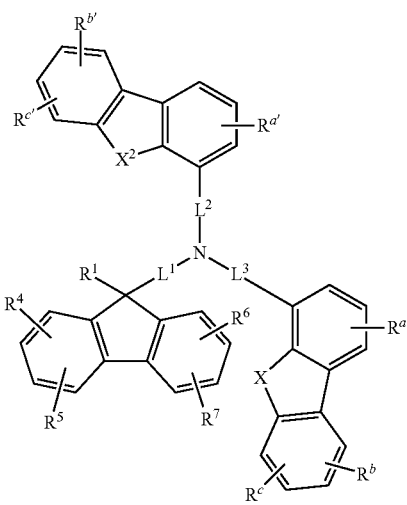

[Chemical Formula 7]

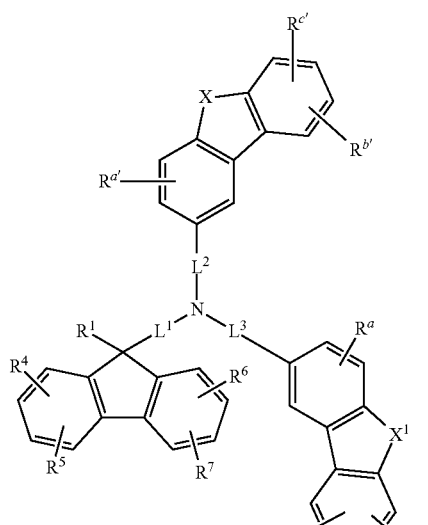

[Chemical Formula 8]

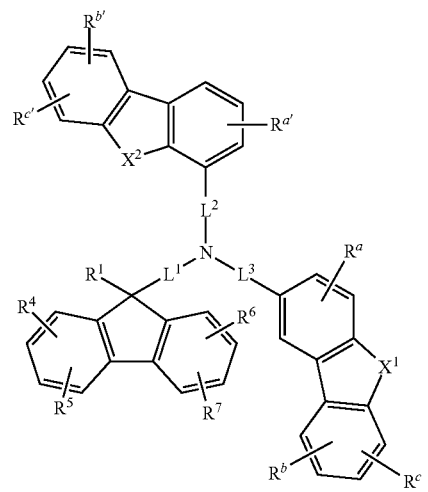

[Chemical Formula 9]

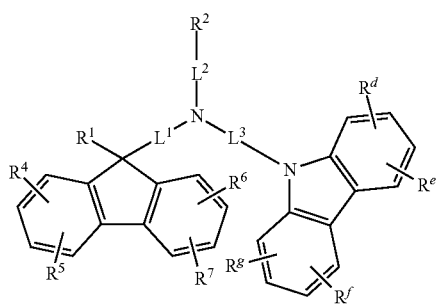

[Chemical Formula 10]

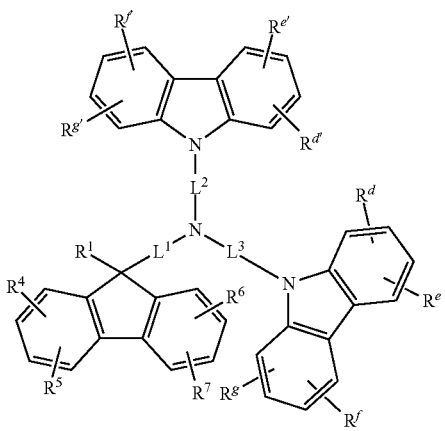

[Chemical Formula 11]

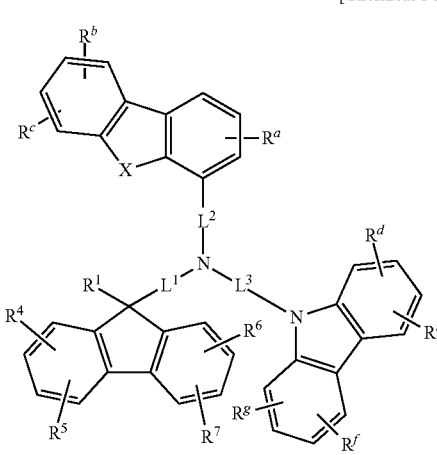

[Chemical Formula 12]

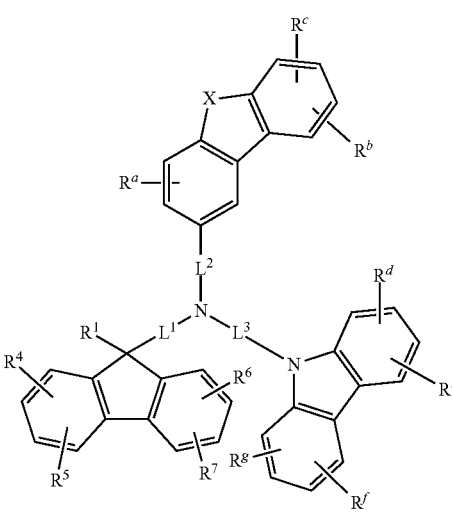

In Chemical Formulae 4 to 12

X, $X^1$ and $X^2$ are each independently O or S, $R^1$, $R^2$, $R^4$ to $R^7$, $R^a$ to $R^g$ and $R^{a'}$ to $R^{9'}$ are each independently hydrogen, deuterium, a substituted or unsubstituted C1 to C30 alkyl group, a substituted or unsubstituted C3 to C30 cycloalkyl group, a substituted or unsubstituted C2 to C30 heterocyclic group, a substituted or unsubstituted C6 to C30 aryl group, a substituted or unsubstituted C6 to C30 arylamine group, a substituted or unsubstituted C1 to C30 alkoxy group, a substituted or unsubstituted C2 to C30 alkoxycarbonyl group, a substituted or unsubstituted C2 to C30 alkoxycarbonylamino group, a substituted or unsubstituted C7 to C30 aryloxycarbonylamino group, a substituted or unsubstituted C1 to C30 sulfamoylamino group, a substituted or unsubstituted C2 to C30 alkenyl group, a substituted or unsubstituted C2 to C30 alkynyl group, a substituted or unsubstituted C3 to C40 silyl group, a substituted or unsubstituted C3 to C40 silyloxy group, a substituted or unsubstituted C1 to C30 acyl group, a substituted or unsubstituted C1 to C20 acyloxy group, a substituted or unsubstituted C1 to C20 acylamino group, a substituted or unsubstituted C1 to C30 sulfonyl group, a substituted or unsubstituted C1 to C30 alkylthiol group, a substituted or unsubstituted C6 to C30 arylthiol group, a substituted or unsubstituted C1 to C30 ureide group, a halogen, a halogen-containing group, a cyano group, a hydroxyl group, an amino group, a nitro group, a carboxyl group, a ferrocenyl group, or a combination thereof, and $L^1$ to $L^3$ are the same as defined in Chemical Formula 1.

For example, the $R^2$ and $R^3$ may be each independently selected from a substituted or unsubstituted C2 to C30 heterocyclic group or a substituted or unsubstituted C6 to C30 aryl group, and may be selected from a substituted or unsubstituted phenyl group, a substituted or unsubstituted naphthalene group, a substituted or unsubstituted biphenyl group, a substituted or unsubstituted terphenyl group, a substituted or unsubstituted triphenylenyl group, a substituted or unsubstituted anthracenyl group, a substituted or unsubstituted pyrenyl group, a substituted or unsubstituted dibenzofuranyl group, a substituted or unsubstituted dibenzothiophenyl group, a substituted or unsubstituted thiophenyl group, a substituted or unsubstituted furanyl group, a substituted or unsubstituted benzothiophenyl group, a substituted or unsubstituted benzofuranyl group, a substituted or unsubstituted quinolinyl group, a substituted or unsubstituted isoquinolinyl group, a substituted or unsubstituted benzoquinolinyl group, a substituted or unsubstituted benzoisoquinolinyl group, a substituted or unsubstituted pyridinyl group, a substituted or unsubstituted pyrimidinyl group, a substituted or unsubstituted triazinyl group, a substituted or unsubstituted fluorenyl group, a substituted or unsubstituted carbazolyl group, and the like.

For example, the $R^2$ and $R^3$ may be each independently selected from the substituted or unsubstituted groups listed in Group I, and at least one of $R^2$ and $R^3$ may be selected from the substituted or unsubstituted groups in Group I-1.

[Group I]

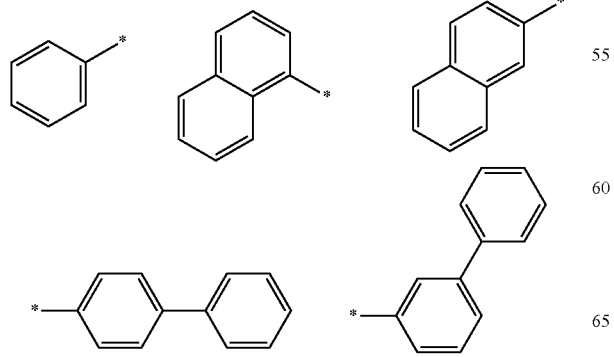
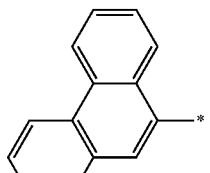
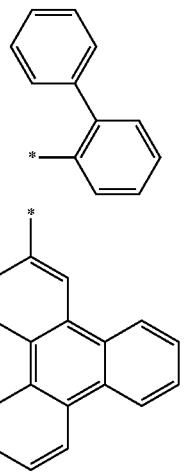
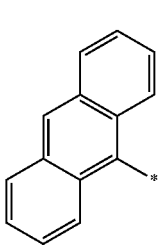
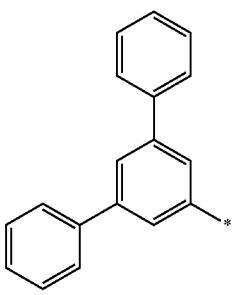
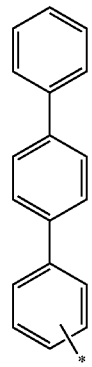
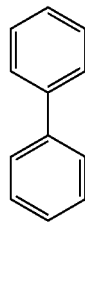
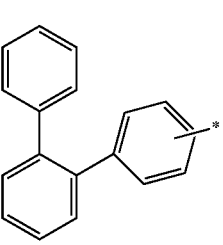
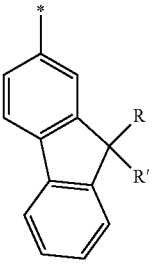
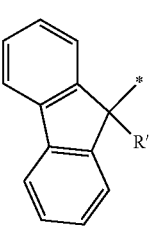
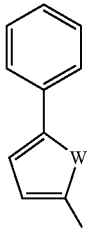
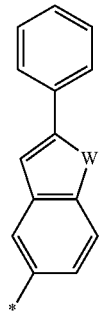

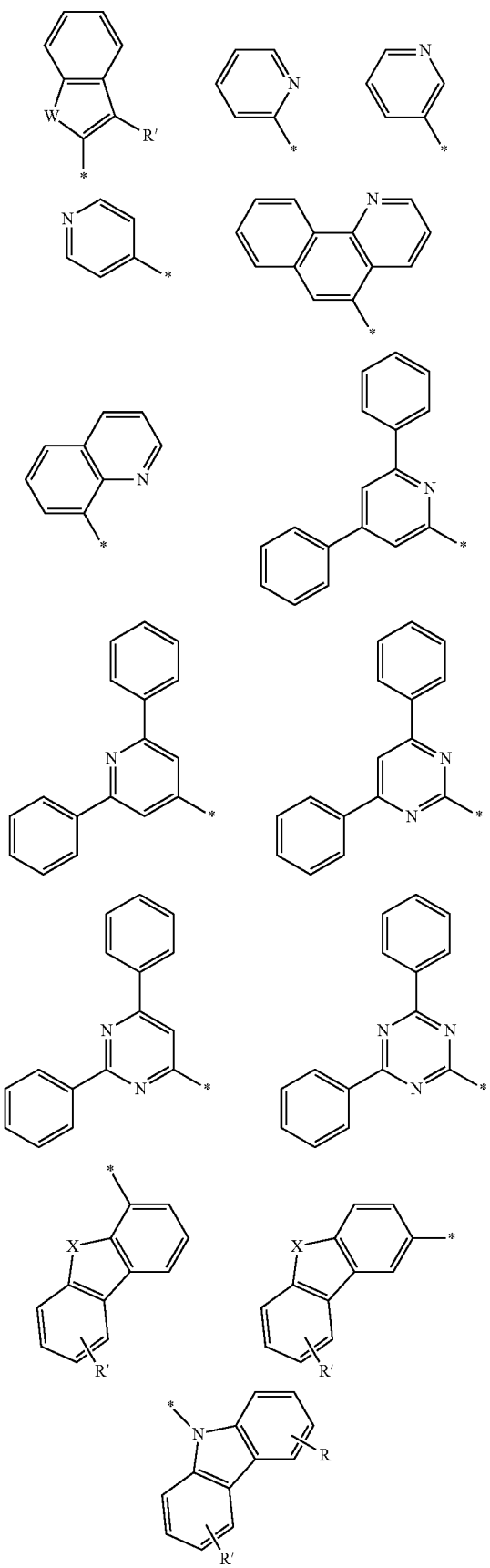

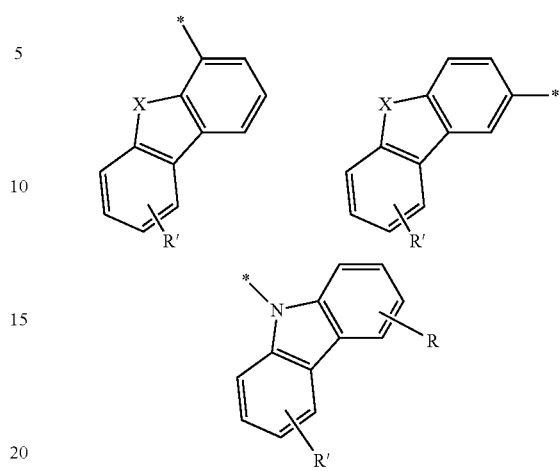

In Groups I and I-1,

X and W are each independently O or S, R and R' are independently hydrogen, deuterium, a substituted or unsubstituted C1 to C30 alkyl group, a substituted or unsubstituted C6 to C30 aryl group, a substituted or unsubstituted C3 to C30 heterocyclic group, or a combination thereof, and * is a linking point.

The $R^1$ may be a substituted or unsubstituted C1 to C30 alkyl group, a substituted or unsubstituted C3 to C30 cycloalkyl group, a substituted or unsubstituted C2 to C30 heterocyclic group, a substituted or unsubstituted C6 to C30 aryl group, or a combination thereof.

Specifically, the $R^1$ may be a methyl group, an ethyl group, a substituted or unsubstituted cyclopentyl group, a substituted or unsubstituted cyclohexyl group, a substituted or unsubstituted phenyl group, a substituted or unsubstituted biphenyl group, a substituted or unsubstituted naphthyl group, a substituted or unsubstituted pyridyl group, a substituted or unsubstituted furanyl group, a substituted or unsubstituted thiophenyl group, a substituted or unsubstituted quinolinyl group, or a combination thereof, and may be, for example selected from a methyl group, an ethyl group, or groups listed in Group II.

[Group II]

-continued

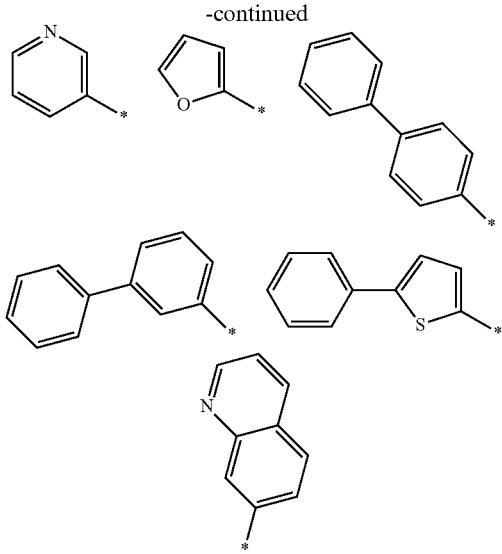

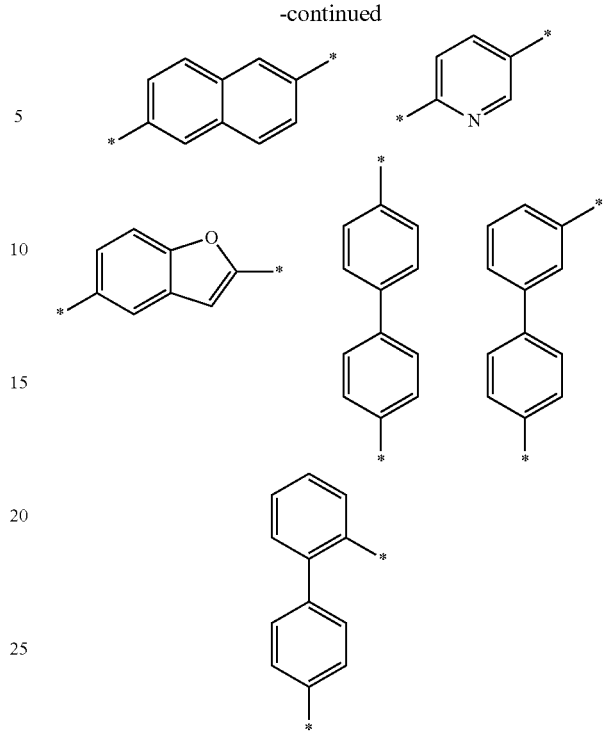

In Group II, * is a linking point.

In examples of the present invention, $R^4$ to $R^7$, $R^a$ to $R^g$ and $R^{a'}$ to $R^{g'}$ of Chemical Formula 1 and Chemical Formulae 4 to 12 may be each independently hydrogen, deuterium, a substituted or unsubstituted C1 to C10 alkyl group, a substituted or unsubstituted C3 to C12 cycloalkyl group, a substituted or unsubstituted C2 to C12 heterocyclic group, or a substituted or unsubstituted C6 to C12 aryl group.

In addition, $R^4$ to $R^7$, $R^a$ to $R^g$ and $R^{a'}$ to $R^{g'}$ of Chemical Formula 1 and Chemical Formulae 4 to 12 may be each independently hydrogen, deuterium, a substituted or unsubstituted C1 to C10 alkyl group, or a substituted or unsubstituted C6 to C12 aryl group.

In examples of the present invention, $L^1$ to $L^3$ of Chemical Formula 1 and Chemical Formulae 4 to 12 may be independently a single bond, a substituted or unsubstituted C6 to C30 arylene group, or a substituted or unsubstituted C2 to C30 heteroarylene group.

The $L^1$ to $L^3$ may be independently a single bond, a substituted or unsubstituted phenylene group, a substituted or unsubstituted biphenylene group, a substituted or unsubstituted naphthylene group, a substituted or unsubstituted pyridylene group, a substituted or unsubstituted pyrimidylene group, a substituted or unsubstituted benzofuranylene group, or a combination thereof, and may be, for example selected from a single bond, or the substituted or unsubstituted groups in Group III.

[Group III]

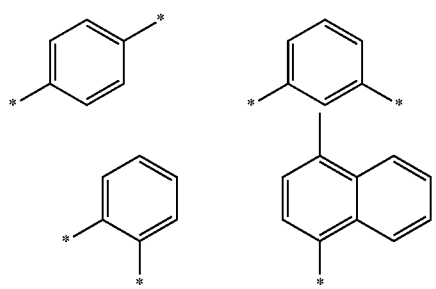

In Group III, * is a linking point.

The compound represented by Chemical Formula 1 may be, for example compounds listed below, but is not limited thereto.

[A-1]

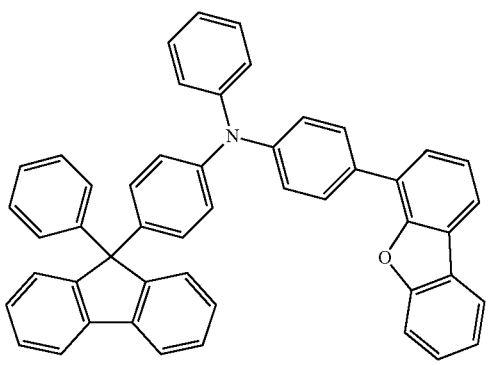

[A-2]

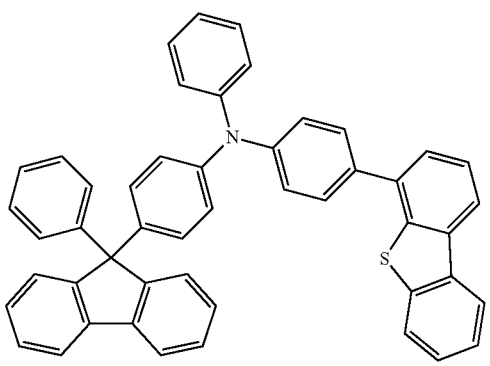

[A-3]
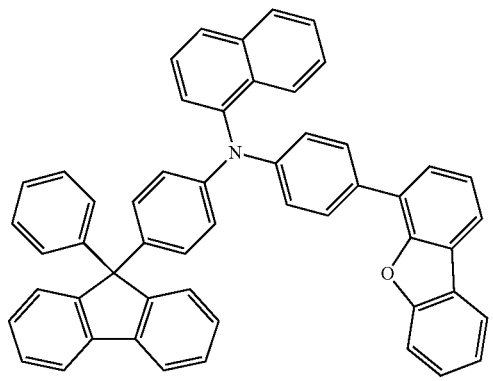
[A-4]
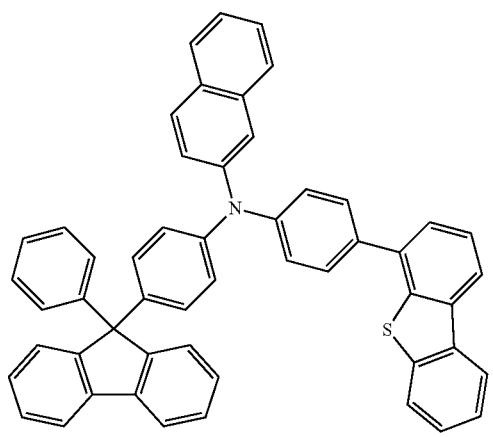
[A-5]
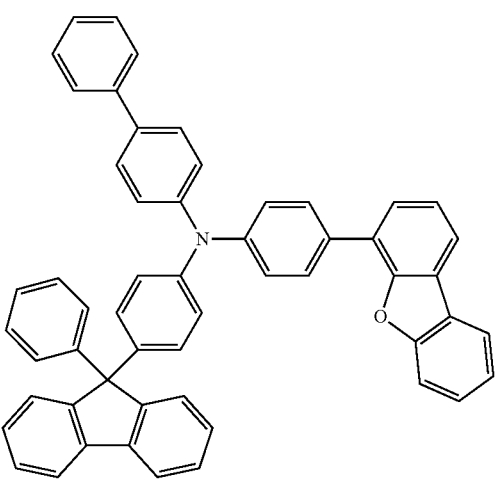
[A-6]
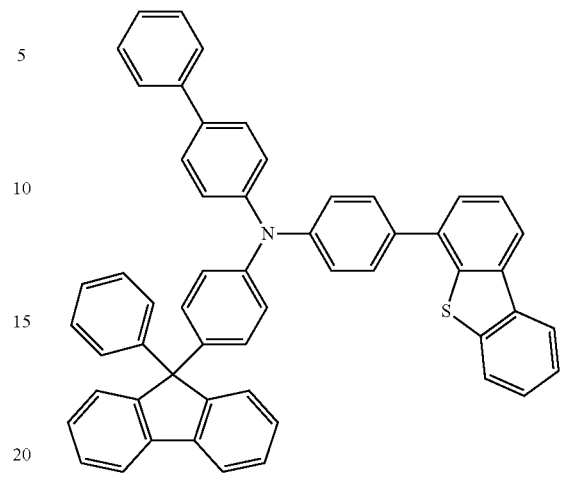
[A-7]
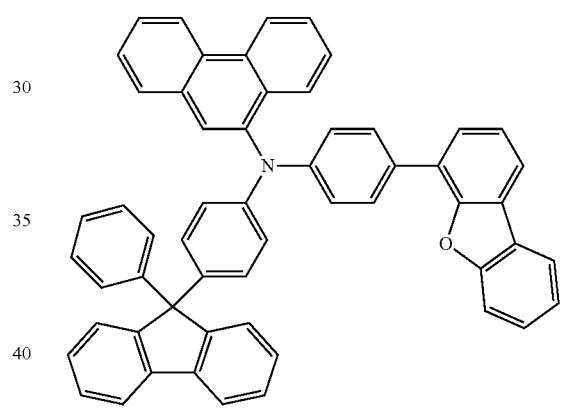
[A-8]
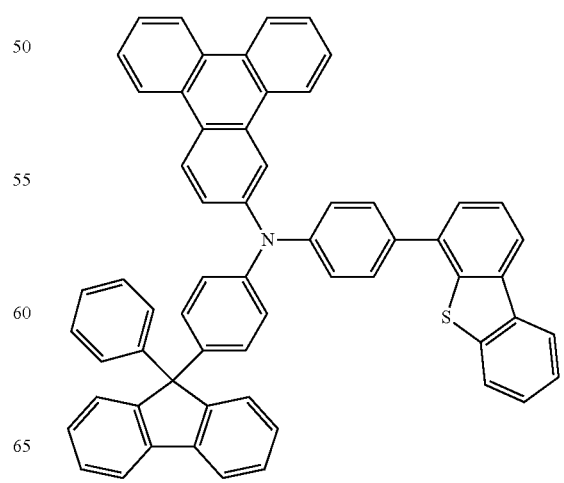

[A-9]
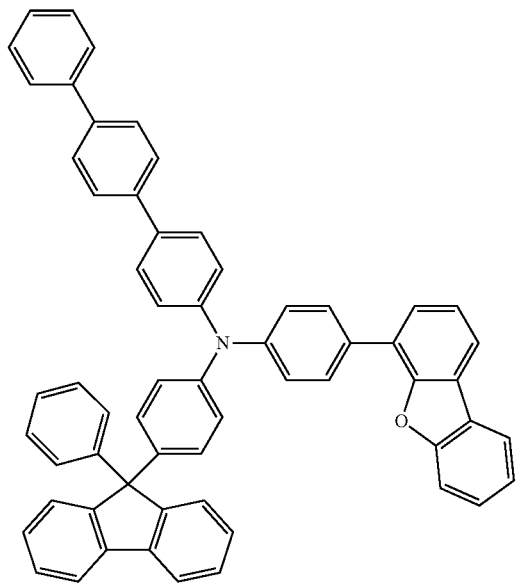
[A-11]
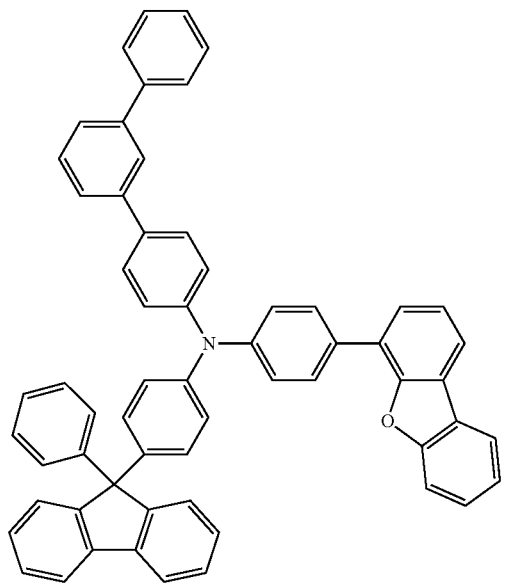
[A-10]
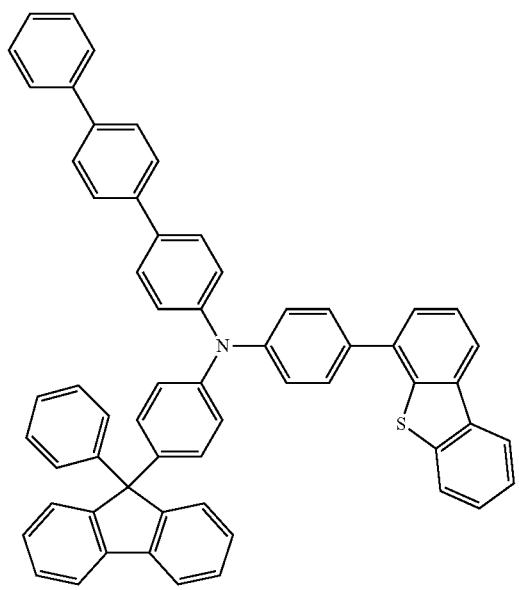
[A-12]
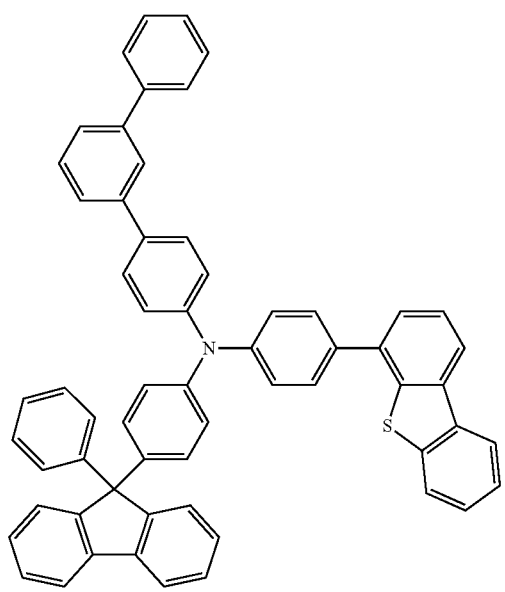

-continued
[A-13]
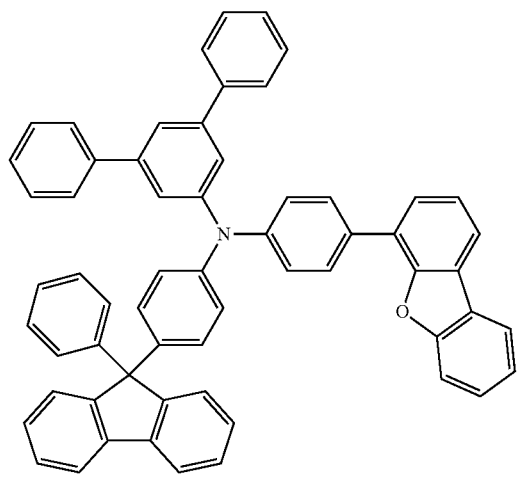
[A-14]
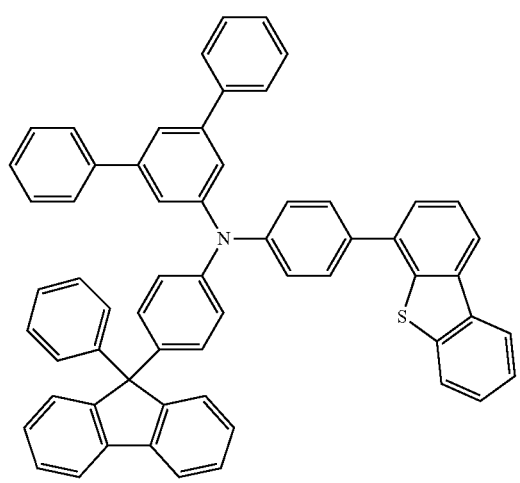
[A-15]
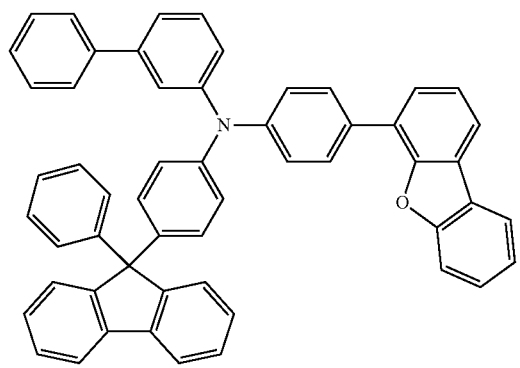
[A-16]
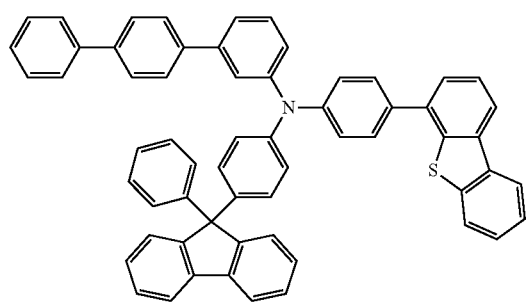
[A-17]
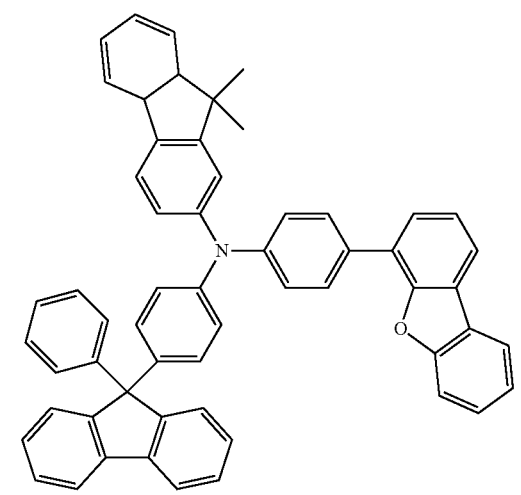
[A-18]
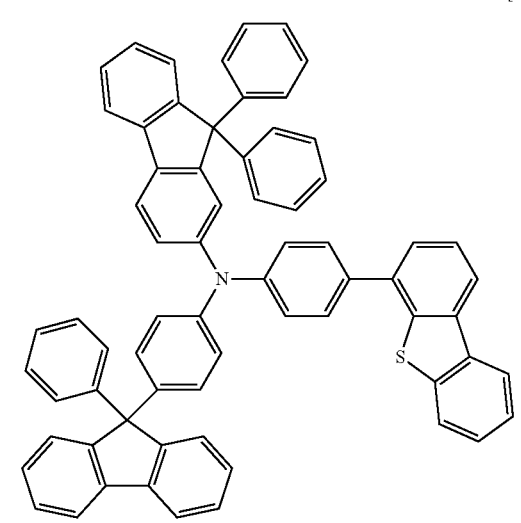

[A-19]
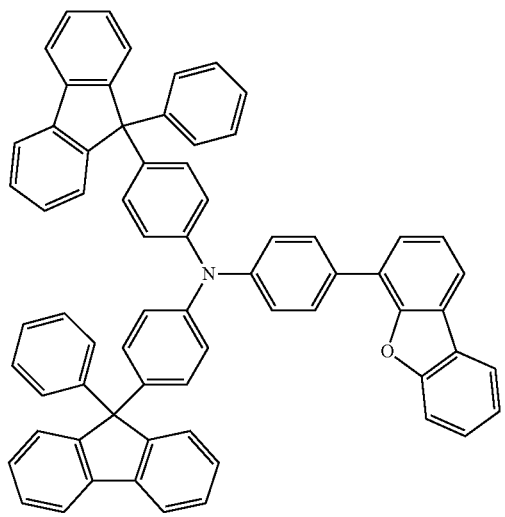
[A-20]
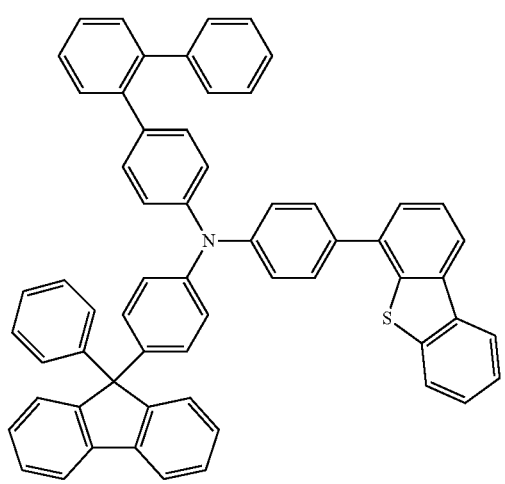
[A-21]
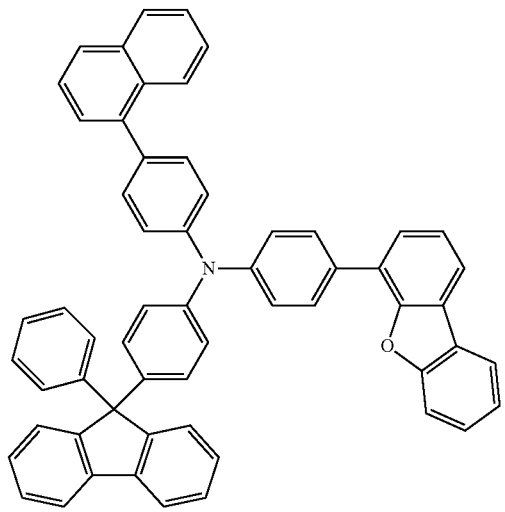
[A-22]
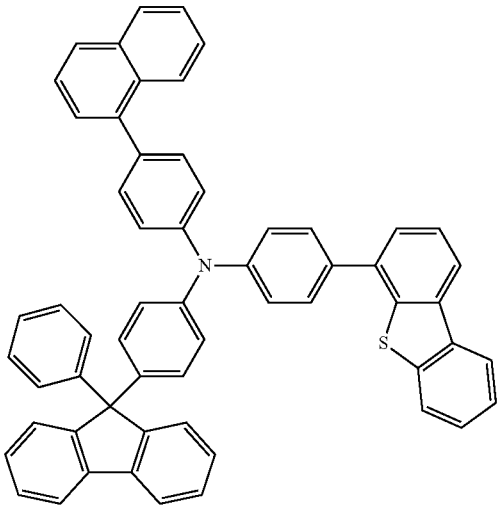
[A-23]
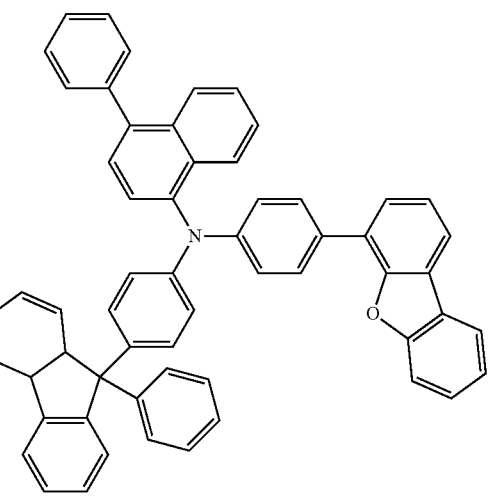
[A-24]
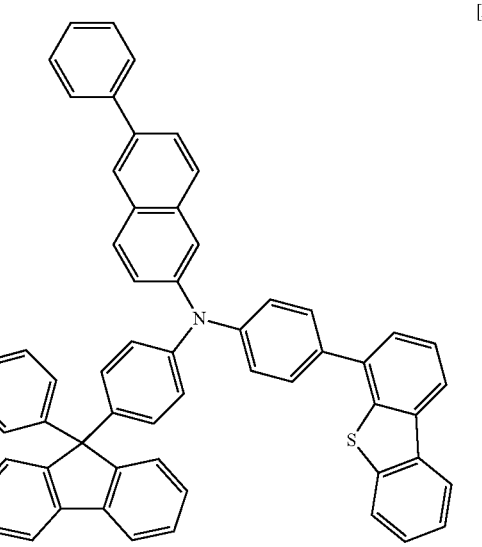

[A-25]
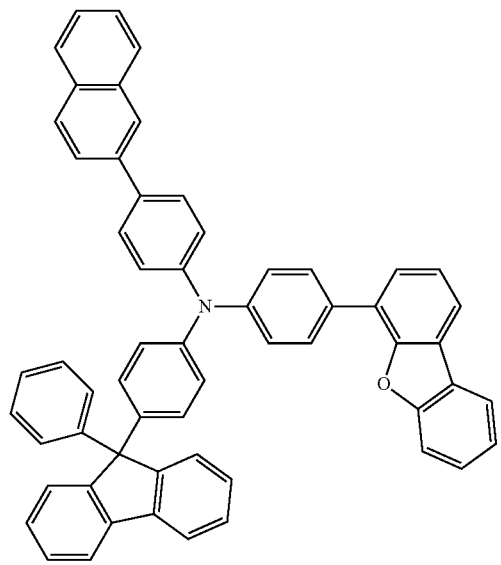
[A-27]
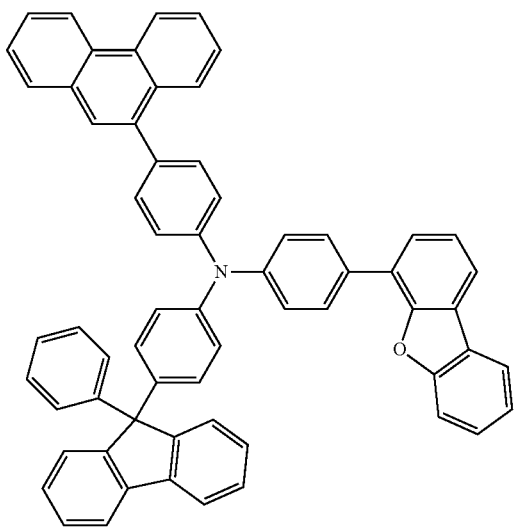
[A-26]
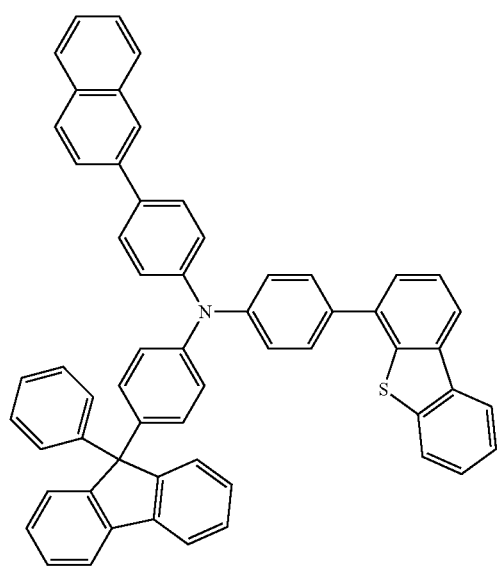
[A-28]
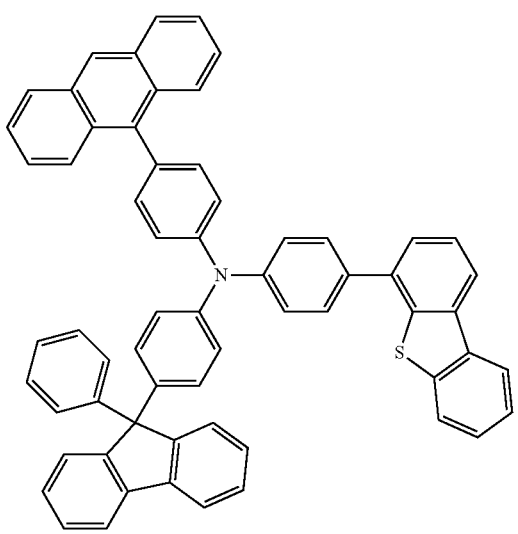

[A-29]
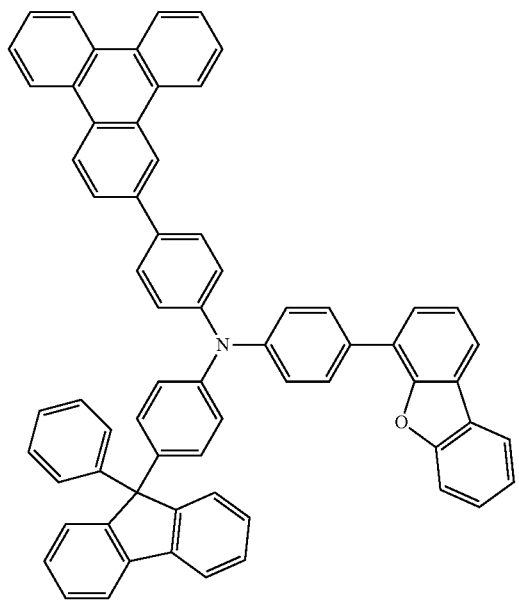
[A-31]
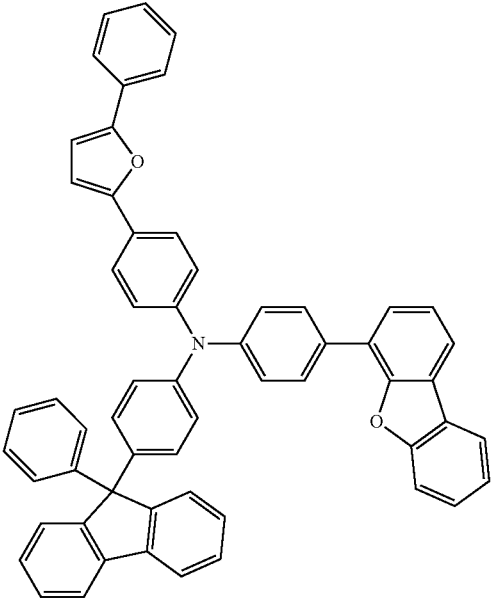
[A-30]
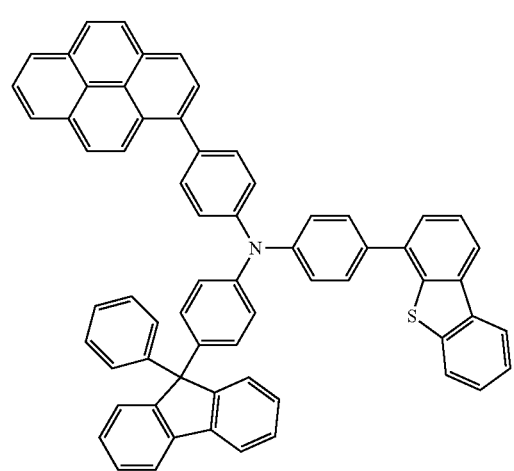
[A-32]
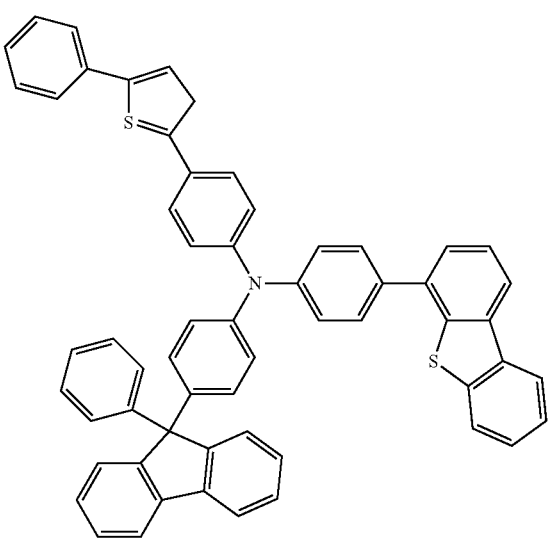

[A-33]
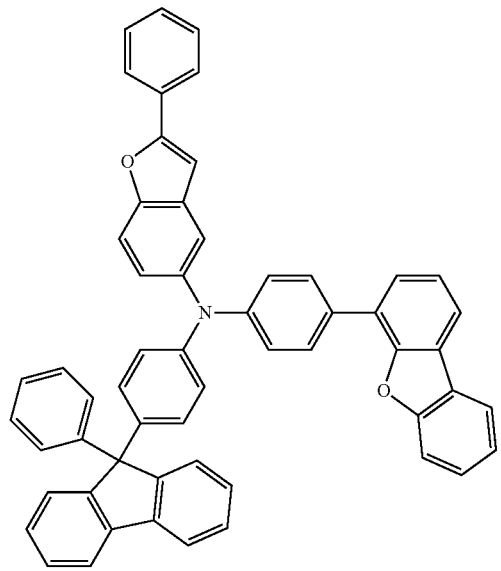
[A-35]
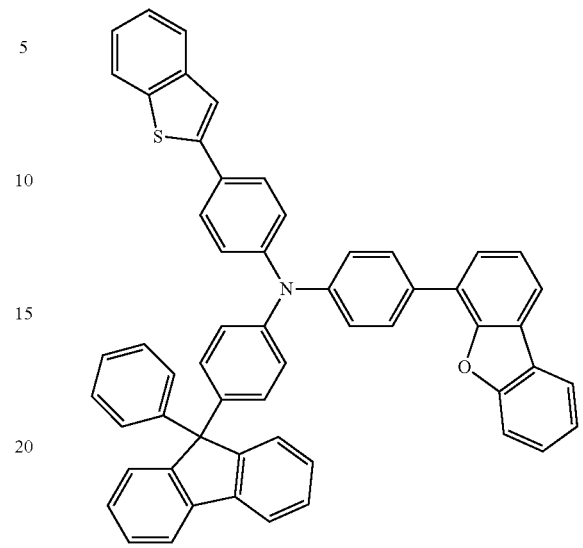
[A-36]
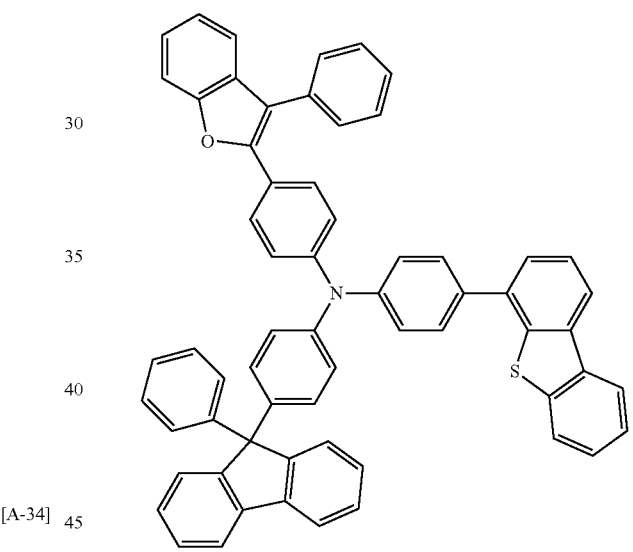
[A-34]
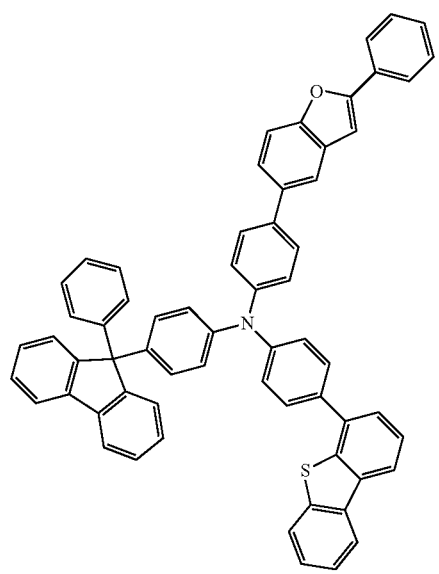
[A-37]
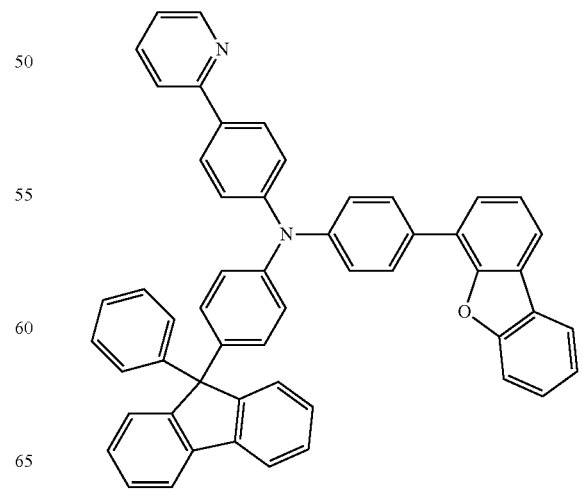

[A-38]
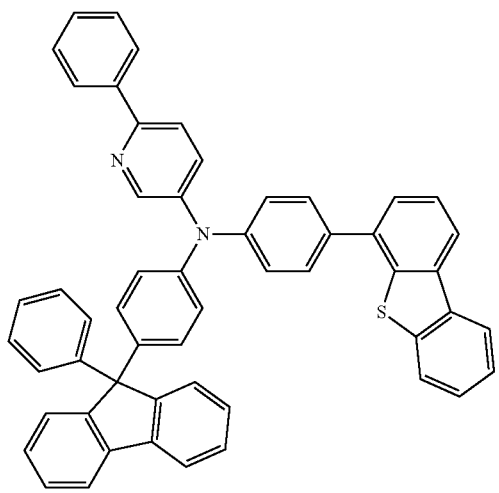
[A-41]
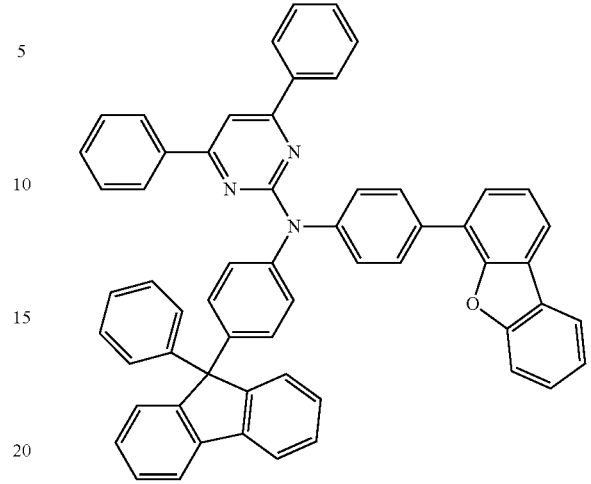
[A-39]
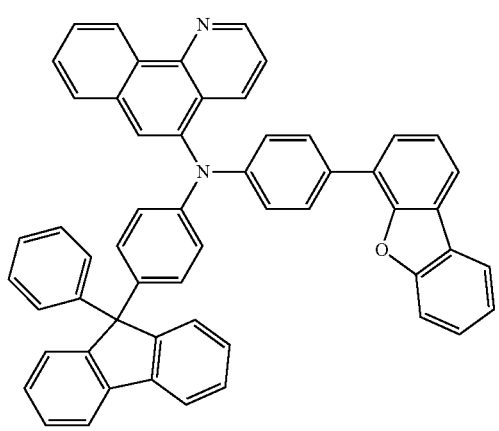
[A-42]
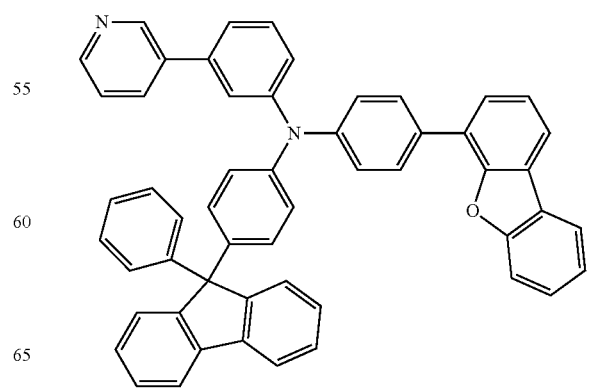
[A-40]
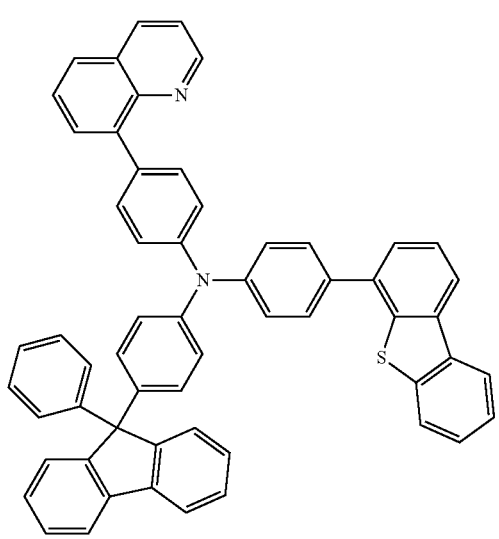
[A-43]

[A-44]
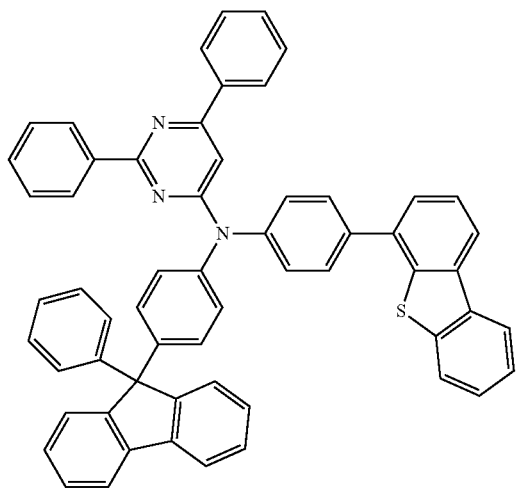
[A-45]
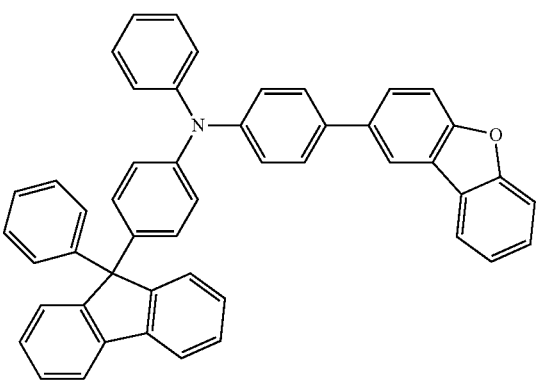
[A-46]
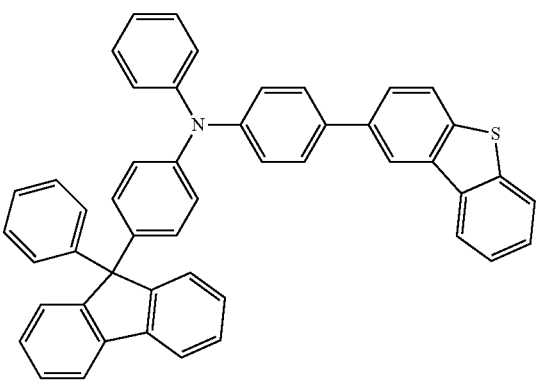
[A-47]
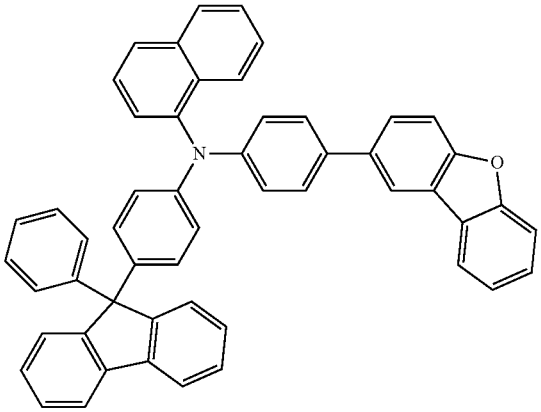
[A-48]
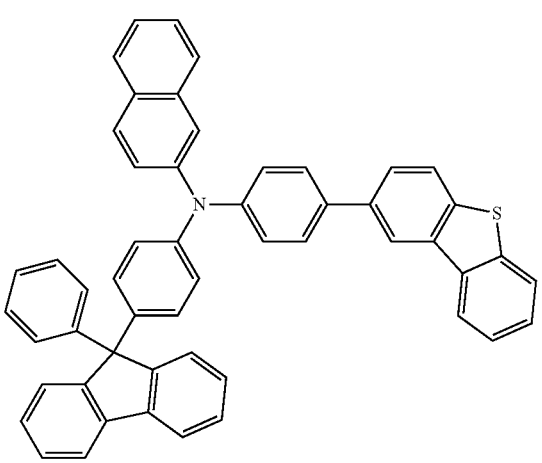
[A-49]
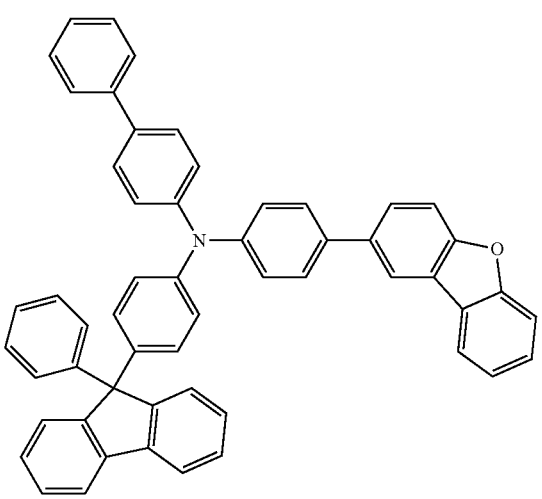

[A-50]
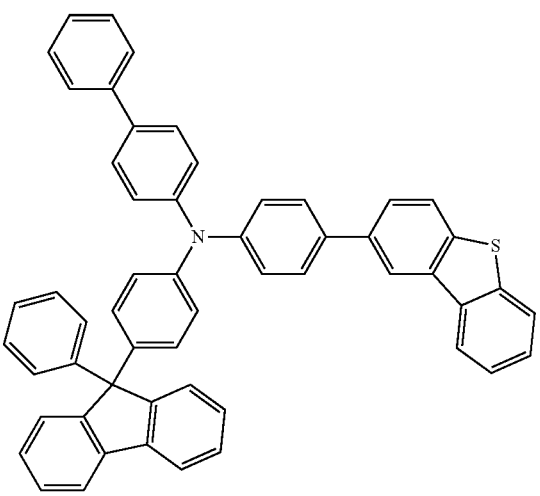
[A-53]
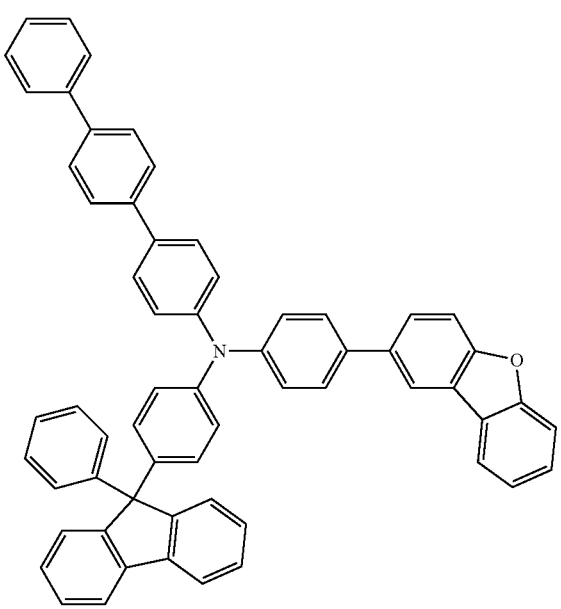
[A-51]
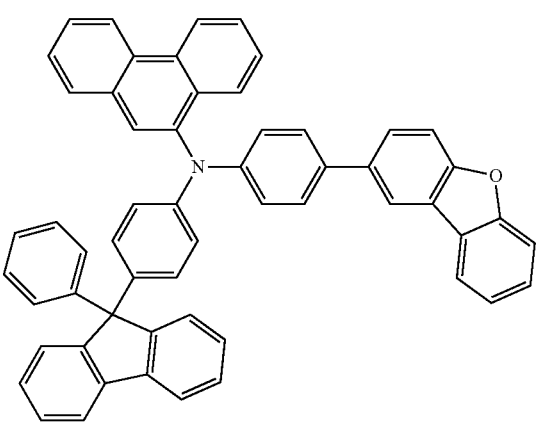
[A-52]
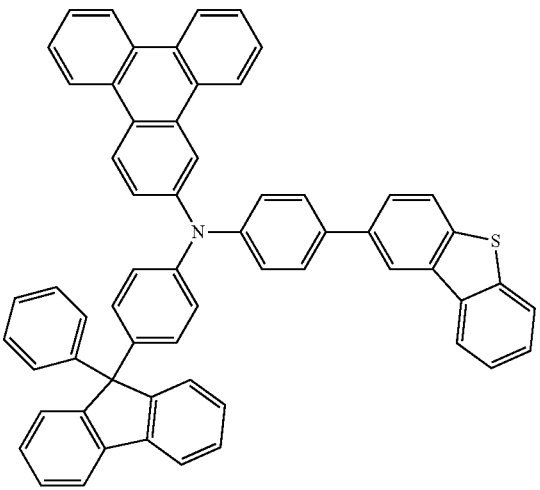
[A-54]
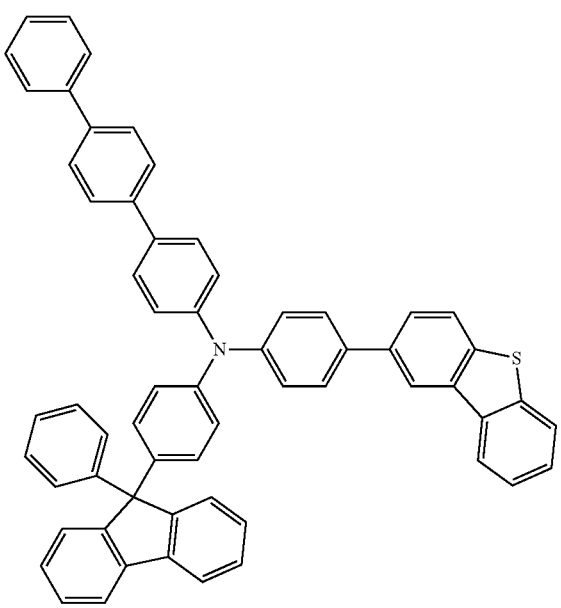

[A-55]
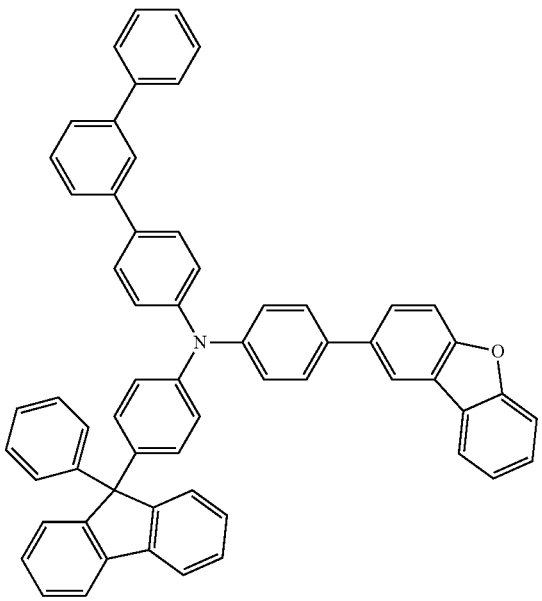
[A-56]
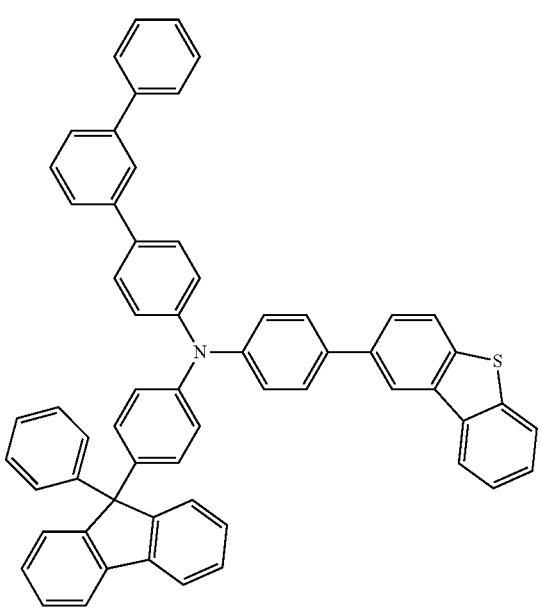
[A-57]
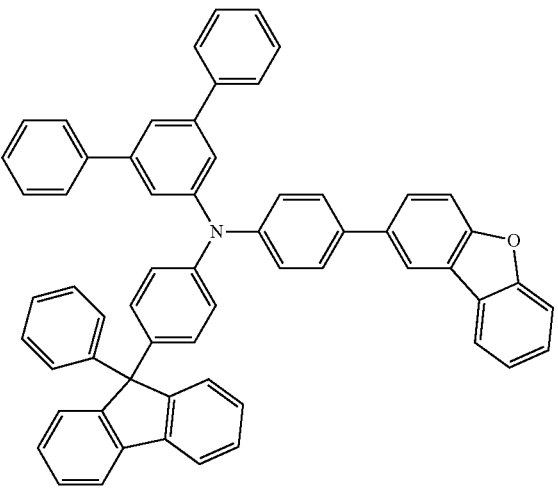
[A-58]
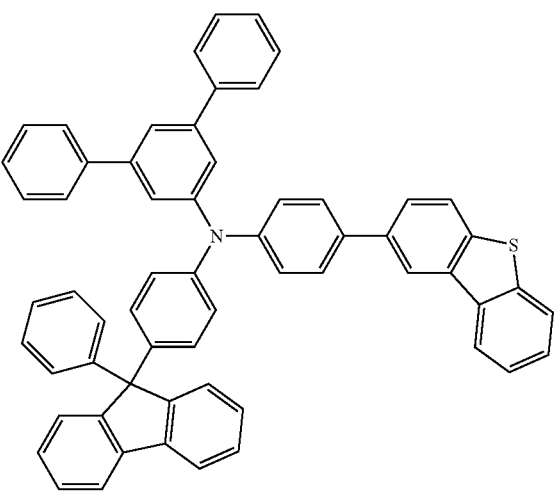
[A-59]
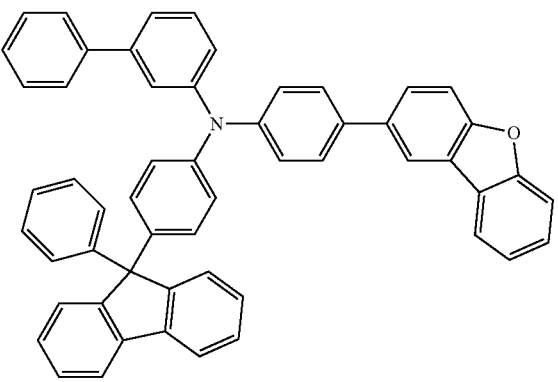

[A-60]
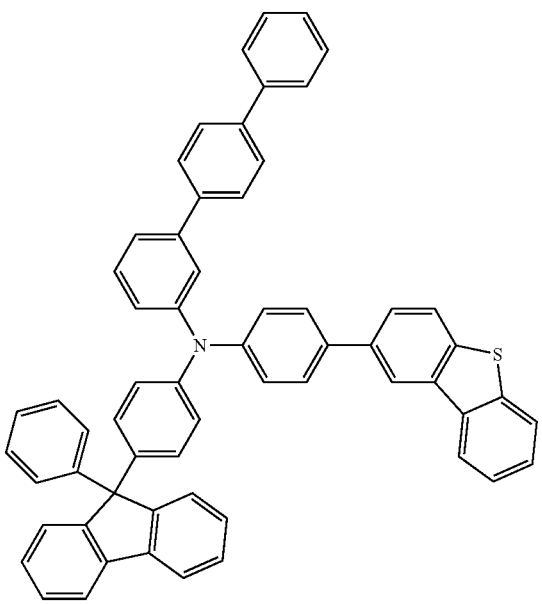
[A-61]
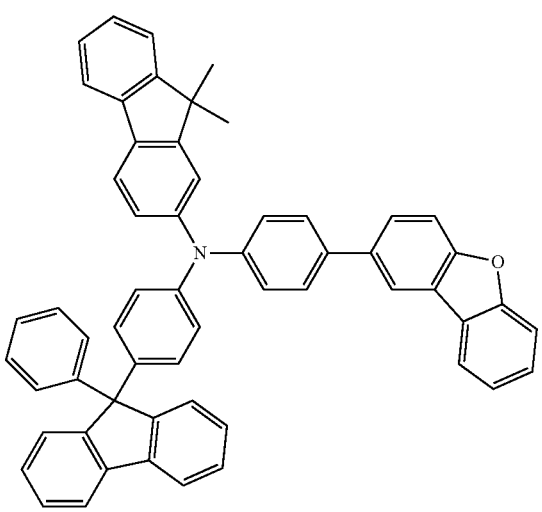
[A-62]
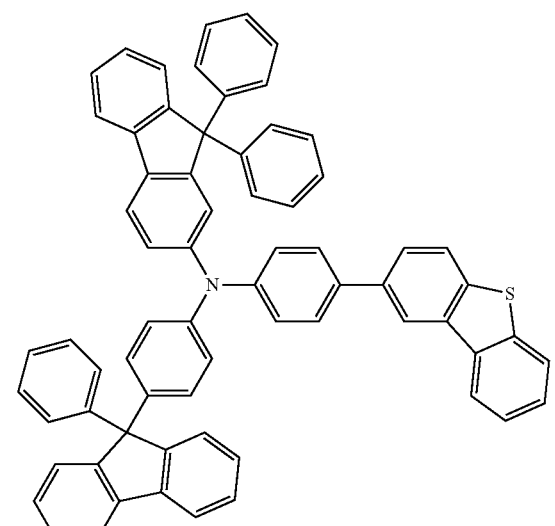
[A-63]
[A-64]
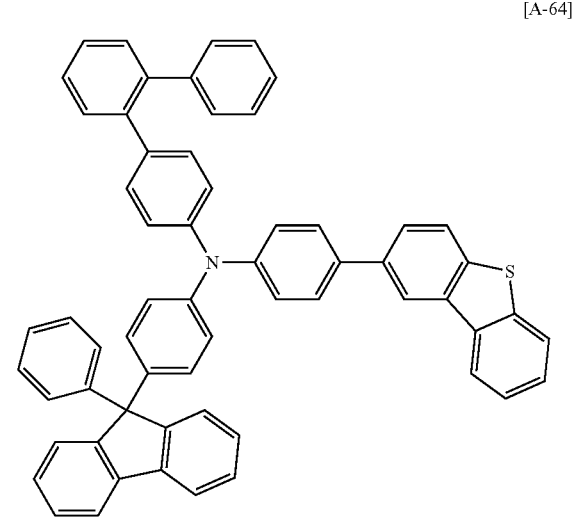

[A-65]
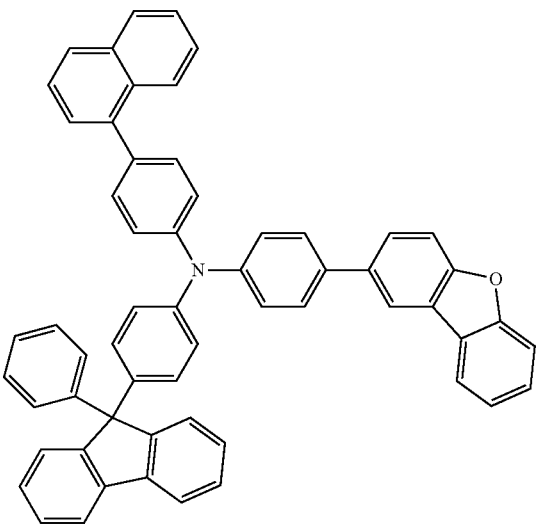
[A-66]
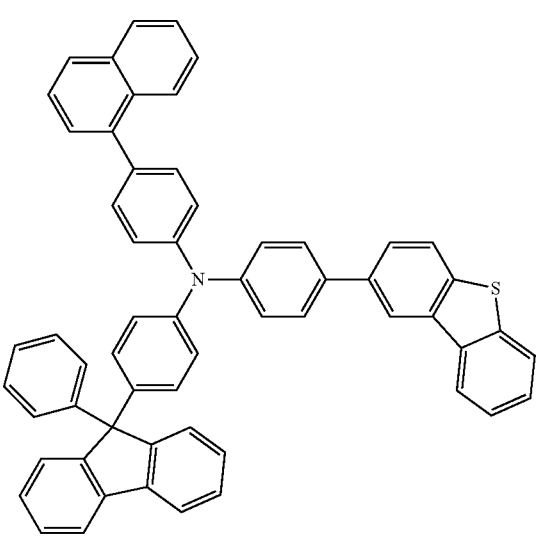
[A-67]
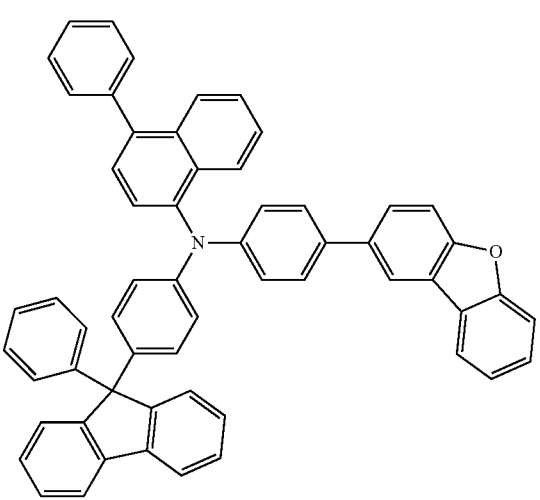
[A-68]
[A-69]
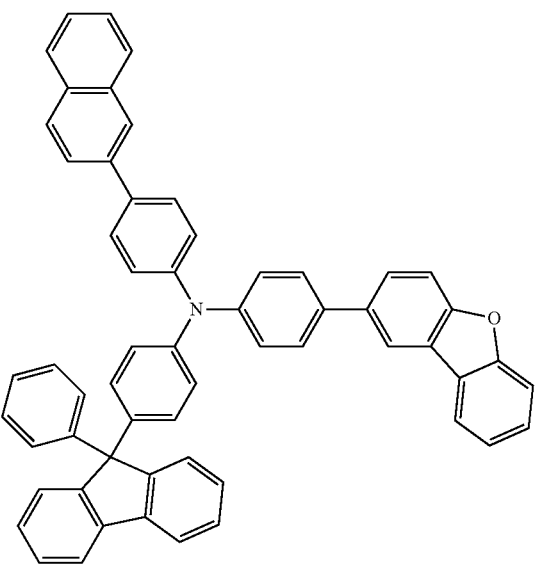

[A-70]
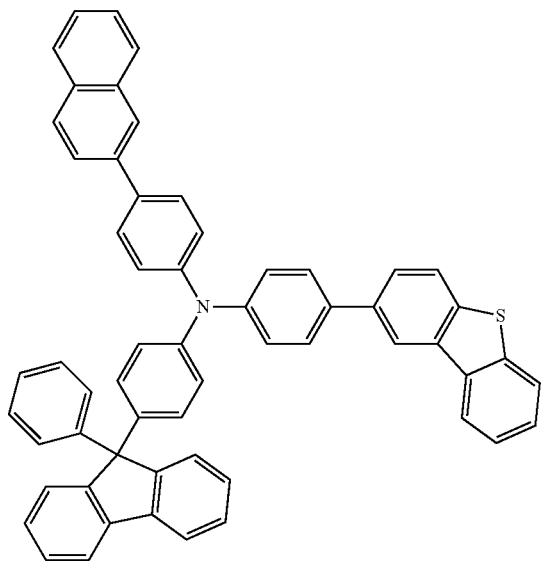
[A-71]
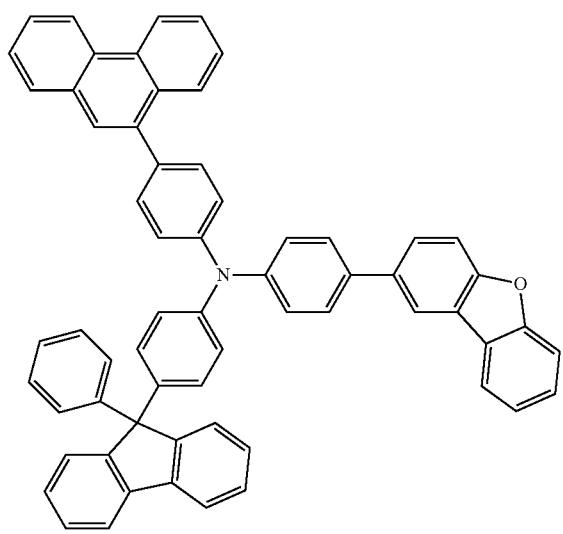
[A-72]
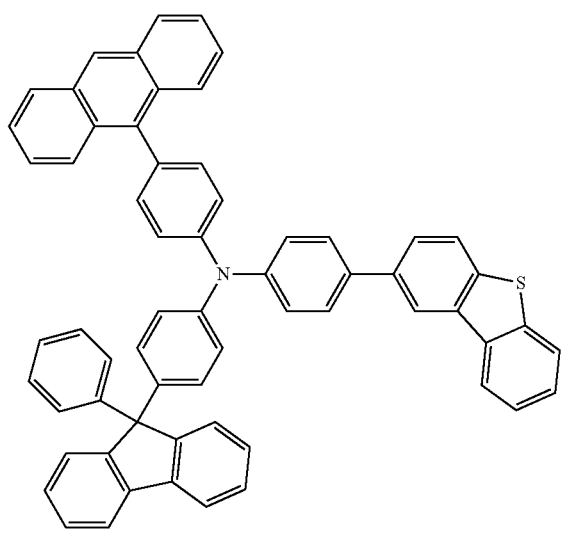
[A-73]
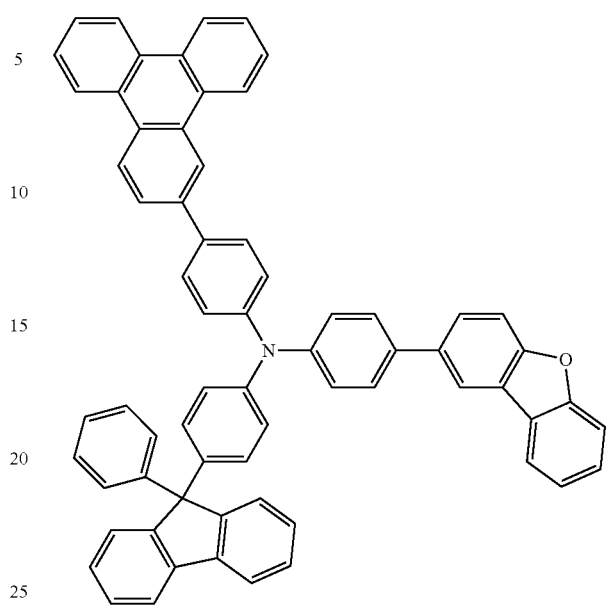
[A-74]
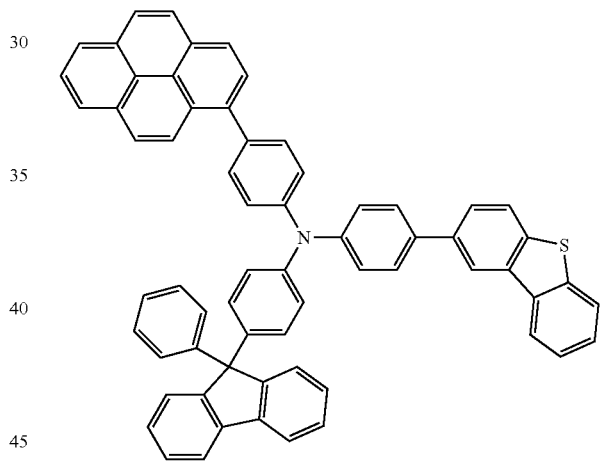
[A-75]
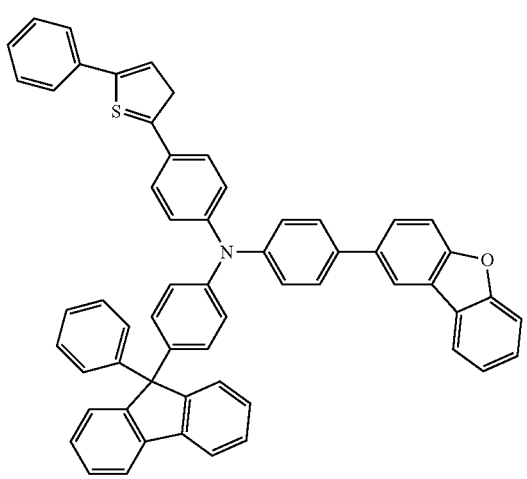

[A-76]
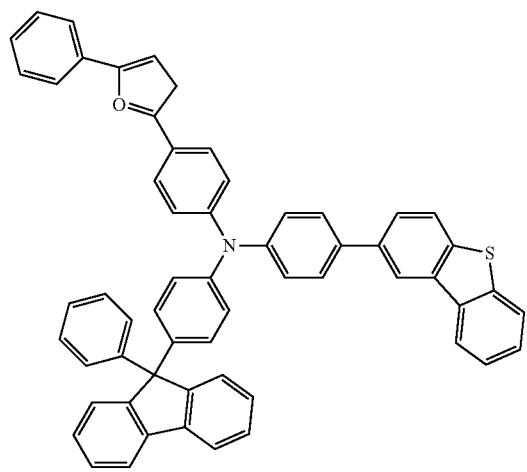
[A-77]
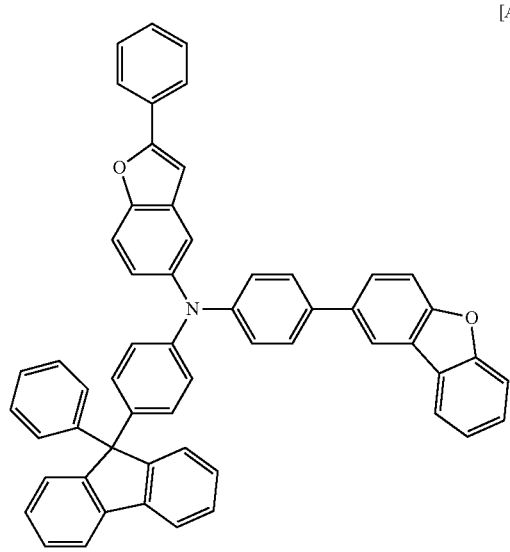
[A-78]
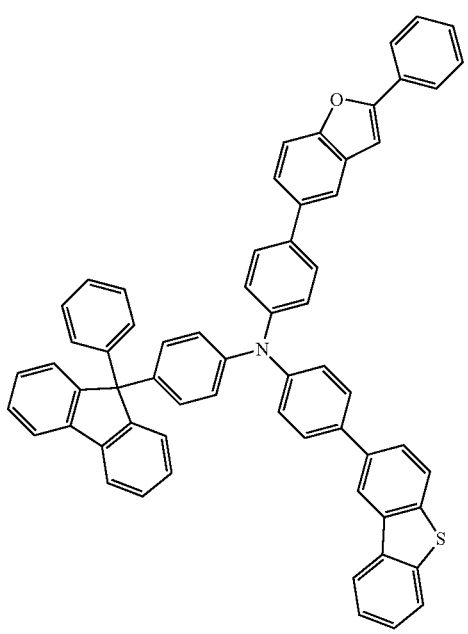
[A-79]
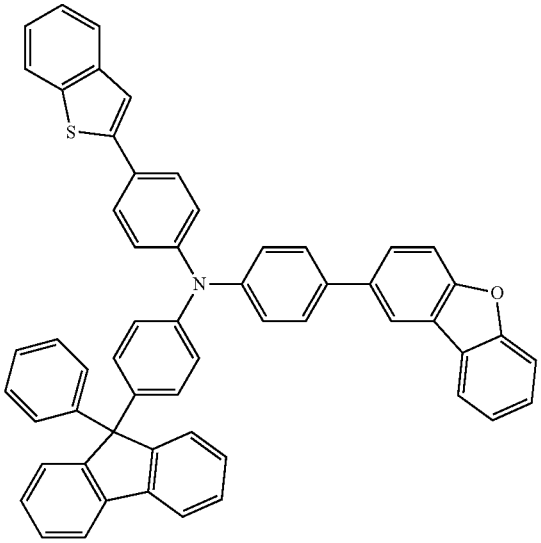
[A-80]
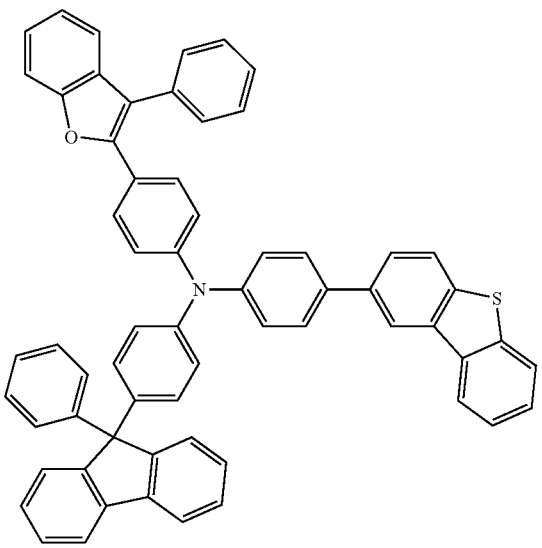
[A-81]
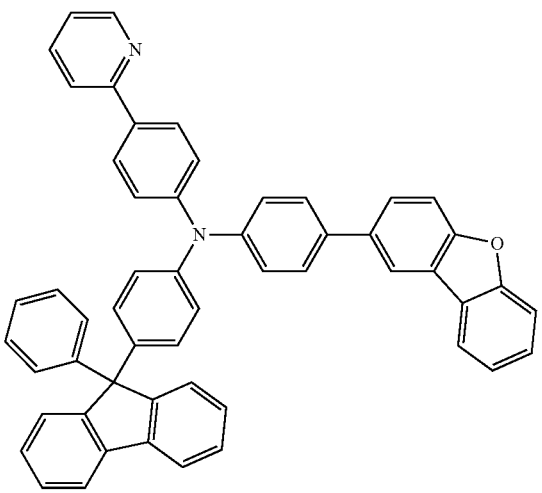

[A-82]
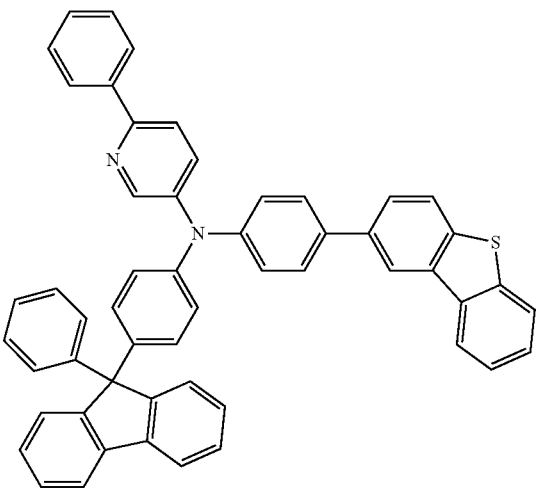
[A-85]
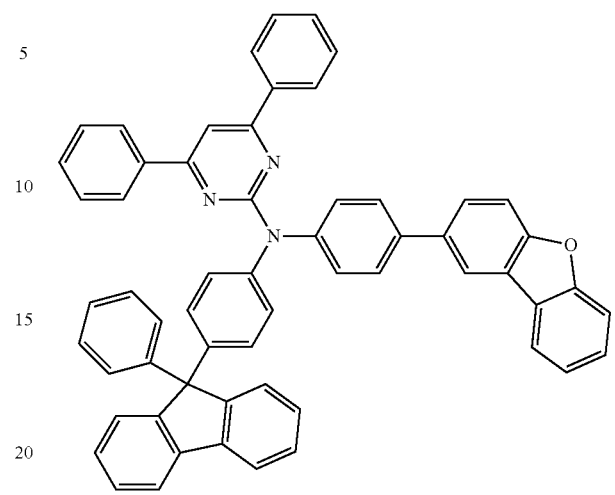
[A-83]
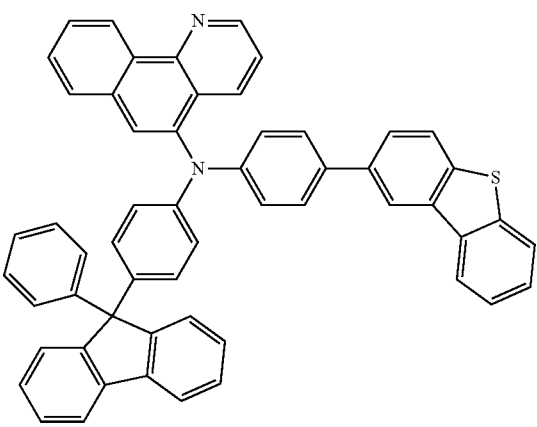
[A-86]
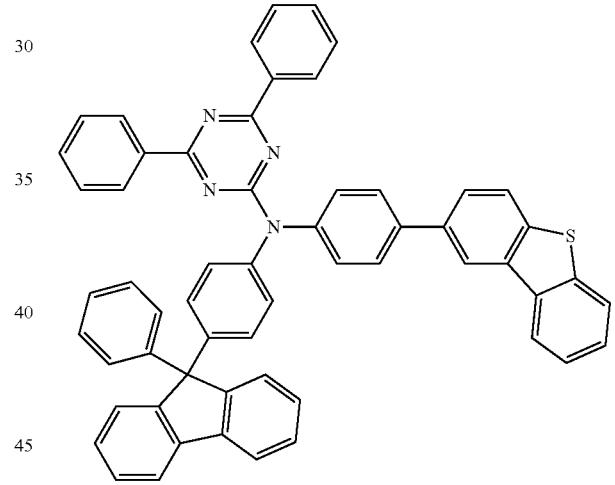
[A-84]
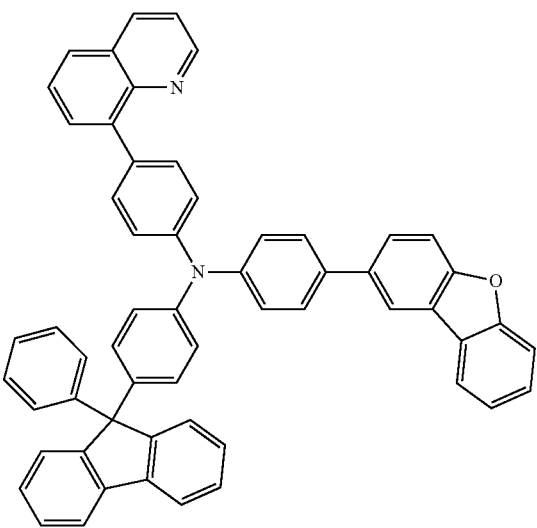
[A-87]
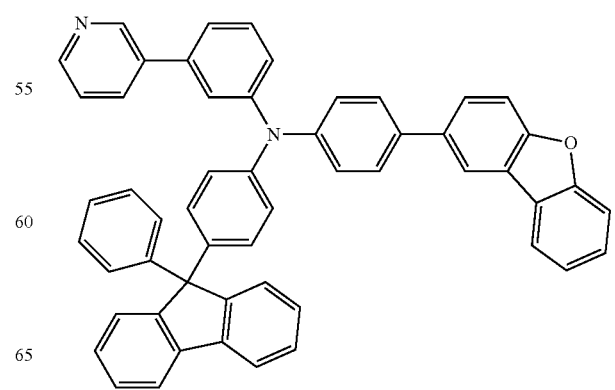

[A-88]
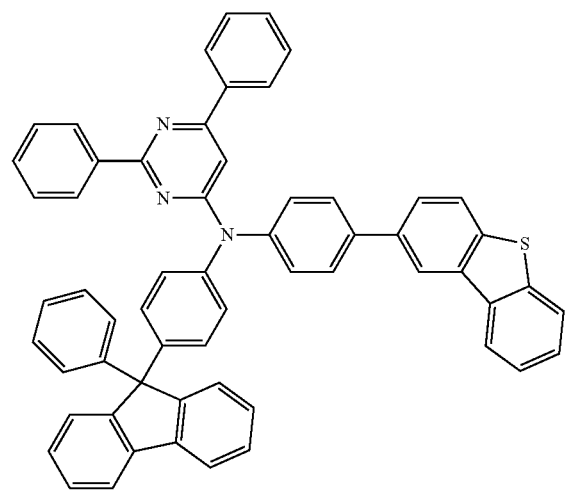
[A-89]
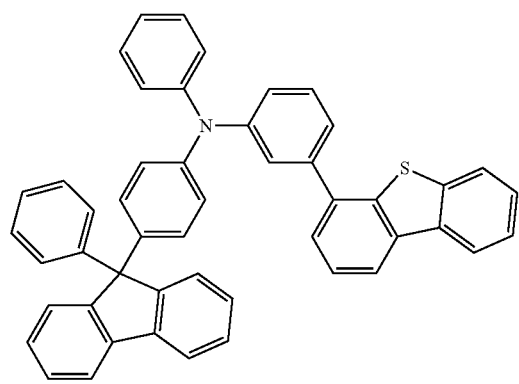
[A-90]
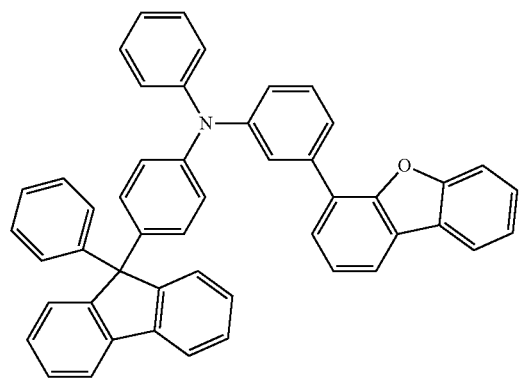
[A-91]
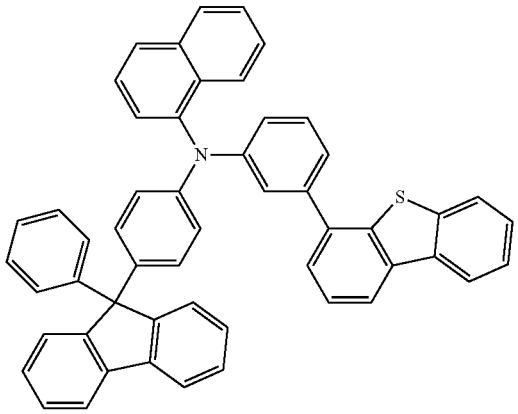
[A-92]
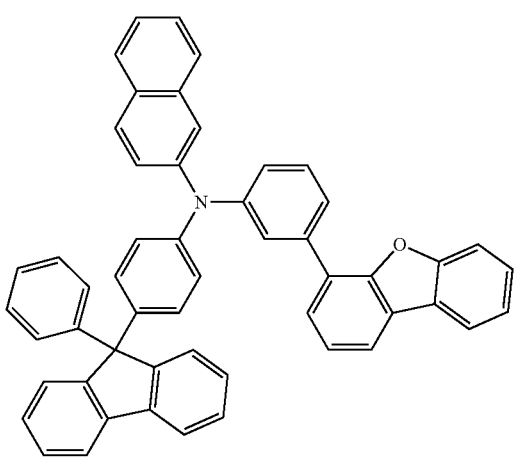
[A-93]
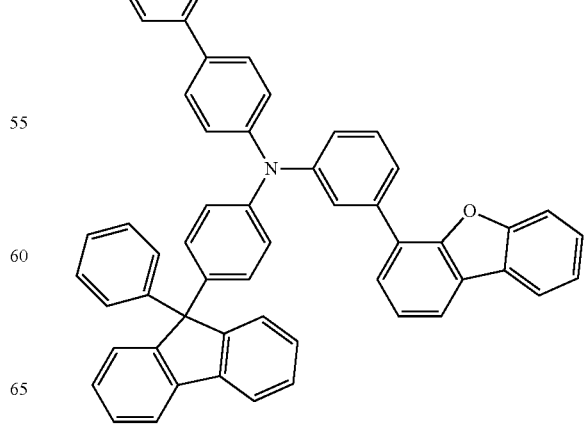

[A-94]
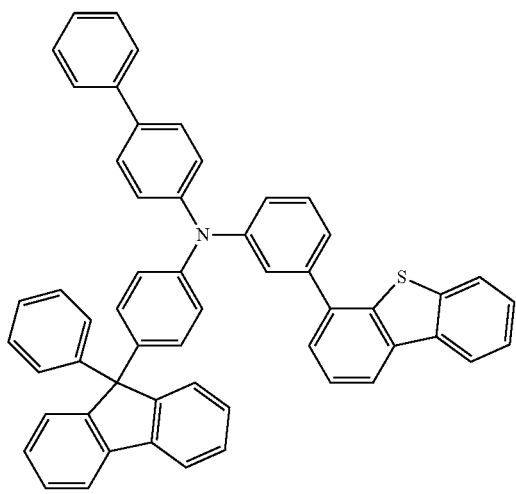
[A-95]
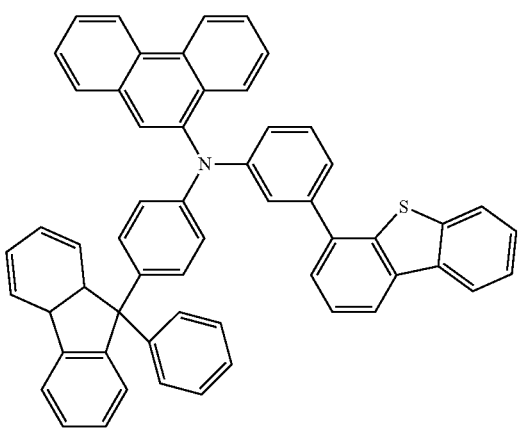
[A-96]
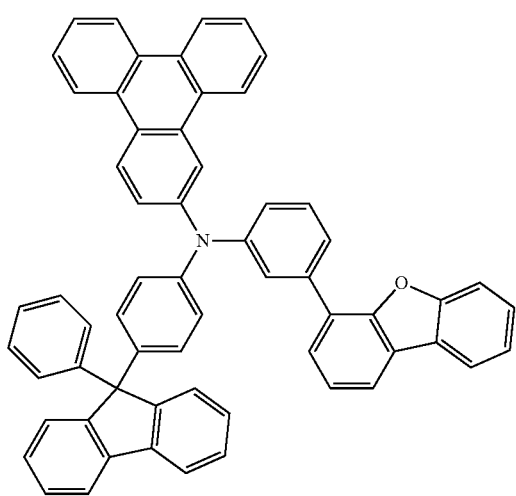
[A-97]
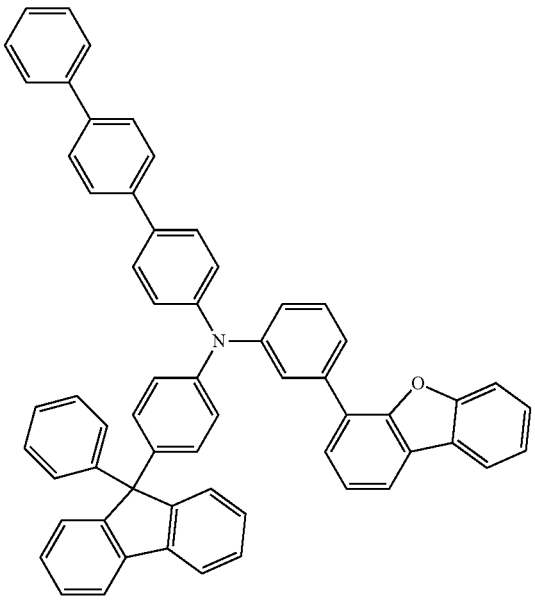
[A-98]
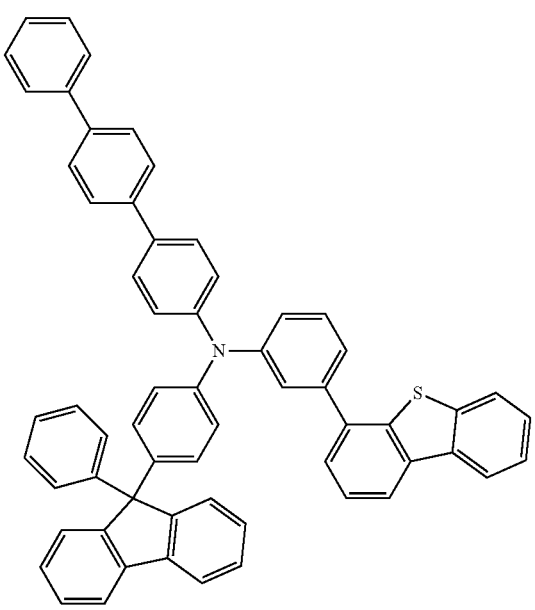

[A-99]
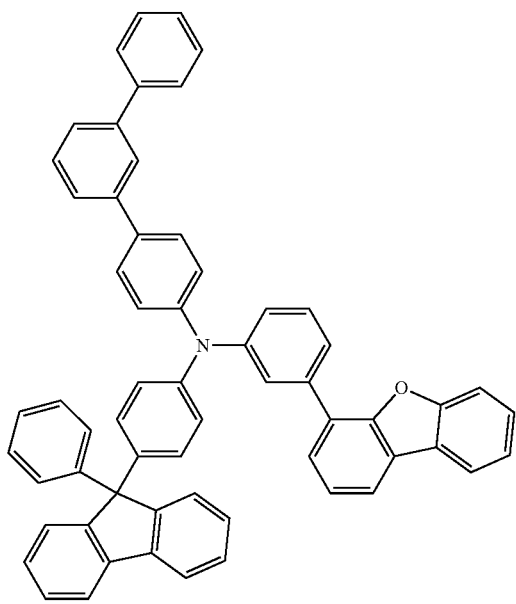
[A-100]
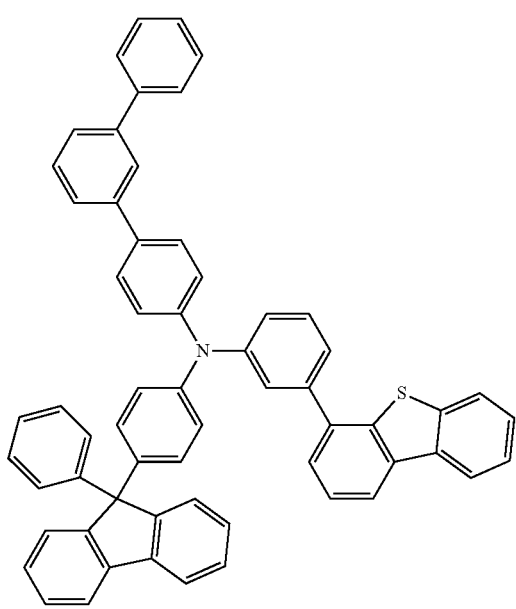
[A-101]
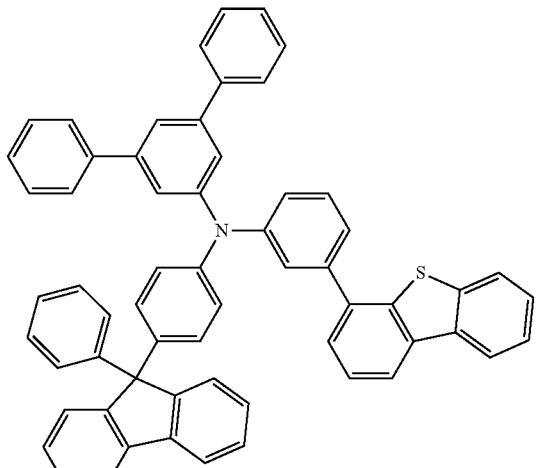
[A-102]
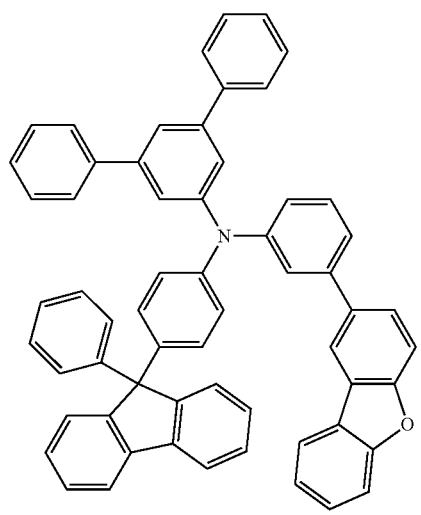
[A-103]
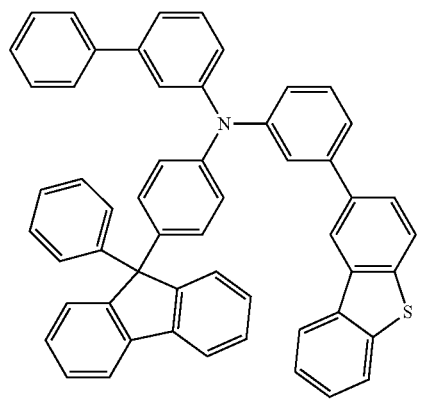

[A-104]
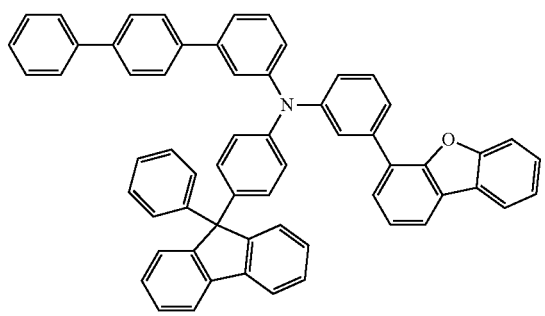
[A-105]
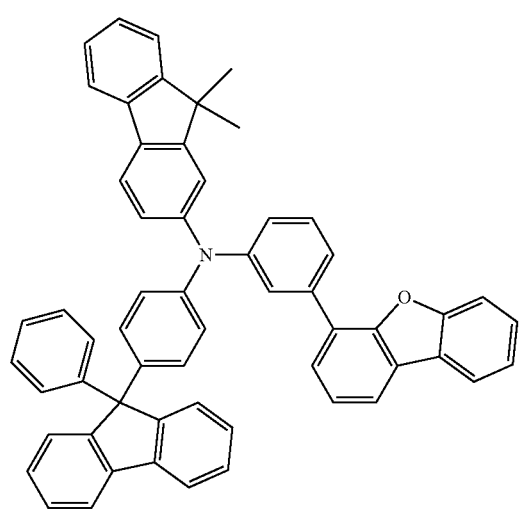
[A-106]
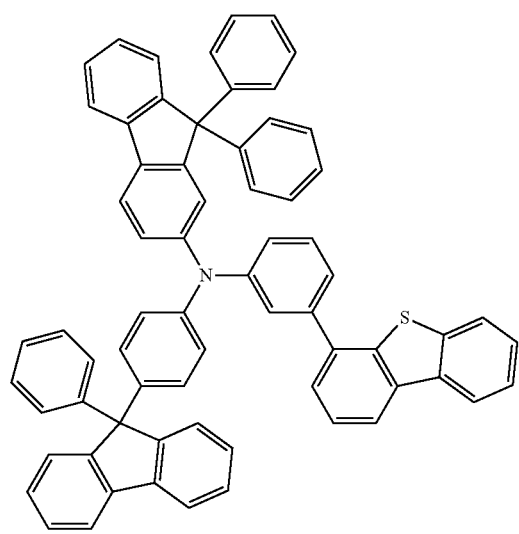
[A-107]
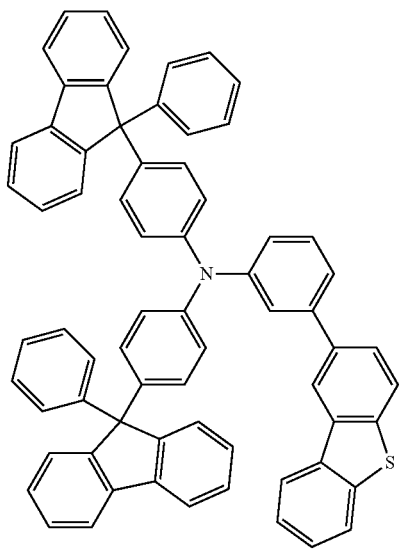
[A-108]
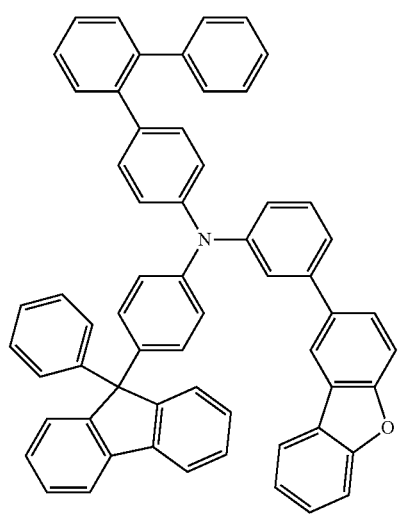
[A-109]
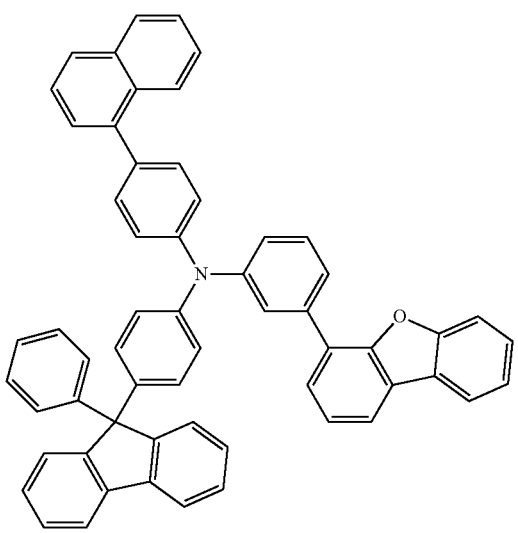

[A-110]
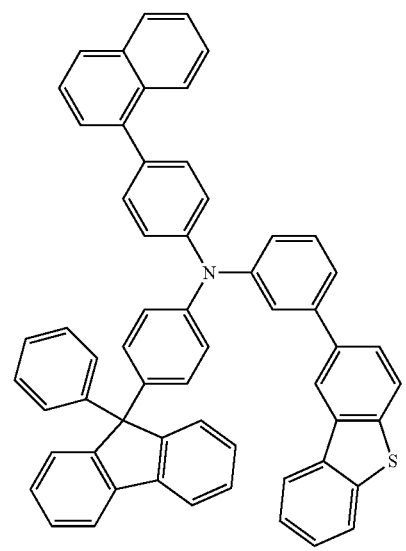
[A-111]
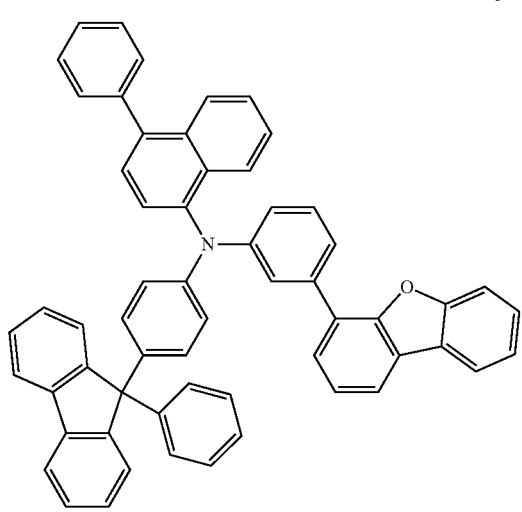
[A-112]
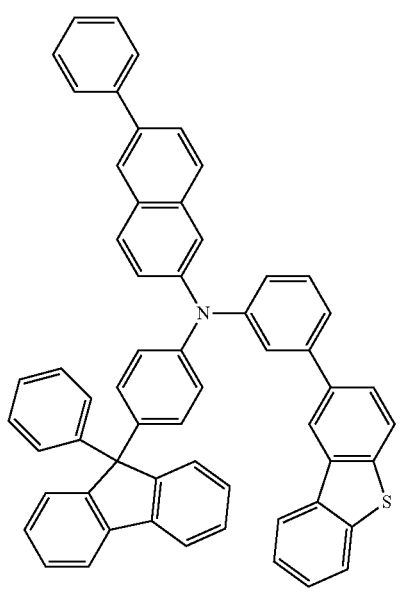
[A-113]
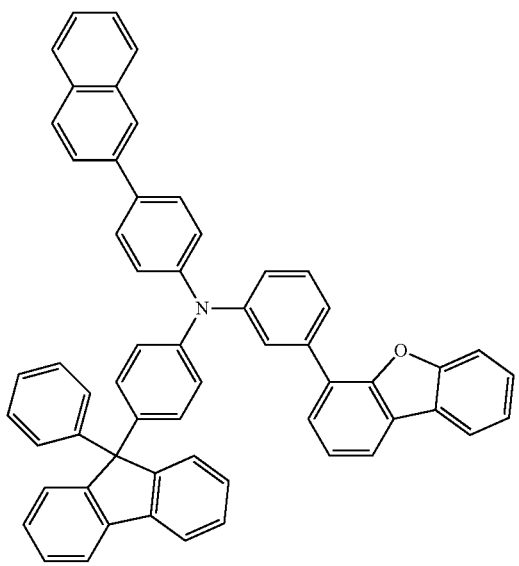
[A-114]
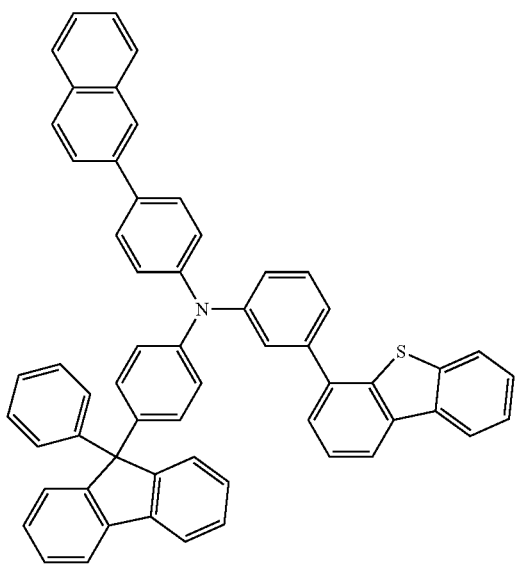

[A-115]
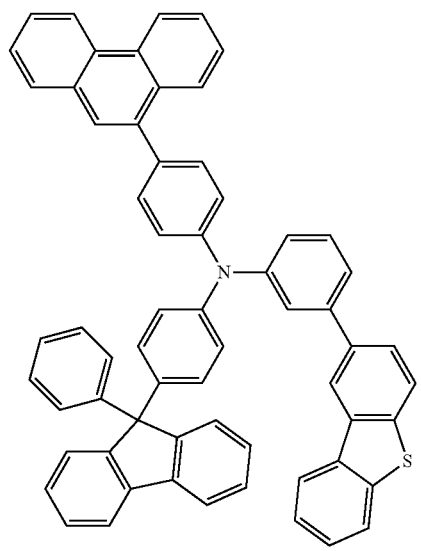
[A-117]
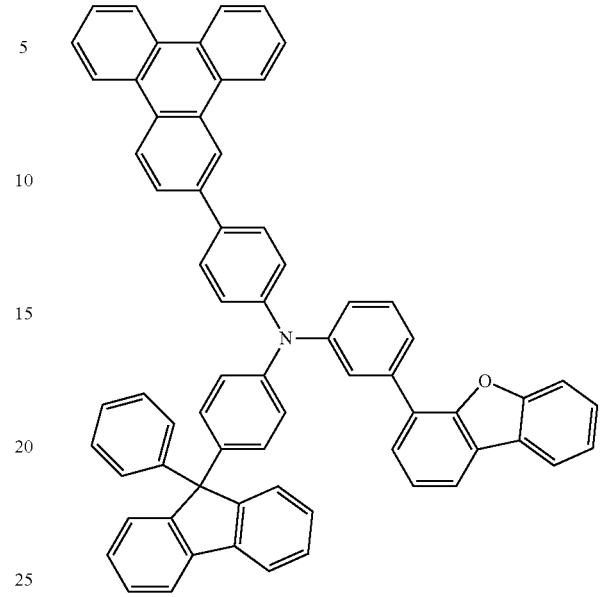
[A-116]
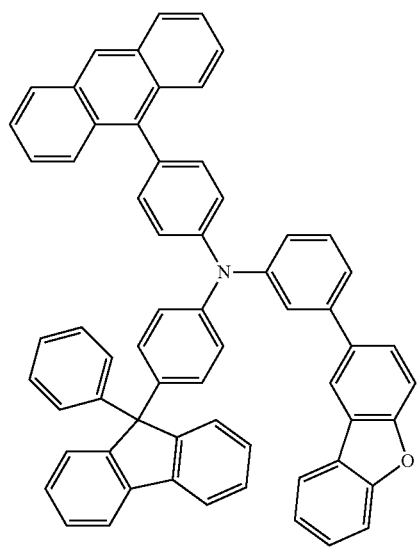
[A-118]
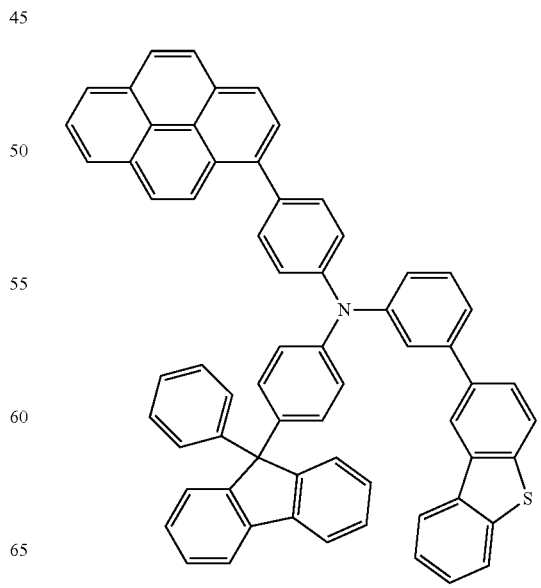

[A-119]
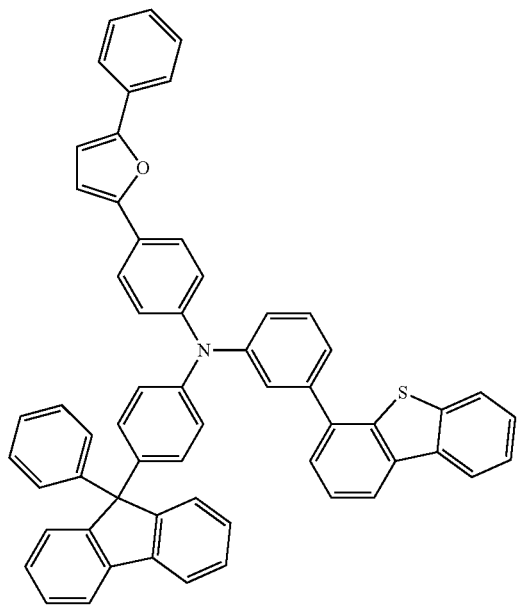
[A-120]
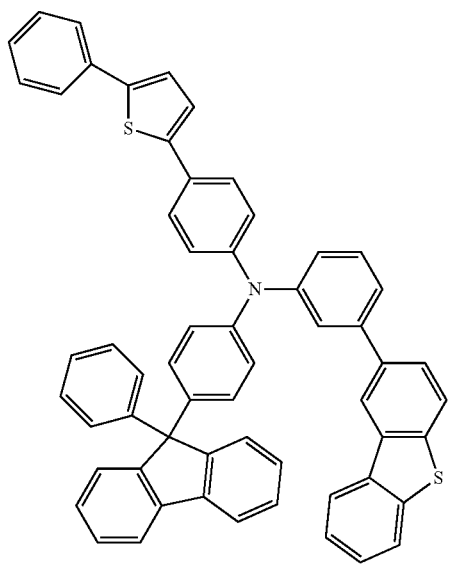
[A-121]
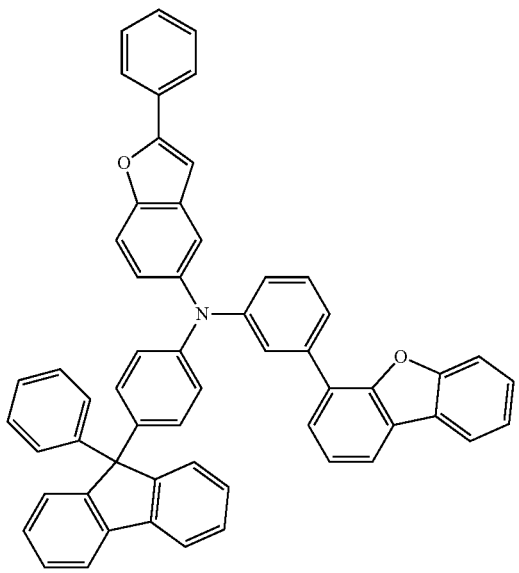
[A-122]
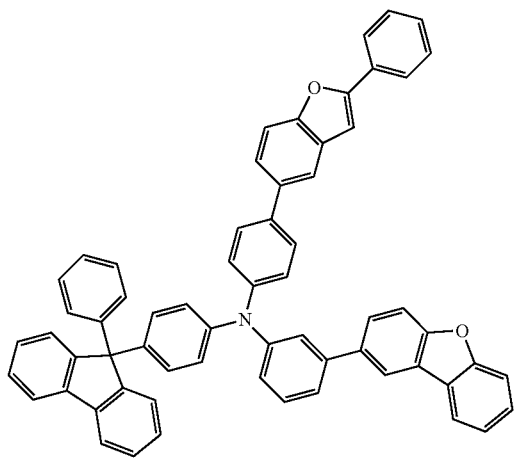
[A-123]
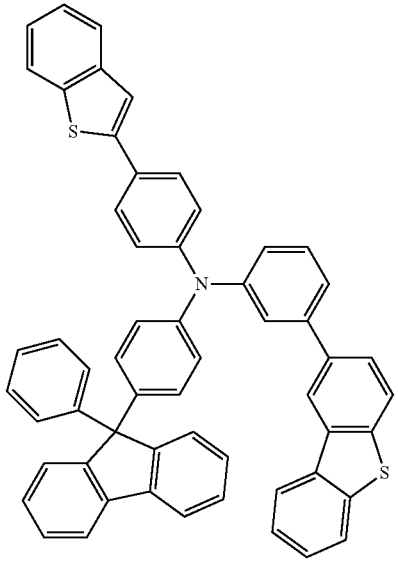

[A-124]
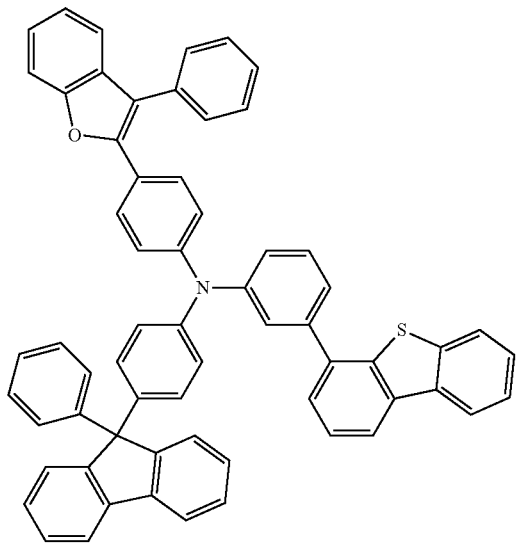
[A-125]
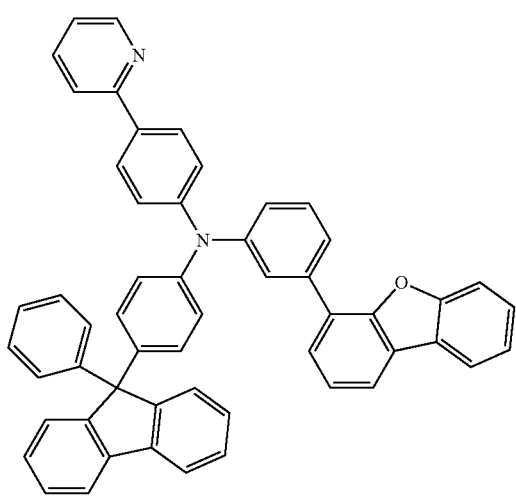
[A-126]
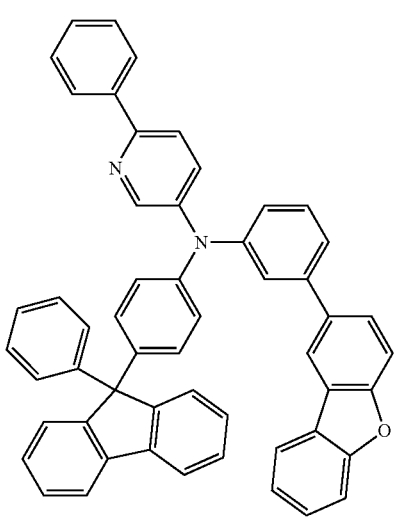
[A-127]
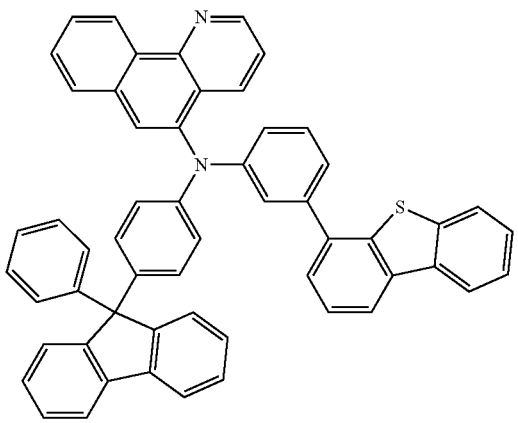
[A-128]
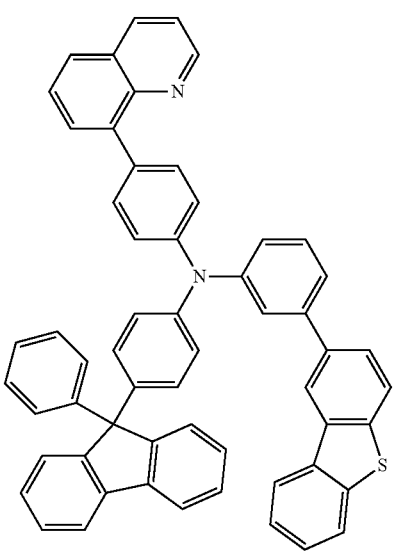
[A-129]
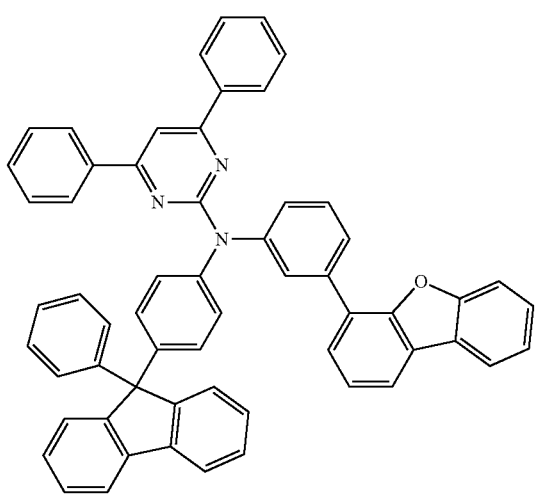

[A-130]
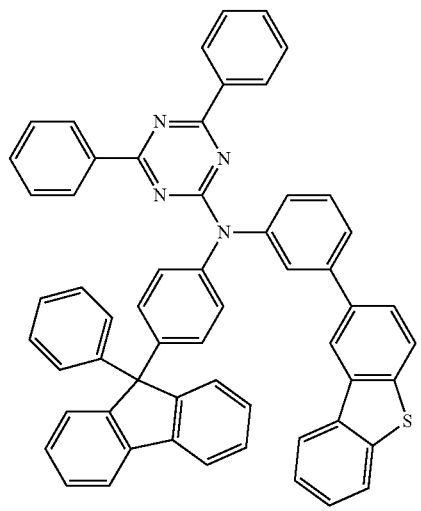
[A-131]
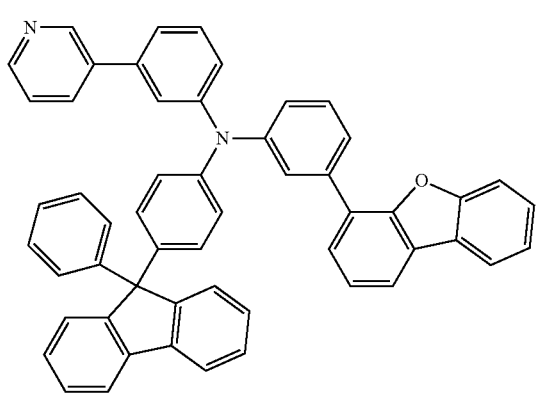
[A-132]
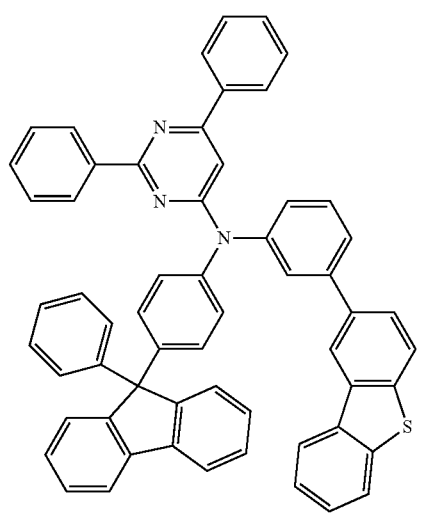
[A-133]
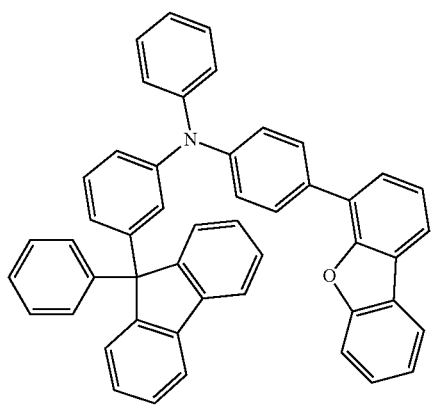
[A-134]
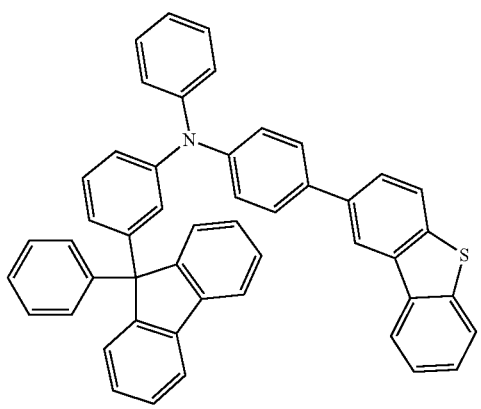
[A-135]
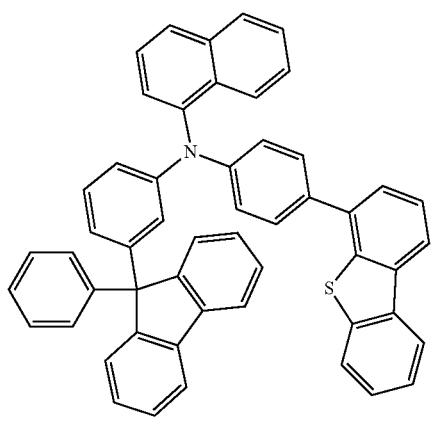

-continued
[A-136]
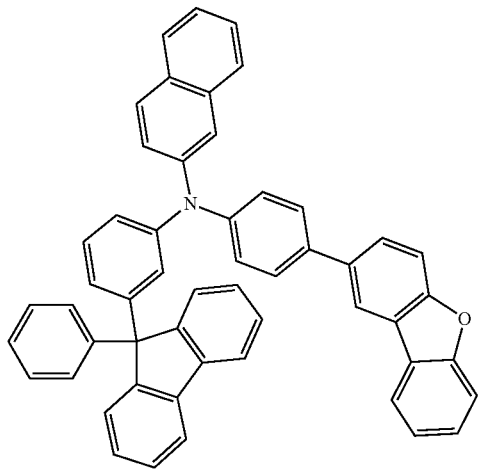
[A-137]
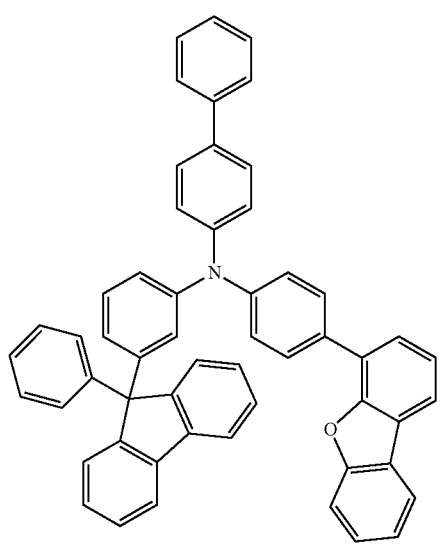
[A-138]
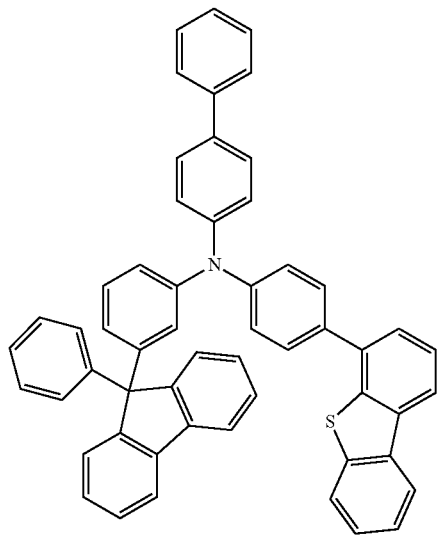
-continued
[A-139]
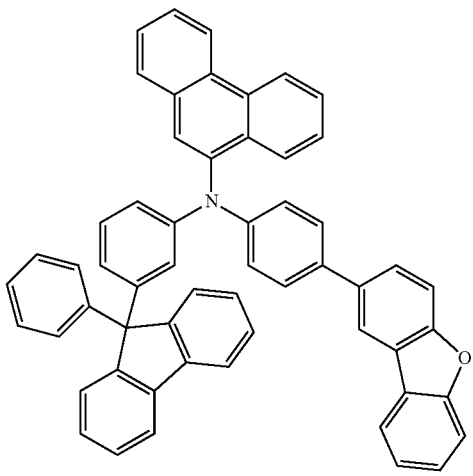
[A-140]
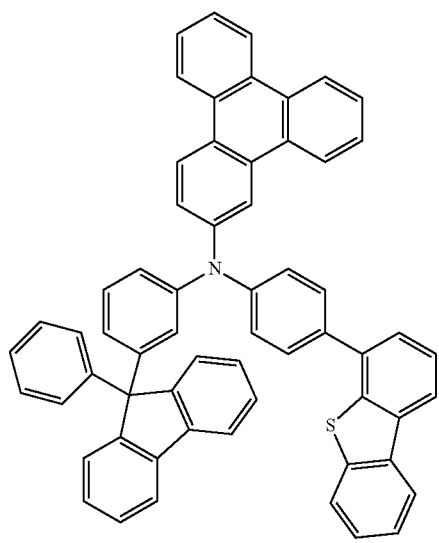
[A-141]
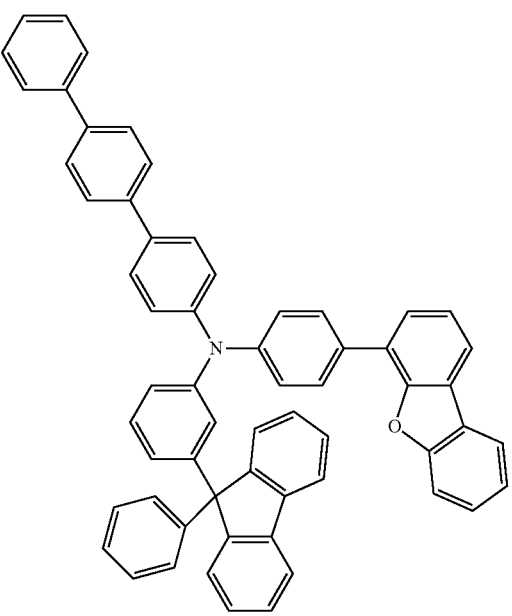

[A-142]
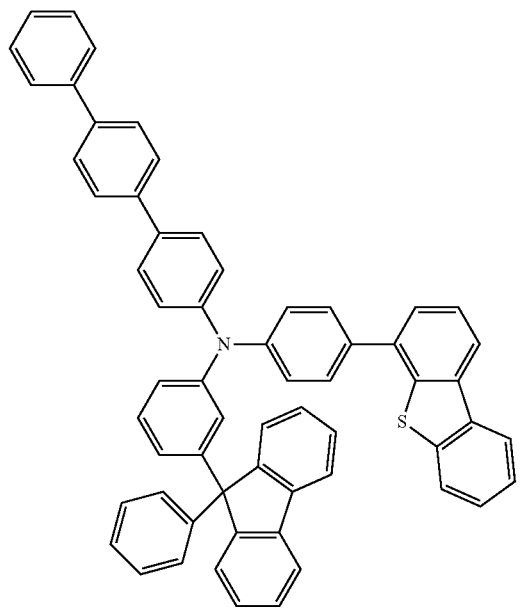
[A-143]
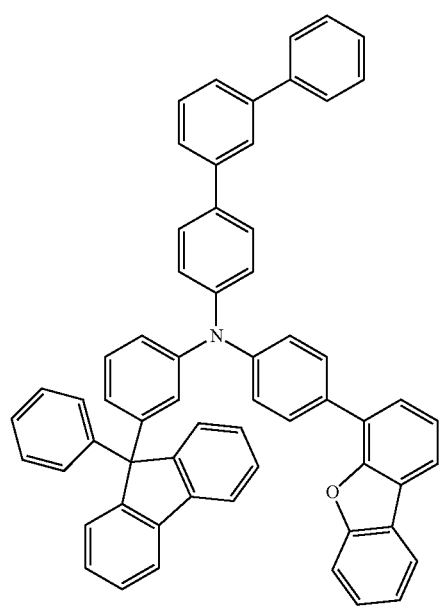
[A-144]
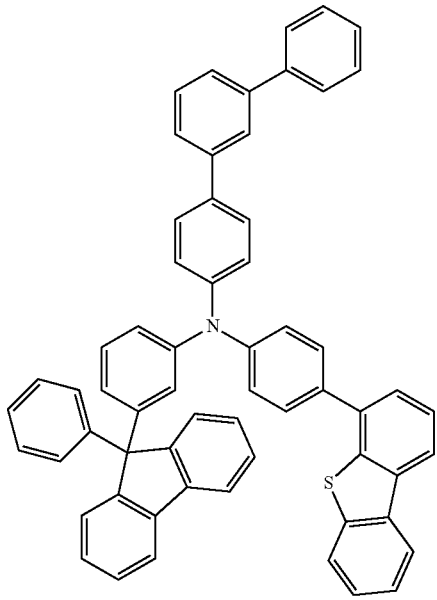
[A-145]
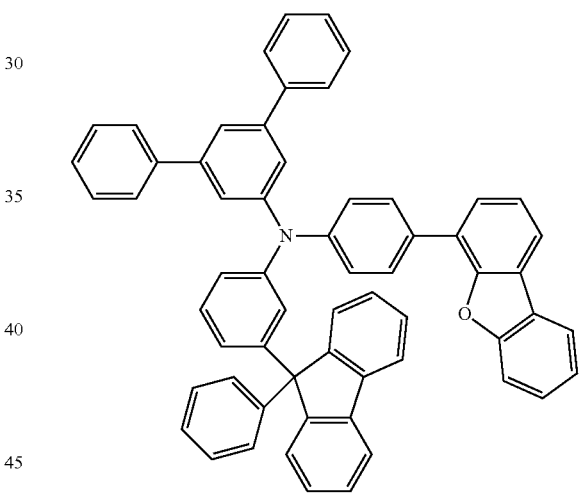
[A-146]
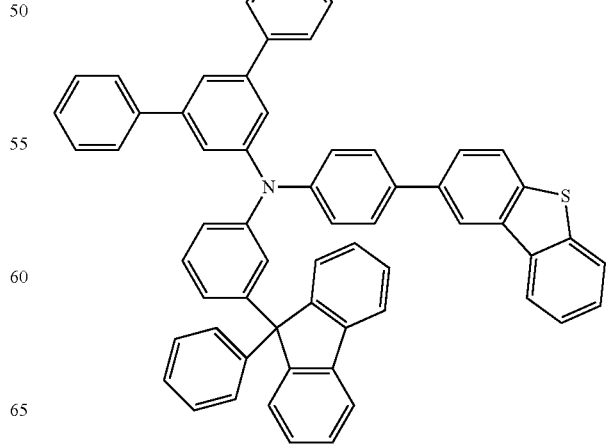

[A-147] 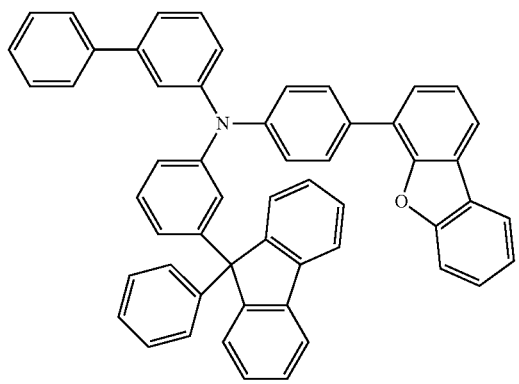
[A-148] 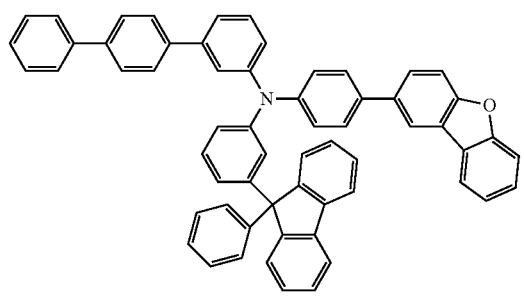
[A-149] 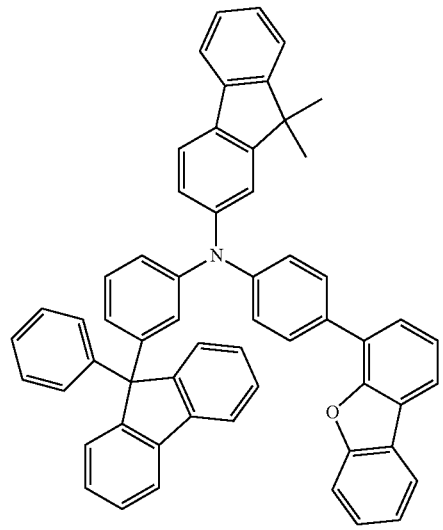
[A-150] 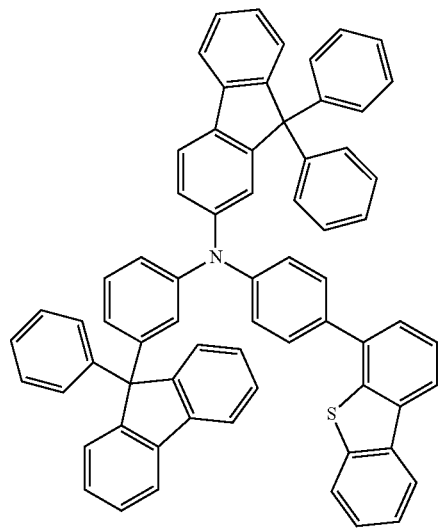
[A-151] 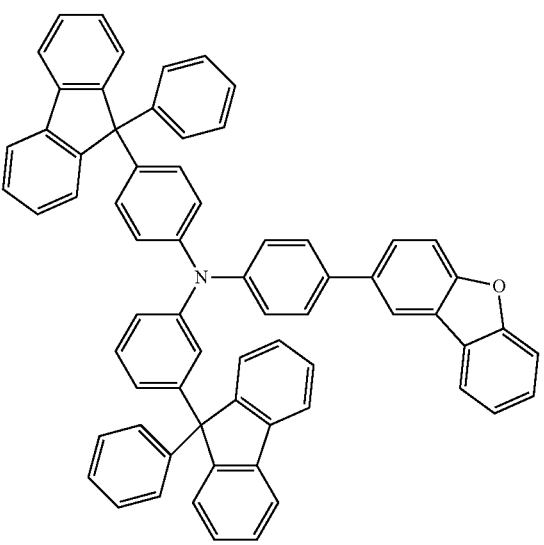
[A-152] 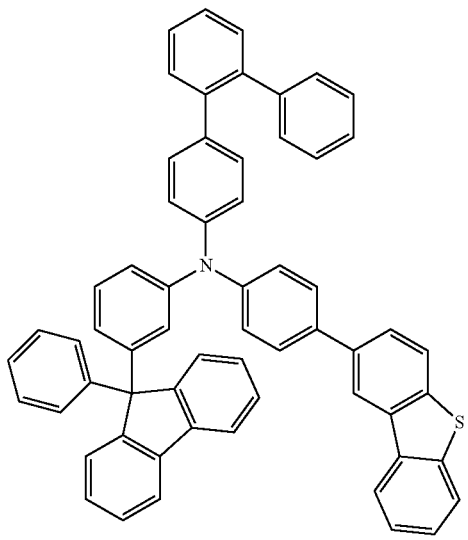

[A-153]
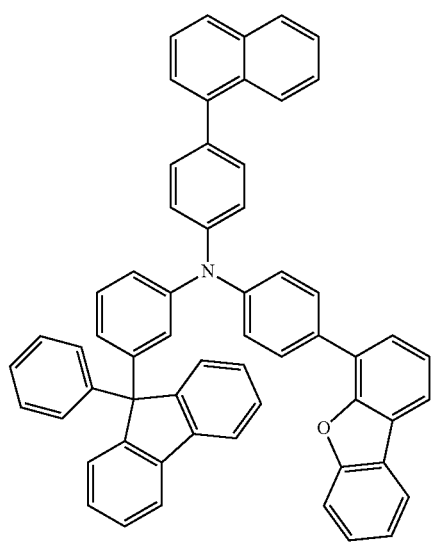
[A-154]
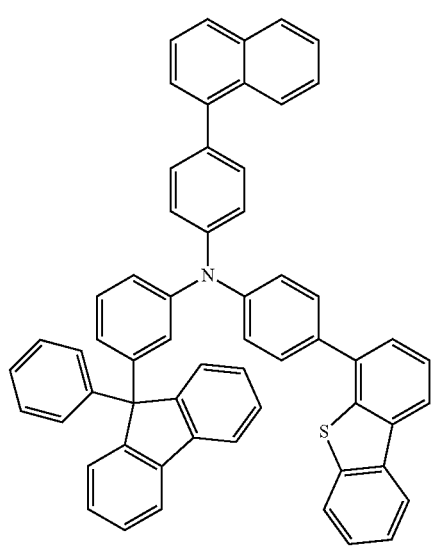
[A-155]
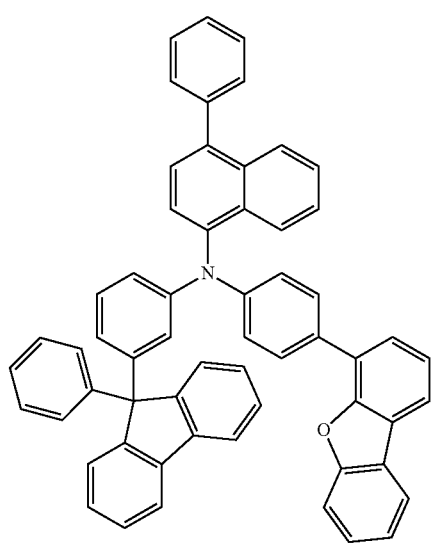
[A-156]
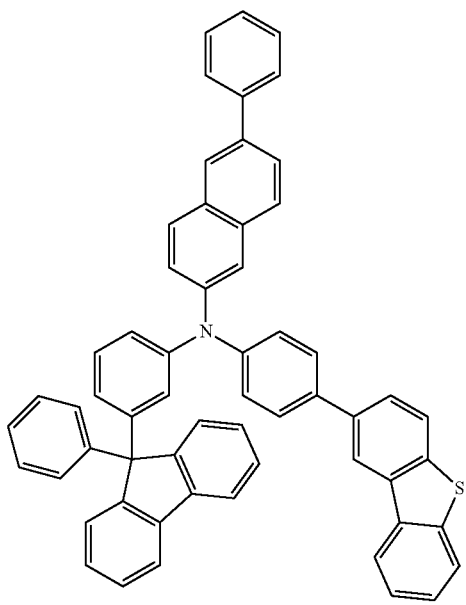
[A-157]
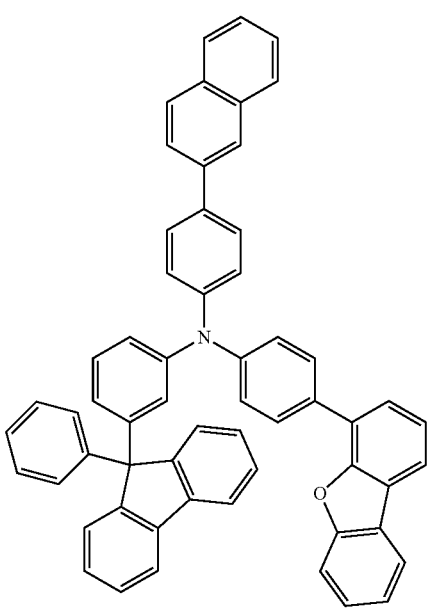

[A-158]
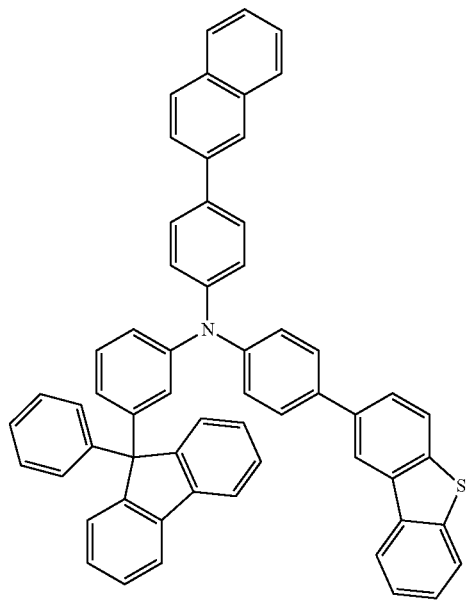
[A-160]
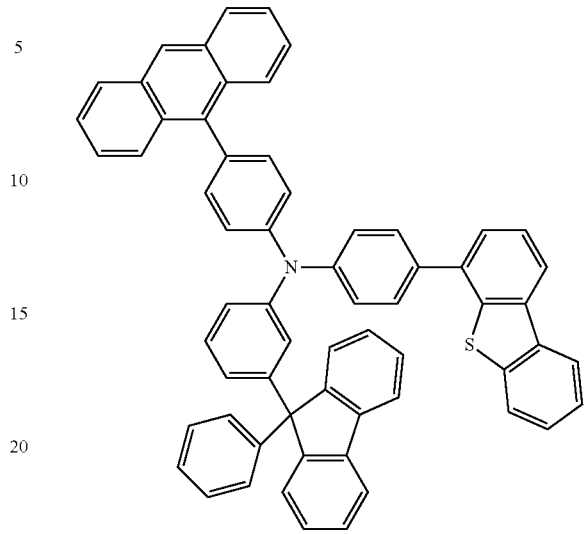
[A-159]
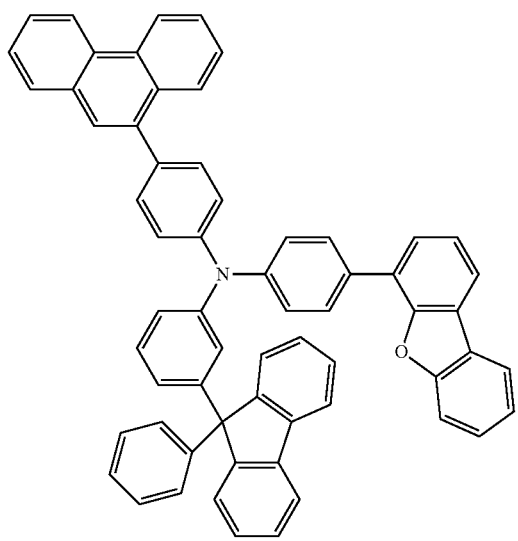
[A-161]
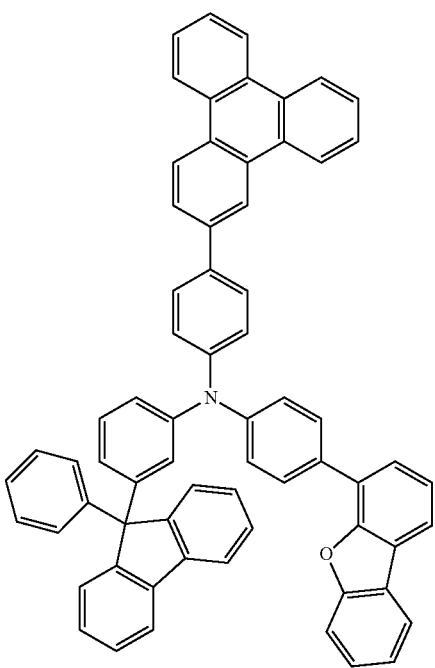

[A-162]
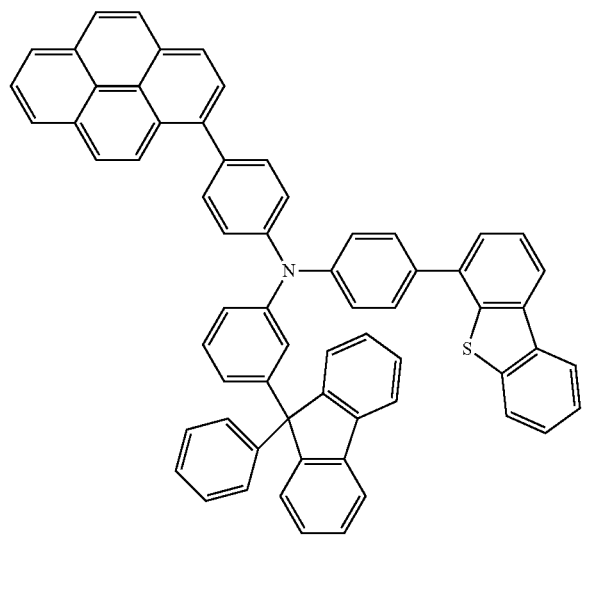
[A-164]
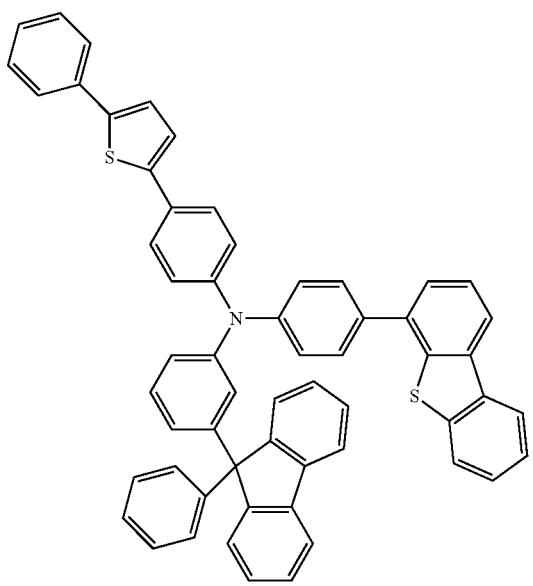
[A-163]
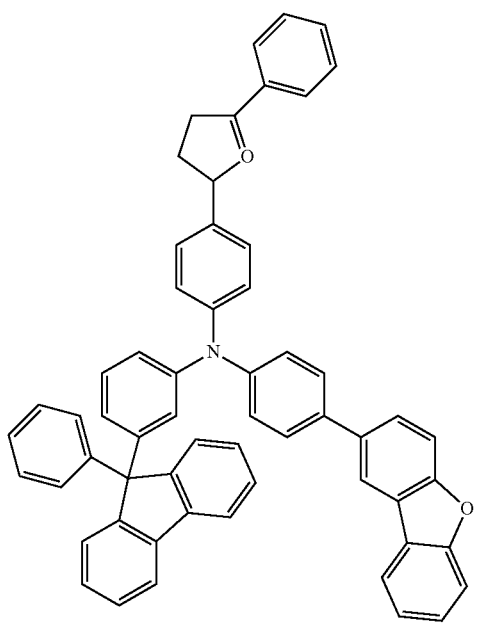
[A-165]
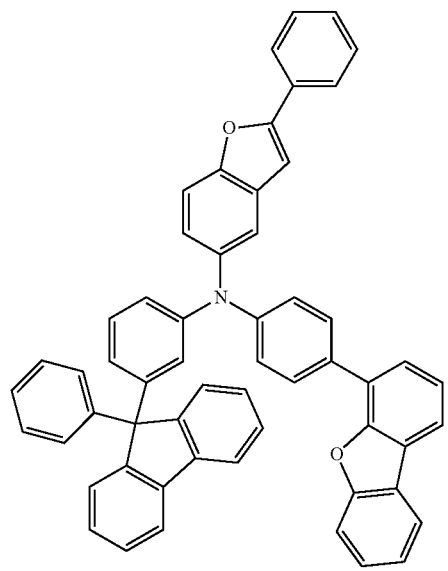

[A-166]
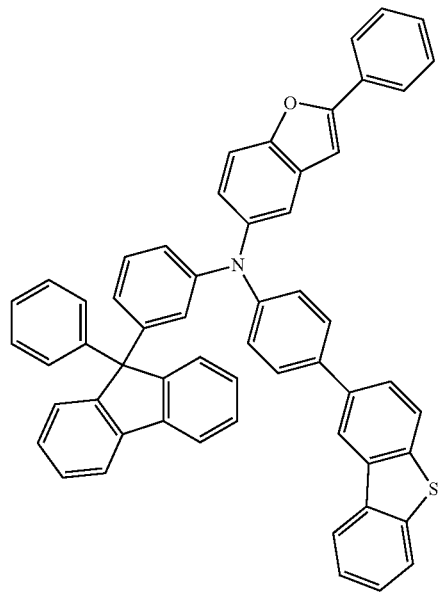
[A-168]
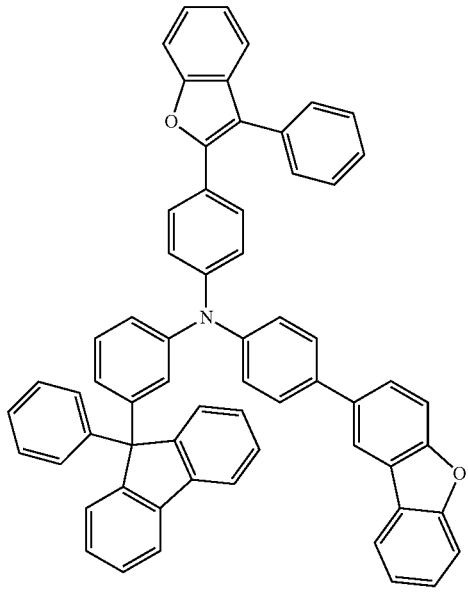
[A-167]
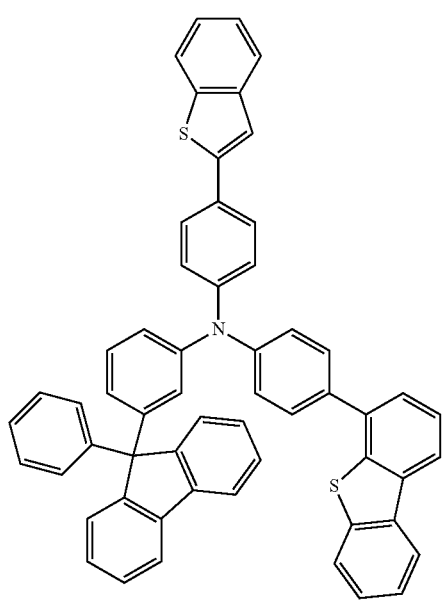
[A-169]

[A-170]
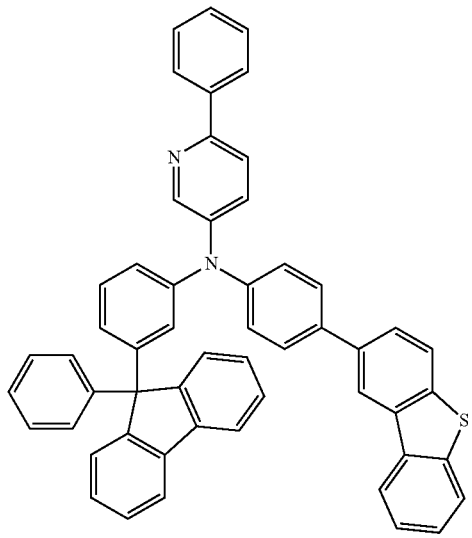
[A-173]
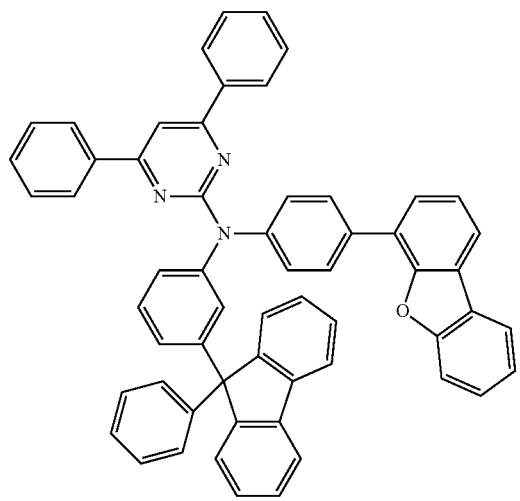
[A-171]
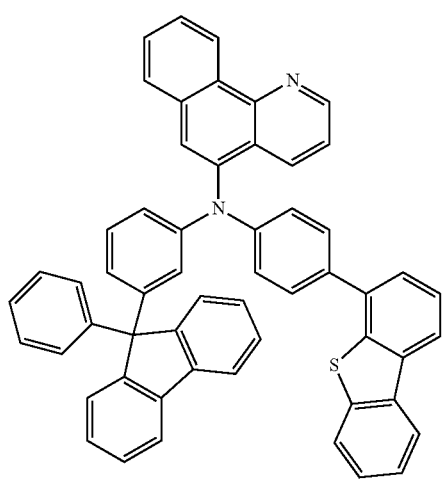
[A-174]
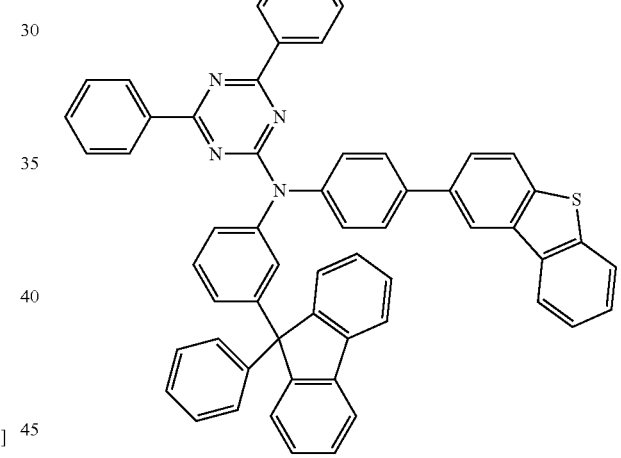
[A-172]
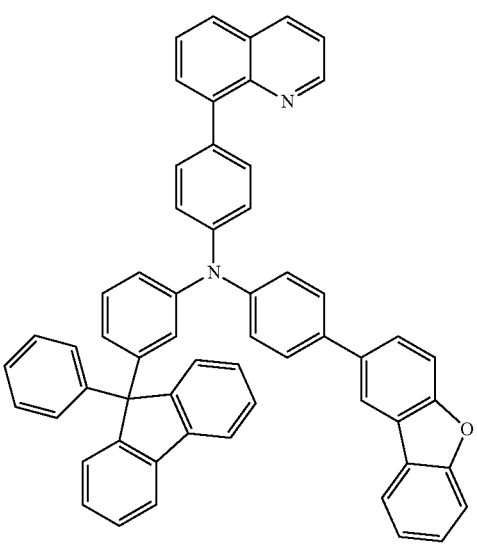
[A-175]
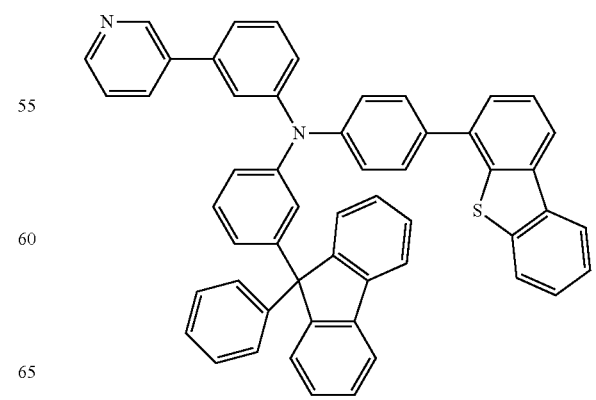

[A-176]
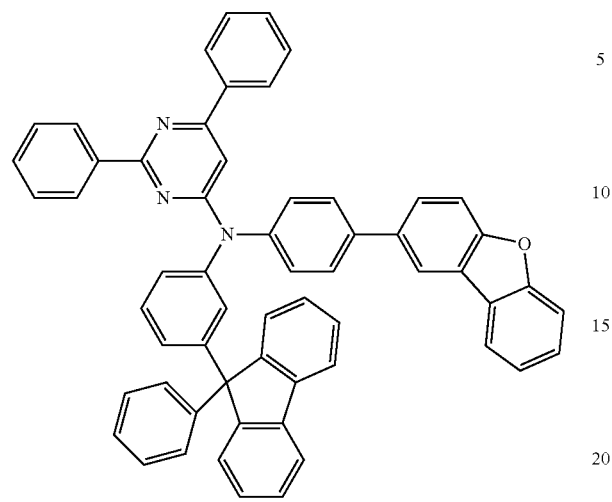
[A-179]
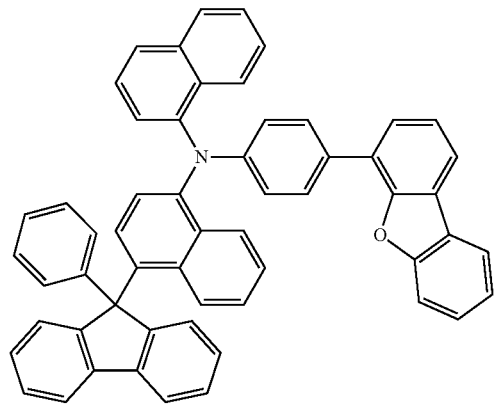
[A-177]
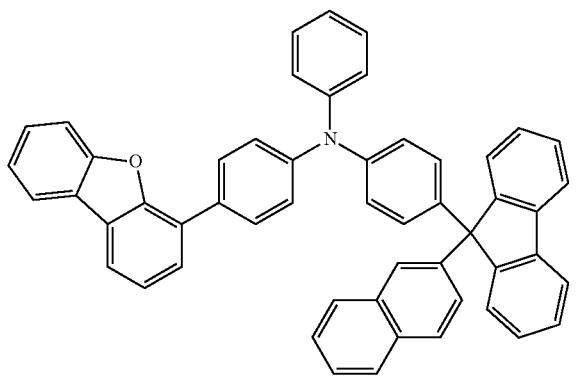
[A-180]
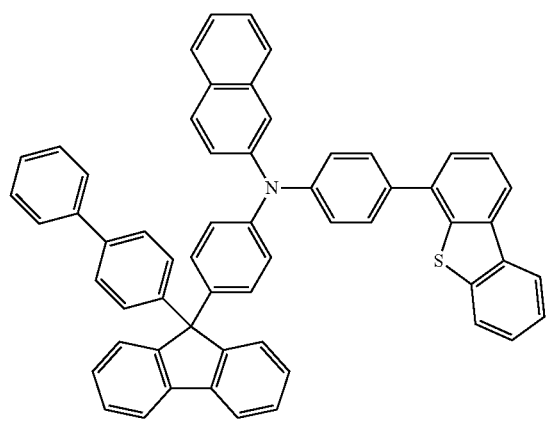
[A-178]
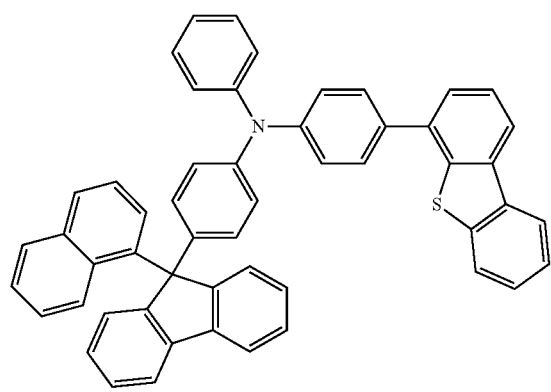
[A-181]
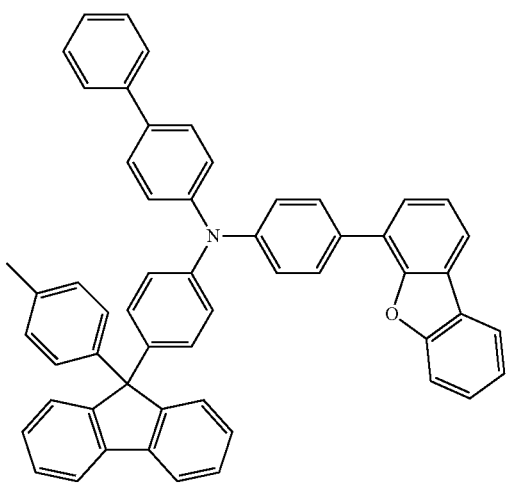

[A-182]
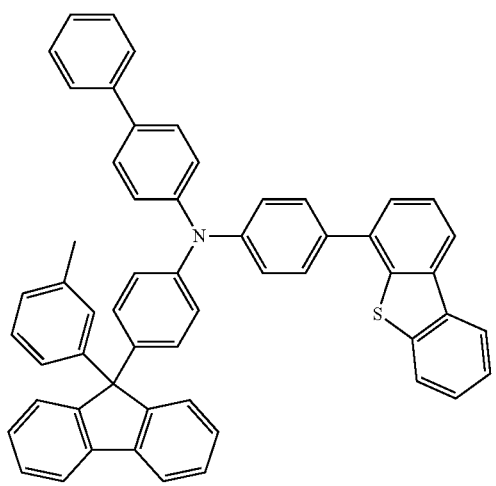
[A-185]
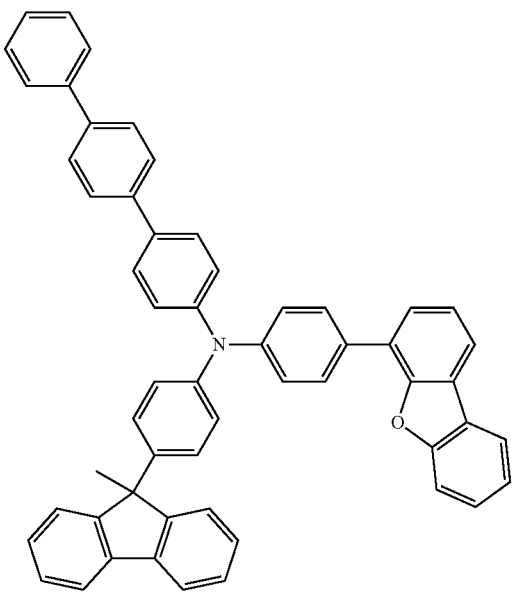
[A-183]
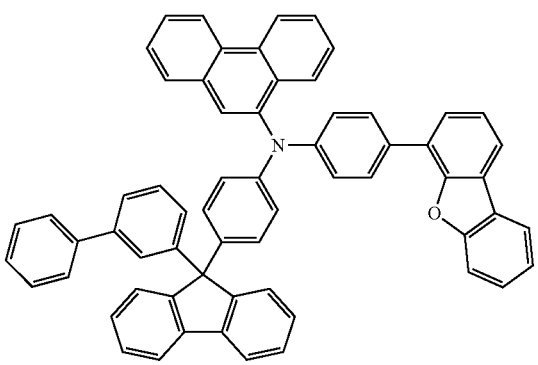
[A-184]
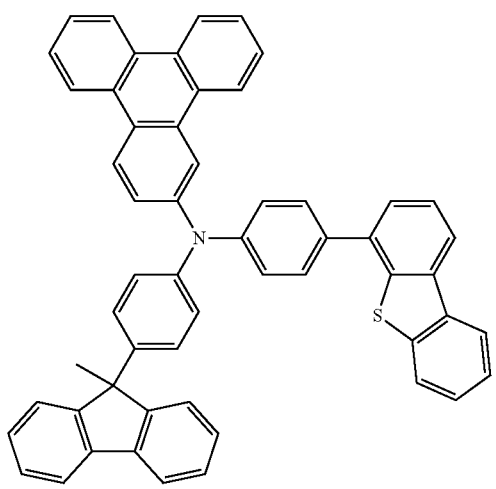
[A-186]
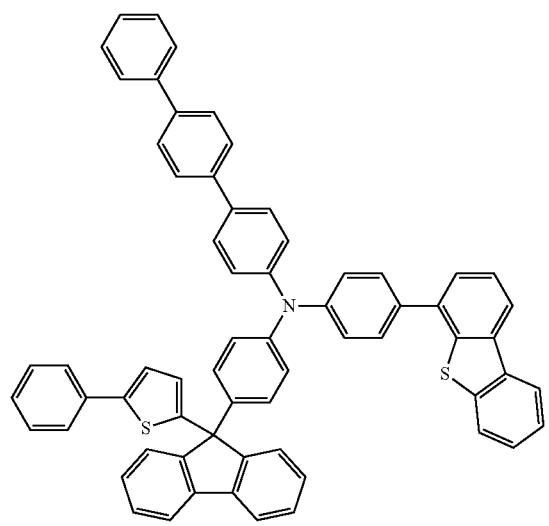

[A-187]
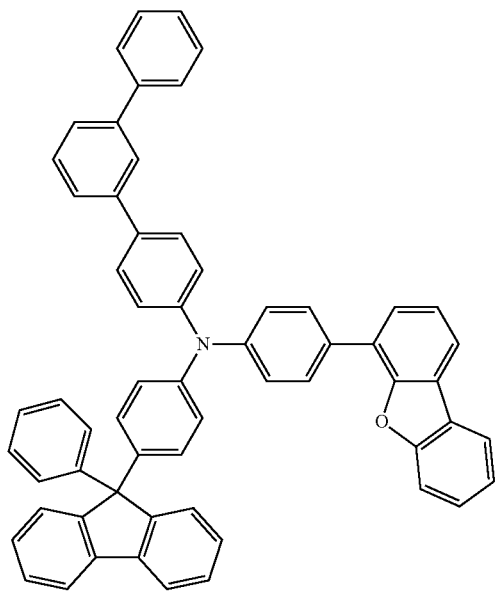
[A-189]
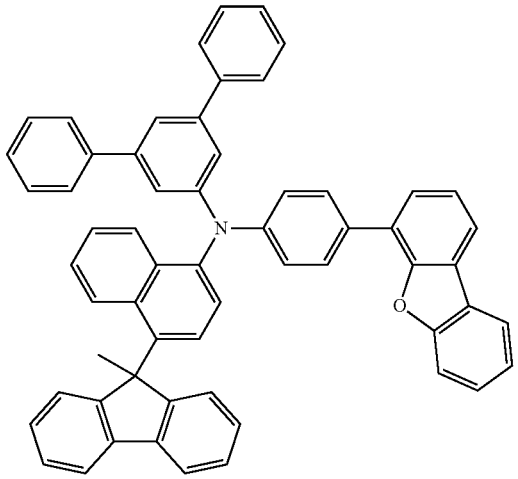
[A-188]
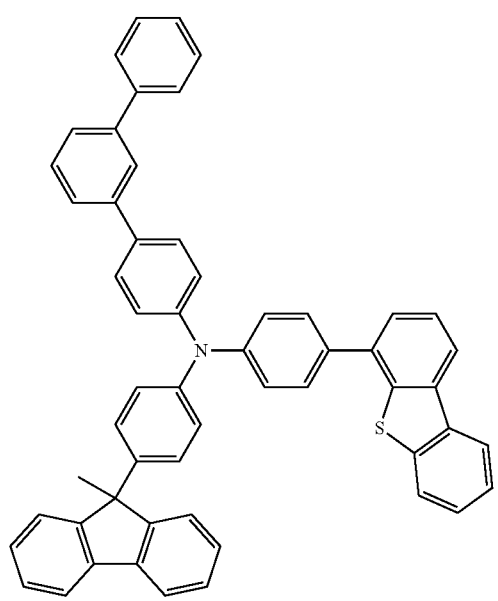
[A-190]
[A-191]
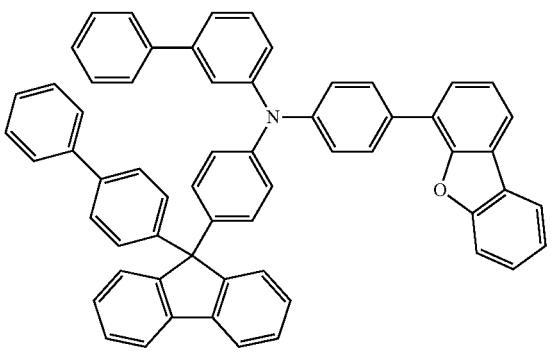

[A-192]
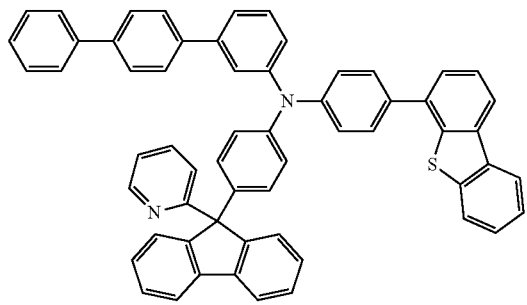
[A-193]
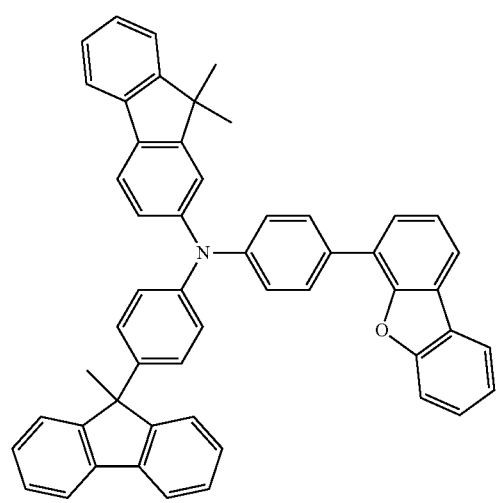
[A-194]
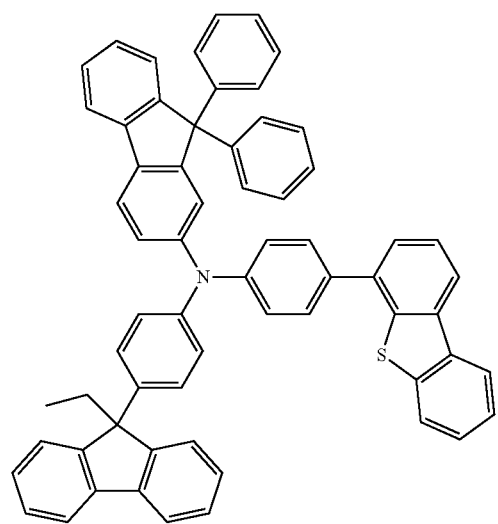
[A-195]
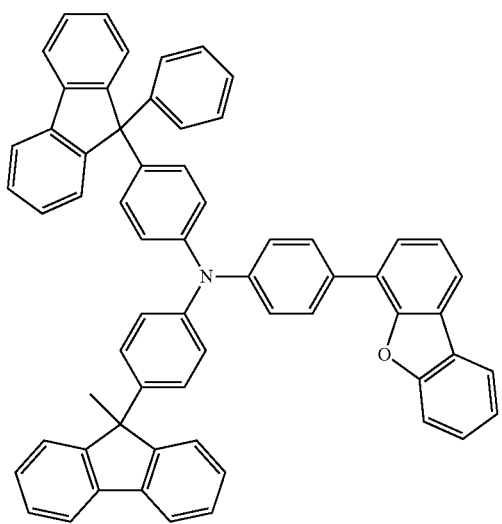
[A-196]
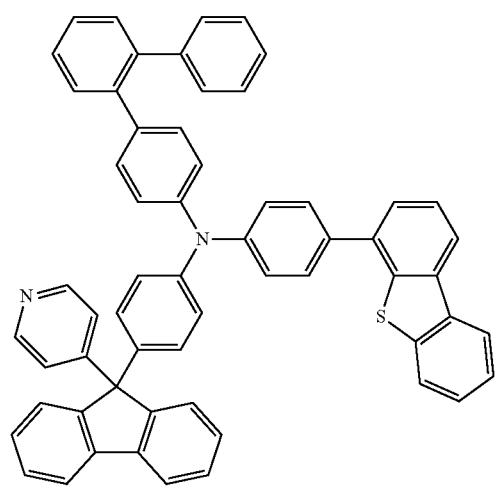

[A-197]
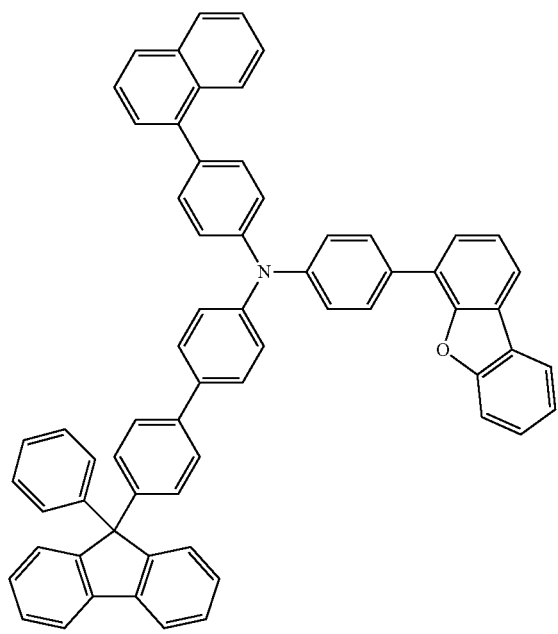
[A-199]
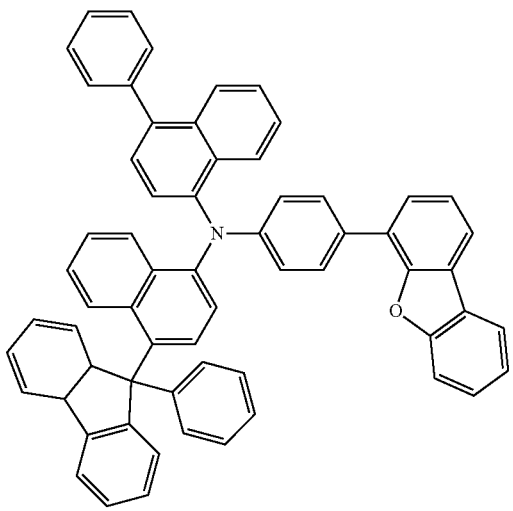
[A-198]
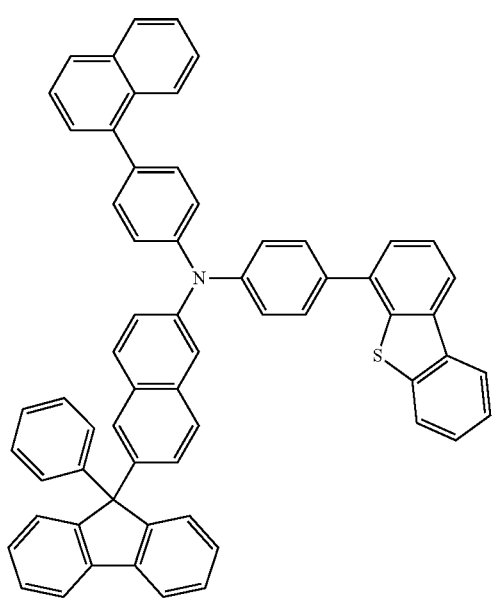
[A-200]
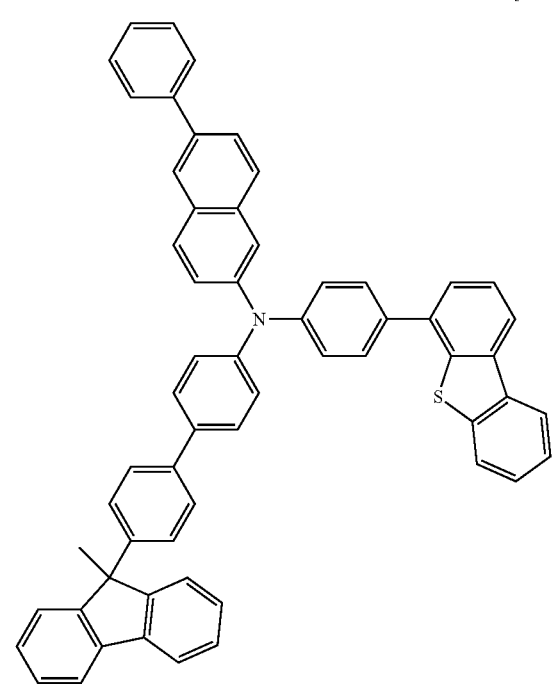

[A-201]
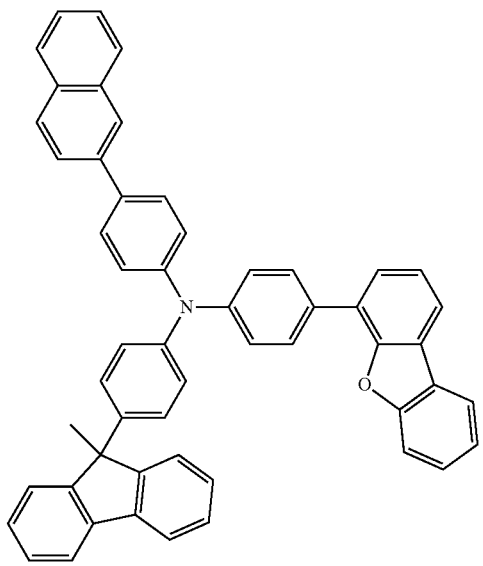
[A-203]
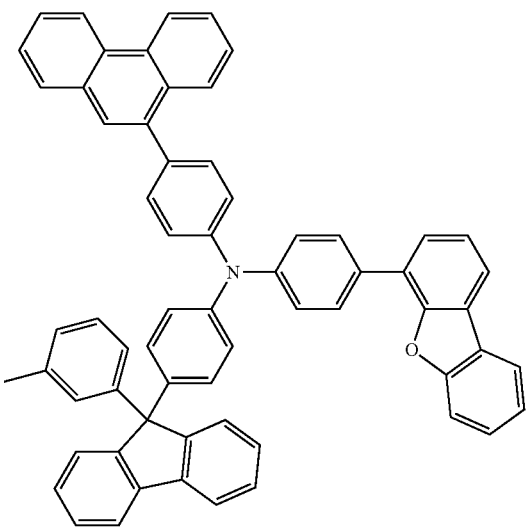
[A-202]
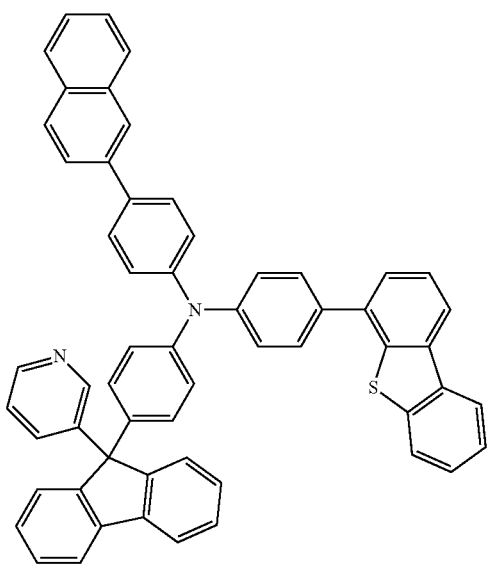
[A-204]
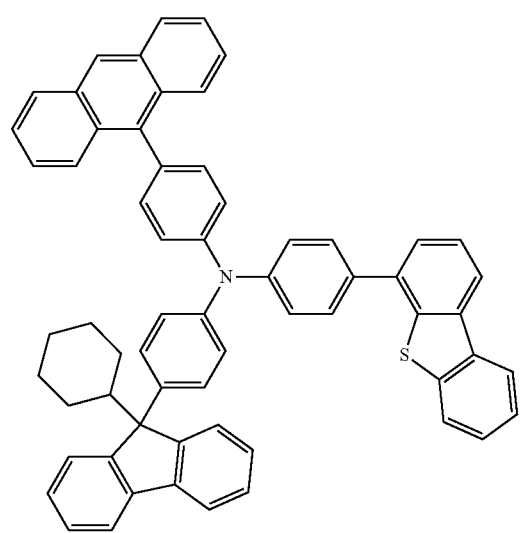

[A-205]
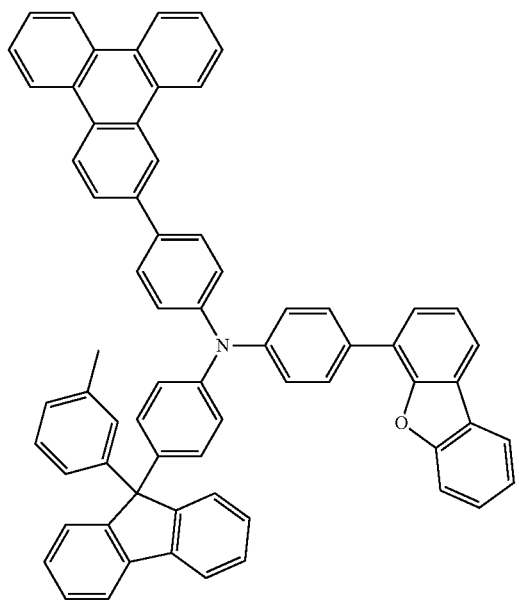
[A-206]
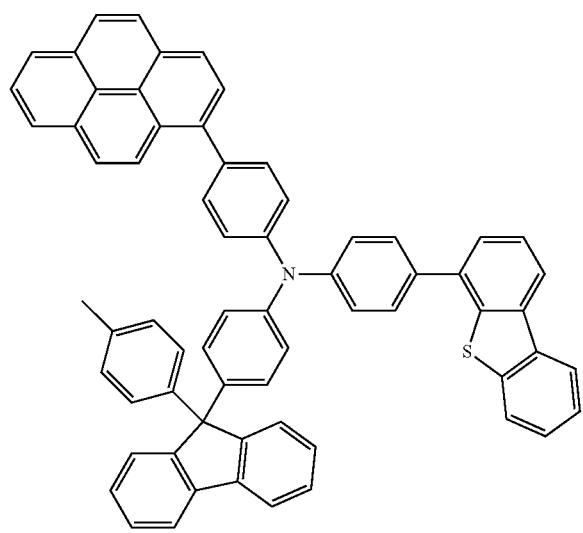
[A-207]
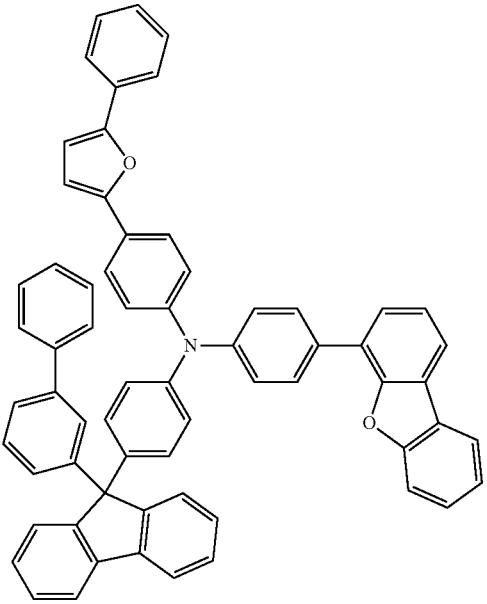
[A-208]
[A-209]
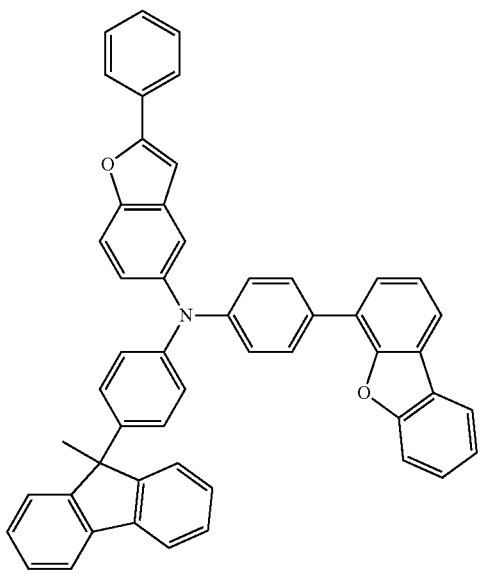

[A-210]
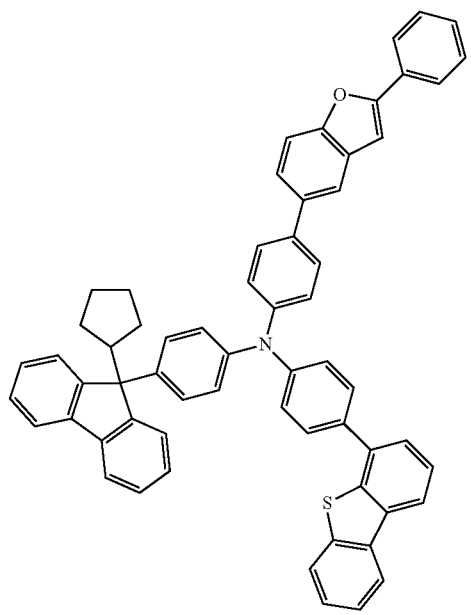
[A-212]
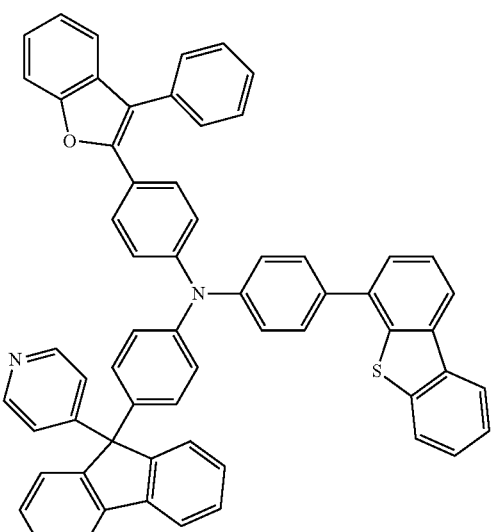
[A-213]
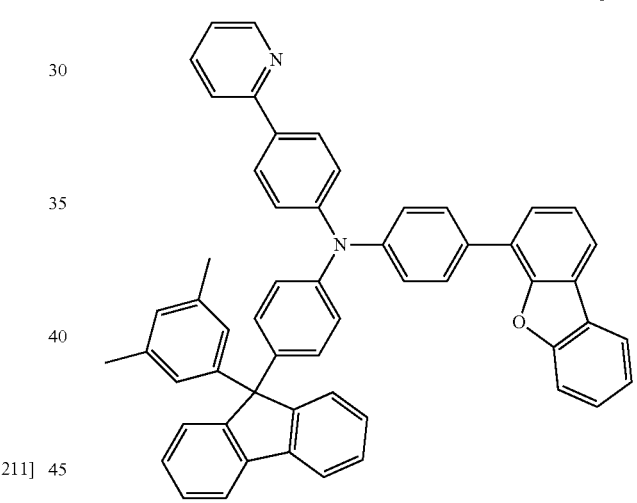
[A-211]
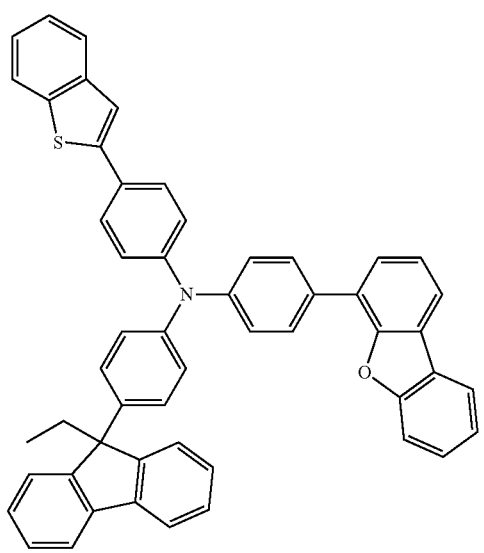
[A-214]
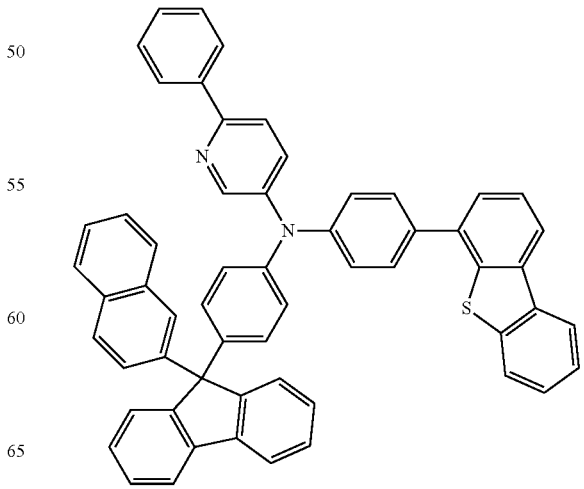

[A-215]
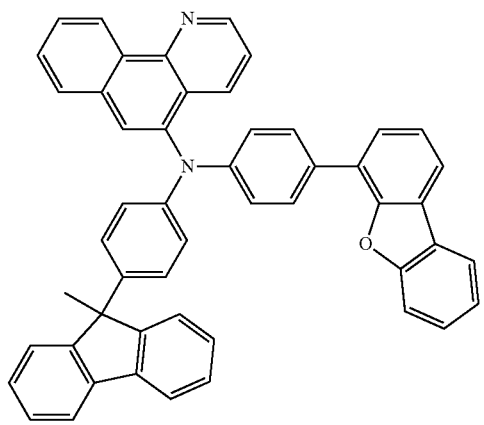
[A-218]
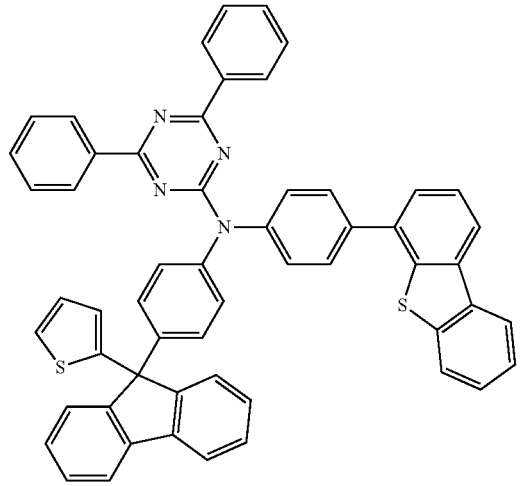
[A-216]
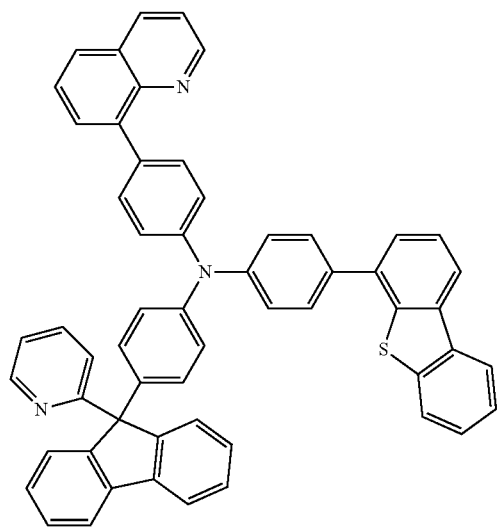
[A-219]
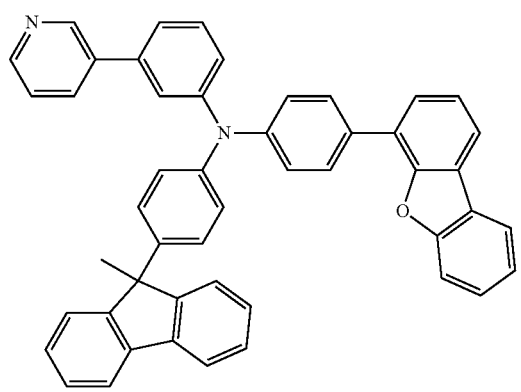
[A-217]
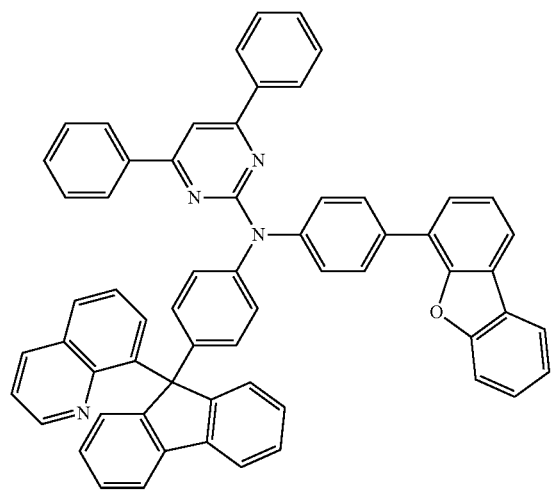
[A-220]
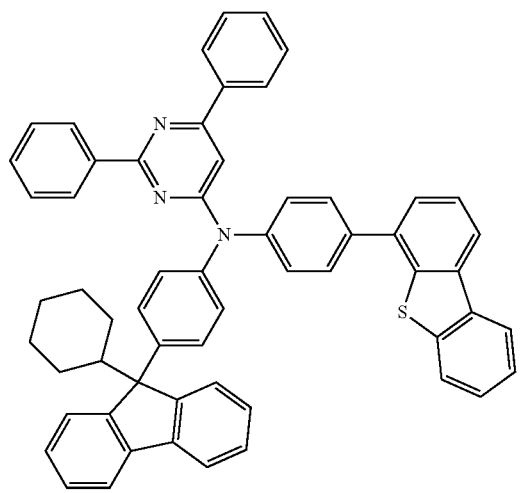

[A-221]
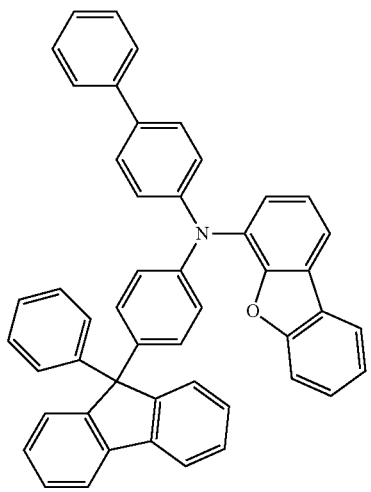
[A-224]
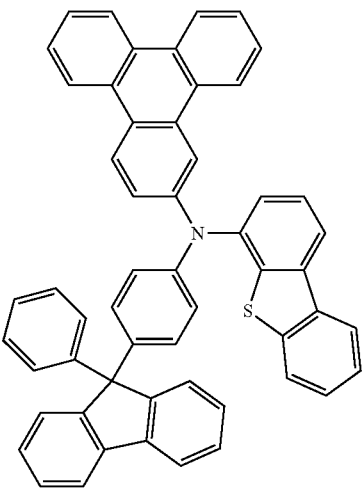
[A-222]
[A-225]
[A-223]
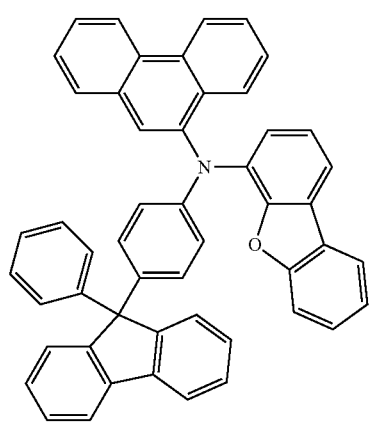

[A-226]
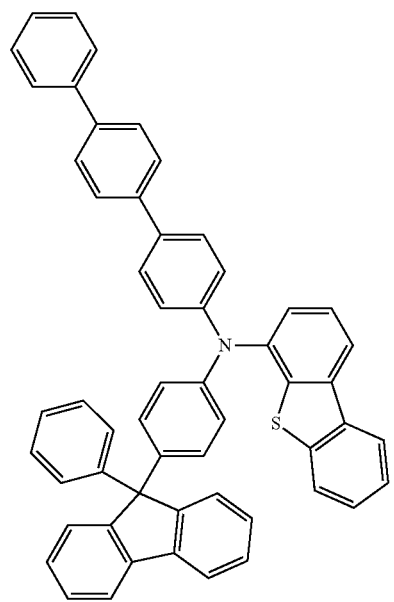
[A-227]
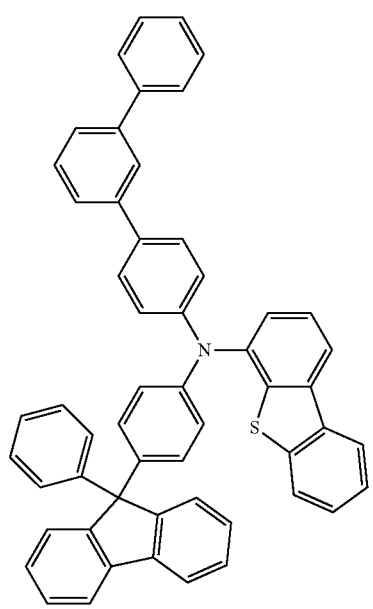
[A-228]
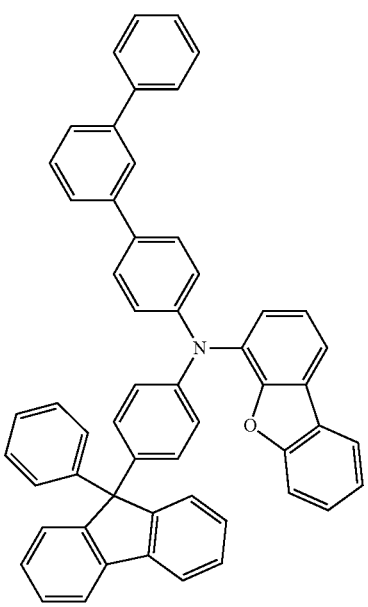
[A-229]
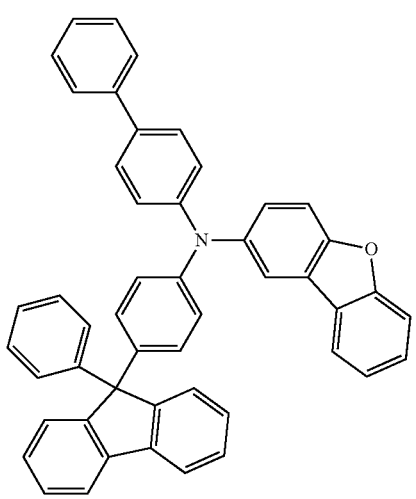
[A-230]
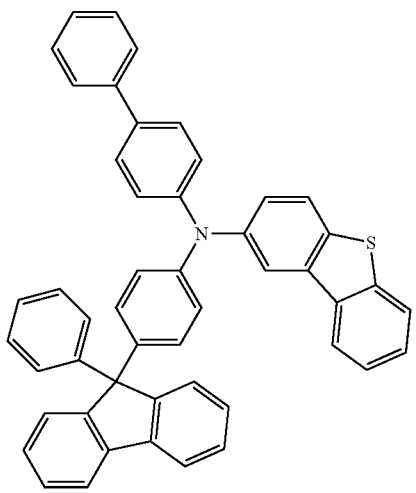

[A-231]
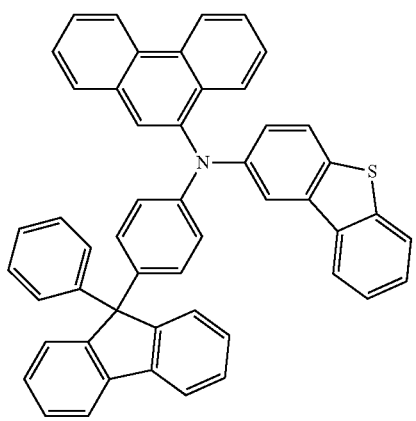
[A-232]
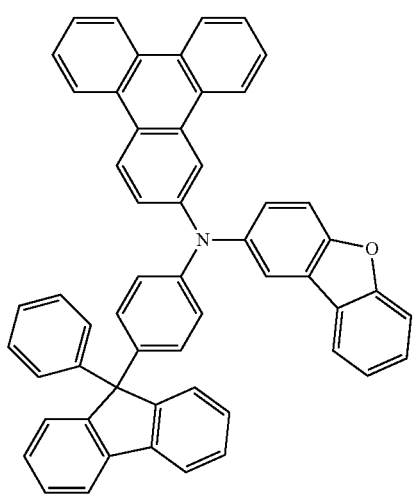
[A-233]
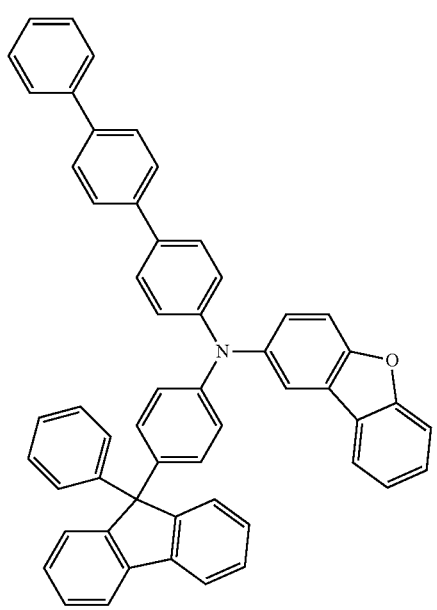
[A-234]
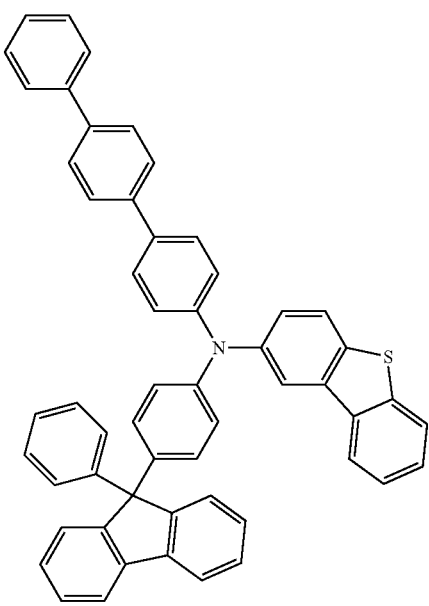
[A-235]
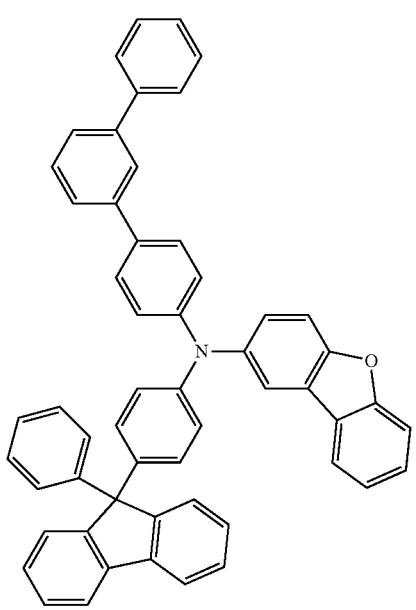

[A-236]
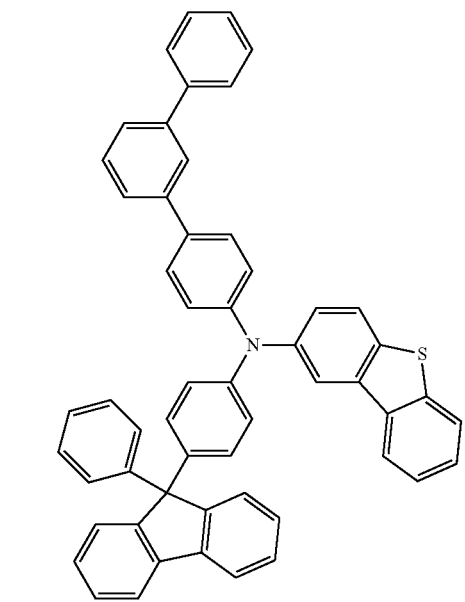
[A-237]
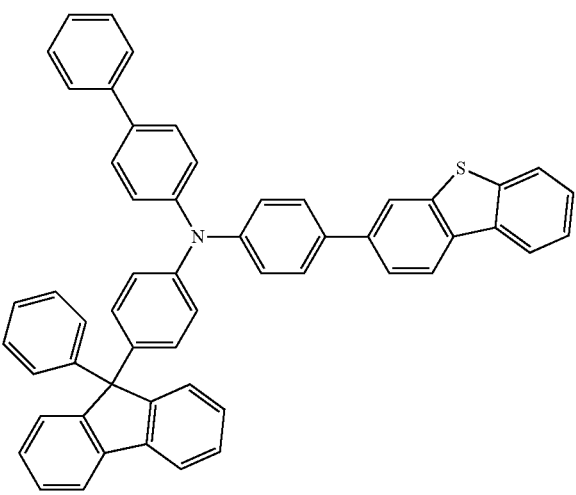
[A-238]
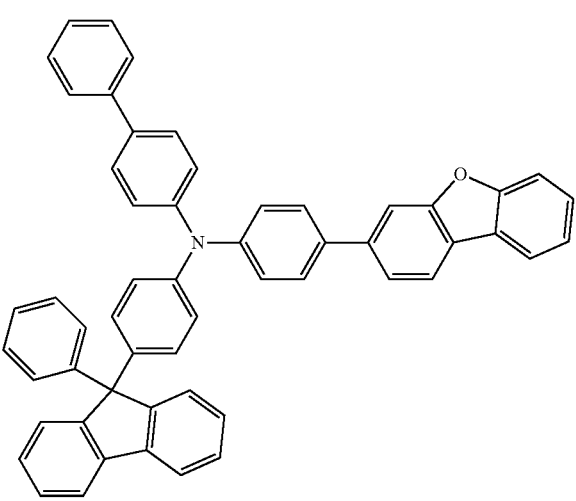
[A-239]
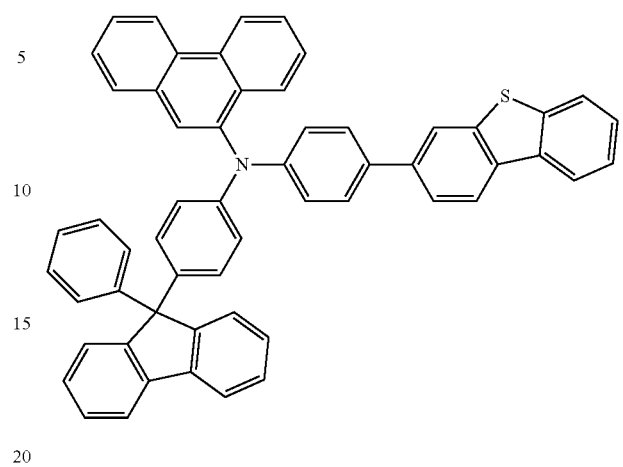
[A-240]
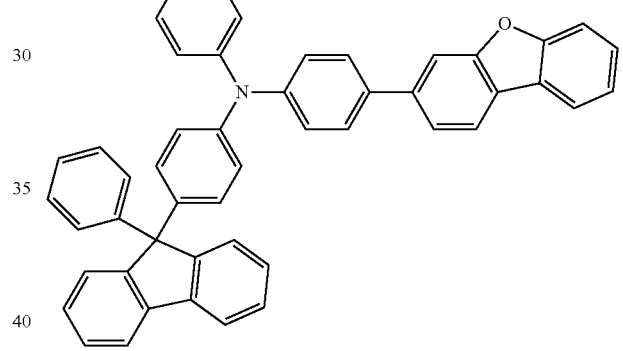
[A-241]
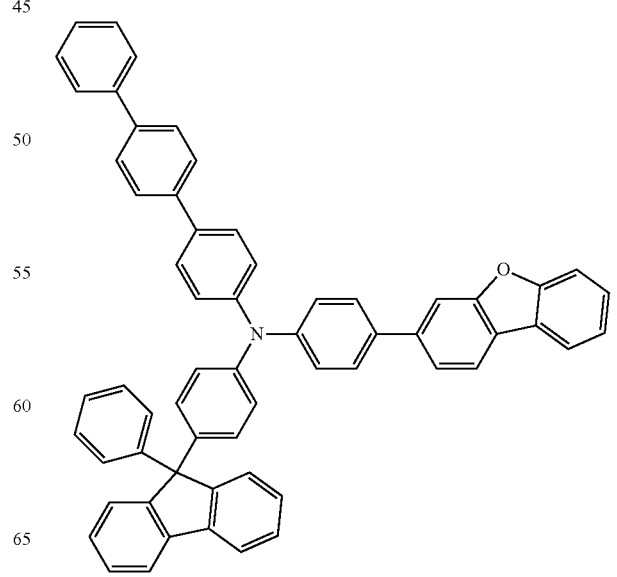

[A-242]
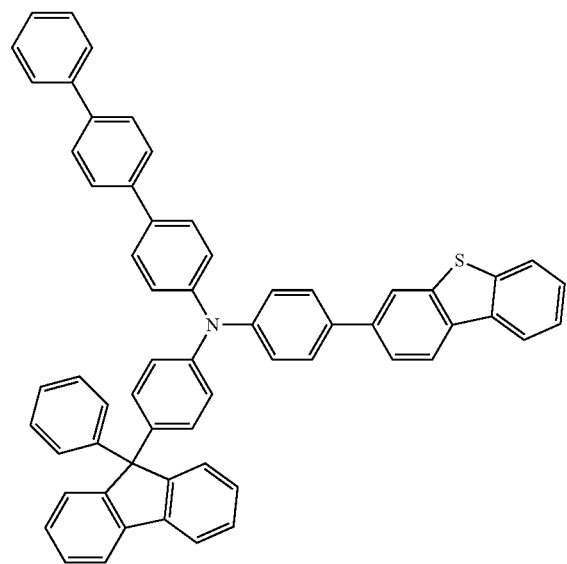
[A-244]
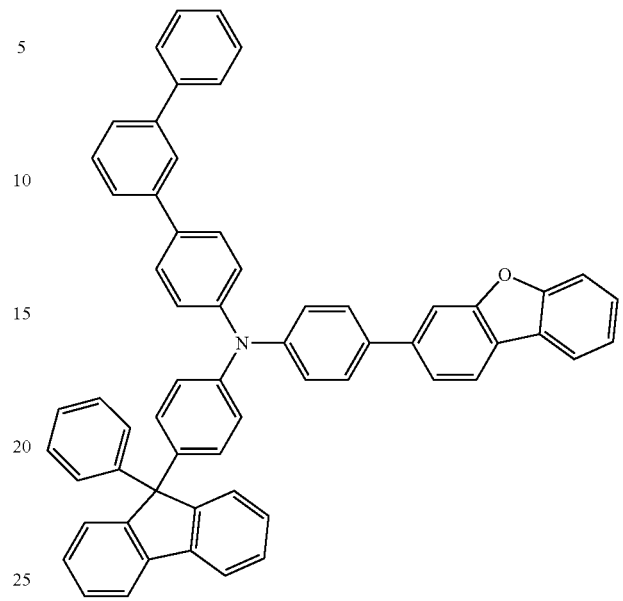
[A-243]
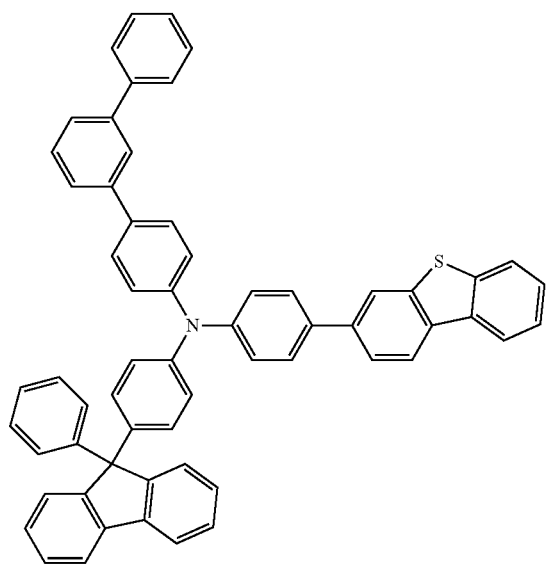
[A-245]
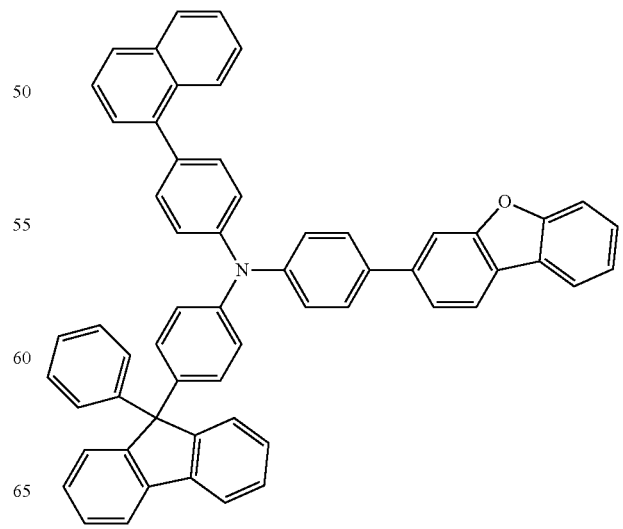

[A-246]
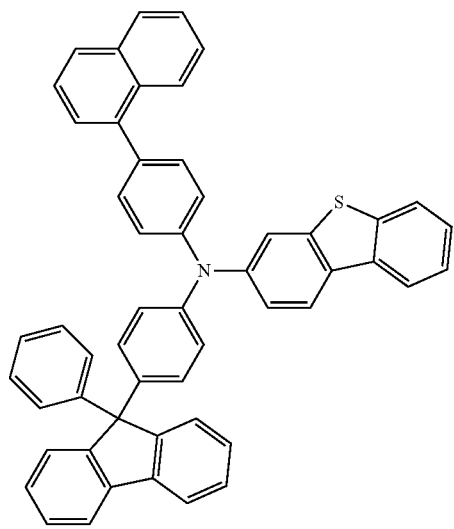
[A-249]
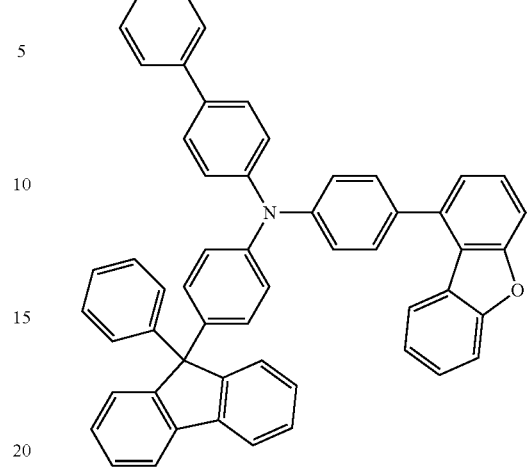
[A-247]
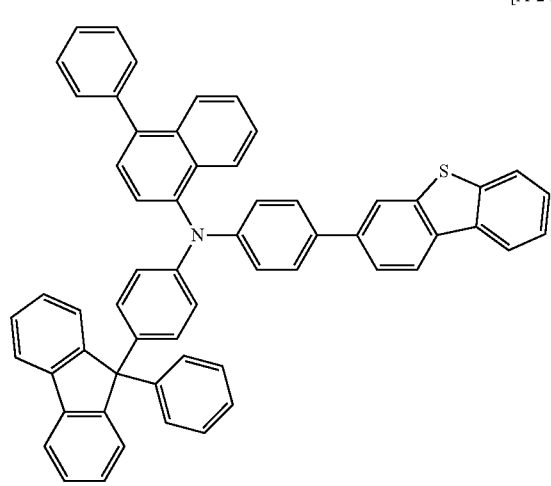
[A-250]
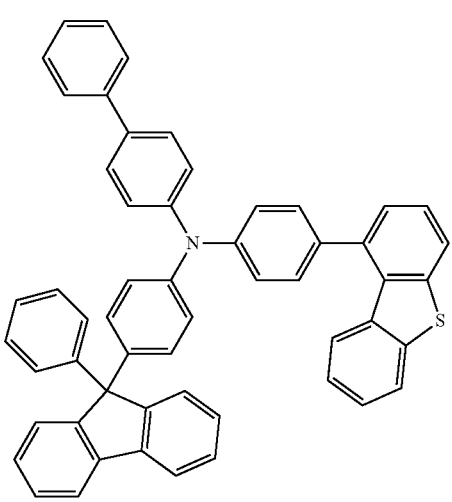
[A-248]
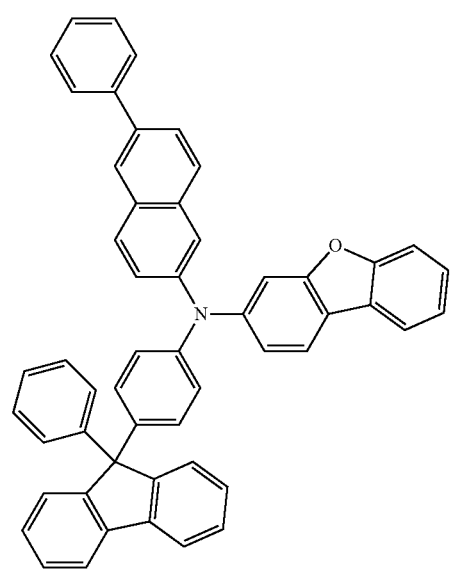
[A-251]
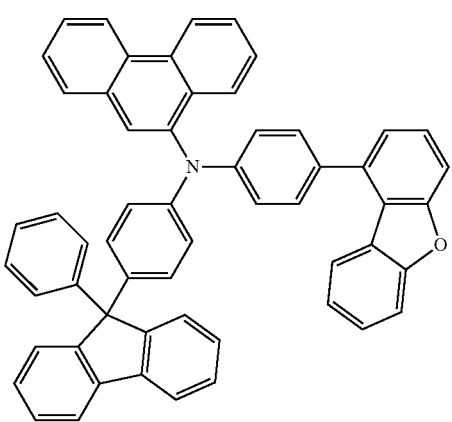

[A-252]
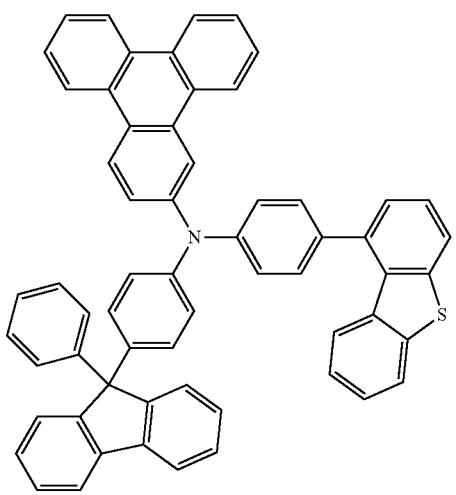
[A-253]
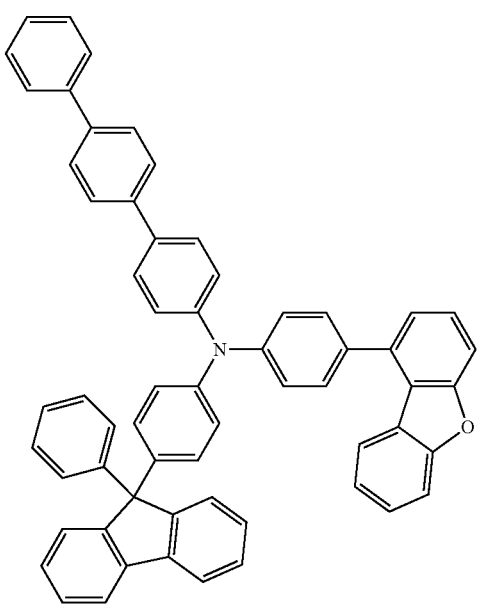
[A-254]
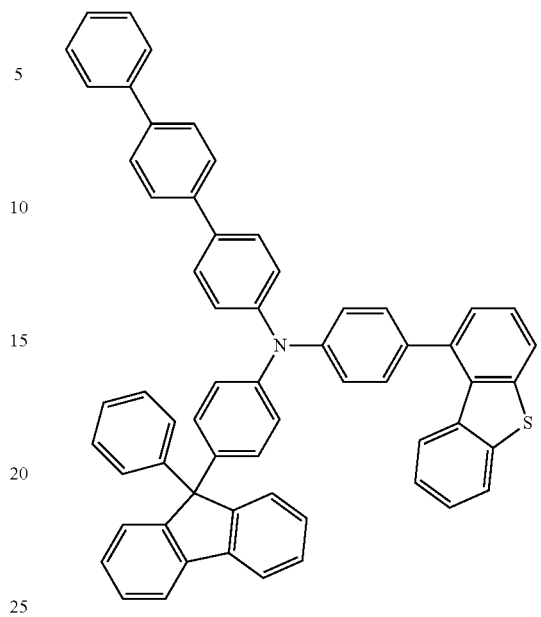
[A-255]
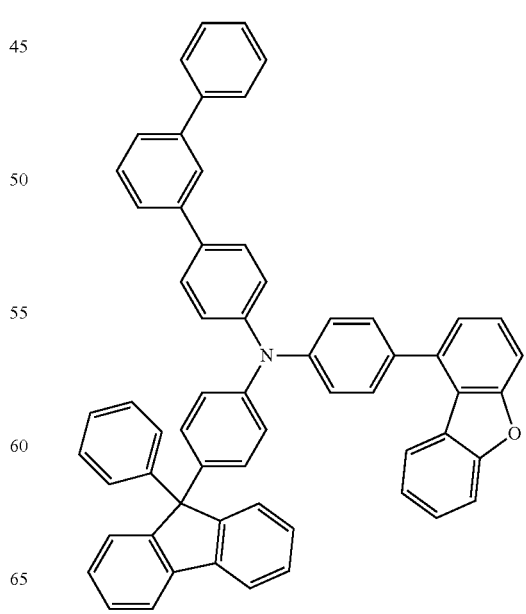

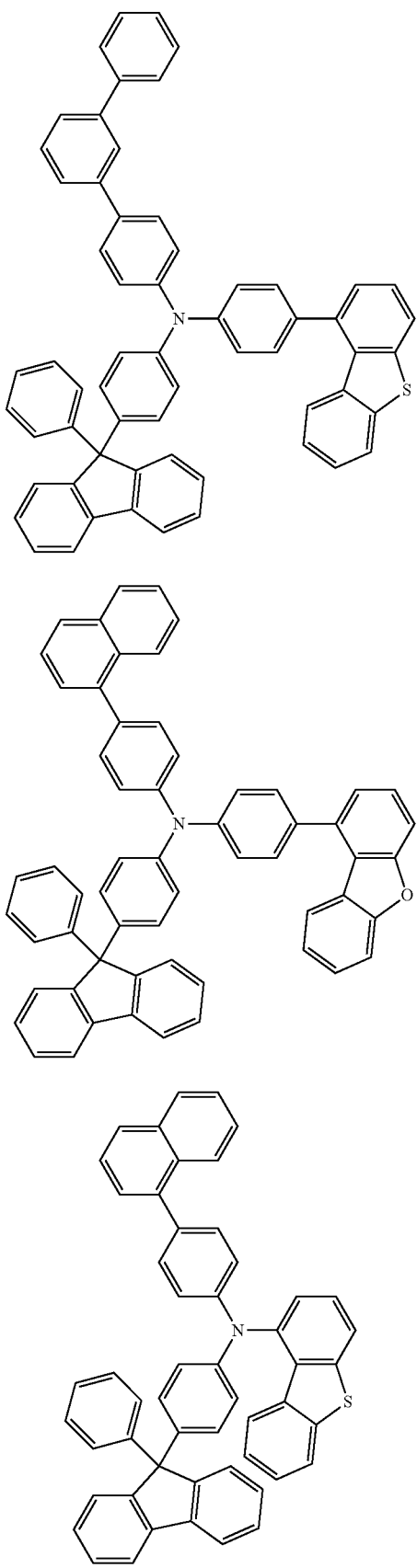
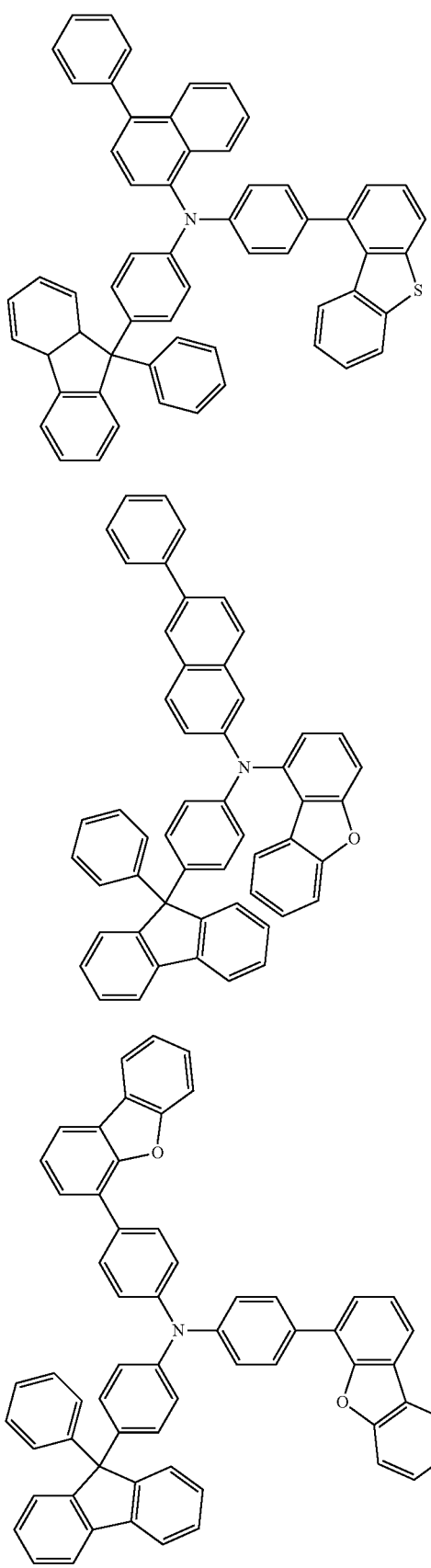

[B-2]
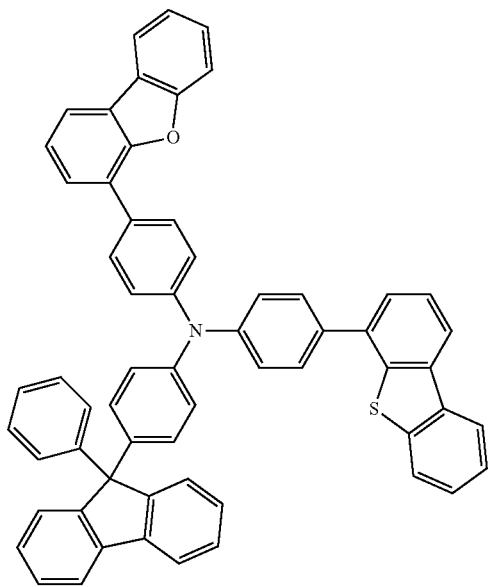
[B-3]
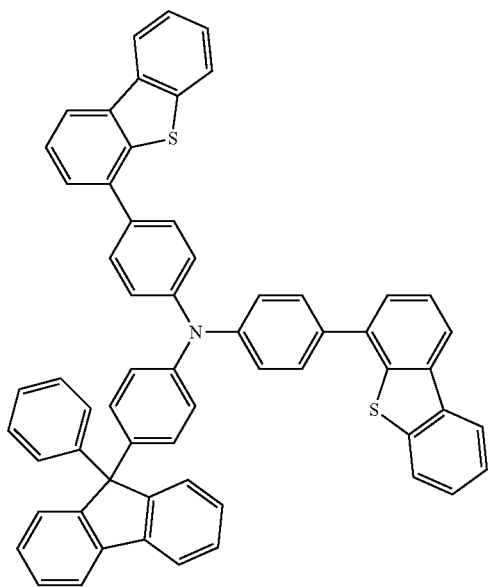
[B-4]
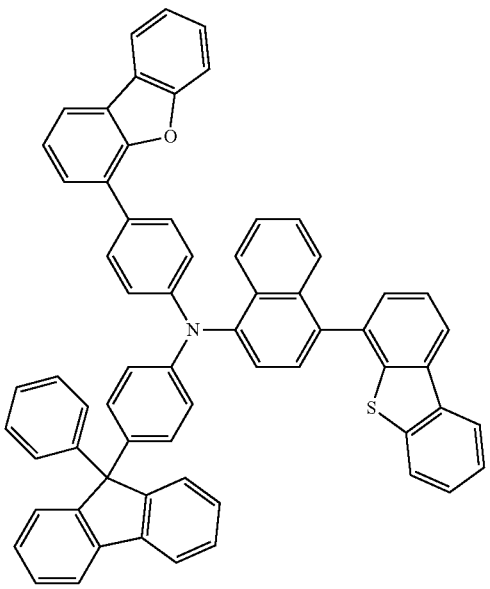
[B-5]
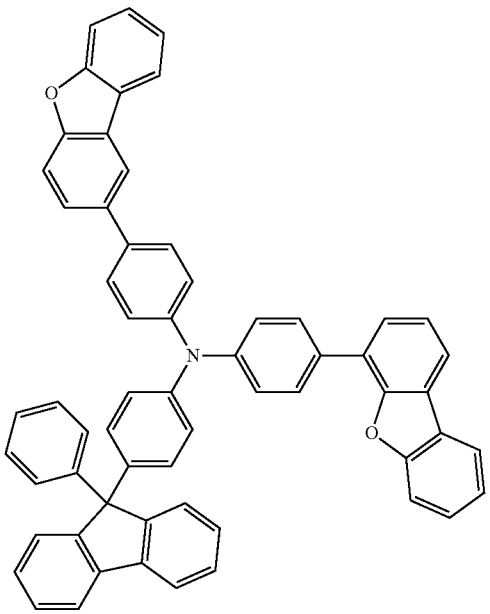

[B-6]
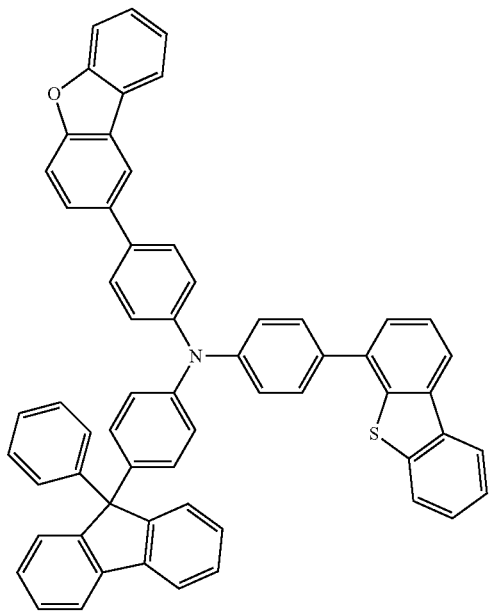
[B-8]
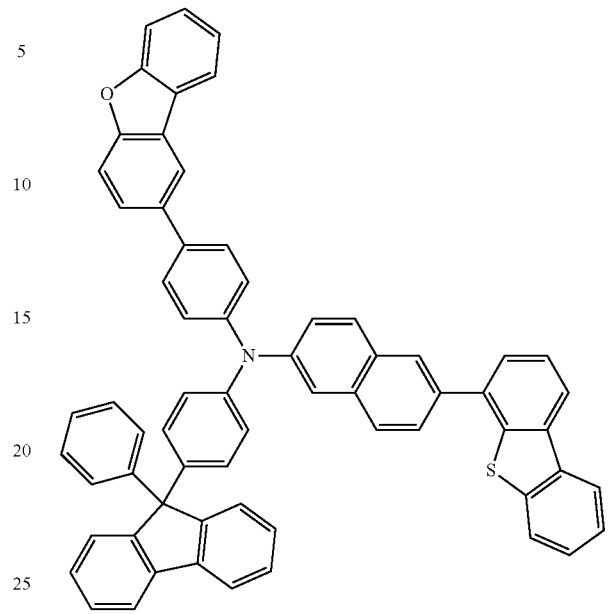
[B-7]
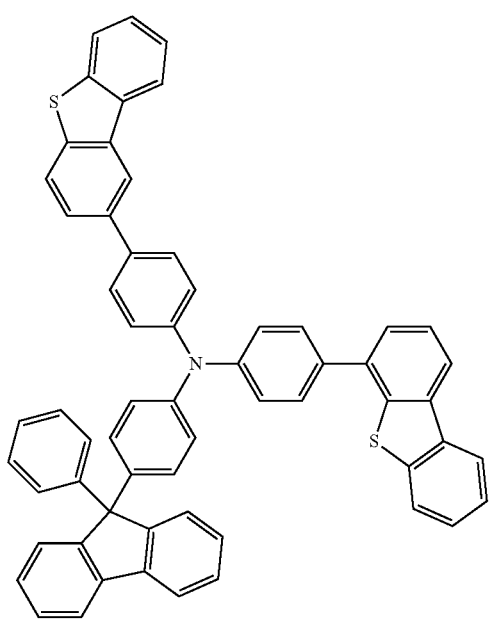
[B-9]
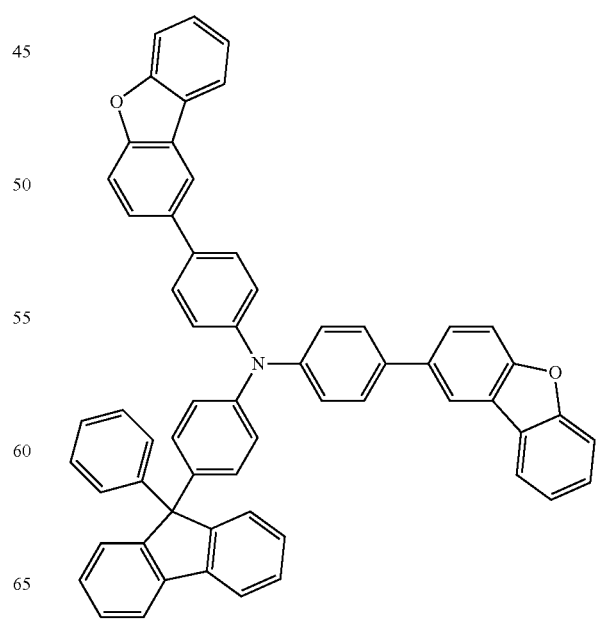

[B-10]
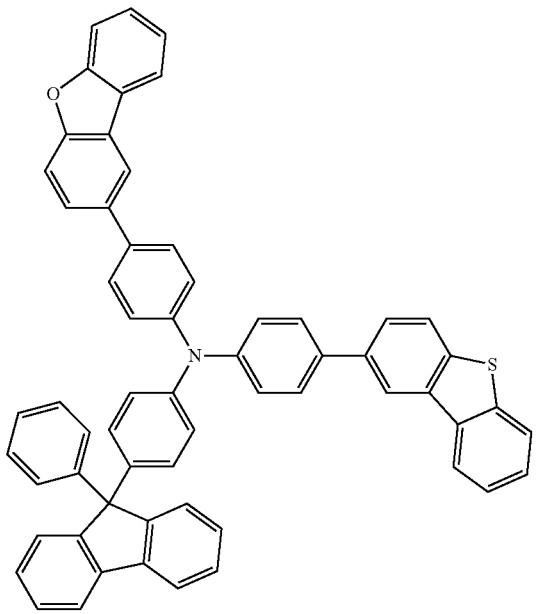
[B-11]
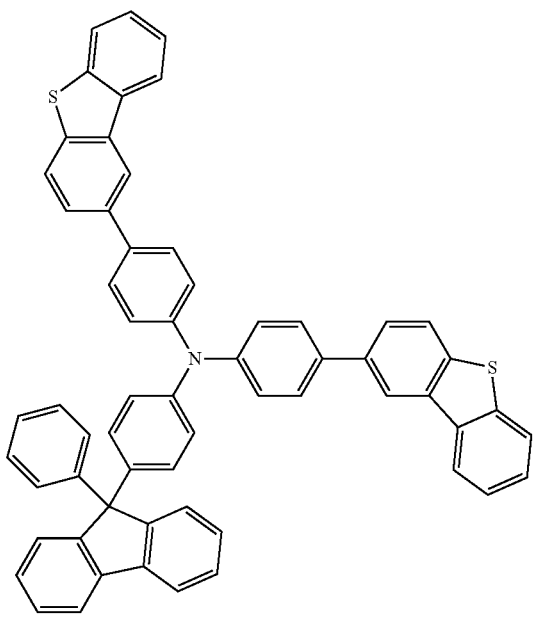
[B-12]
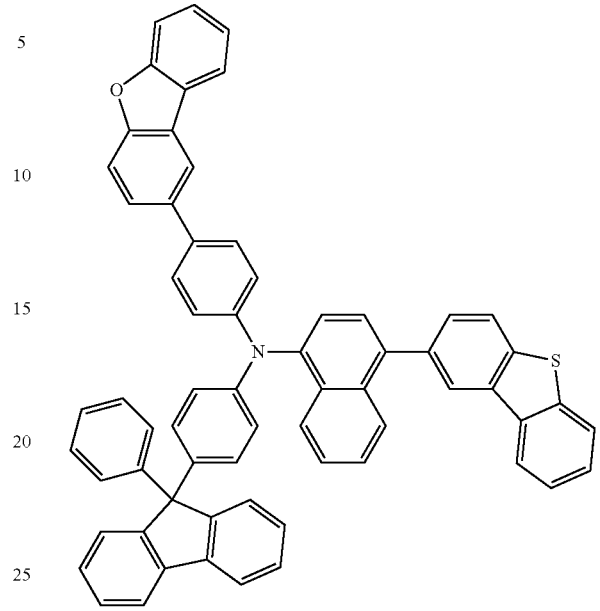
[B-13]
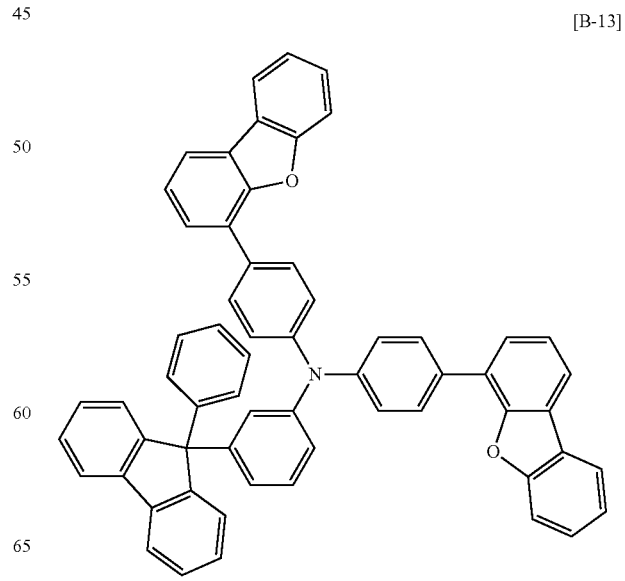

[B-14]
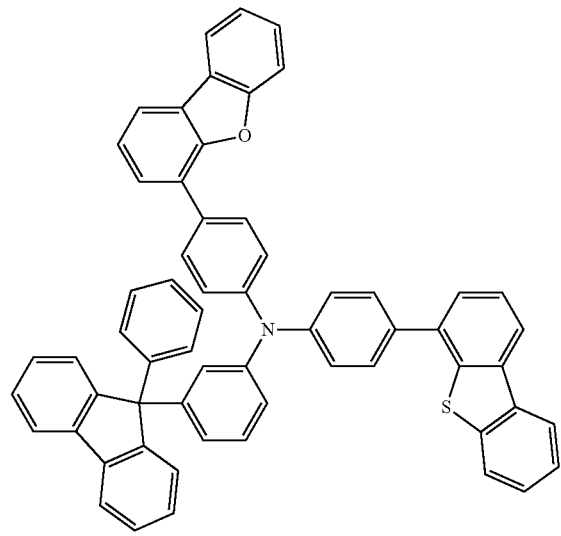
[B-17]
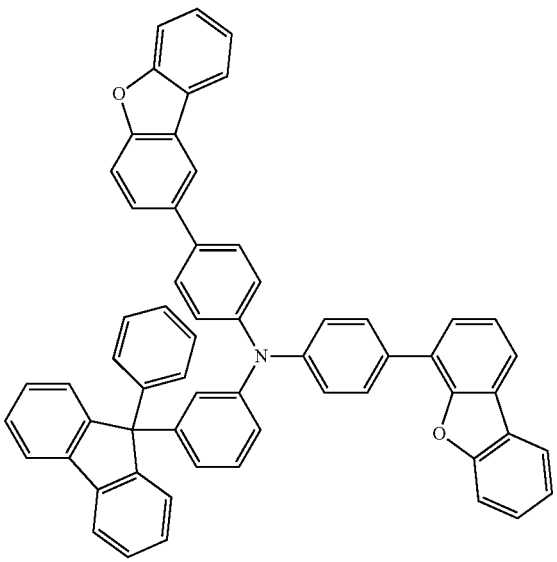
[B-15]
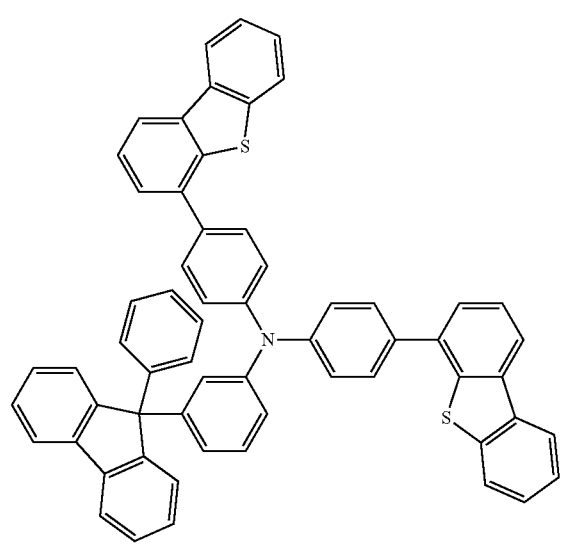
[B-16]
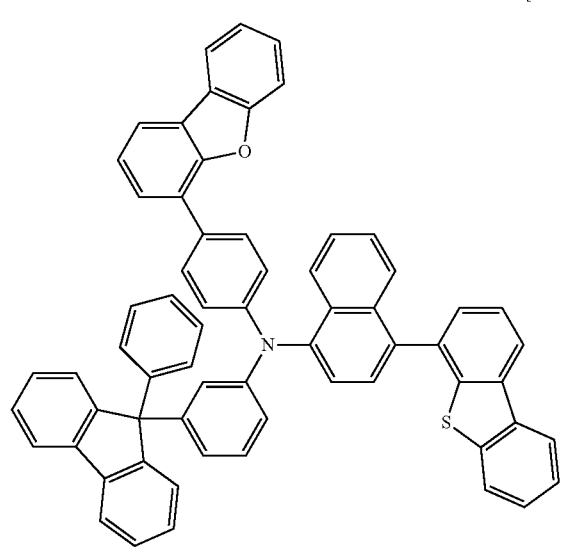
[B-18]
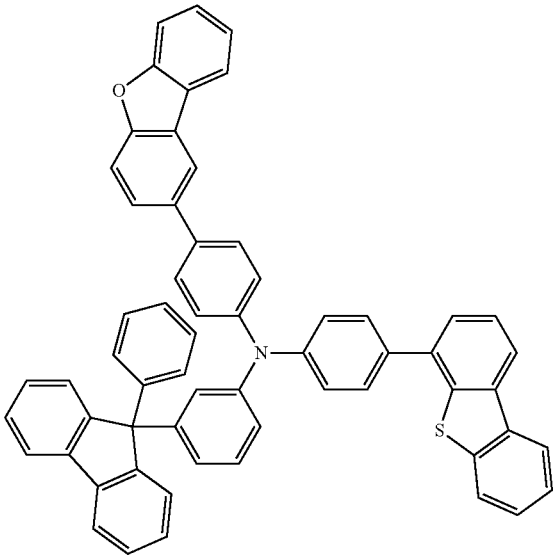

-continued
[B-19]
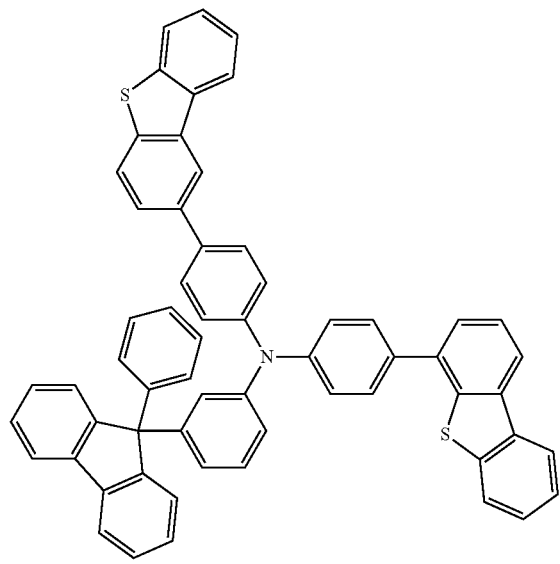
[B-20]
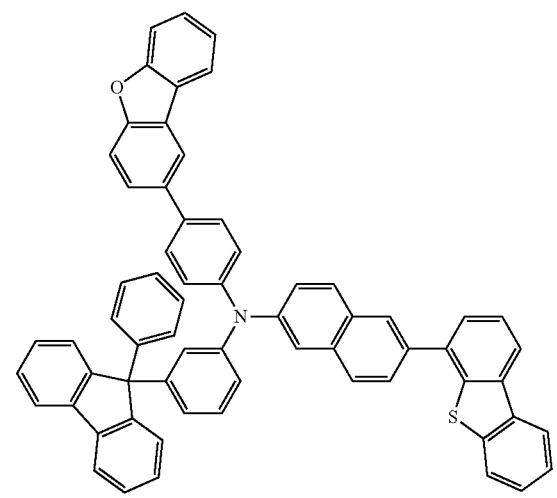
[B-21]
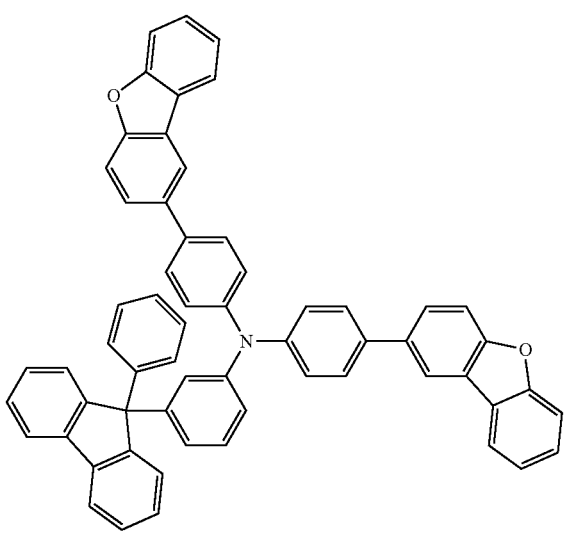
-continued
[B-22]
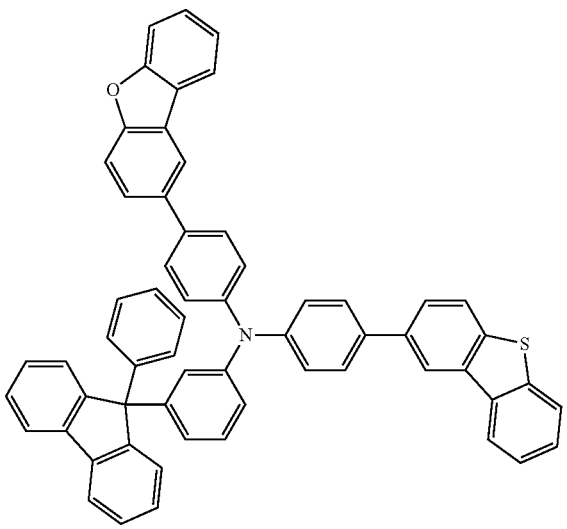
[B-23]
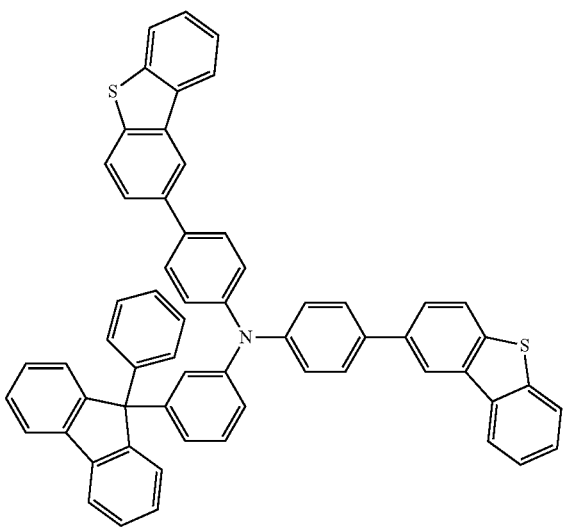
[B-24]
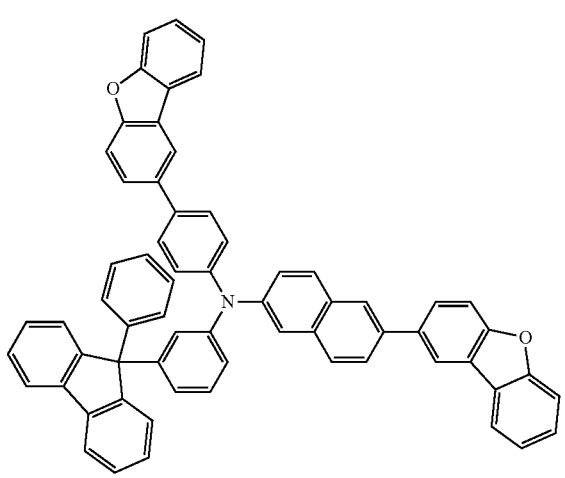

[B-25]
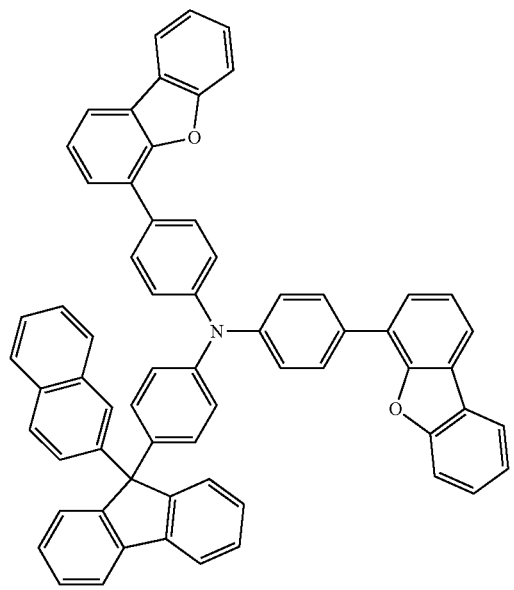
[B-27]
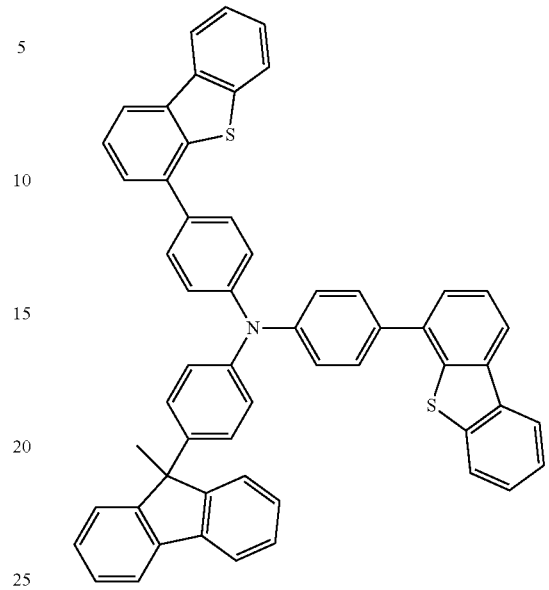
[B-26]
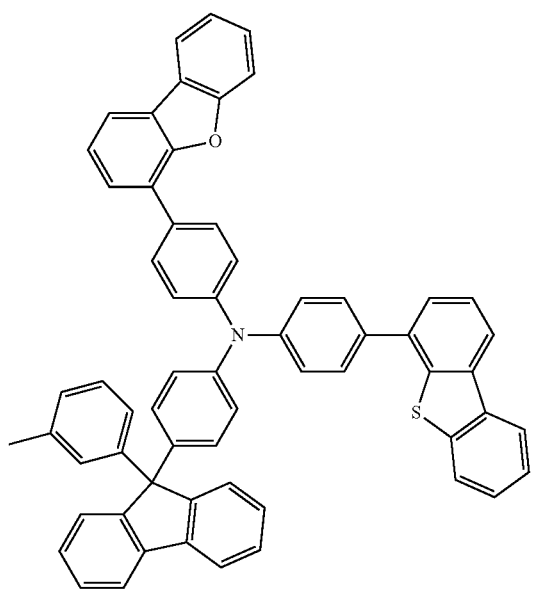
[B-28]
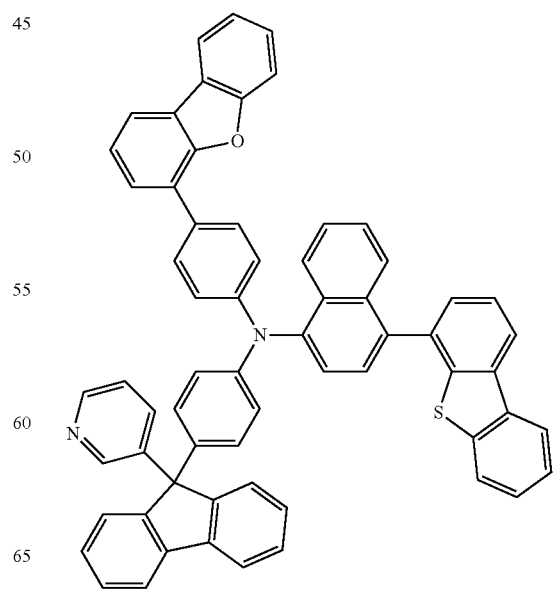

[B-29]
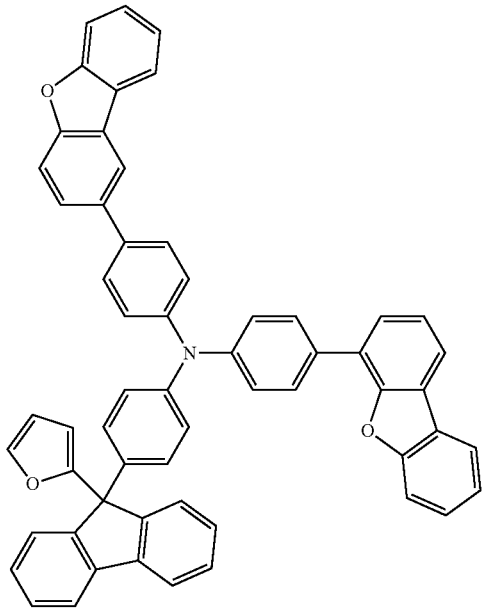
[B-31]
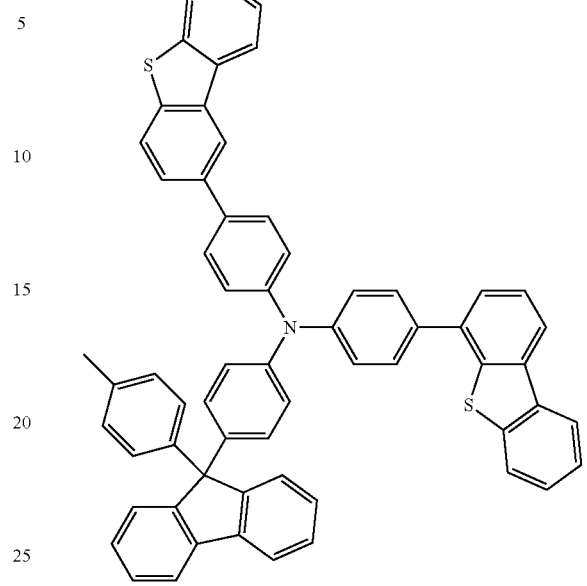
[B-30]
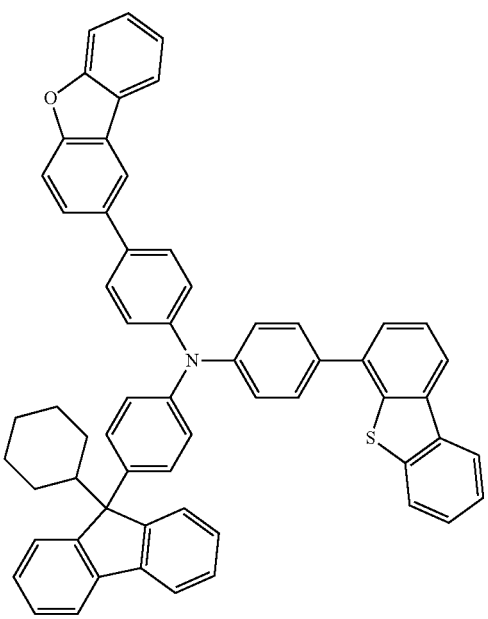
[B-32]
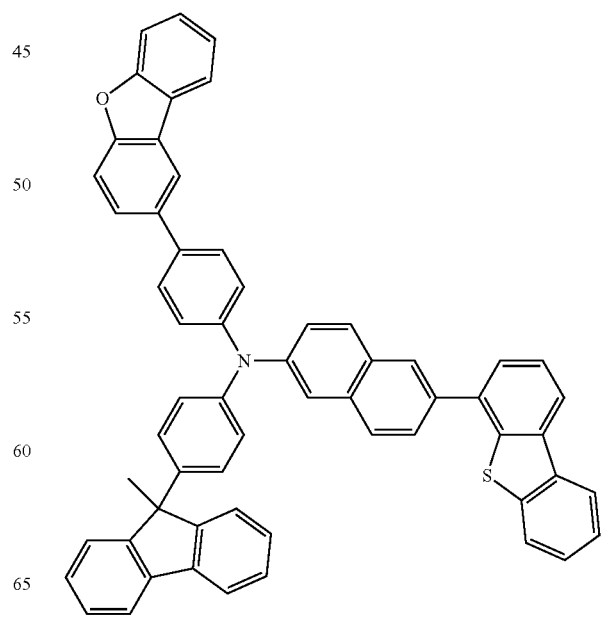

[B-33]
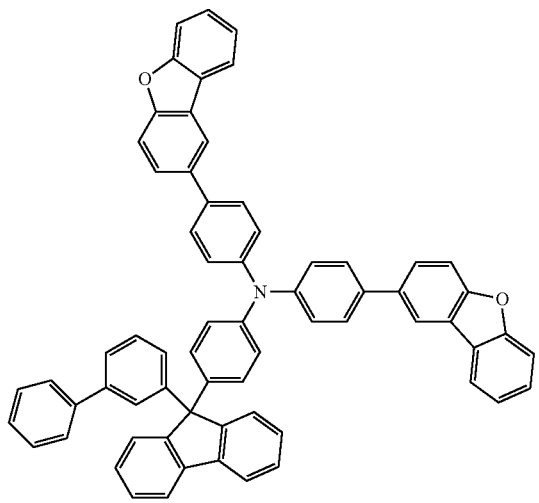
[B-34]
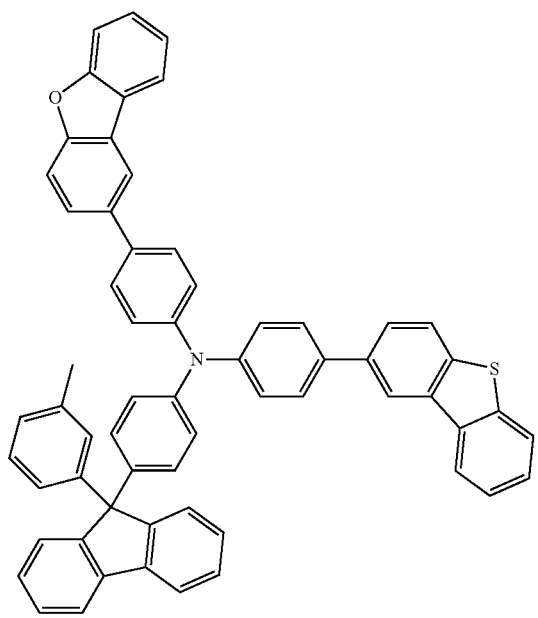
[B-35]
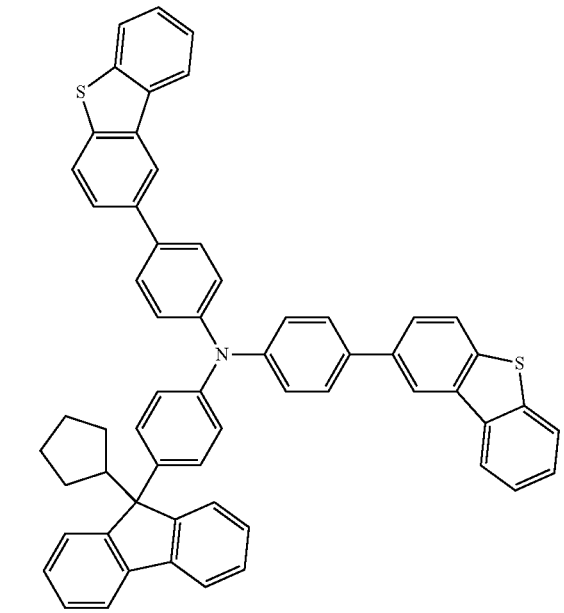
[B-36]
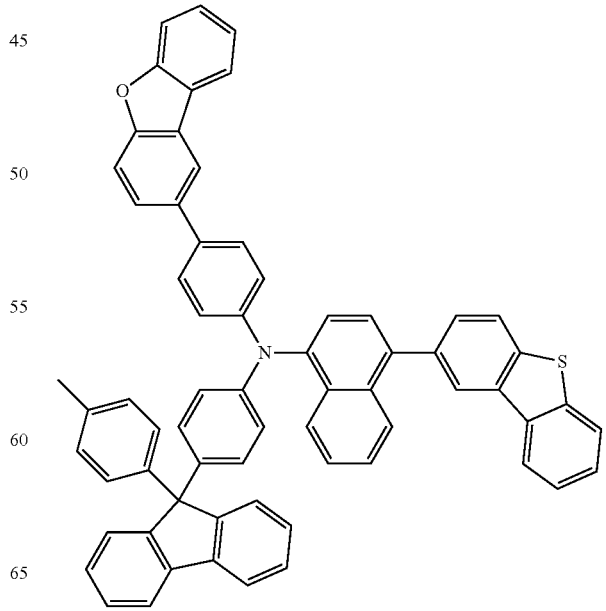

[B-37]
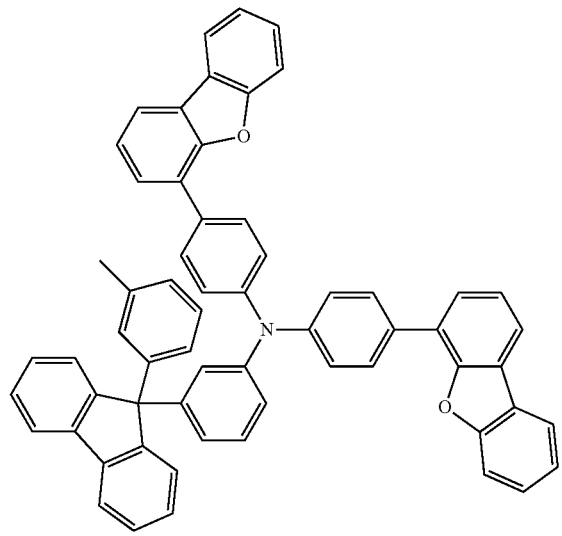
[B-38]
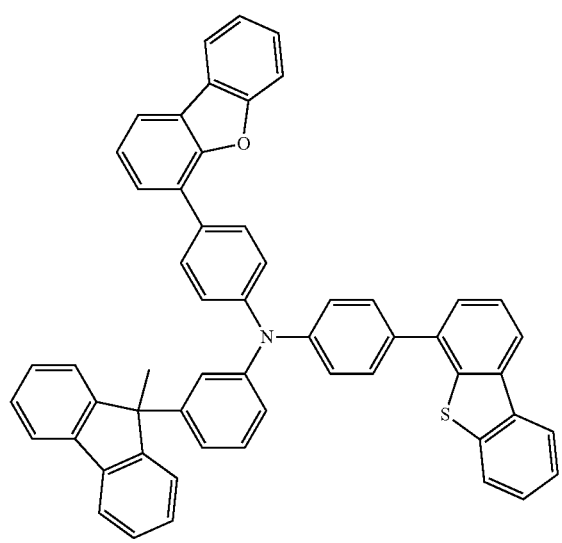
[B-39]
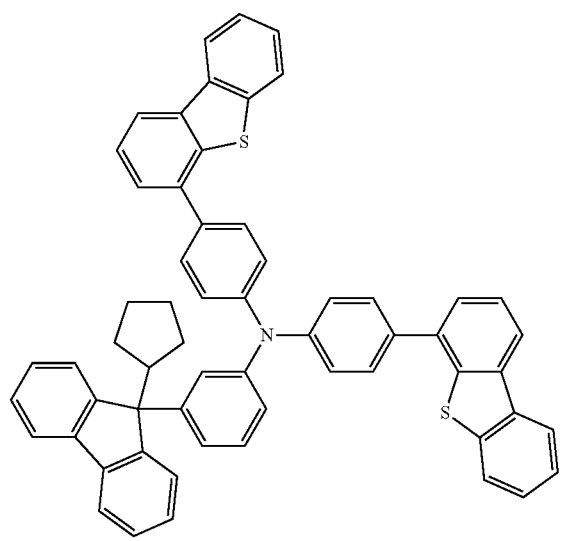
[B-40]
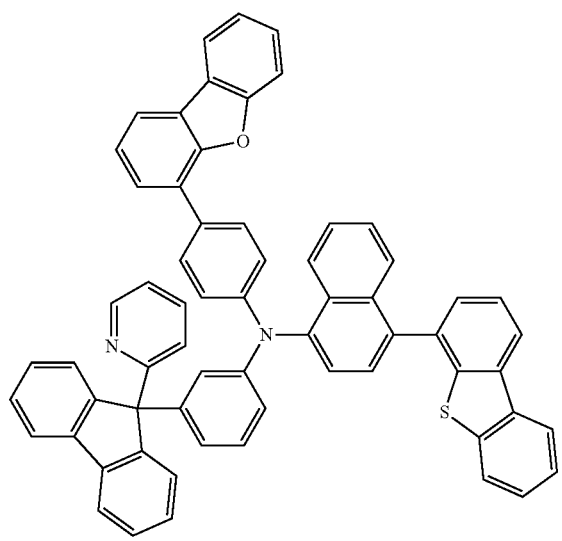
[B-41]
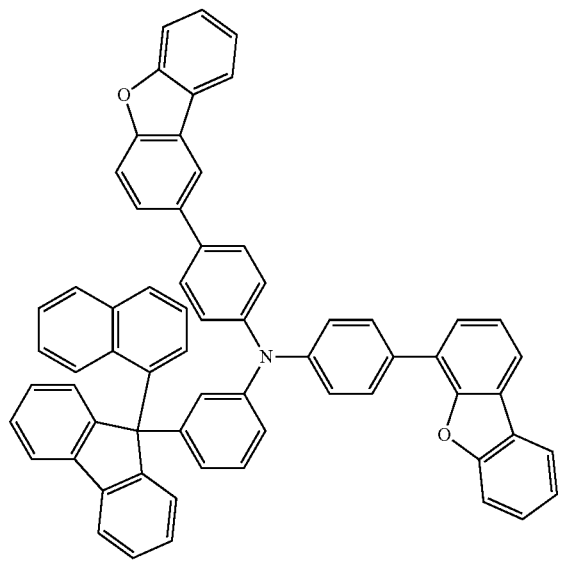

[B-42]
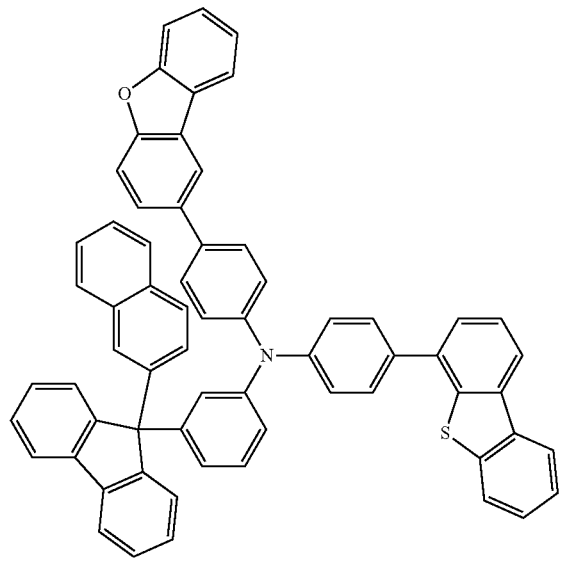
[B-43]
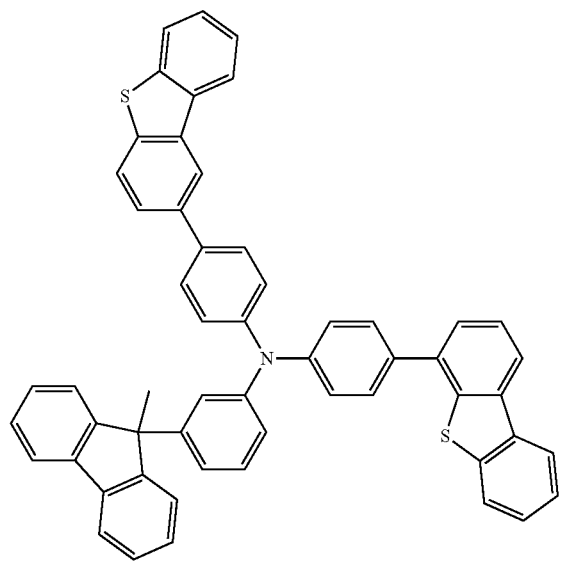
[B-44]
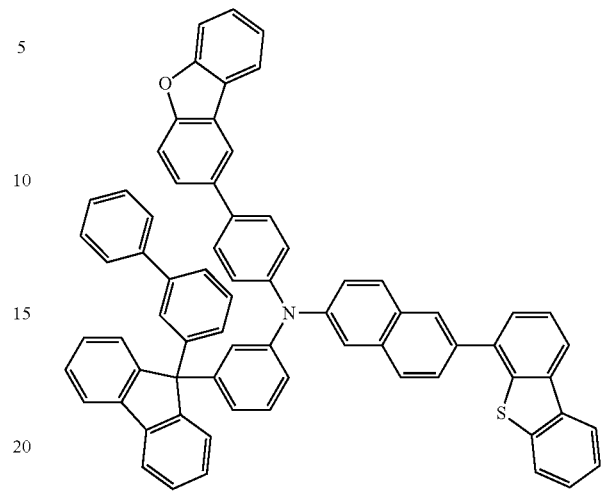
[B-45]
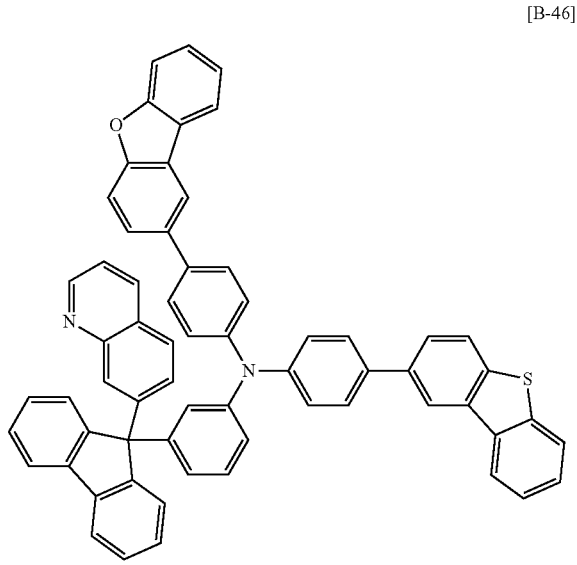
[B-46]

[B-47]
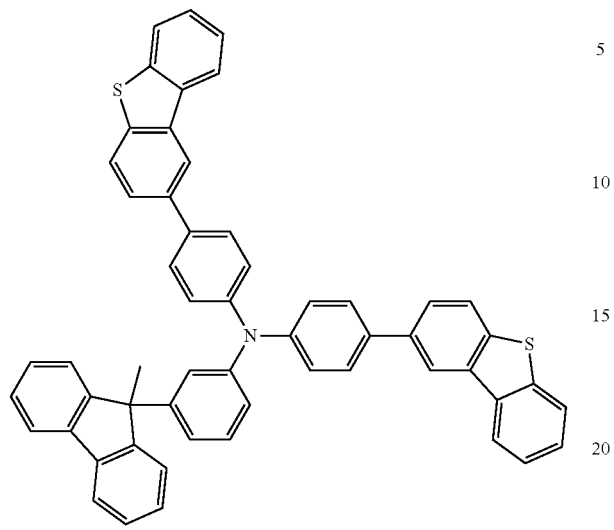
[C-2]
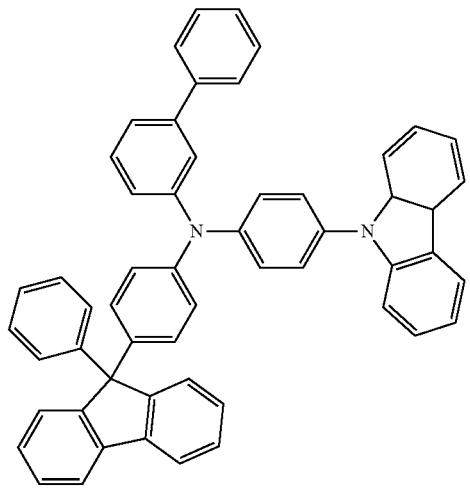
[B-48]
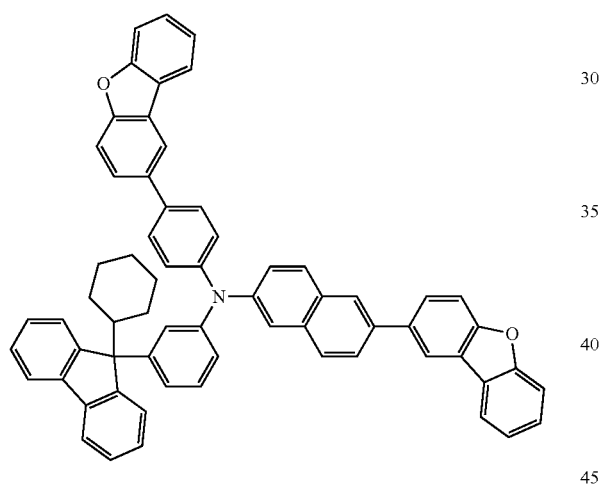
[C-3]
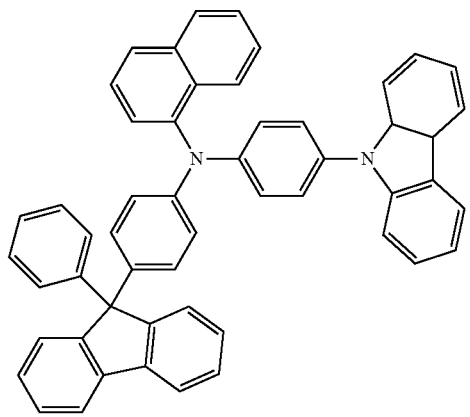
[C-1]
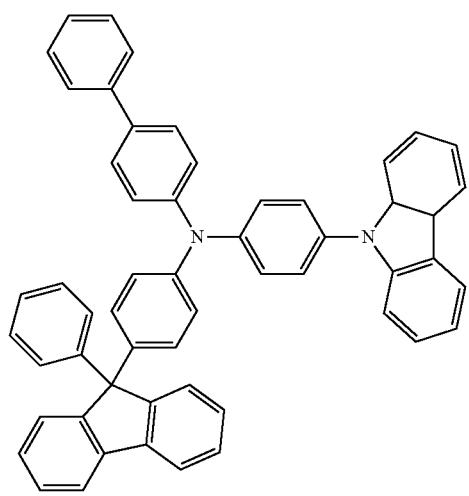
[C-4]
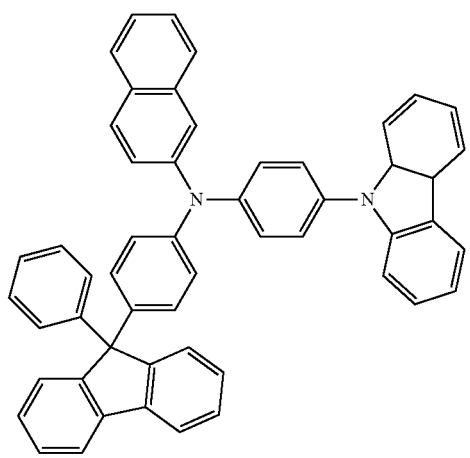

[C-5]
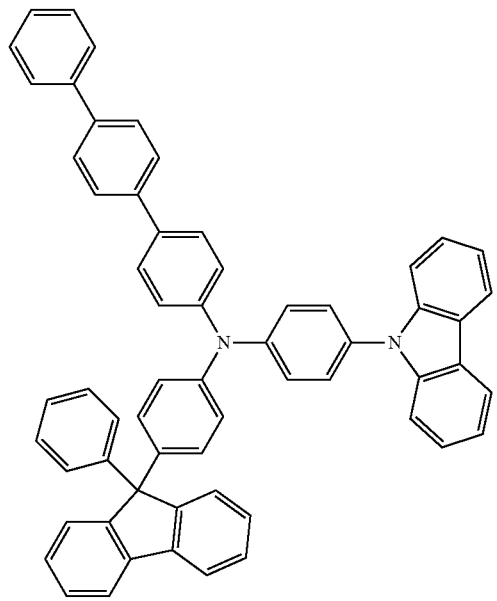
[C-6]
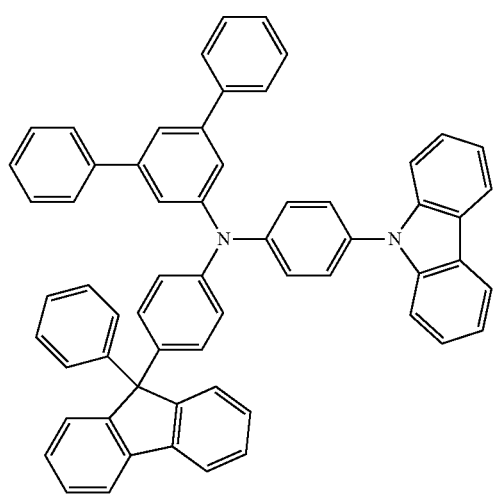
[C-7]
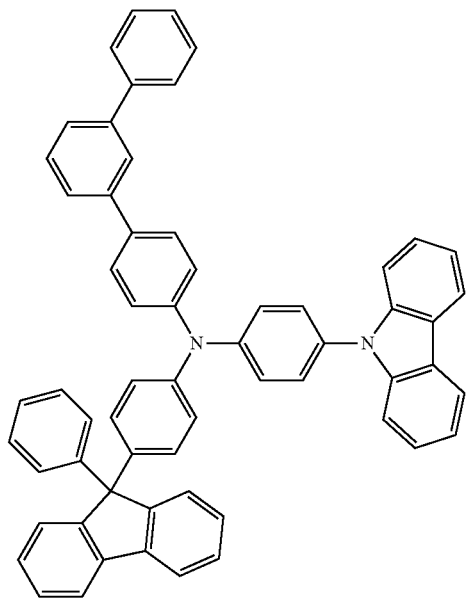
[C-8]
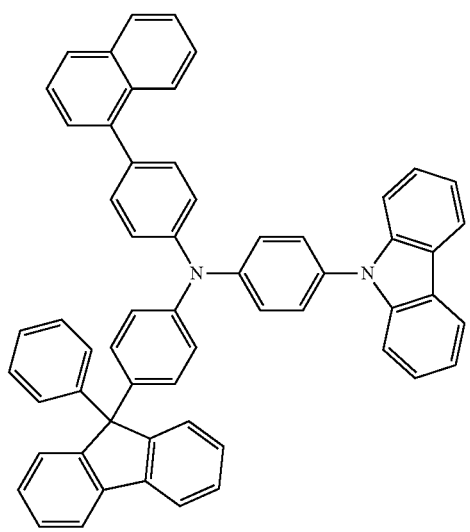
[C-9]
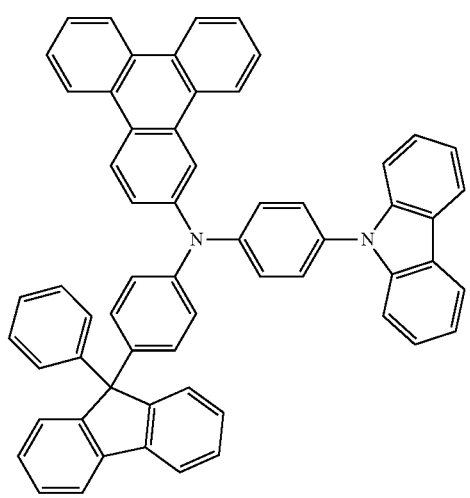

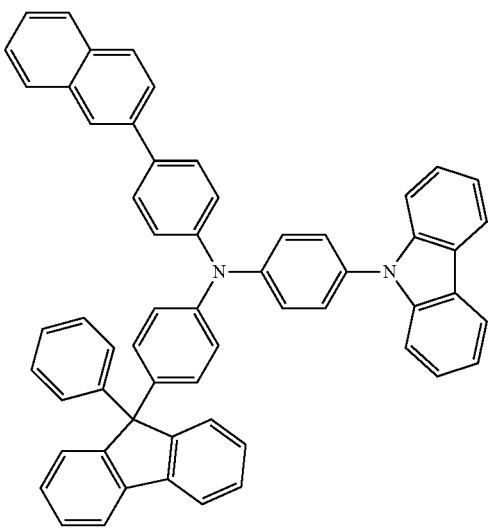
[C-10]
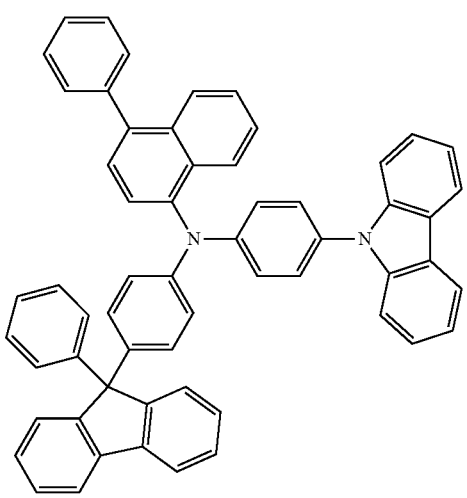
[C-11]
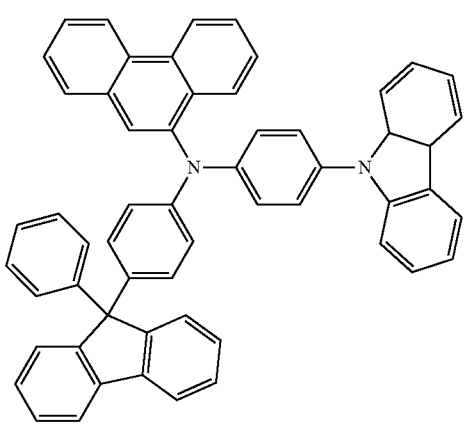
[C-12]
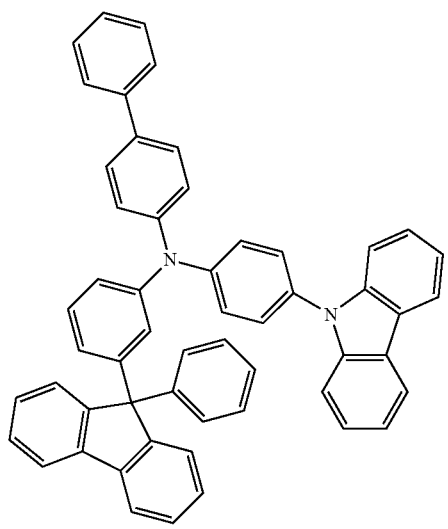
[C-13]
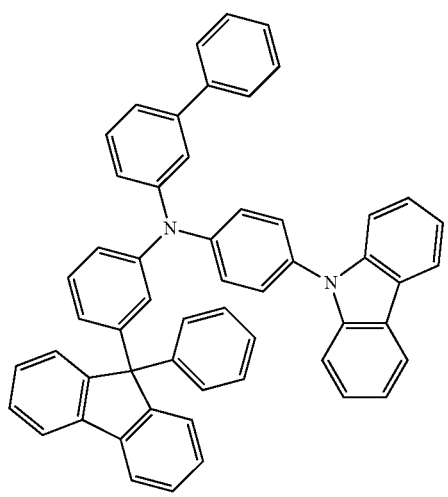
[C-14]
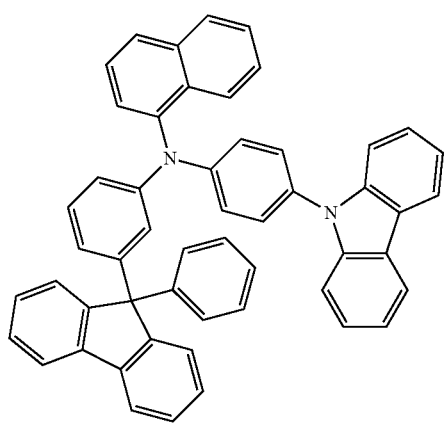
[C-15]

-continued
[C-16]
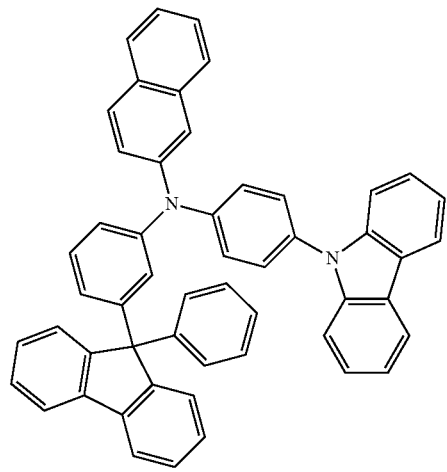
[C-17]
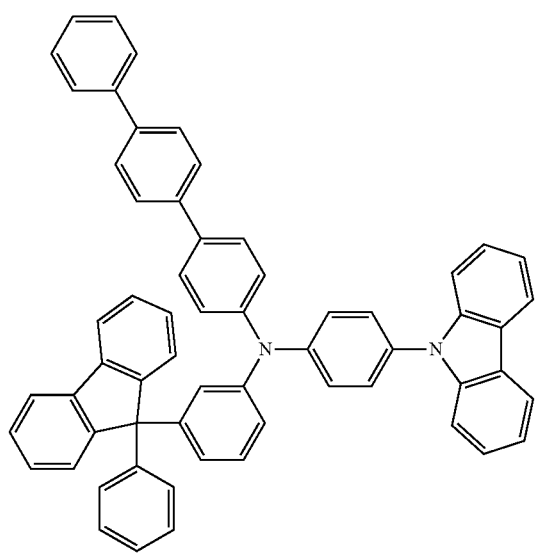
[C-18]
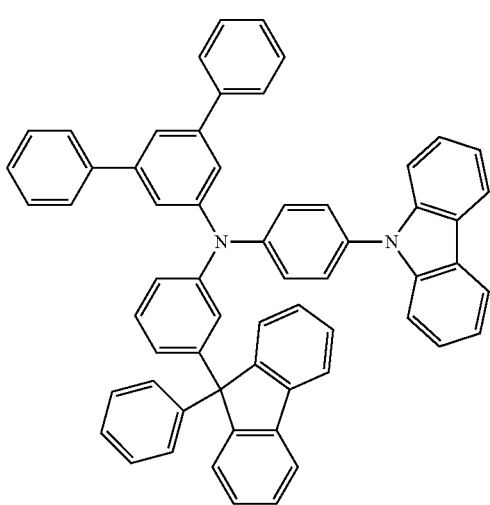
[C-19]
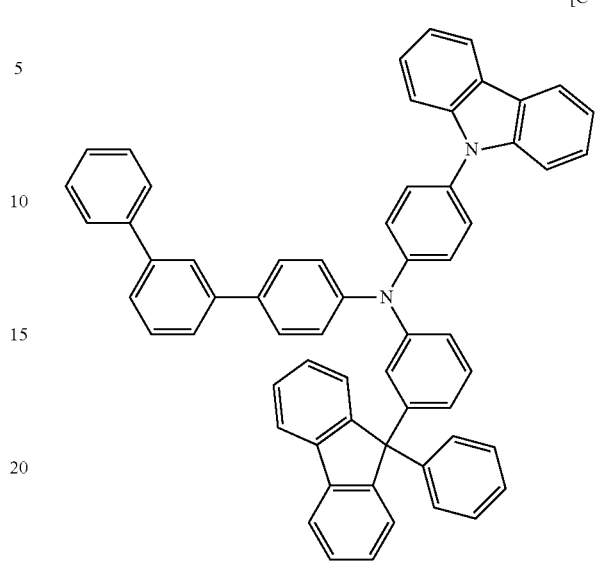
[C-20]
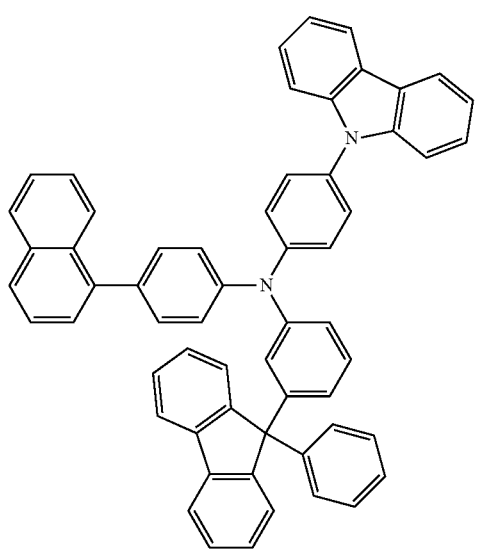
[C-21]
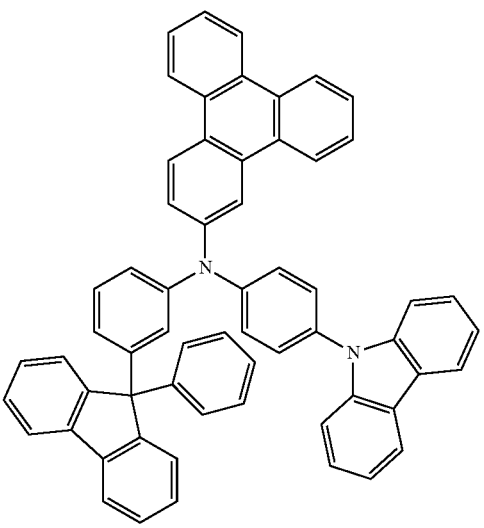

[C-22]
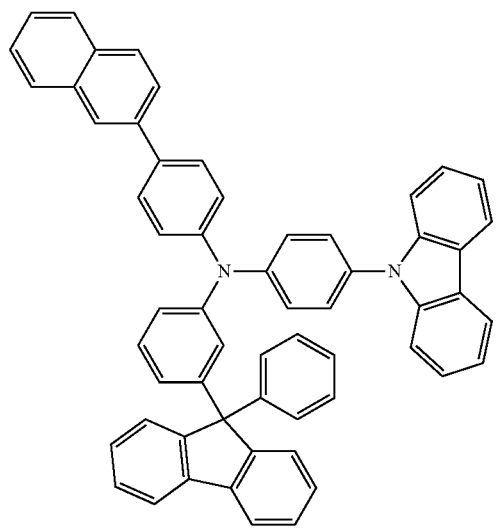
[C-25]
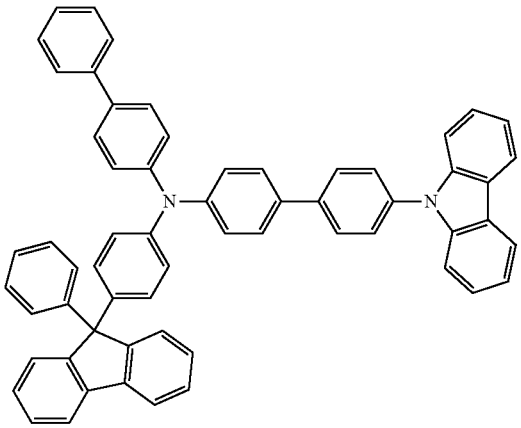
[C-23]
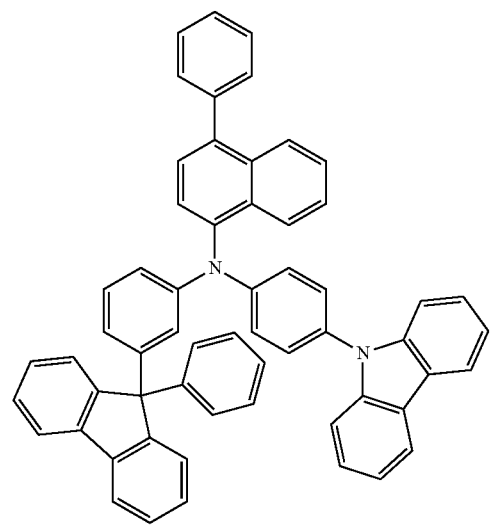
[C-26]
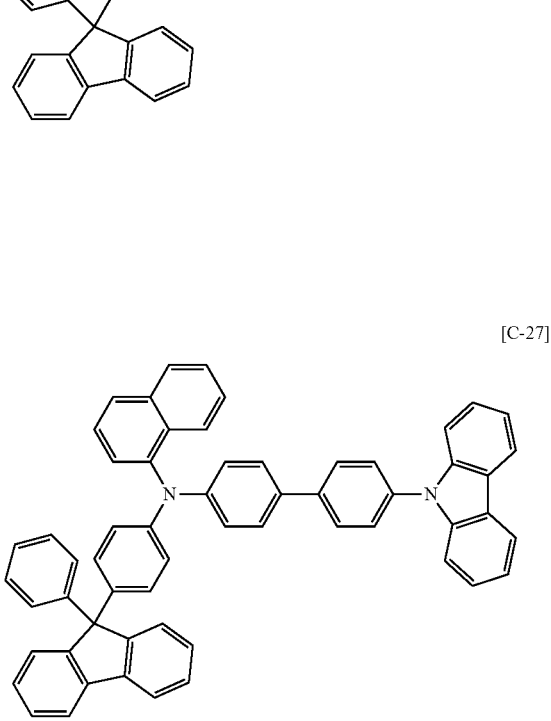
[C-24]
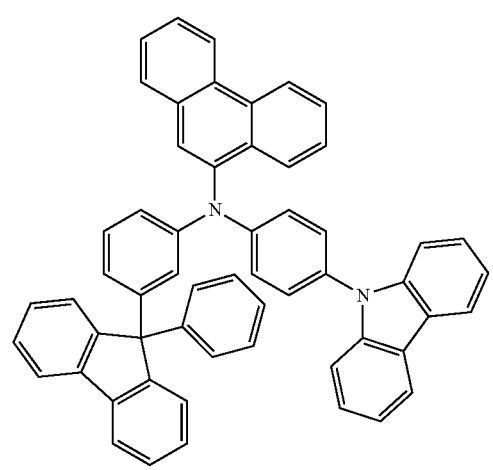
[C-27]

-continued
[C-28]
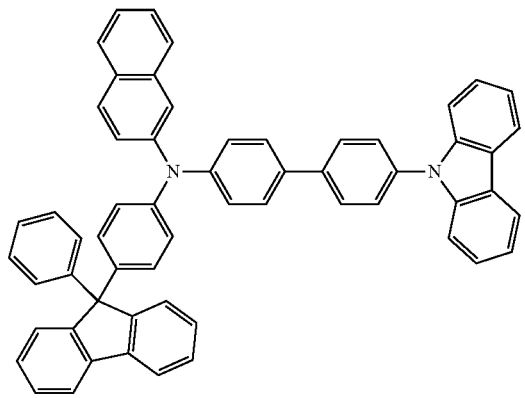
[C-29]
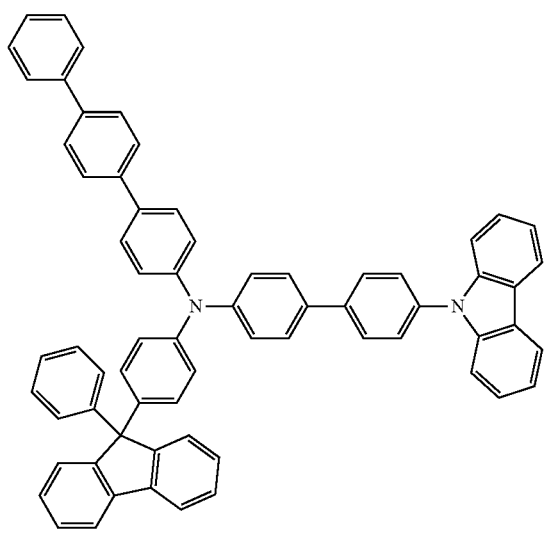
[C-30]
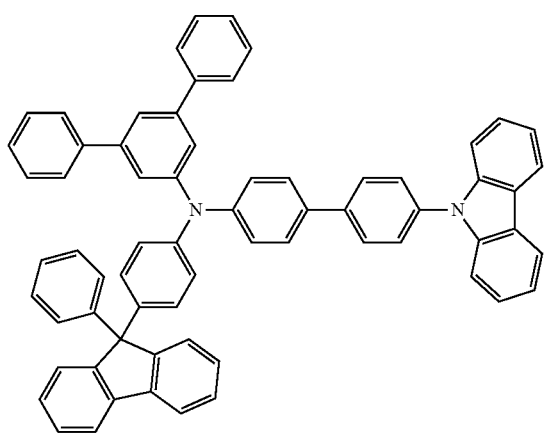
[C-31]
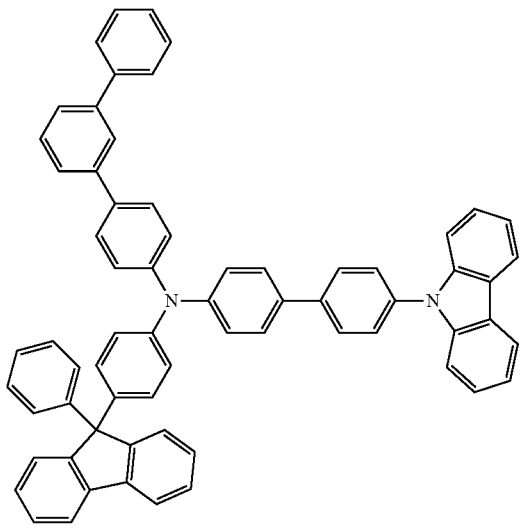
[C-32]
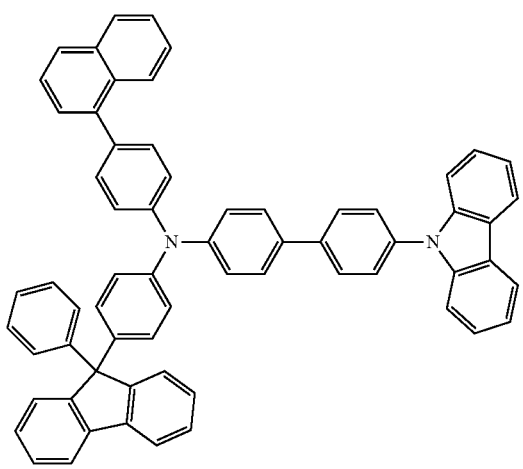
[C-33]
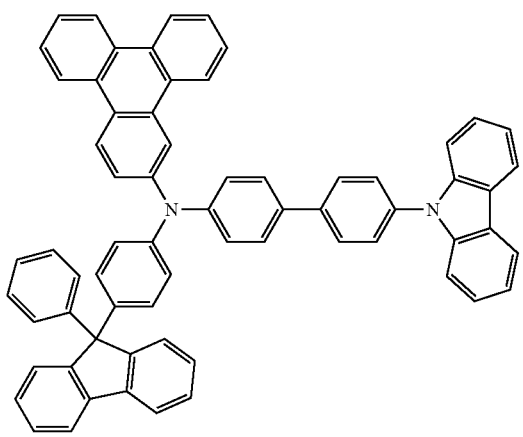

-continued
[C-34]
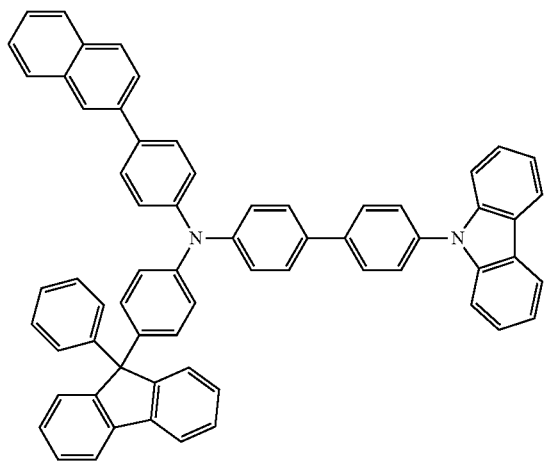
[C-35]
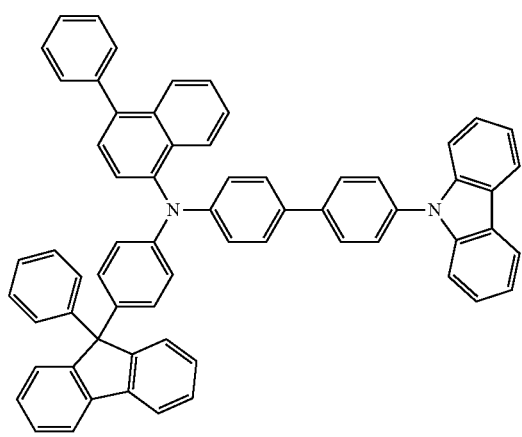
[C-36]
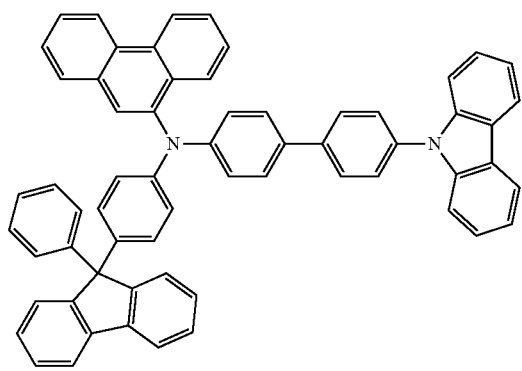
[C-37]
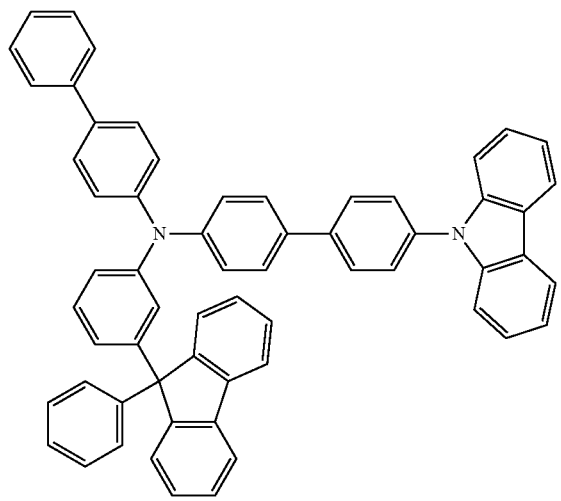
[C-38]
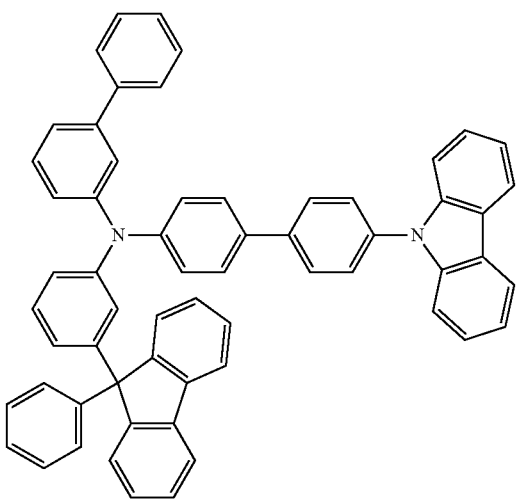
[C-39]
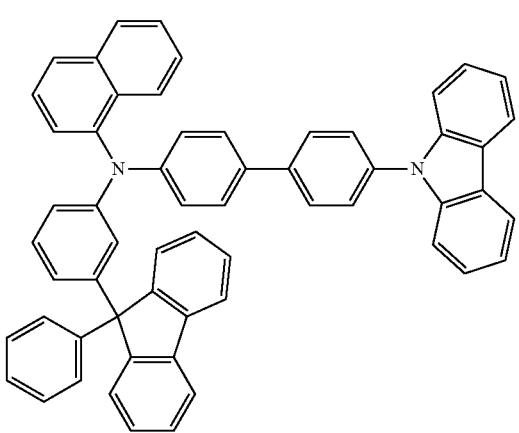

[C-40]
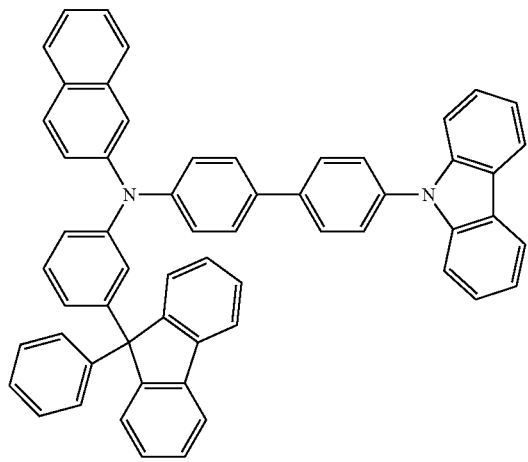
[C-41]
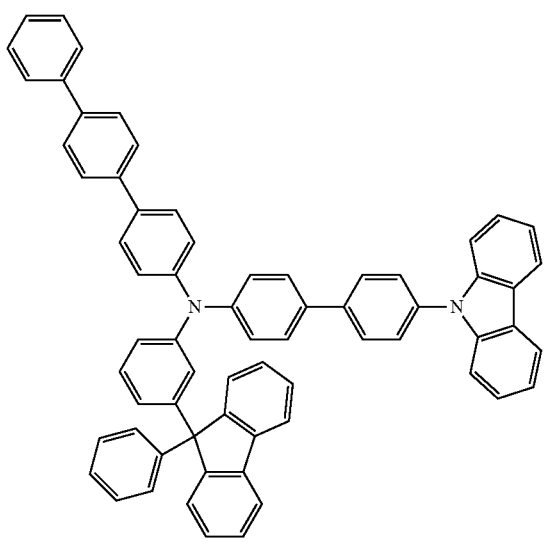
[C-42]
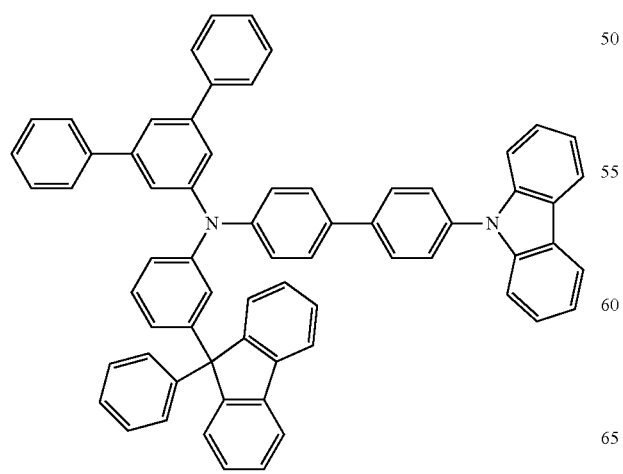
[C-43]
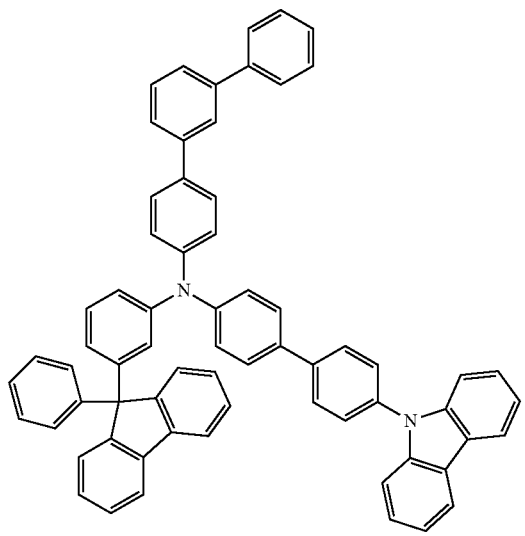
[C-44]
[C-45]
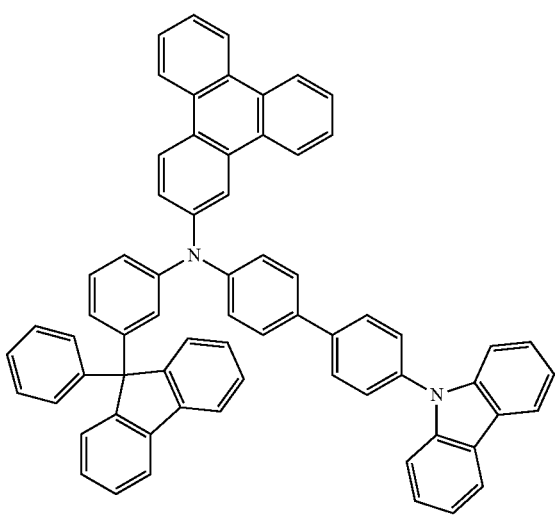

[C-46]
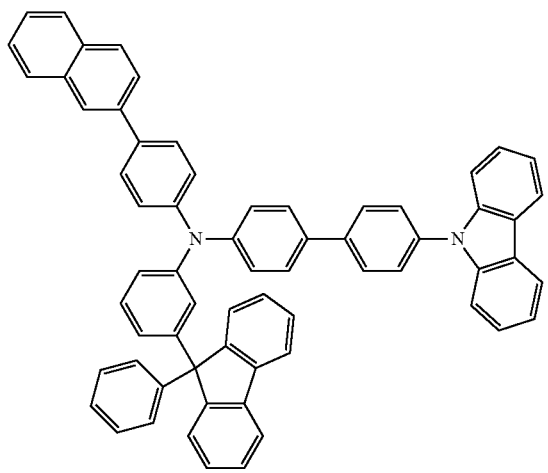
[C-49]
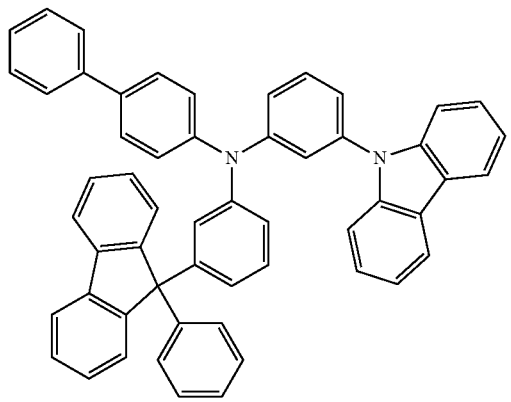
[C-48]
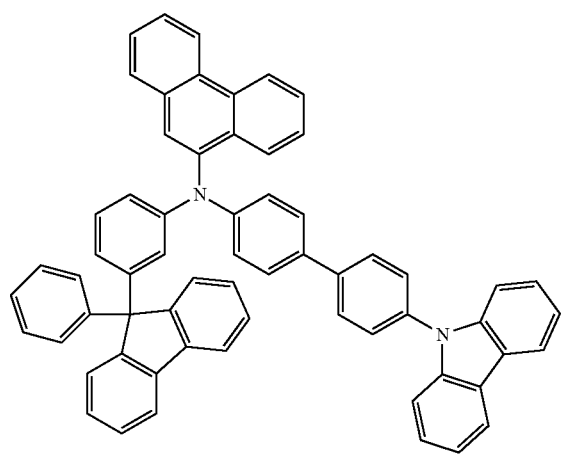
[C-50]
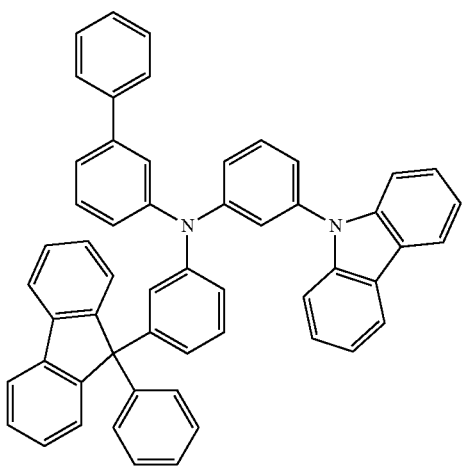
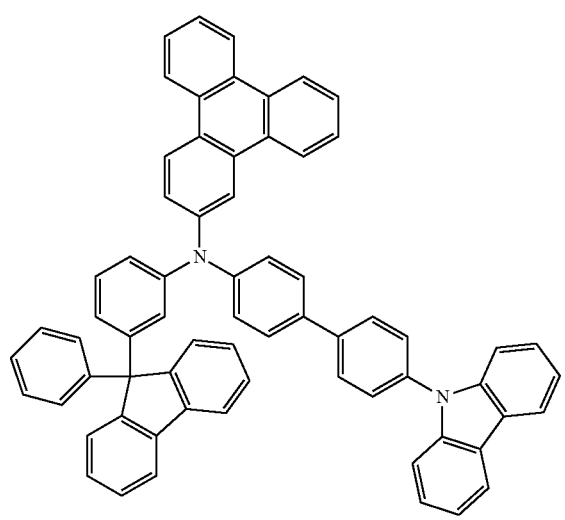
[C-51]
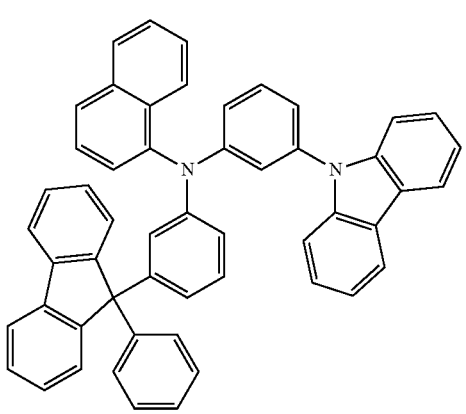

[C-52]
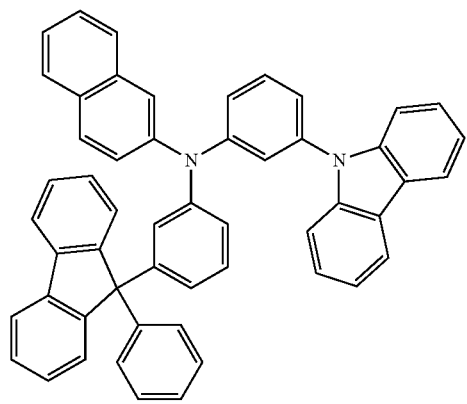
[C-53]
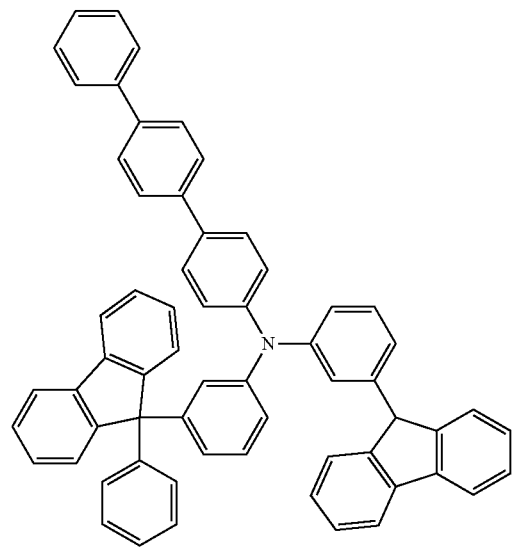
[C-54]
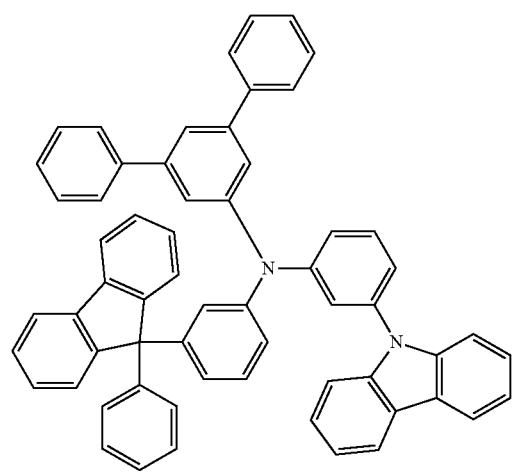
[C-55]
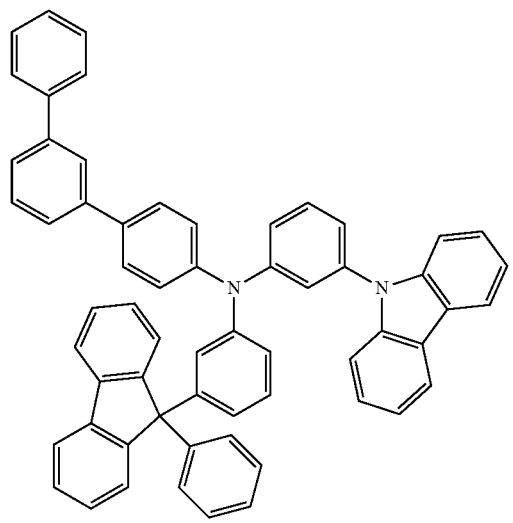
[C-56]
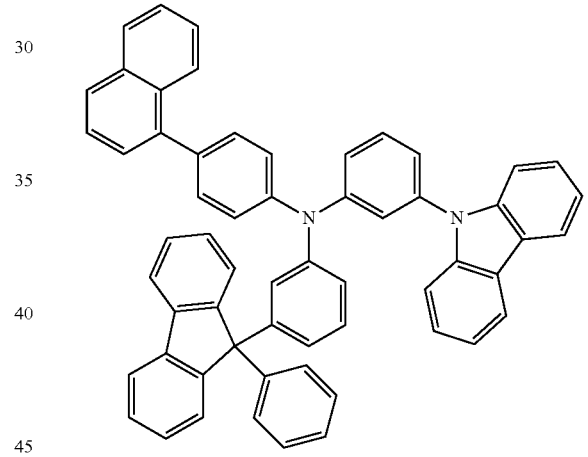
[C-57]
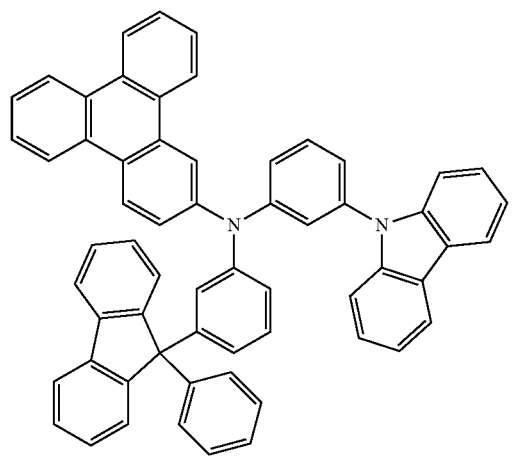

[C-58]
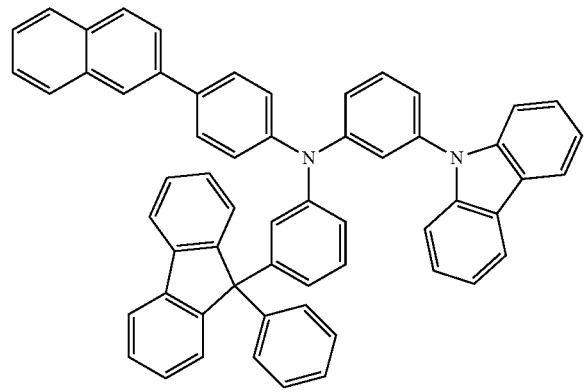
[C-59]
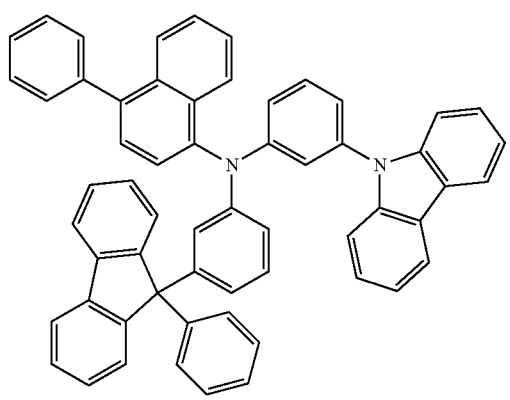
[C-60]
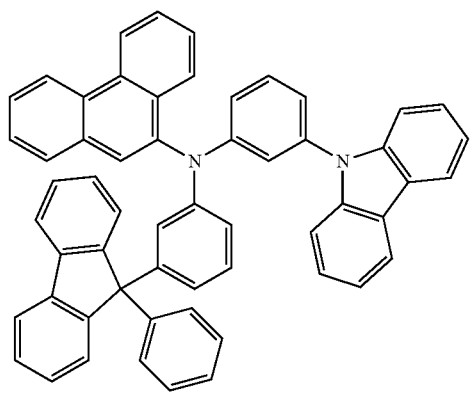
[C-61]
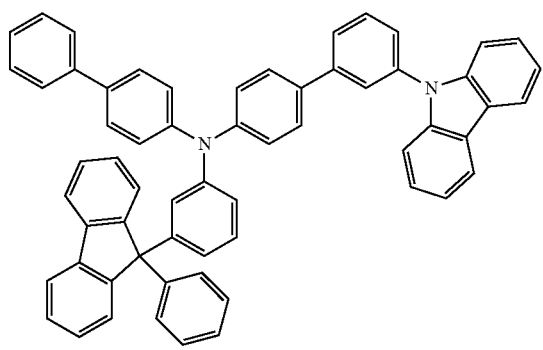
[C-62]
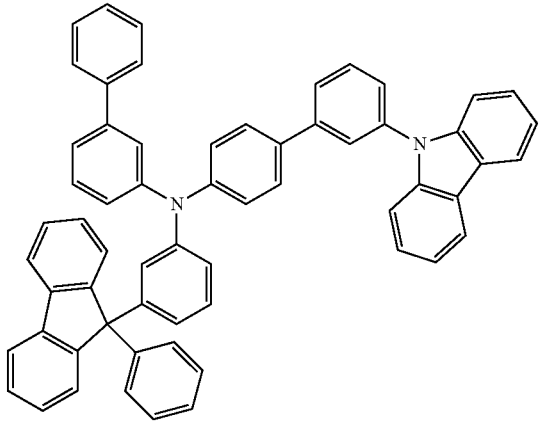
[C-63]
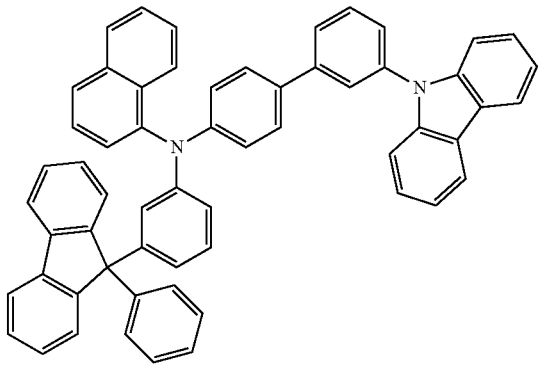
[C-64]
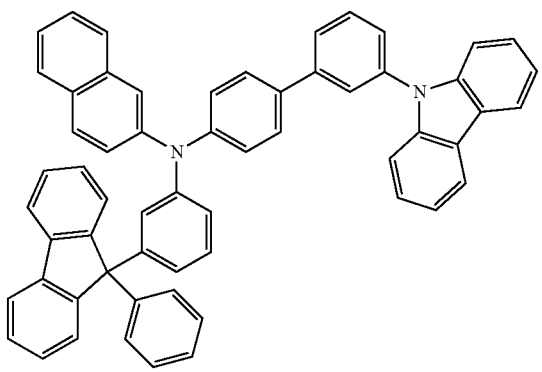

[C-65]
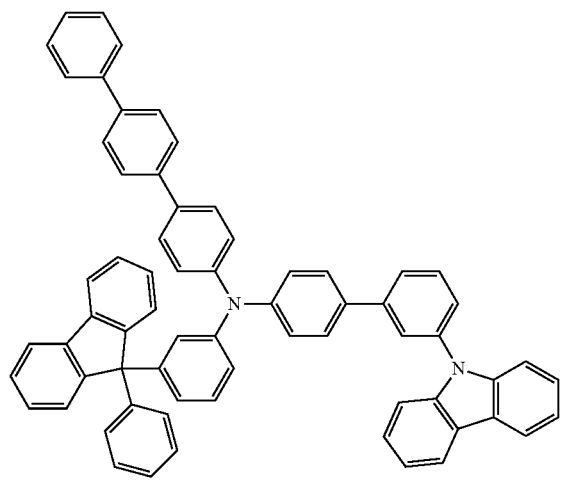
[C-68]
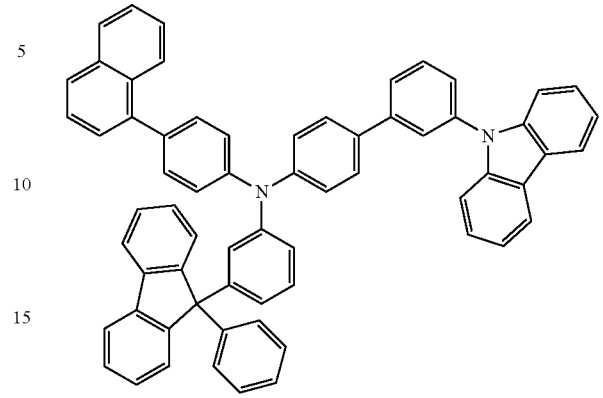
[C-66]
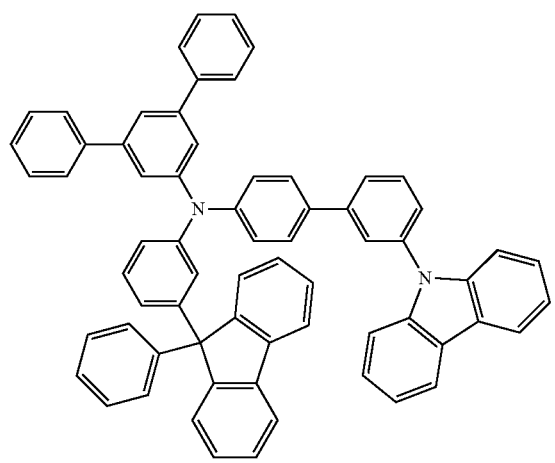
[C-69]
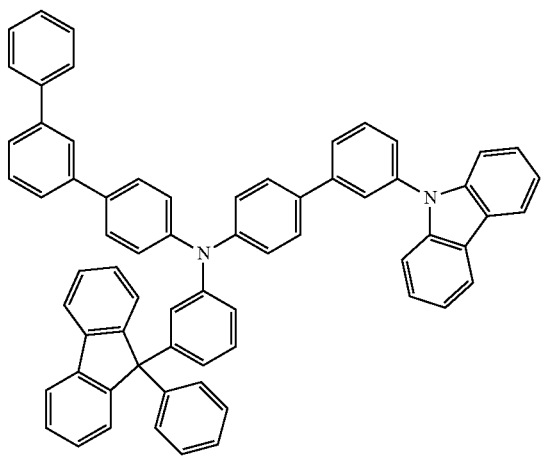
[C-67]
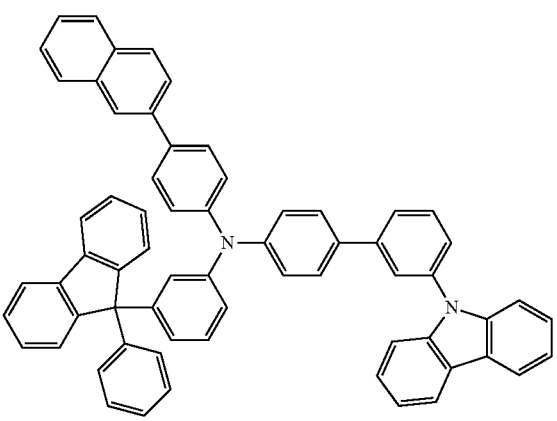
[C-70]

[C-71]
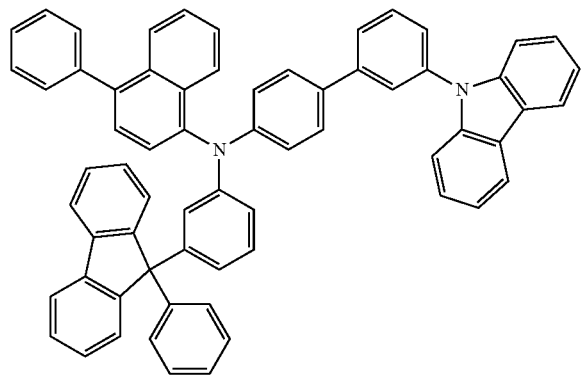
[C-72]
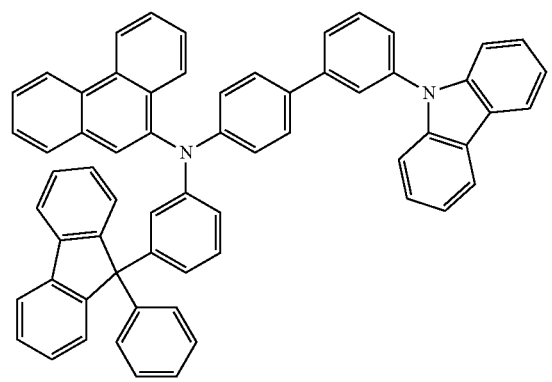
[D-2]
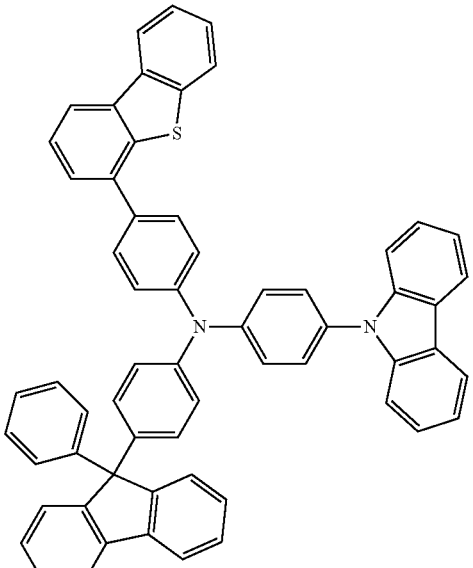
[D-1]
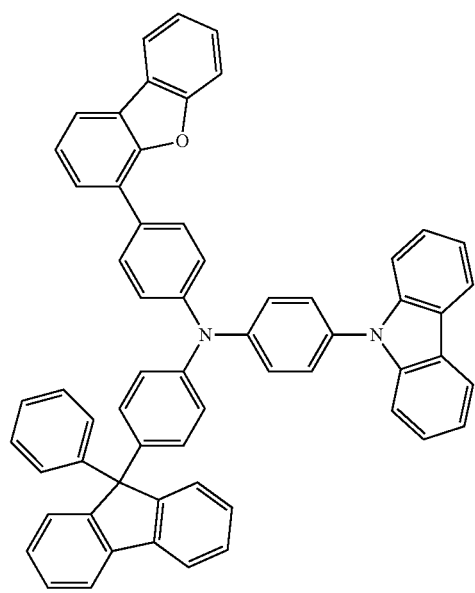
[D-3]
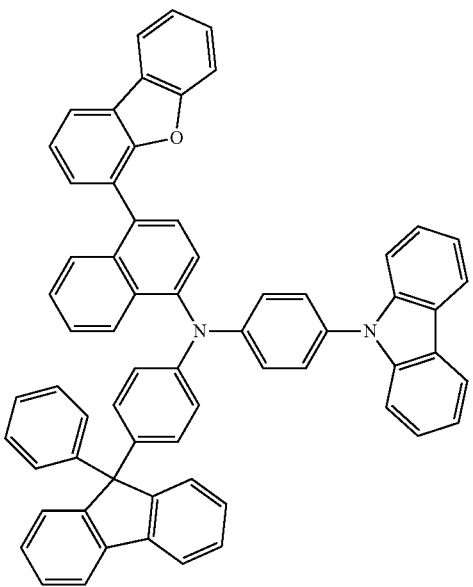

[D-4]
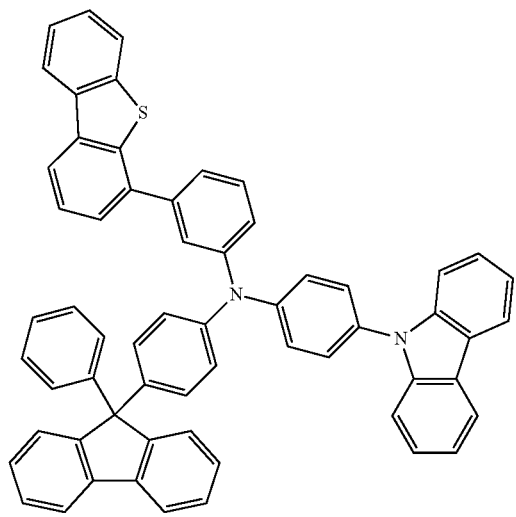
[D-5]
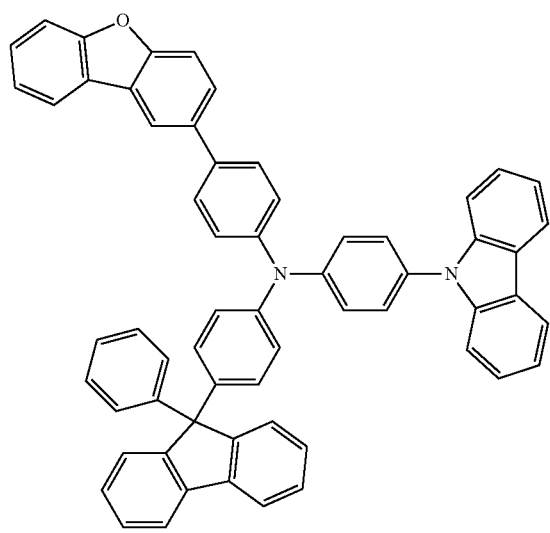
[D-6]
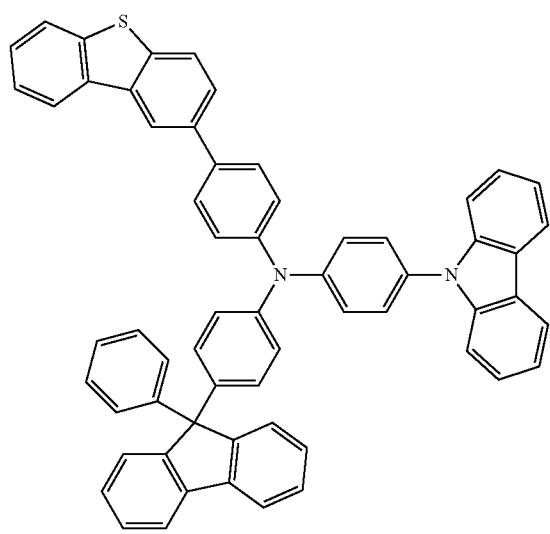
[D-7]
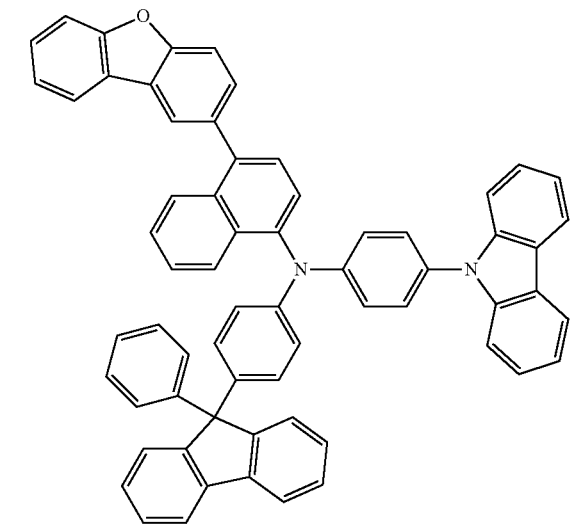
[D-8]
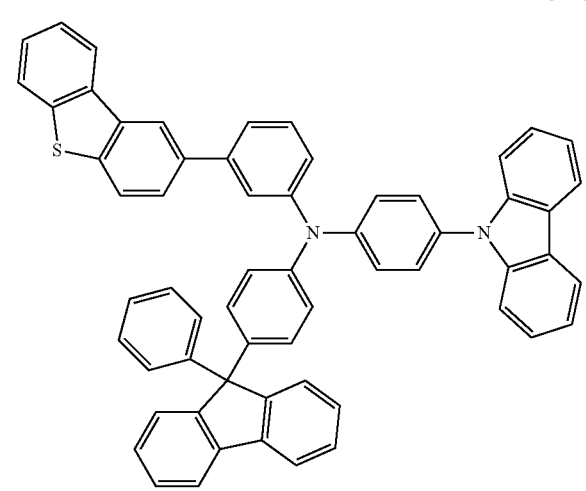
[D-9]
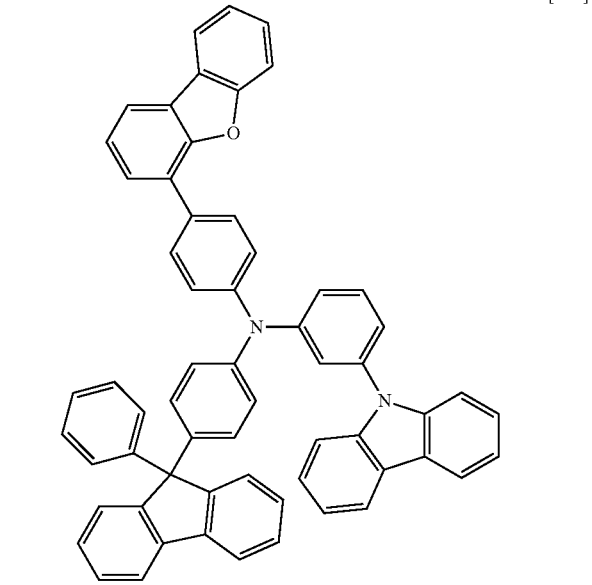

[D-10]
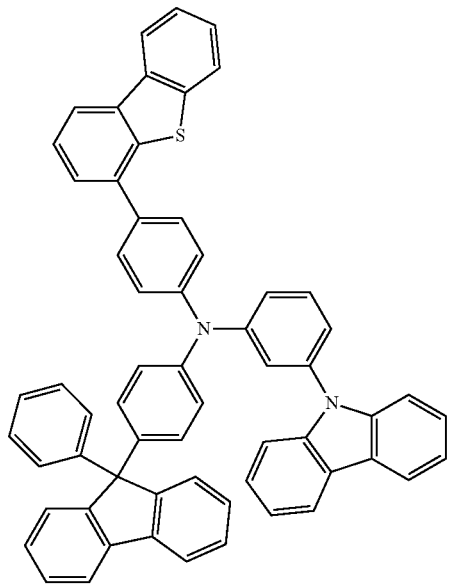
[D-11]
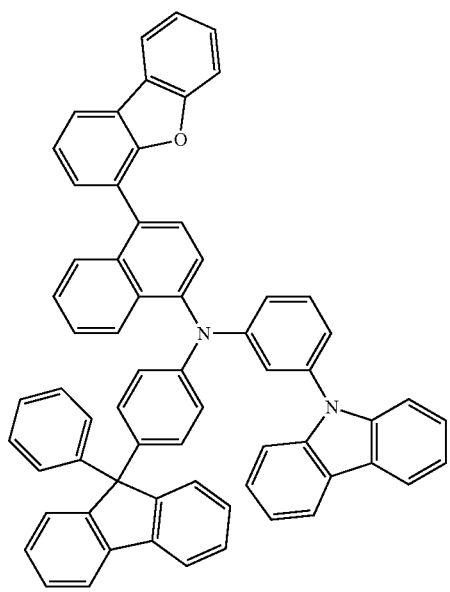
[D-12]
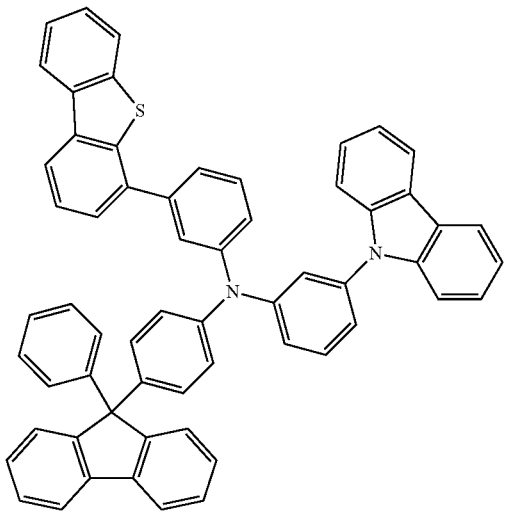
[D-13]
[D-14]
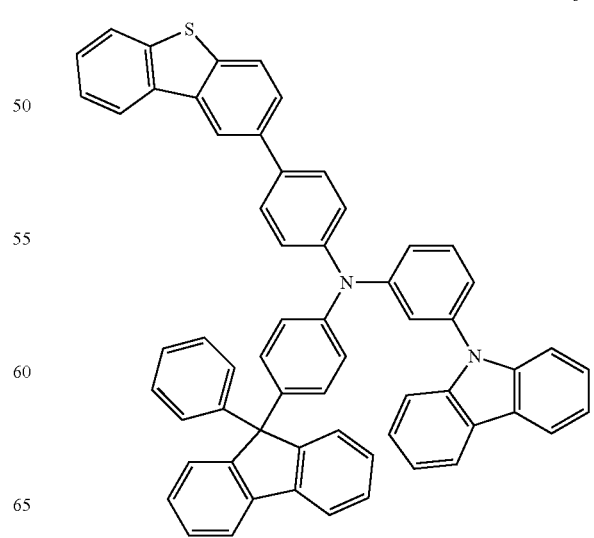

[D-15]
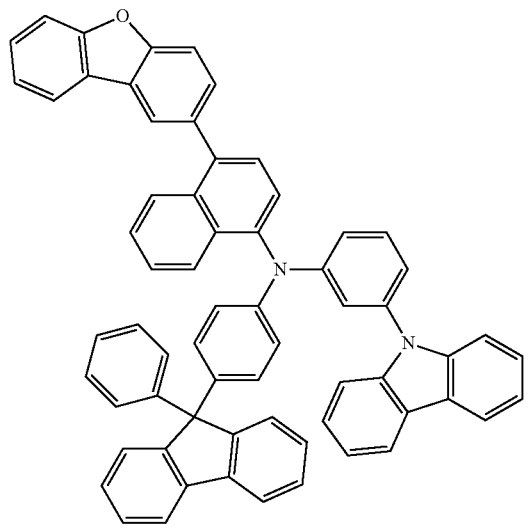
[D-16]
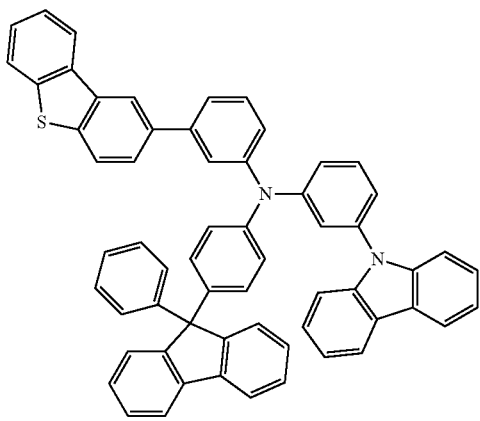
[D-17]
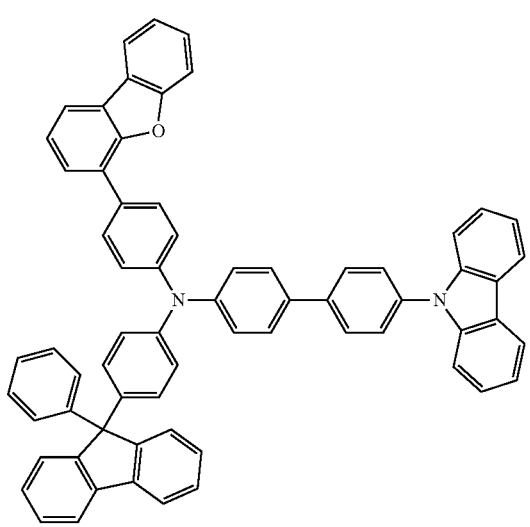
[D-18]
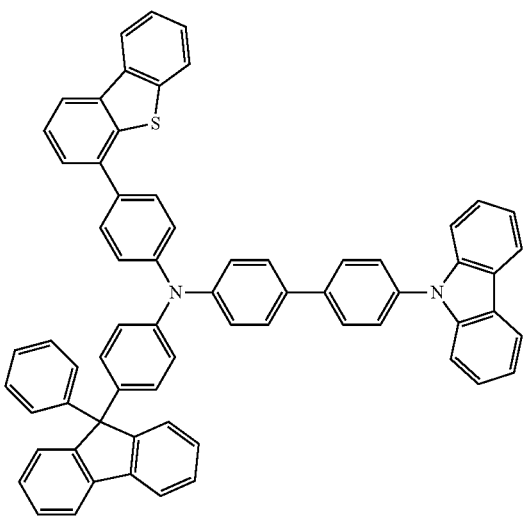
[D-19]
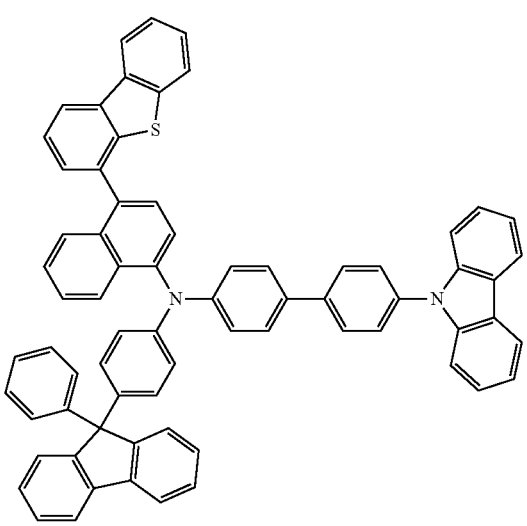
[D-20]
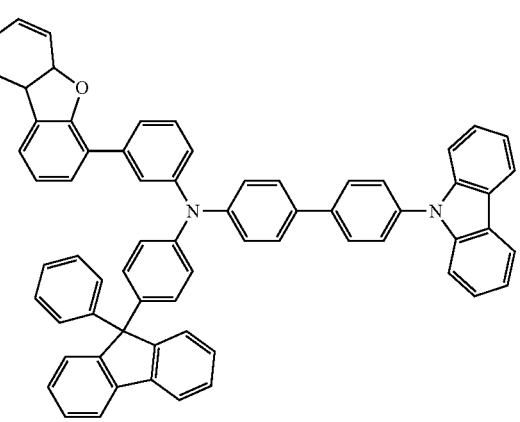

-continued
[D-21]
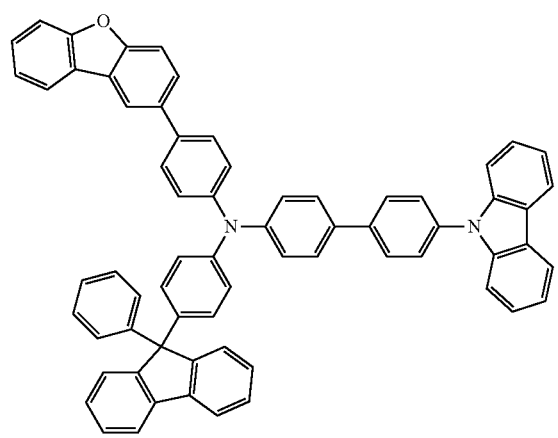
[D-22]
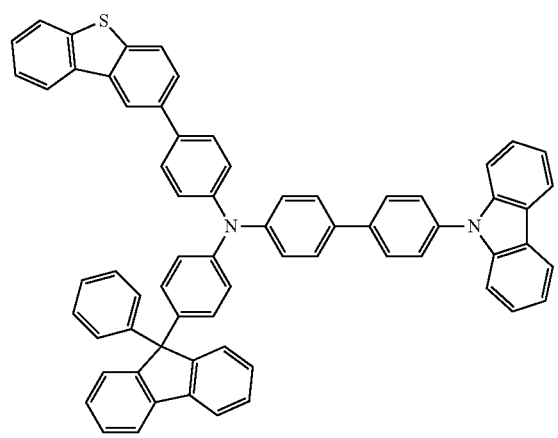
[D-23]
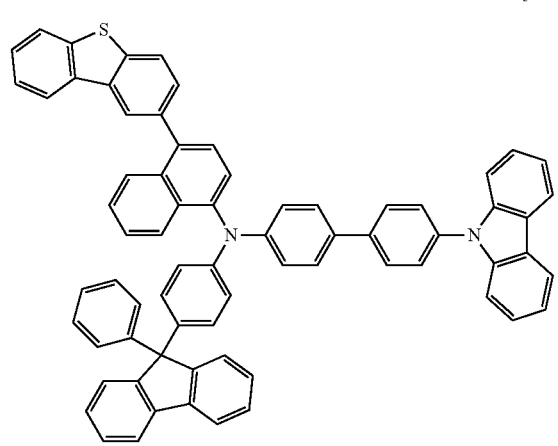
-continued
[D-24]
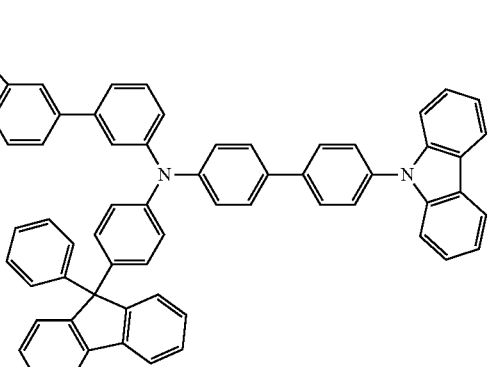
[D-25]
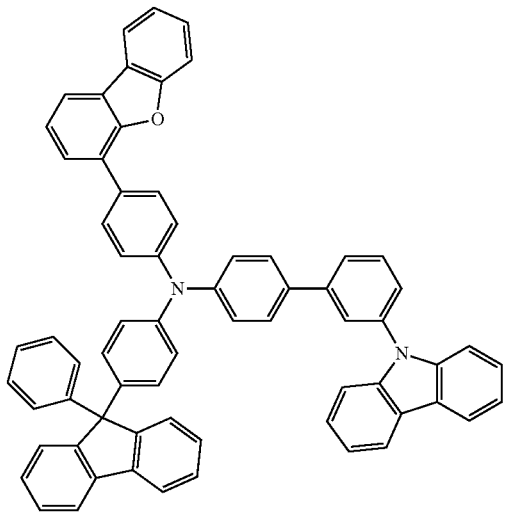
[D-26]
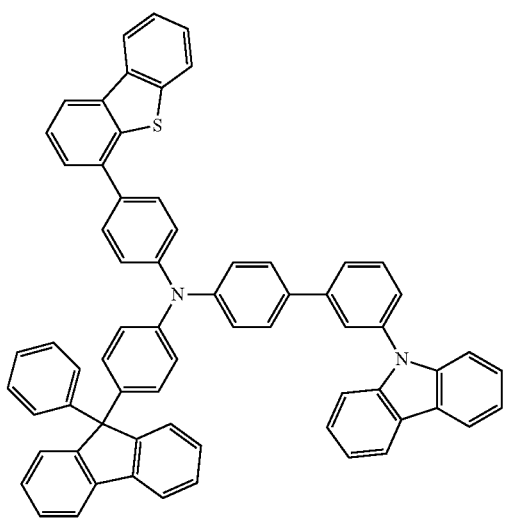

[D-27]
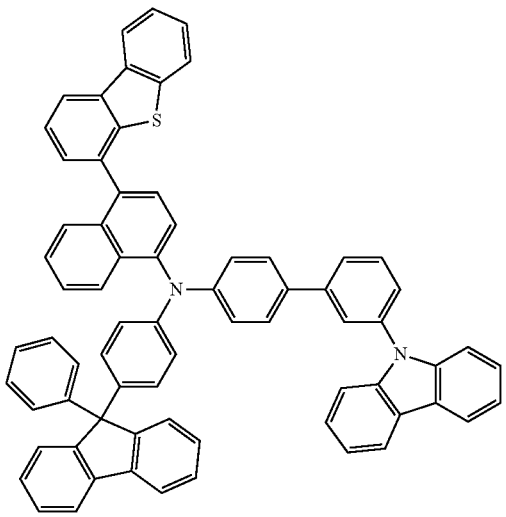
[D-28]
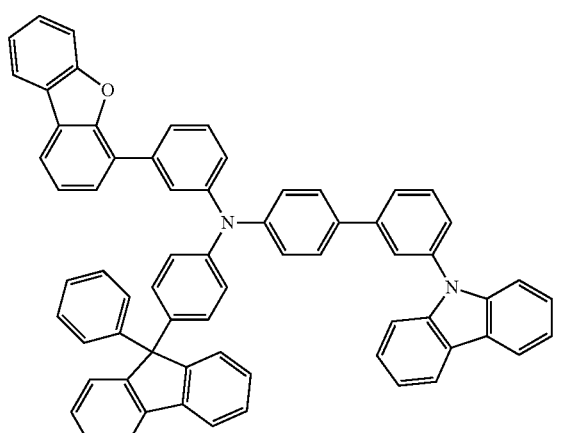
[D-29]
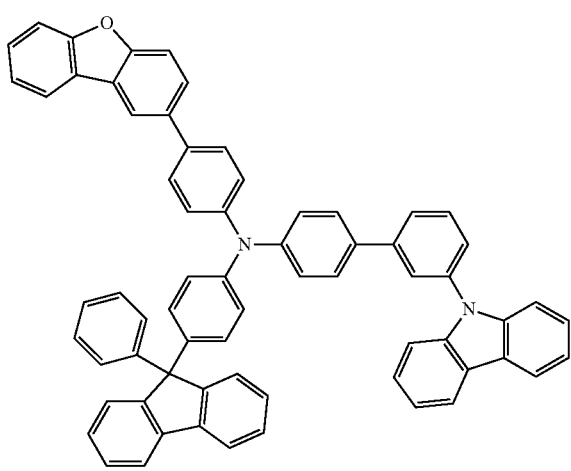
[D-30]
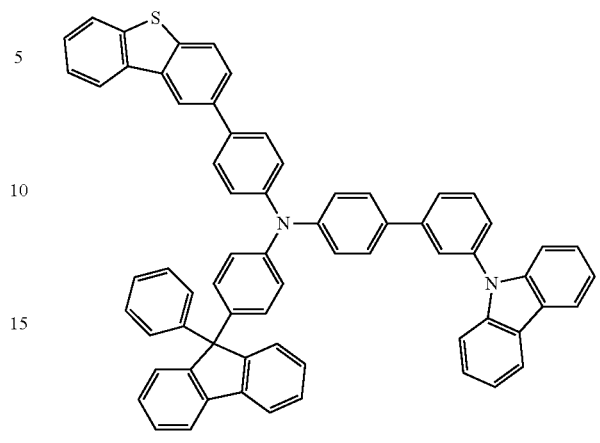
[D-31]
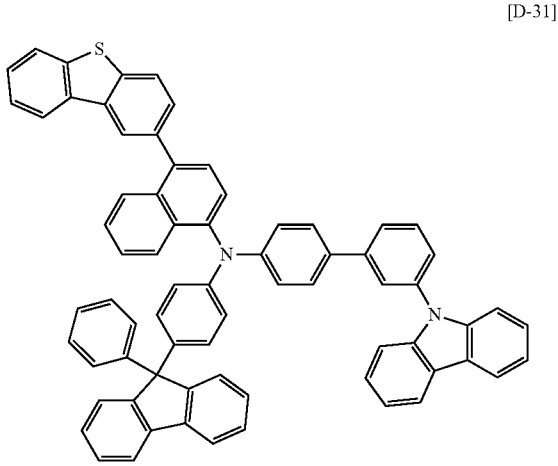
[D-32]
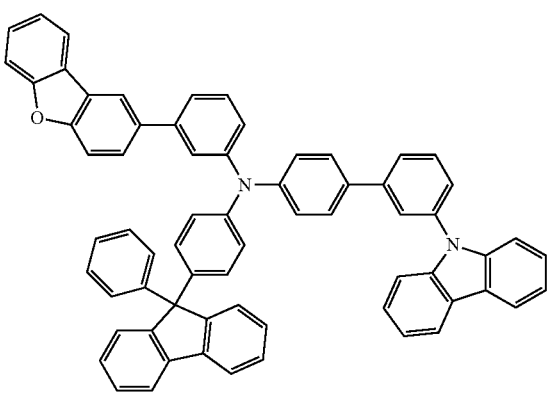

[E-1]
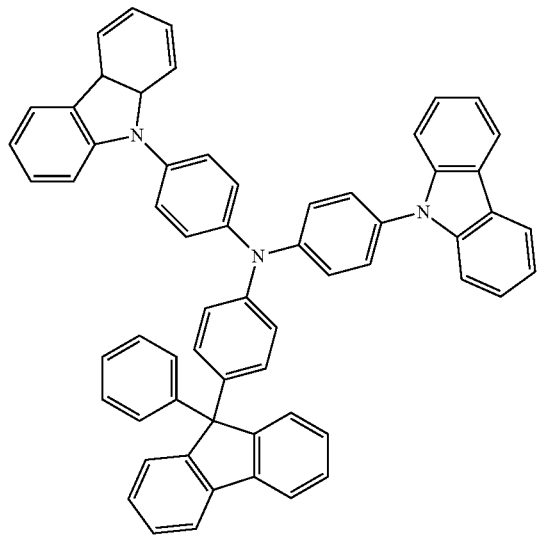
[E-2]
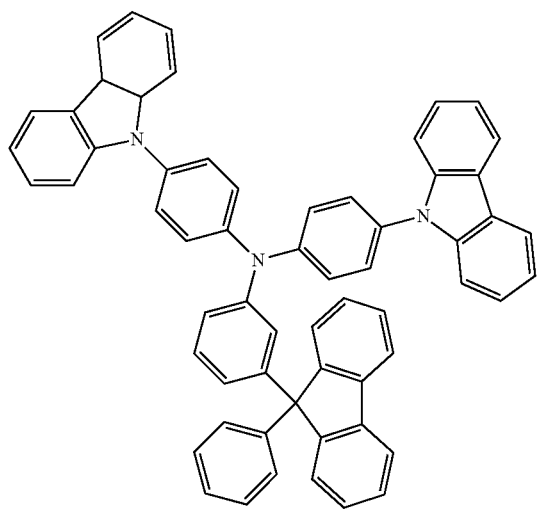
[E-3]
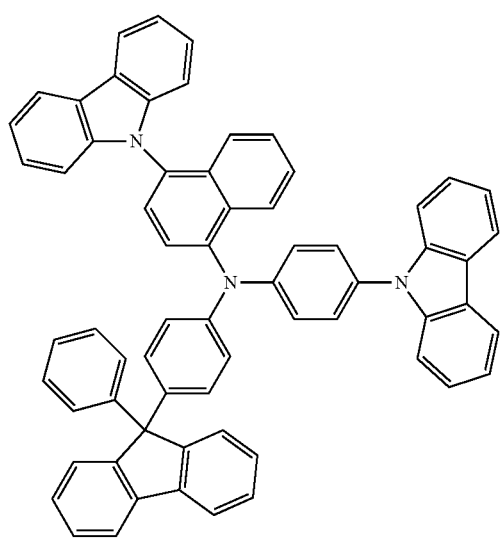
[E-4]
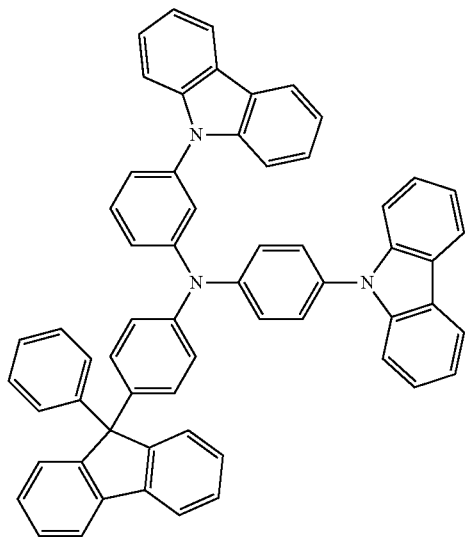
[E-5]
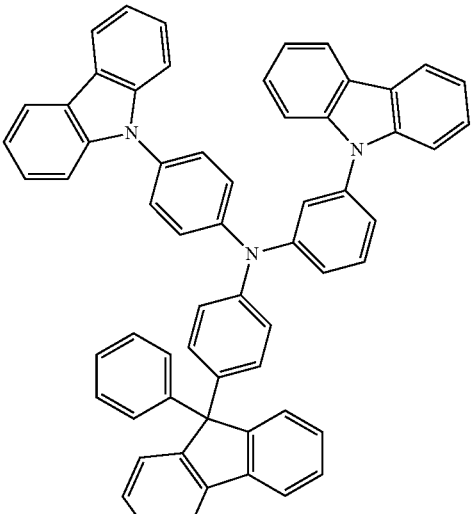
[E-6]
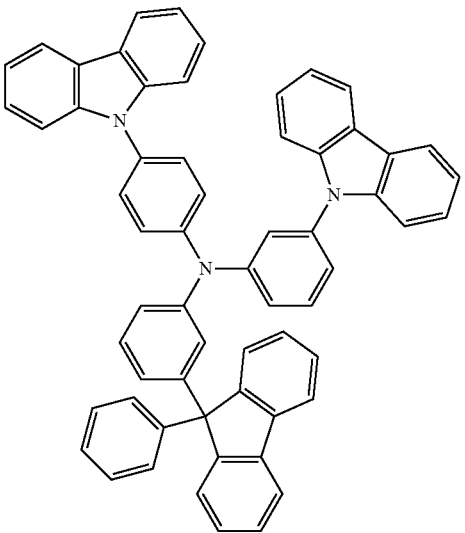

[E-7]
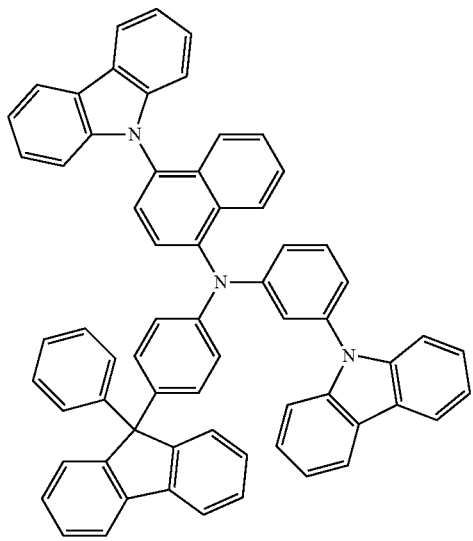
[E-8]
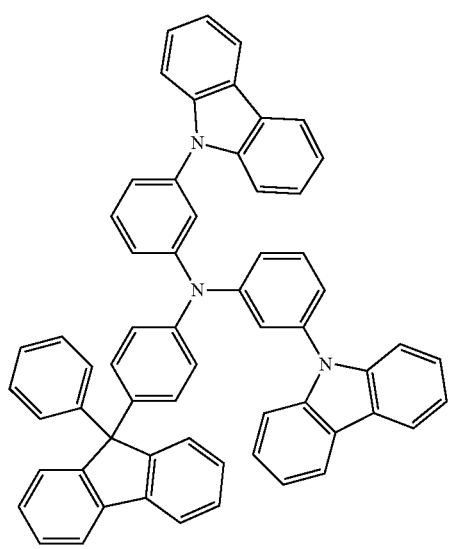
[E-9]
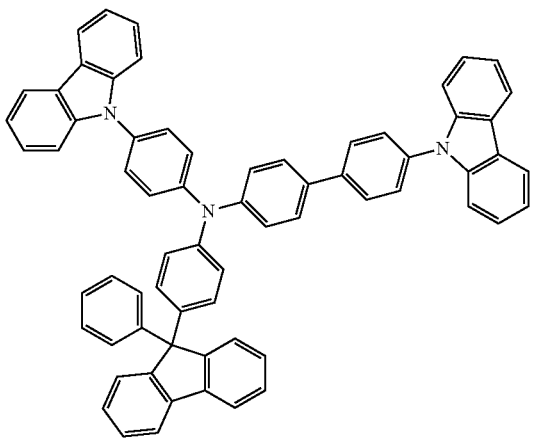
[E-10]
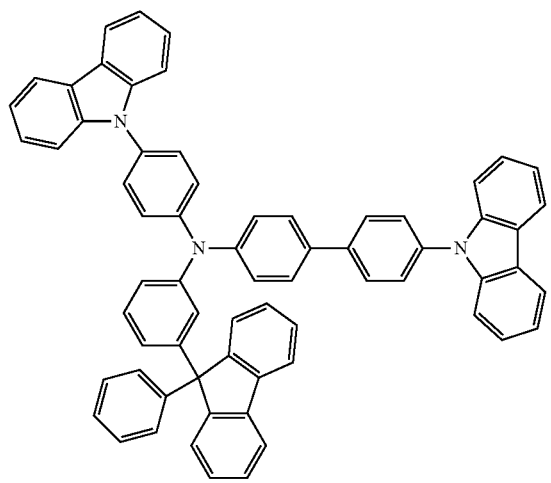
[E-11]
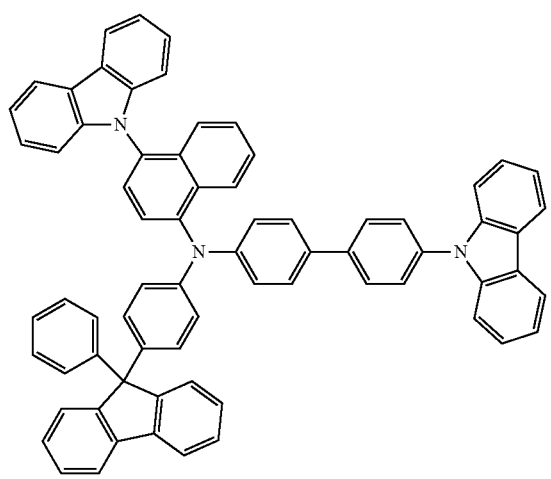
[E-12]
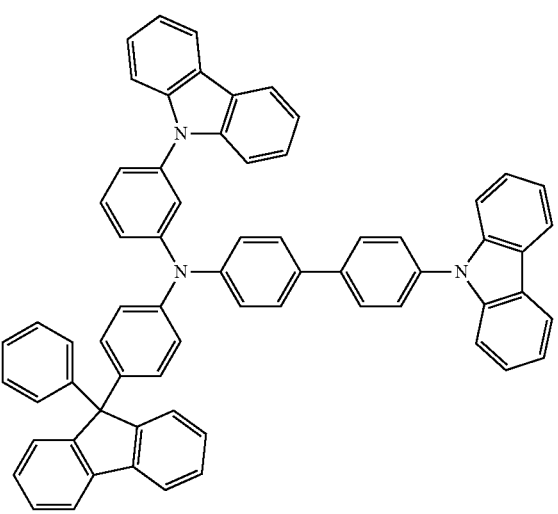

[E-13]

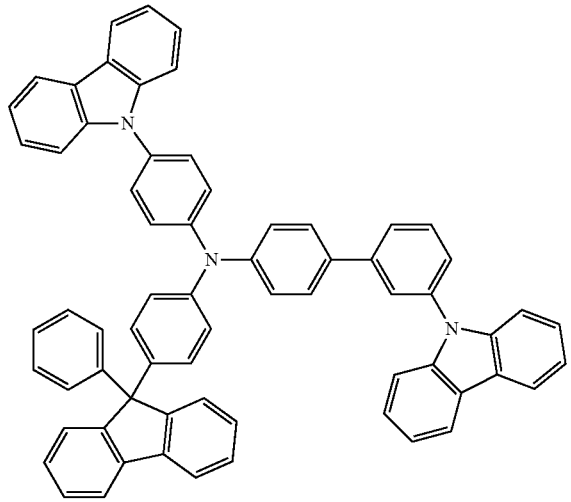

[E-14]

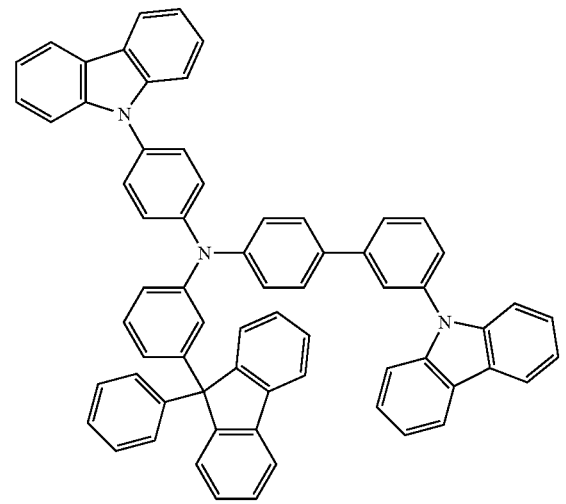

[E-15]

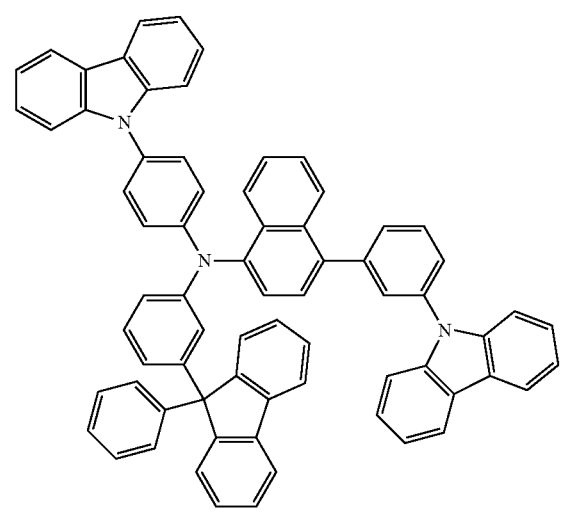

[E-16]

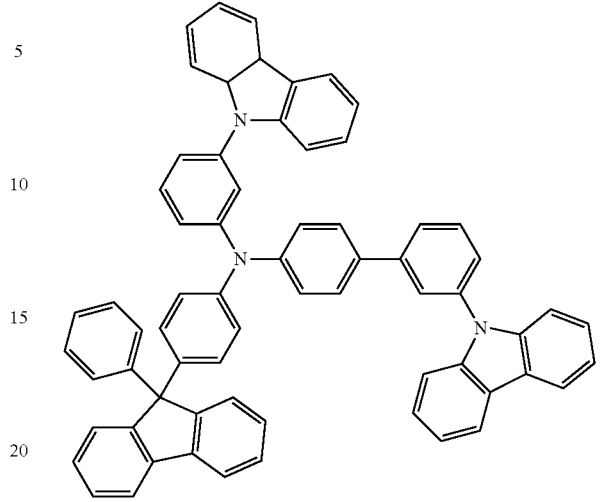

The compound may be used for an organic optoelectric device.

Hereinafter, an organic optoelectric device including the compound is described.

In another embodiment of the present invention, an organic optoelectric device includes an anode and a cathode facing each other and at least one organic layer between the anode and the cathode, wherein the organic layer includes an emission layer and at least one auxiliary layer selected from a hole injection layer, a hole transport layer, an electron blocking layer, electron transport layer, electron injection layer, and hole blocking layer, and the auxiliary layer includes the compound.

Specifically, the auxiliary layer may be a hole transport layer.

The organic optoelectric device may be any device to convert electrical energy into photoenergy and vice versa without particular limitation, and may be, for example an organic photoelectric device, an organic light emitting diode, an organic solar cell, and an organic photo-conductor drum.

Herein, an organic light emitting diode as one example of an organic optoelectric device is described referring to drawings.

FIGS. 1 and 2 are cross-sectional views of each organic light emitting diode according to one embodiment.

Referring to FIG. 1, an organic optoelectric device 100 according to one embodiment includes an anode 120 and a cathode 110 facing each other and an organic layer 105 interposed between the anode 120 and cathode 110.

The anode 120 may be made of a conductor having a large work function to help hole injection, and may be for example metal, metal oxide and/or a conductive polymer. The anode 120 may be, for example a metal such as nickel, platinum, vanadium, chromium, copper, zinc, gold, and the like or an alloy thereof; metal oxide such as zinc oxide, indium oxide, indium tin oxide (ITO), indium zinc oxide (IZO), and the like; a combination of a metal and an oxide such as ZnO and Al or $SnO_2$ and Sb; a conductive polymer such as poly(3-methylthiophene), poly(3,4-(ethylene-1,2-dioxy)thiophene) (PEDT), polypyrrole, and polyaniline, but is not limited thereto.

The cathode 110 may be made of a conductor having a small work function to help electron injection, and may be for example metal, metal oxide and/or a conductive polymer. The cathode 110 may be for example a metal or an alloy thereof such as magnesium, calcium, sodium, potassium, titanium, indium, yttrium, lithium, gadolinium, aluminum, silver, tin, lead, cesium, barium, and the like; a multi-layer structure material such as LiF/Al, LiO$_2$/Al, LiF/Ca, LiF/Al and BaF$_2$/Ca, but is not limited thereto.

The organic layer 105 includes an emission layer 130.

The emission layer 130 may include, for example the organic compound at alone, or a mixture of at least two kinds. In the case of a mixture of at least two kinds, they may be, for example a host and a dopant. The host may be, for example a phosphorescent host or fluorescent host.

The dopant may include an inorganic, organic, or organic/inorganic compound, and may be selected from known dopants.

Referring to FIG. 2, an organic light emitting diode 200 further includes a hole auxiliary layer 140 in addition to an emission layer 230. The hole auxiliary layer 140 may improve hole injection and/or hole mobility between the anode 120 and the emission layer 230 and may block electrons. The hole auxiliary layer 140 may include, for example at least one of a hole transport layer, a hole injection layer and/or an electron blocking layer. The compound may be included in the hole auxiliary layer 140.

Even not shown in FIG. 1 or 2, the organic layer 105 may further include an electron injection layer, an electron transport layer, an auxiliary electron transport layer, a hole transport layer, an auxiliary hole transport layer, a hole injection layer or a combination thereof. The compound may be included in the auxiliary hole transport layer.

The emission layer 230 and the auxiliary hole transport layer may be positioned to be adjacent to each other.

The compound of the present invention may be included in the organic layers. The organic light emitting diodes 100 and 200 may be manufactured by forming an anode or a cathode on a substrate, forming an organic layer in accordance with a dry coating method such as evaporation, sputtering, plasma plating, and ion plating or a wet coating method such as spin coating, dipping, and flow coating; and forming a cathode or an anode thereon.

The compound may be included as a fluorescent material.

The fluorescent material may have a maximum light emitting wavelength of less than or equal to 550 nm, and specifically 420 nm to 550 nm.

The compound represented by Chemical Formula 1 may have a HOMO level of greater than or equal to 5.4 eV and less than or equal to 5.8 eV.

The compound represented by Chemical Formula 1 may have a triplet excitation energy (T1) of greater than or equal to 2.4 eV and less than or equal to 2.7 eV.

The organic light emitting diode may be applied to an organic light emitting diode (OLED) display.

MODE FOR INVENTION

Hereinafter, the embodiments are illustrated in more detail with reference to examples. These examples, however, are not in any sense to be interpreted as limiting the scope of the invention.

Hereinafter, a starting material and a reaction material used in Examples and Synthesis Examples were purchased from Sigma-Aldrich Co. Ltd. or TCI Inc. unless there was particularly mentioned.

(Preparation of Compound)

A compound was synthesized through the following steps as specific examples of a compound according to the present invention.

Synthesis Example 1

Synthesis of Intermediate M-1

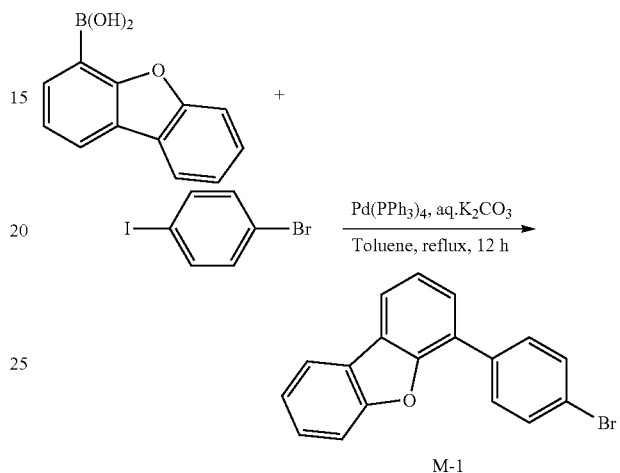

20 g (94.3 mmol) of 4-dibenzofuranboronic acid and 26.7 g (94.3 mmol) of 1-bromo-4-iodobenzene were put in a round-bottomed flask, 313 ml of toluene was added thereto to dissolve them, 117 ml of an aqueous solution in which 19.5 g (141.5 mmol) of potassium carbonate was dissolved was added thereto, and the mixture was agitated. Then, 1.09 g (0.94 mmol) of tetrakistriphenyl phosphine palladium was added thereto, and the obtained mixture was refluxed and agitated under a nitrogen atmosphere for 12 hours. When the reaction was complete, the resultant was extracted with ethyl acetate, the obtained extraction solution was dried with magnesium sulfate and filtered, and the filtered solution was concentrated under a reduced pressure. Then, a product obtained therefrom was purified with n-hexane/dichloromethane (9:1 of a volume ratio) through silica gel column chromatography, obtaining 27 g (a yield of 89%) of a white solid intermediate M-1 as a target compound.

LC-Mass (a theoretical value: 322.00 g/mol, a measured value: M+=322.09 g/mol, M+2=324.04 g/mol)

Synthesis Example 2

Synthesis of Intermediate M-2

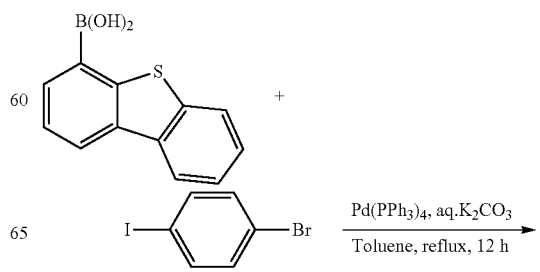

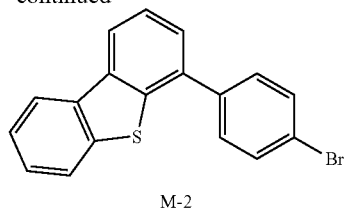

M-2

21.5 g (94.3 mmol) of 4-dibenzothiopheneboronic acid and 26.7 g (94.3 mmol) of 1-bromo-4-iodobenzene were put in a round-bottomed flask, 313 ml of toluene was added thereto to dissolve them, 117 ml of an aqueous solution in which 19.5 g (141.5 mmol) of potassium carbonate was dissolved was added thereto, and the mixture was agitated. Then, 1.09 g (0.94 mmol) of tetrakistriphenyl phosphine palladium was added thereto, and the obtained mixture was refluxed and agitated under a nitrogen atmosphere for 12 hours. When the reaction was complete, the resultant was extracted with ethyl acetate, the extraction solution was dried with magnesium sulfate and filtered, and the filtered solution was concentrated under a reduced pressure. Then, a product obtained therefrom was purified with n-hexane/dichloromethane (9:1 of a volume ratio) through silica gel column chromatography, obtaining 29 g (a yield of 91%) of a white solid intermediate M-2 as a target compound.

LC-Mass (a theoretical value: 337.98 g/mol, a measured value: M+=338.04 g/mol, M+2=340.11 g/mol)

Synthesis Example 3

Synthesis of Intermediate M-3

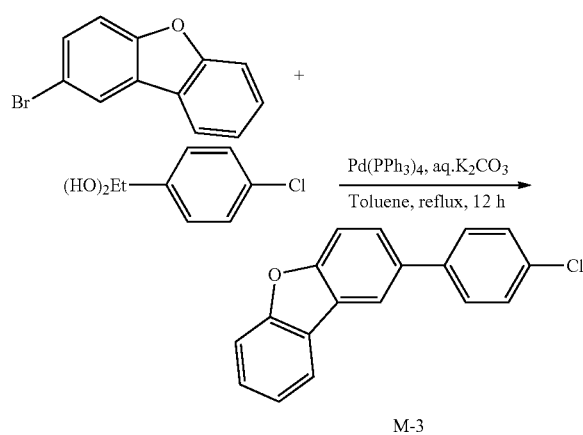

M-3

14.7 g (94.3 mmol) of 4-chlorophenylboronic acid and 23.3 g (94.3 mmol) of 2-bromodibenzofuran were put in a round-bottomed flask, 313 ml of toluene was added thereto to dissolve them, 117 ml of an aqueous solution in which 19.5 g (141.5 mmol) of potassium carbonate were dissolved was added thereto, and the mixture was agitated. Then, 1.09 g (0.94 mmol) of tetrakistriphenyl phosphine palladium was added thereto, and the obtained mixture was refluxed and agitated under a nitrogen atmosphere for 12 hours. When the reaction was complete, the resultant was extracted with ethyl acetate, the extraction solution was dried with magnesium sulfate and filtered, and the filtered solution was concentrated under a reduced pressure. Then, a product obtained therefrom was purified with n-hexane/dichloromethane (9:1 of a volume ratio) through silica gel column chromatography, obtaining 23.9 g (a yield of 91%) of a white solid intermediate M-3 as a target compound.

LC-Mass (a theoretical value: 278.05 g/mol, a measured value: M+=278.12 g/mol, M+2=280.13 g/mol)

Synthesis Example 4

Synthesis of Intermediate M-4

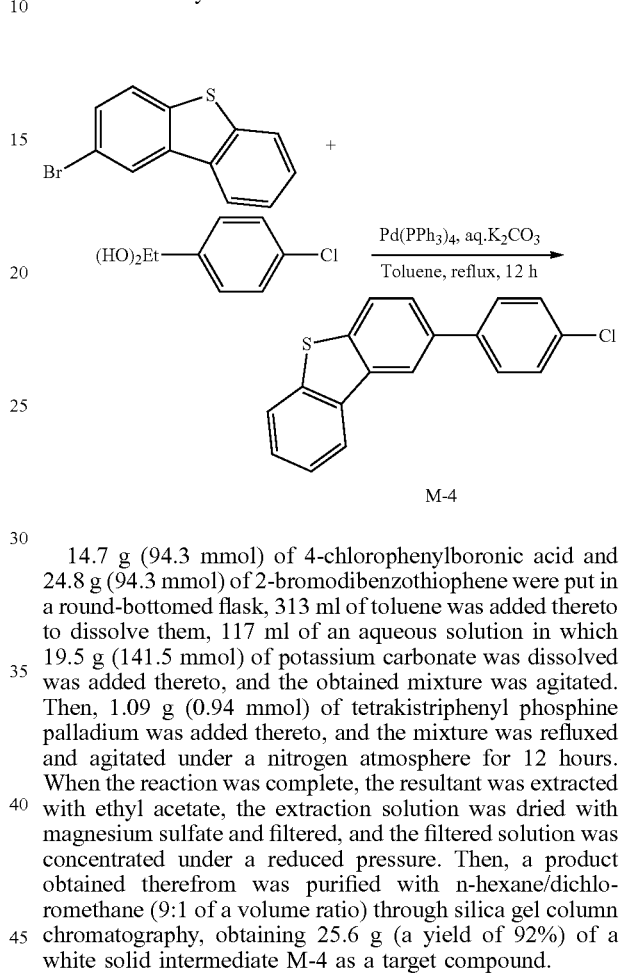

M-4

14.7 g (94.3 mmol) of 4-chlorophenylboronic acid and 24.8 g (94.3 mmol) of 2-bromodibenzothiophene were put in a round-bottomed flask, 313 ml of toluene was added thereto to dissolve them, 117 ml of an aqueous solution in which 19.5 g (141.5 mmol) of potassium carbonate was dissolved was added thereto, and the obtained mixture was agitated. Then, 1.09 g (0.94 mmol) of tetrakistriphenyl phosphine palladium was added thereto, and the mixture was refluxed and agitated under a nitrogen atmosphere for 12 hours. When the reaction was complete, the resultant was extracted with ethyl acetate, the extraction solution was dried with magnesium sulfate and filtered, and the filtered solution was concentrated under a reduced pressure. Then, a product obtained therefrom was purified with n-hexane/dichloromethane (9:1 of a volume ratio) through silica gel column chromatography, obtaining 25.6 g (a yield of 92%) of a white solid intermediate M-4 as a target compound.

LC-Mass (a theoretical value: 294.03 g/mol, a measured value: M+=294.16 g/mol, M+2=296.13 g/mol)

Synthesis Example 5

Synthesis of Intermediate M-5

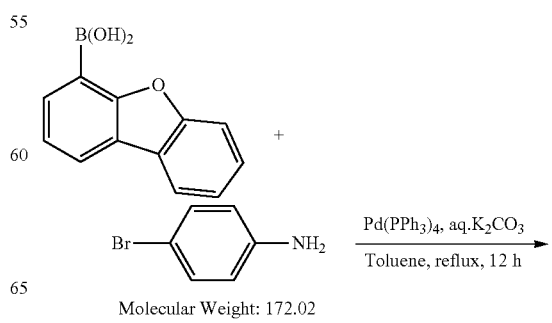

Molecular Weight: 172.02

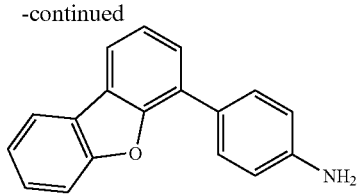

Exact Mass: 259.1
Molecular Weight: 259.3

M-5

20 g (94.3 mmol) of 4-dibenzofuranboronic acid and 16.2 g (94.3 mmol) of 4-bromoaniline were put in a round-bottomed flask, 300 ml of toluene was added thereto to dissolve them, 117 ml of an aqueous solution in which 19.5 g (141.5 mmol) of potassium carbonate was dissolved was added thereto, and the mixture was agitated. Then, 1.09 g (0.94 mmol) of tetrakistriphenyl phosphine palladium was added thereto, and the obtained mixture was refluxed and agitated under a nitrogen atmosphere for 12 hours. When the reaction was complete, the resultant was extracted with ethyl acetate, the extraction solution was dried with magnesium sulfate and filtered, and the filtered solution was concentrated under a reduced pressure. Then, a product obtained therefrom was purified with n-hexane/dichloromethane (9:1 of a volume ratio) through silica gel column chromatography, obtaining 17.4 g (a yield of 71%) of a white solid intermediate M-5 as a target compound.

LC-Mass (a theoretical value: 259.1 g/mol, a measured value: M+=259.21 g/mol)

Synthesis Example 6

Synthesis of Intermediate M-6

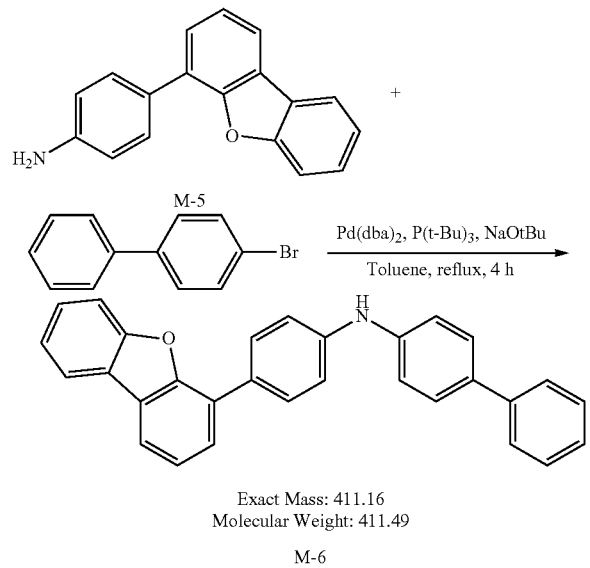

Exact Mass: 411.16
Molecular Weight: 411.49

M-6

9.6 g (37.08 mmol) of the intermediate M-5, 7.2 g (30.9 mmol) of 4-bromobiphenyl and 5.35 g (55.6 mmol) of sodium t-butoxide were put in a round-bottomed flask, and 155 ml of toluene was added thereto to dissolve them. Then, 0.178 g (0.31 mmol) of Pd(dba)$_2$ and 0.125 g (0.62 mmol) of tri-tertiary-butylphosphine were sequentially added thereto, and the mixture was refluxed and agitated under a nitrogen atmosphere for 4 hours. When the reaction was complete, the resultant was extracted with toluene and distilled water, an organic layer obtained after the extraction was dried with magnesium sulfate and filtered, and the filtered solution was concentrated under a reduced pressure. Then, a product obtained therefrom was purified with n-hexane/dichloromethane (7:3 of a volume ratio) through silica gel column chromatography, obtaining 11.1 g of a white solid intermediate M-6 as a target compound.

Synthesis Example 7

Synthesis of Intermediate M-7

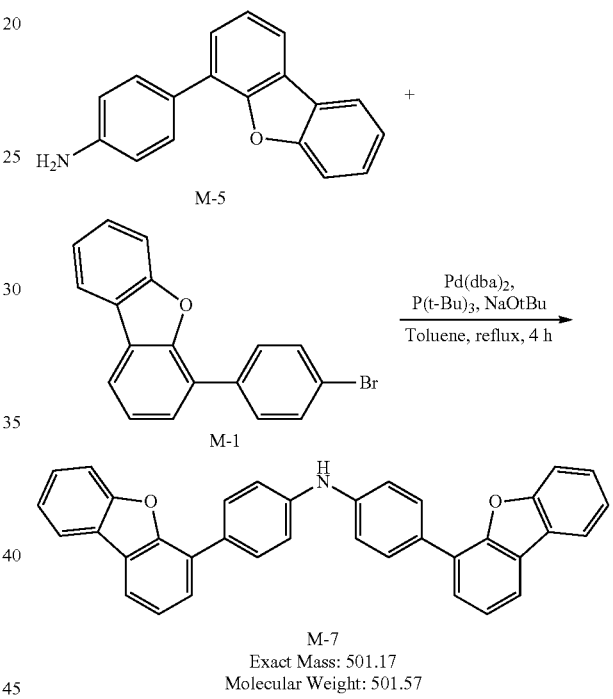

M-7
Exact Mass: 501.17
Molecular Weight: 501.57

10 g (30.9 mmol) of the intermediate M-1, 9.6 g (37.08 mmol) of the intermediate M-5 and 5.35 g (55.6 mmol) of sodium t-butoxide were put in a round-bottomed flask, and 155 ml of toluene was added thereto to dissolve them. Then, 0.178 g (0.31 mmol) of Pd(dba)$_2$ and 0.125 g (0.62 mmol) of tri-tertiary-butylphosphine were sequentially added thereto, and the mixture was refluxed and agitated under a nitrogen atmosphere for 4 hours. When the reaction was complete, the resultant was extracted with toluene and distilled water, an organic layer obtained after the extraction was dried with magnesium sulfate and filtered, and the filtered solution was concentrated under a reduced pressure. Then, a product obtained therefrom was purified with n-hexane/dichloromethane (7:3 of a volume ratio) through silica gel column chromatography, obtaining 11.2 g (a yield of 72%) of a white solid intermediate M-7 as a target compound.

LC-Mass (a theoretical value: 501.17 g/mol, a measured value: M+=501.31 g/mol)

Synthesis Example 8

Synthesis of Intermediate M-8

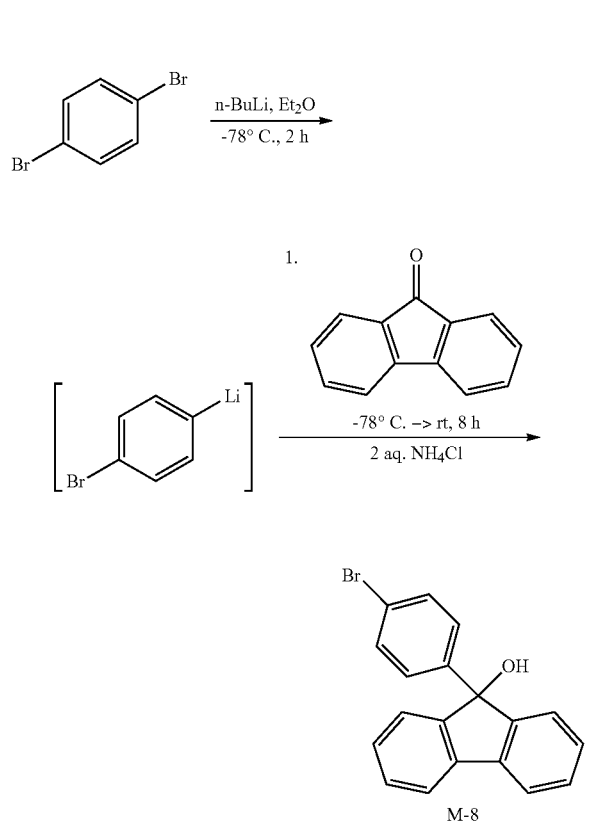

56.2 g (238.1 mmol) of 1,4-dibromobenzene was put in a round-bottomed flask heated and dried under a reduced pressure, 500 ml of anhydrous diethylether was added there to dissolve it, and the solution was cooled down to −78° C. and agitated under a nitrogen atmosphere. Then, 100 ml (250 mmol) of a 2.5 M n-butyllithium normal hexane solution was slowly added thereto, and the mixed solution was agitated at −78° C. under a nitrogen atmosphere for 2 hours. Subsequently, a solution obtained by dissolving 41 g (226 mmol) of 9-fluorenone in 100 ml of anhydrous tetrahydrofuran was slowly added thereto, and the obtained mixture was agitated at room temperature under a nitrogen atmosphere for 8 hours. The reaction solution was cooled down to 0° C., 250 ml of a 1.0 M ammonium chloride aqueous solution was added thereto, the mixture was extracted with diethylether, an organic layer obtained after the extraction was dried with magnesium sulfate and filtered, and the filtered solution was concentrated under a reduced pressure. The residue was separated with a 10% ethyl acetate/normal-hexane solution through silica gel column chromatography, obtaining 70 g (a yield of 92%) of an intermediate M-8 as a target compound.

LC-Mass (a theoretical value: 336.01 g/mol, a measured value: M+=336.17 g/mol)

Synthesis Example 9

Synthesis of Intermediate M-9

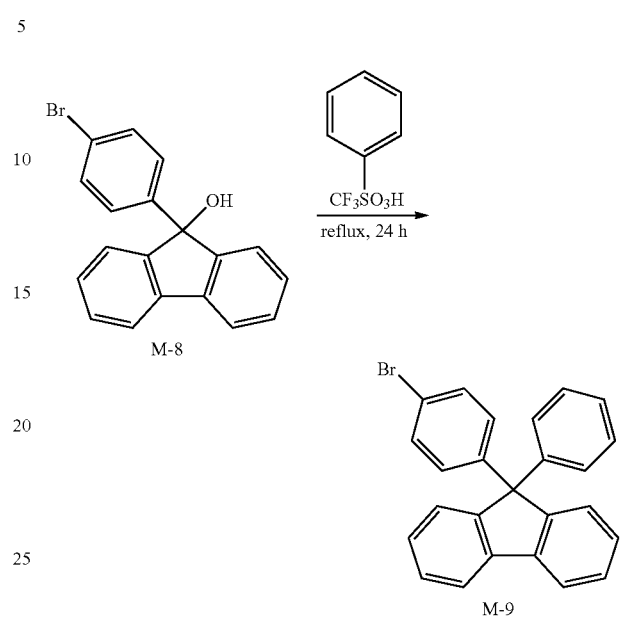

67.4 g (200 mmol) of the intermediate M-8 was put in a round-bottomed flask, and 534 mL of benzene was added thereto to dissolve it. Then, 30 g (200 mmol) of trifluoromethanesulfonic acid was slowly added thereto, and the mixture was refluxed and agitated under a nitrogen atmosphere for 24 hours. When the reaction was complete, 240 ml of a 1.0 M sodium bicarbonate aqueous solution was slowly added thereto, the mixture was extracted with ethyl acetate and distilled water, an organic layer obtained therefrom was dried with magnesium sulfate and filtered, and the filtered solution was concentrated under a reduced pressure. Then, a product obtained therefrom was purified with n-hexane/dichloromethane (9:1 of a volume ratio) through silica gel column chromatography, obtaining 27.8 g (a yield of 35%) of an intermediate M-9 as a target compound.

LC-Mass (a theoretical value: 396.05 g/mol, a measured value: M+=396.14 g/mol)

Synthesis Example 10

Synthesis of Intermediate M-10

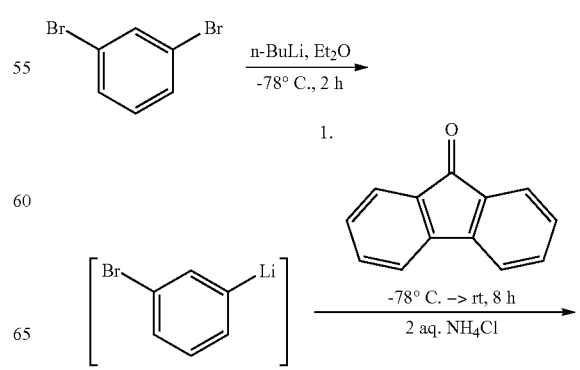

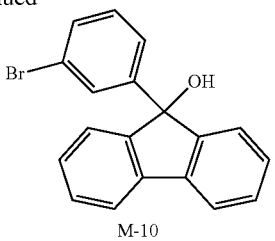

M-10

56.2 g (238.1 mmol) of 1,3-dibromobenzene was put in a round-bottomed flask dried under a reduced pressure, 500 ml of anhydrous diethylether was added thereto, and the mixture was cooled down to −78° C. and agitated under a nitrogen atmosphere. Then, a 2.5 M n-butyllithium normal hexane solution 100 ml (250 mmol) was slowly added thereto, and the mixture was cooled down to −78° C. and agitated under a nitrogen atmosphere for 2 hours. Subsequently, 41 g (226 mmol) of 9-fluorenone dissolved in 100 ml of anhydrous tetrahydrofuran was slowly added thereto, and the mixture was agitated at room temperature under a nitrogen atmosphere for 8 hours. The reaction solution was cooled down to 0° C., 250 ml of a 1.0 M ammonium chloride aqueous solution was added thereto, the mixture was extracted with diethylether, an organic layer obtained therefrom was dried with magnesium sulfate and filtered, and the filtered solution was concentrated under a reduced pressure. The residue was separated with a 10% ethyl acetate/normal-hexane solution through silica gel column chromatography, obtaining 65 g (a yield of 85%) of an intermediate M-10 as a target compound.

LC-Mass (a theoretical value: 336.01 g/mol, a measured value: M+=336.21 g/mol)

Synthesis Example 11

Synthesis of Intermediate M-11

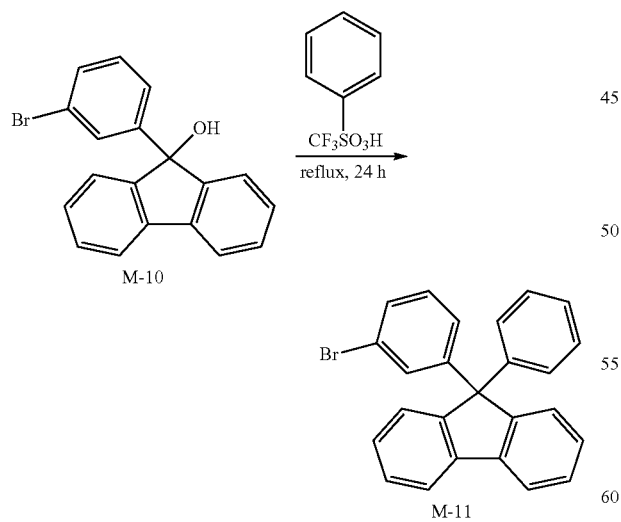

60 g (178 mmol) of the intermediate M-10 was put in a round-bottomed flask, and 476 mL of benzene was added thereto to dissolve it. Then, 26.7 g (200 mmol) of trifluoromethanesulfonic acid was slowly added thereto, and the mixture was refluxed and agitated under a nitrogen atmosphere for 24 hours. When the reaction was complete, 214 ml of a 1.0 M sodium bicarbonate aqueous solution was slowly added thereto, the mixture was extracted with ethyl acetate and distilled water, an organic layer obtained therefrom was dried with magnesium sulfate and filtered, and the filtered solution was concentrated under a reduced pressure. Then, a product obtained therefrom was purified with n-hexane/dichloromethane (9:1 of a volume ratio) through silica gel column chromatography, obtaining 30.4 g (a yield of 43%) of an intermediate M-11 as a target compound.

LC-Mass (a theoretical value: 396.05 g/mol, a measured value: M+=396.19 g/mol)

Synthesis Example 12

Synthesis of Intermediate M-12

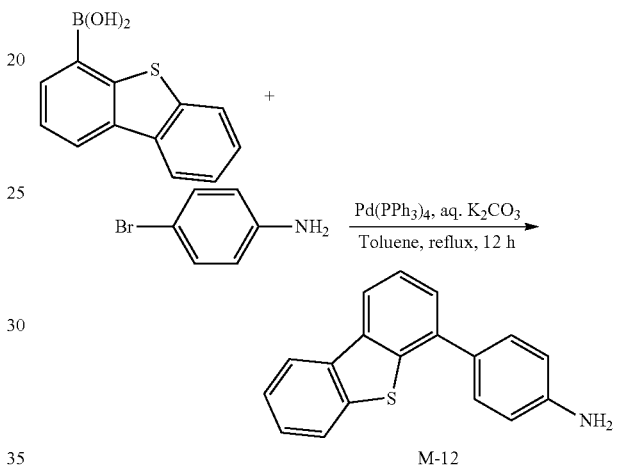

M-12

21.5 g (94.3 mmol) of 4-dibenzothiopheneboronic acid and 16.2 g (94.3 mmol) of 4-bromoaniline were put in a round-bottomed flask, 300 ml of toluene was added thereto to dissolve them, 117 ml of an aqueous solution in which 19.5 g (141.5 mmol) of potassium carbonate was dissolved was added thereto, and the mixture was agitated. Then, 1.09 g (0.94 mmol) of tetrakistriphenyl phosphine palladium was added thereto, and the mixture was refluxed and agitated under a nitrogen atmosphere for 12 hours. When the reaction was complete, the resultant was extracted with ethyl acetate, and the extraction solution was dried with magnesium sulfate and filtered, and the filtered solution was concentrated under a reduced pressure. Then, a product obtained therefrom was purified with n-hexane/dichloromethane (7:3 of a volume ratio) through silica gel column chromatography, obtaining 19.2 g (a yield of 74%) of a white solid intermediate M-12 as a target compound.

LC-Mass (a theoretical value: 275.08 g/mol, a measured value: M+=275.14 g/mol)

Synthesis Example 13

Synthesis of Intermediate M-13

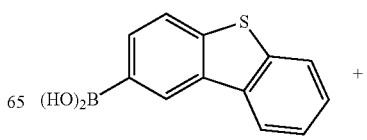

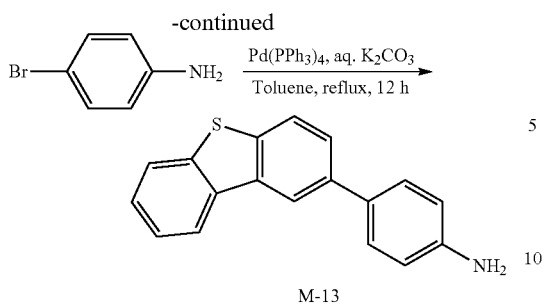

M-13

21.5 g (94.3 mmol) of 2-dibenzothiopheneboronic acid and 16.2 g (94.3 mmol) of 4-bromoaniline were put in a round-bottomed flask, 300 ml of toluene was added to dissolve them, 117 ml of an aqueous solution in which 19.5 g (141.5 mmol) of potassium carbonate was dissolved was added thereto, and the mixture was agitated. Then, 1.09 g (0.94 mmol) of tetrakistriphenyl phosphine palladium was added thereto, and the resulting mixture was refluxed and agitated under a nitrogen atmosphere for 12 hours. When the reaction was complete, the resultant was extracted with ethyl acetate, the extraction solution was dried with magnesium sulfate and filtered, and the filtered solution was concentrated under a reduced pressure. Then, a product obtained therefrom was purified with n-hexane/dichloromethane (7:3 of a volume ratio) through silica gel column chromatography, obtaining 17.9 g (a yield of 69%) of a white solid intermediate M-13 as a target compound.

LC-Mass (a theoretical value: 275.08 g/mol, a measured value: M+=275.21 g/mol)

Synthesis Example 14

Synthesis of Intermediate M-14

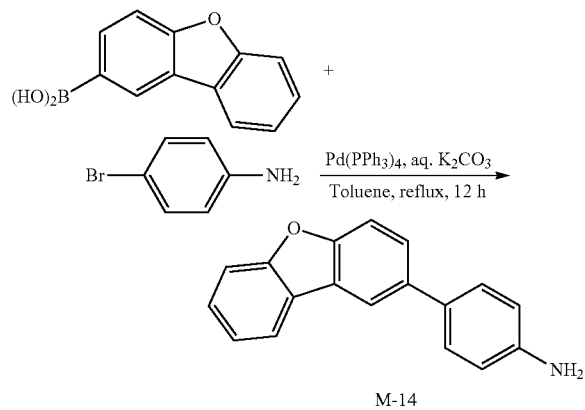

M-14

20 g (94.3 mmol) of 2-dibenzofuranboronic acid and 16.2 g (94.3 mmol) of 4-bromoaniline were put in a round-bottomed flask, 300 ml of toluene was added thereto to dissolve them, 117 ml of an aqueous solution in which 19.5 g (141.5 mmol) of potassium carbonate was dissolved was added thereto, and the mixture was agitated. Then, 1.09 g (0.94 mmol) of tetrakistriphenyl phosphine palladium was added thereto, and the mixture was refluxed and agitated under a nitrogen atmosphere for 12 hours. When the reaction was complete, the resultant was extracted with ethyl acetate, the extraction solution was dried with magnesium sulfate and filtered, and the filtered solution was concentrated under a reduced pressure. Then, a product obtained therefrom was purified with n-hexane/dichloromethane (7:3 of a volume ratio) through silica gel column chromatography, obtaining 17.4 g (a yield of 71%) of a white solid intermediate M-14 as a target compound.

LC-Mass (a theoretical value: 259.1 g/mol, a measured value: M+=259.12 g/mol)

Synthesis Example 15

Synthesis of Intermediate M-15

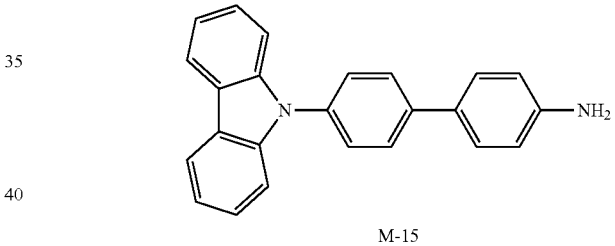

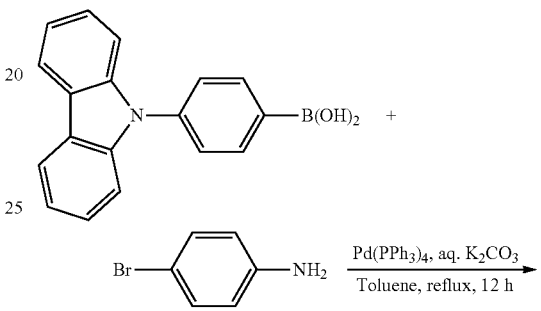

M-15

27.1 g (94.3 mmol) of 4-(9H-carbazole-9-yl)phenylboronic acid and 16.2 g (94.3 mmol) of 4-bromoaniline were put in a round-bottomed flask, 300 ml of toluene was added thereto to dissolve them, 117 ml of an aqueous solution in which 19.5 g (141.5 mmol) of potassium carbonate was dissolved was added thereto, and the mixture was agitated. Then, 1.09 g (0.94 mmol) of tetrakistriphenyl phosphine palladium was added thereto, and the mixture was refluxed and agitated under a nitrogen atmosphere for 12 hours. When the reaction was complete, the resultant was extracted with ethyl acetate, the extraction solution was dried with magnesium sulfate and filtered, and the filtered solution was concentrated under a reduced pressure. Then, a product obtained therefrom was purified with n-hexane/dichloromethane (7:3 of a volume ratio) through silica gel column chromatography, obtaining 23.3 g (a yield of 74%) of a white solid intermediate M-15 as a target compound.

LC-Mass (a theoretical value: 334.15 g/mol, a measured value: M+=334.23 g/mol)

Synthesis Example 16

Synthesis of Intermediate M-16

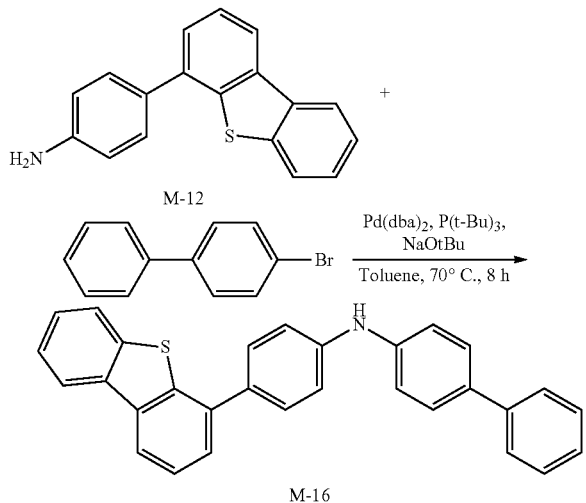

10.2 g (37.08 mmol) of the intermediate M-12, 7.2 g (30.9 mmol) of 4-bromobiphenyl and 5.35 g (55.6 mmol) of sodium t-butoxide were put in a round-bottomed flask, and 155 ml of toluene was added thereto to dissolve them. Then, 0.178 g (0.31 mmol) of Pd(dba)$_2$ and 0.125 g (0.62 mmol) of tri-tertiary-butylphosphine were sequentially added thereto, and the mixture was agitated at 70° C. under a nitrogen atmosphere for 8 hours. When the reaction was complete, the resultant was extracted with toluene and distilled water, an organic layer obtained from the extraction was dried with magnesium sulfate and filtered, and the filtered solution was concentrated under a reduced pressure. Then, a product obtained therefrom was purified with n-hexane/dichloromethane (7:3 of a volume ratio) through silica gel column chromatography, obtaining 10 g (a yield: 76%) of a white solid intermediate M-16 as a target compound.

LC-Mass (a theoretical value: 427.14 g/mol, a measured value: M+=427.25 g/mol)

Synthesis Example 17

Synthesis of Intermediate M-17

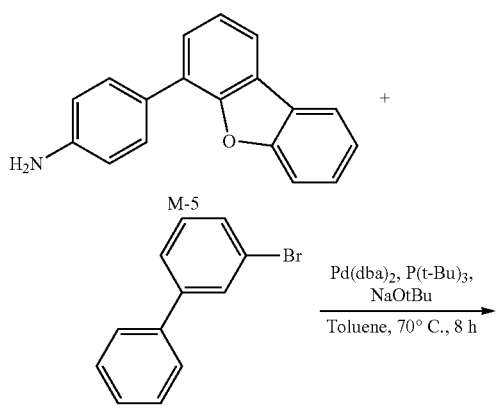

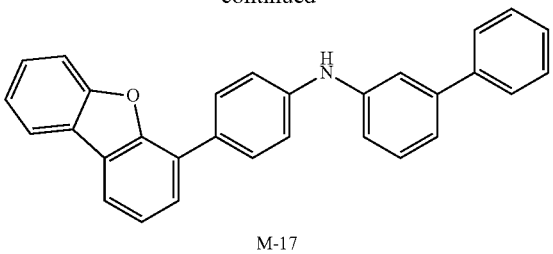

9.6 g (37.08 mmol) of the intermediate M-5, 7.2 g (30.9 mmol) of 3-bromobiphenyl, and 5.35 g (55.6 mmol) of sodium t-butoxide were put in a round-bottomed flask, 155 ml of toluene was added thereto to dissolve them. Herein, 0.178 g (0.31 mmol) of Pd(dba)$_2$ and 0.125 g (0.62 mmol) of tri-tertiary-butylphosphine were sequentially added thereto, and the resulting mixture was agitated at 70° C. under a nitrogen atmosphere for 8 hours. When the reaction was complete, the resultant was extracted with toluene and distilled water, an organic layer obtained after the extraction was dried with magnesium sulfate and filtered, and the filtered solution was concentrated under a reduced pressure. Then, a product obtained therefrom was purified with n-hexane/dichloromethane (7:3 of a volume ratio) through silica gel column chromatography, obtaining 9.7 g (a yield: 76%) of a white solid intermediate M-17 as a target compound.

LC-Mass (a theoretical value: 411.16 g/mol, a measured value: M+=411.24 g/mol)

Synthesis Example 18

Synthesis of Intermediate M-18

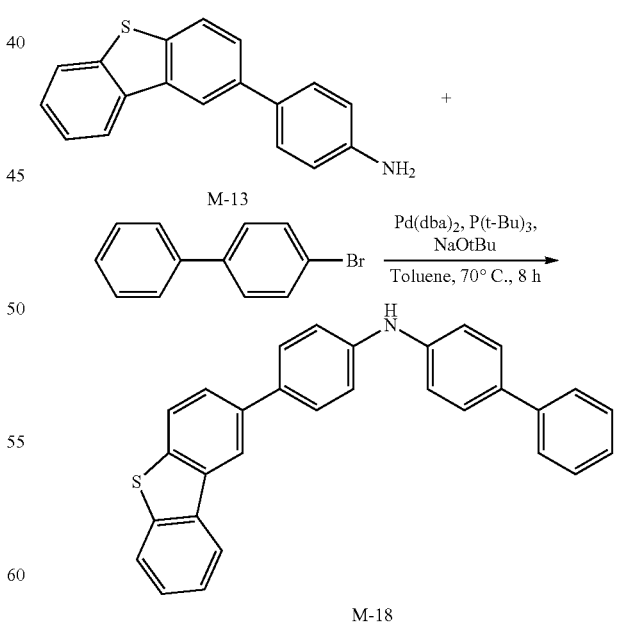

10.2 g (37.08 mmol) of the intermediate M-13, 7.2 g (30.9 mmol) of 4-bromobiphenyl, and 5.35 g (55.6 mmol) of sodium t-butoxide were put in a round-bottomed flask, and 155 ml of toluene was added thereto to dissolve them. Then, 0.178 g (0.31 mmol) of Pd(dba)$_2$ and 0.125 g (0.62 mmol) of tri-tertiary-butylphosphine were sequentially added thereto, and the mixture was agitated at 70° C. under a nitrogen atmosphere for 8 hours. When the reaction was complete, the resultant was extracted with toluene and distilled water, an organic layer obtained after the extraction was dried with magnesium sulfate and filtered, and the filtered solution was concentrated under a reduced pressure. Then, a product obtained therefrom was purified with n-hexane/dichloromethane (7:3 of a volume ratio) through silica gel column chromatography, obtaining 9.8 g (a yield: 74%) of a white solid intermediate M-18 as a target compound.

LC-Mass (a theoretical value: 427.14 g/mol, a measured value: M+=427.21 g/mol)

Synthesis Example 19

Synthesis of Intermediate M-19

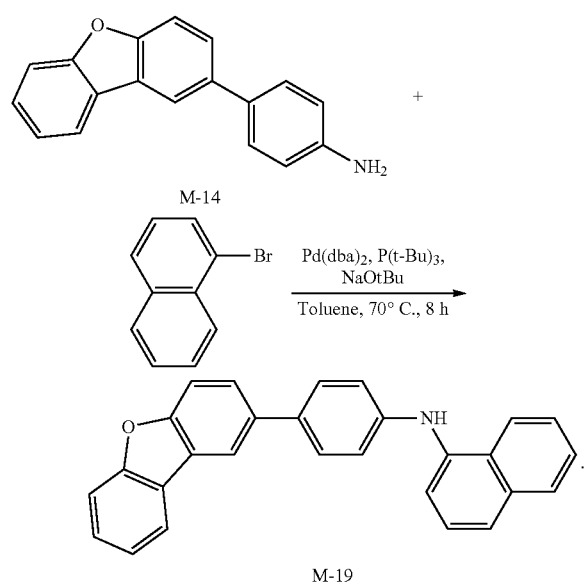

9.6 g (37.08 mmol) of the intermediate M-14, 6.4 g (30.9 mmol) of 1-bromonaphthalene, and 5.35 g (55.6 mmol) of sodium t-butoxide were put in a round-bottomed flask, and 155 ml of toluene was added thereto to dissolve them. Then, 0.178 g (0.31 mmol) of Pd(dba)$_2$ and 0.125 g (0.62 mmol) of tri-tertiary-butylphosphine were sequentially added thereto, and the mixture was agitated at 70° C. under a nitrogen atmosphere for 8 hours. When the reaction was complete, the resultant was extracted with toluene and distilled water, an organic layer obtained therefrom was dried with magnesium sulfate and filtered, and the filtered solution was concentrated under a reduced pressure. Then, a product obtained therefrom was purified with n-hexane/dichloromethane (7:3 of a volume ratio) through silica gel column chromatography, obtaining 9.2 g (a yield: 77%) of a white solid intermediate M-19 as a target compound.

LC-Mass (a theoretical value: 385.15 g/mol, a measured value: M+=385.28 g/mol)

Synthesis Example 20

Synthesis of Intermediate M-20

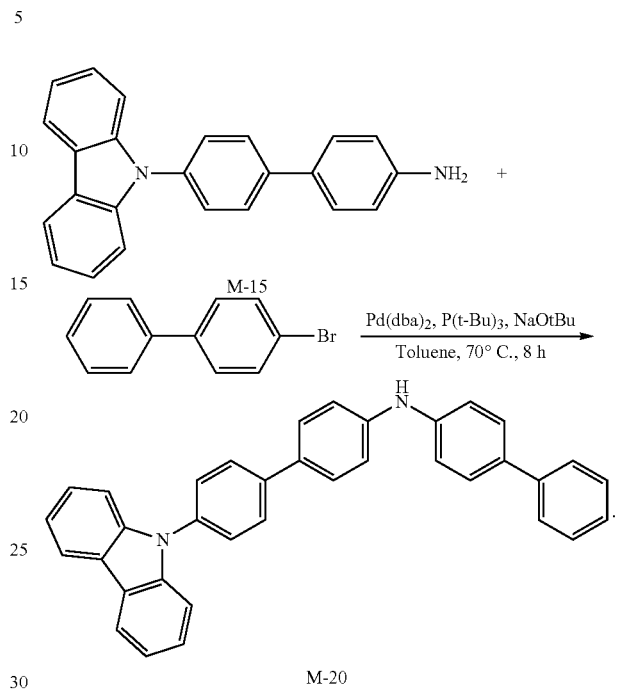

12.4 g (37.08 mmol) of the intermediate M-15, 7.2 g (30.9 mmol) of 4-bromobiphenyl, and 5.35 g (55.6 mmol) of sodium t-butoxide were put in a round-bottomed flask, and 155 ml of toluene was added thereto to dissolve them. Then, 0.178 g (0.31 mmol) of Pd(dba)$_2$ and 0.125 g (0.62 mmol) of tri-tertiary-butylphosphine were sequentially added thereto, and the mixture was agitated at 70° C. under a nitrogen atmosphere for 8 hours. When the reaction was complete, the resultant was extracted with toluene and distilled water, an organic layer obtained from the extraction was dried with magnesium sulfate and filtered, and then, the filtered solution was concentrated under a reduced pressure. Then, a product obtained therefrom was purified with n-hexane/dichloromethane (7:3 of a volume ratio) through silica gel column chromatography, obtaining 10.5 g (a yield: 70%) of a white solid intermediate M-20 as a target compound.

LC-Mass (a theoretical value: 486.21 g/mol, a measured value: M+=486.21 g/mol)

Synthesis Example 21

Synthesis of Intermediate M-21

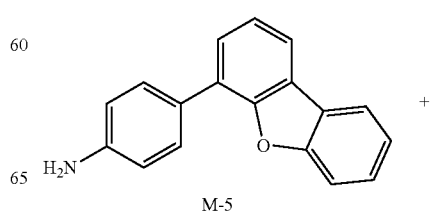

-continued

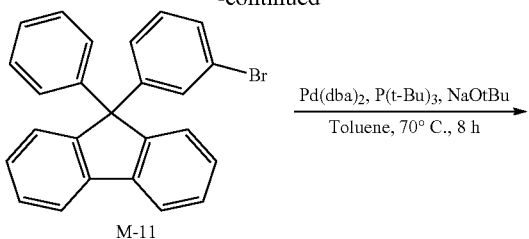

M-11

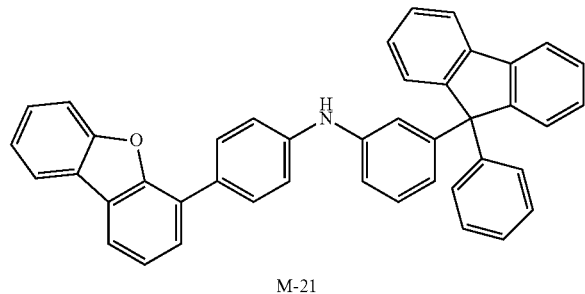

M-21

12.3 g (30.9 mmol) of the intermediate M-11, 9.6 g (37.08 mmol) of the intermediate M-5, and 5.35 g (55.6 mmol) of sodium t-butoxide were put in a round-bottomed flask, and 155 ml of toluene was added thereto to dissolve them. Then, 0.178 g (0.31 mmol) of Pd(dba)$_2$ and 0.125 g (0.62 mmol) of tri-tertiary-butylphosphine were sequentially added thereto, and the mixture was agitated at 70° C. under a nitrogen atmosphere for 8 hours. When the reaction was complete, the resultant was extracted with toluene and distilled water, an organic layer obtained after the extraction was dried with magnesium sulfate and filtered, and the filtered solution was concentrated under a reduced pressure. Then, a product was purified with n-hexane/dichloromethane (7:3 of a volume ratio) through silica gel column chromatography, obtaining 12.5 g (a yield: 70%) of a white solid intermediate M-21.

LC-Mass (a theoretical value: 575.22 g/mol, a measured value: M+=575.24 g/mol)

Synthesis Example 22

Synthesis of Intermediate M-22

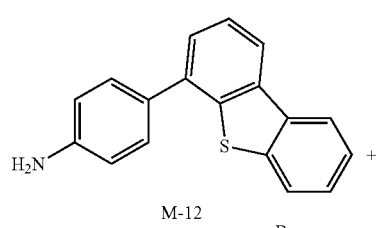

M-12

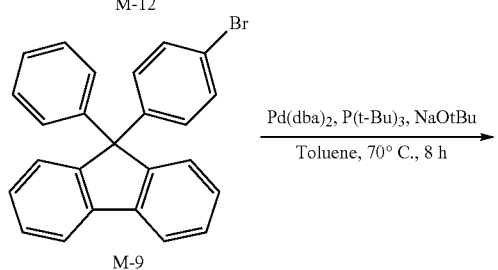

M-9

-continued

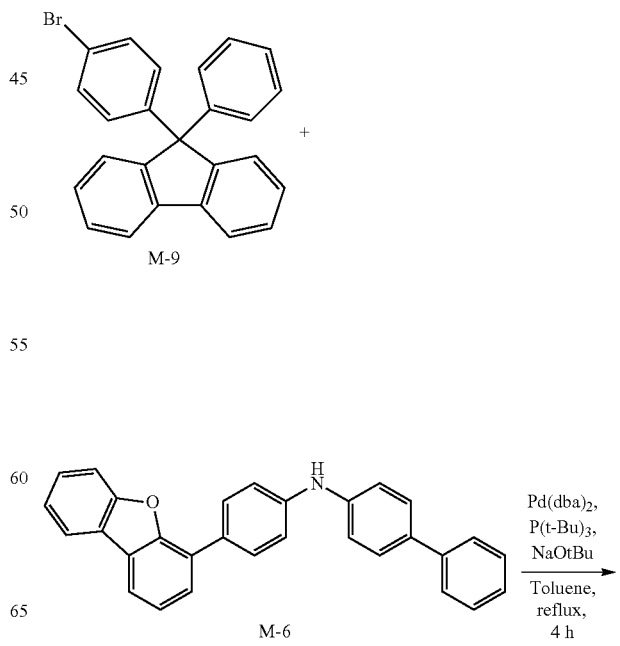

12.3 g (30.9 mmol) of the intermediate M-9, 10.2 g (37.08 mmol) of the intermediate M-12 and 5.35 g (55.6 mmol) of sodium t-butoxide were put in a round-bottomed flask, and 155 ml of toluene was added thereto to dissolve them. Then, 0.178 g (0.31 mmol) of Pd(dba)$_2$ and 0.125 g (0.62 mmol) of tri-tertiary-butylphosphine were sequentially added thereto, and the mixture was agitated at 70° C. under a nitrogen atmosphere for 8 hours. When the reaction was complete, the resultant was extracted with toluene and distilled water, an organic layer obtained after the extraction was dried with magnesium sulfate and filtered, and the filtered solution was concentration under a reduced pressure. Then, a product obtained therefrom was purified with n-hexane/dichloromethane (7:3 of a volume ratio) through silica gel column chromatography, obtaining 13.2 g (a yield: 72%) of a white solid intermediate M-22.

LC-Mass (a theoretical value: 591.2 g/mol, a measured value: M+=591.31 g/mol)

Example 1

Synthesis of Compound A-5

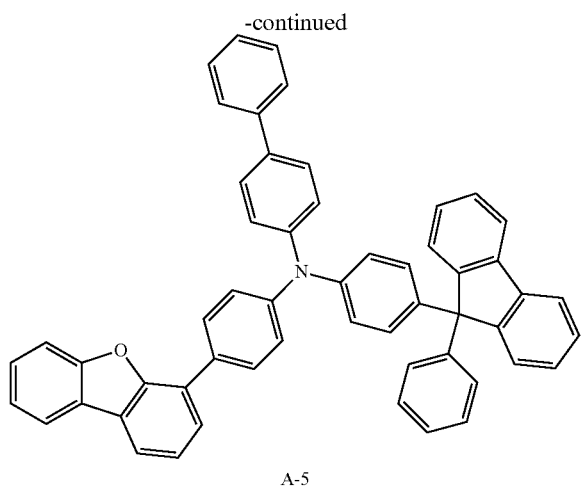

A-5

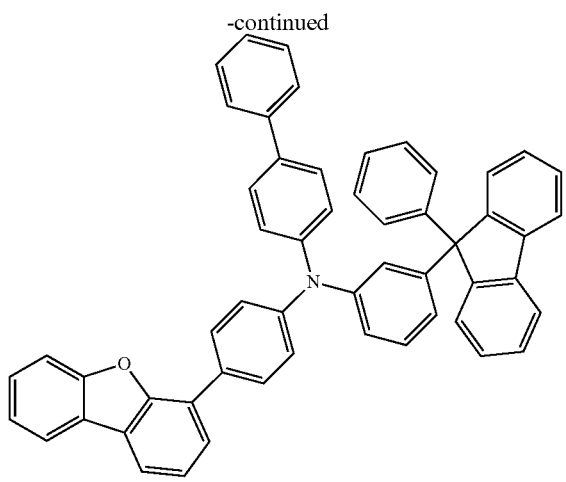

7.95 g (20 mmol) of the intermediate M-9, 8.23 g (20 mmol) of the intermediate M-6, and 2.9 g (30 mmol) of sodium t-butoxide were put in a round-bottomed flask, and 155 ml of toluene was added thereto to dissolve them. Then, 0.115 g (0.2 mmol) of Pd(dba)$_2$ and 0.101 g (0.5 mmol) of tri-tertiary-butylphosphine were sequentially added thereto, and the mixture was refluxed and agitated under a nitrogen atmosphere for 4 hours. When the reaction was complete, the resultant was extracted with toluene and distilled water, an organic layer obtained after the extraction was dried with magnesium sulfate and filtered, and the filtered solution was concentrated under a reduced pressure. Then, a product obtained therefrom was purified with n-hexane/dichloromethane (8:2 of a volume ratio) through silica gel column chromatography, obtaining 13.5 g (a yield of 93%) of a target compound A-5.

LC-Mass (a theoretical value: 727.29 g/mol, a measured value: M+=727.34 g/mol)

Example 2

Synthesis of Compound A-137

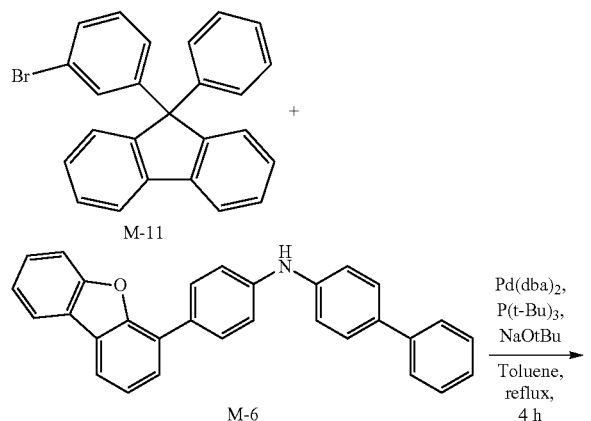

7.95 g (20 mmol) of the intermediate M-11, 8.23 g (20 mmol) of the intermediate M-6, and 2.9 g (30 mmol) of sodium t-butoxide were put in a round-bottomed flask, and 155 ml of toluene was added thereto to dissolve them. Then, 0.115 g (0.2 mmol) of Pd(dba)$_2$ and 0.101 g (0.5 mmol) of tri-tertiary-butylphosphine were sequentially added thereto, and the mixture was refluxed and agitated under a nitrogen atmosphere for 4 hours. When the reaction was complete, the resultant was extracted with toluene and distilled water, an organic layer obtained after the extraction was dried with magnesium sulfate and filtered, and the filtered solution was concentrated under a reduced pressure. Then, a product obtained therefrom was purified with n-hexane/dichloromethane (8:2 of a volume ratio) through silica gel column chromatography, obtaining 13.2 g (a yield: 91%) of a target compound A-137.

LC-Mass (a theoretical value: 727.29 g/mol, a measured value: M+=727.31 g/mol)

Example 3

Synthesis of Compound B-1

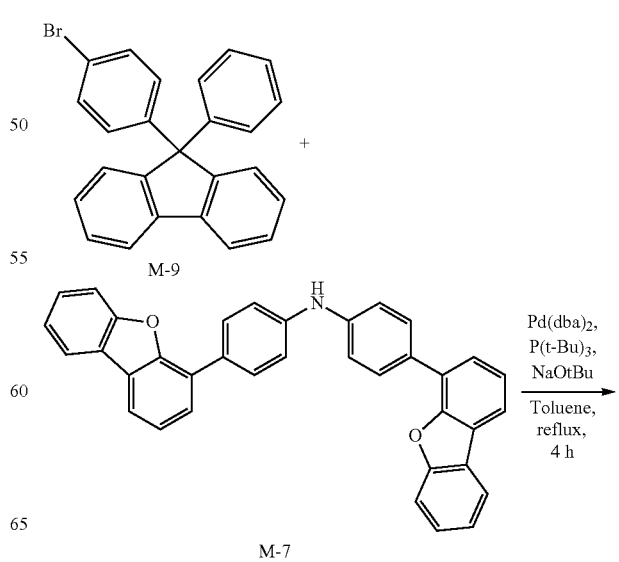

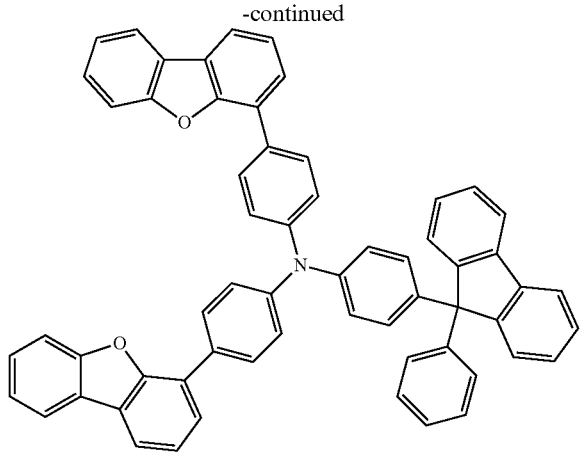

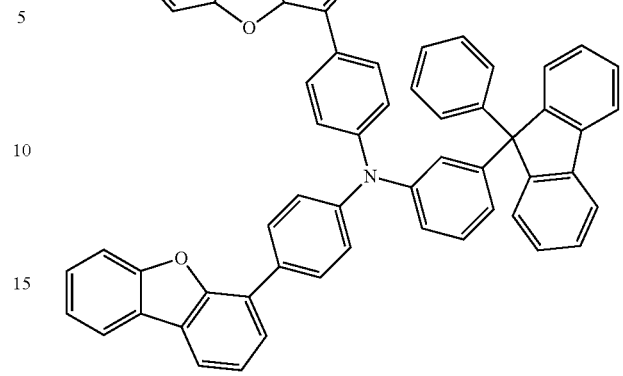

7.95 g (20 mmol) of the intermediate M-9, 10 g (20 mmol) of the intermediate M-7, and 2.9 g (30 mmol) of sodium t-butoxide were put in a round-bottomed flask, and 155 ml of toluene was added thereto to dissolve them. Then, 0.115 g (0.2 mmol) of Pd(dba)$_2$ and 0.101 g (0.5 mmol) of tri-tertiary-butylphosphine were sequentially added thereto, and the mixture was refluxed and agitated under a nitrogen atmosphere for 4 hours. When the reaction was complete, the resultant was extracted with toluene and distilled water, an organic layer obtained after the extraction was dried with magnesium sulfate and filtered, and the filtered solution was concentrated under a reduced pressure. Then, a product obtained therefrom was purified with n-hexane/dichloromethane (8:2 of a volume ratio) through silica gel column chromatography, obtaining 15.1 g (a yield of 92%) of a target compound B-1.

LC-Mass (a theoretical value: 817.30 g/mol, a measured value: M+=817.36 g/mol)

Example 4

Synthesis of Compound B-13

7.95 g (20 mmol) of the intermediate M-11, 10 g (20 mmol) of the intermediate M-7, and 2.9 g (30 mmol) of sodium t-butoxide were put in a round-bottomed flask, and 155 ml of toluene was added thereto to dissolve them. Then, 0.115 g (0.2 mmol) of Pd(dba)$_2$ and 0.101 g (0.5 mmol) of tri-tertiary-butylphosphine were sequentially added thereto, and the mixture was refluxed and agitated under a nitrogen atmosphere for 4 hours. When the reaction was complete, the resultant was extracted with toluene and distilled water, an organic layer obtained after the extraction was dried with magnesium sulfate and filtered, and the filtered solution was concentrated under a reduced pressure. Then, a product was purified with n-hexane/dichloromethane (8:2 of a volume ratio) through silica gel column chromatography, obtaining 14.7 g (a yield of 90%) of a target compound B-13.

LC-Mass (a theoretical value: 817.30 g/mol, a measured value: M+=817.38 g/mol)

Example ad-1

Synthesis of Compound A-6

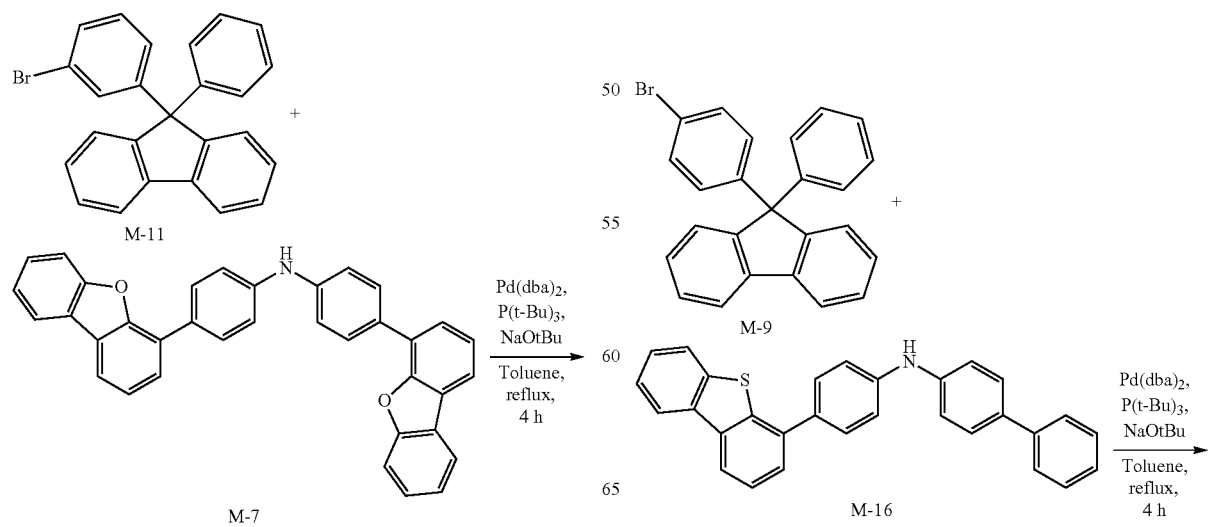

-continued

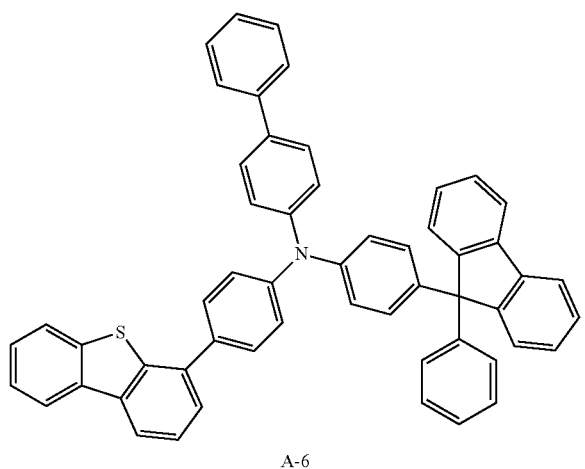

A-6

7.95 g (20 mmol) of the intermediate M-9, 8.6 g (20 mmol) of the intermediate M-16, and 2.9 g (30 mmol) of sodium t-butoxide were put in a round-bottomed flask, and 155 ml of toluene was added thereto to dissolve them. Then, 0.115 g (0.2 mmol) of Pd(dba)$_2$ and 0.101 g (0.5 mmol) of tri-tertiary-butylphosphine were sequentially added thereto, and the mixture was refluxed and agitated under a nitrogen atmosphere for 4 hours. When the reaction was complete, the resultant was extracted with toluene and distilled water, an organic layer obtained after the extraction was dried with magnesium sulfate and filtered, and the filtered solution was concentrated under a reduced pressure. Then, a product therefrom was purified with n-hexane/dichloromethane (8:2 of a volume ratio) through silica gel column chromatography, obtaining 13.8 g (a yield of 93%) of a target compound A-6.

LC-Mass (a theoretical value: 743.26 g/mol, a measured value: M+=743.12 g/mol)

Example ad-2

Synthesis of Compound A-138

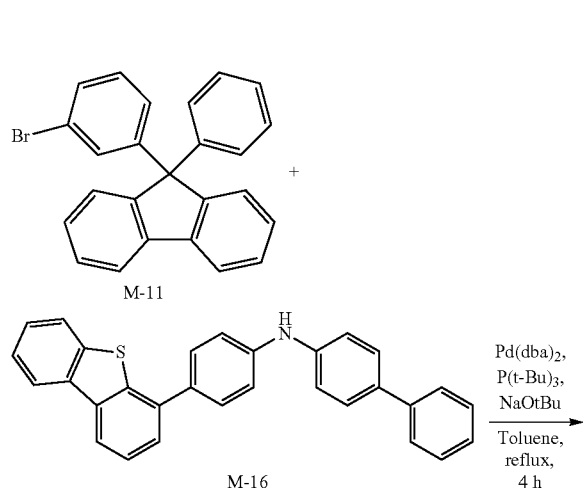

-continued

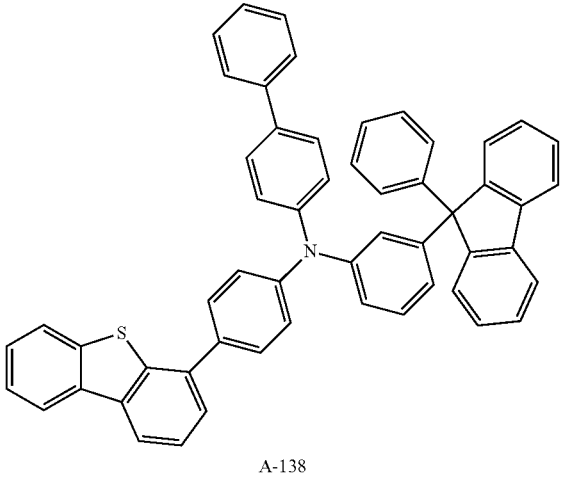

A-138

7.95 g (20 mmol) of the intermediate M-11, 8.6 g (20 mmol) of the intermediate M-16, and 2.9 g (30 mmol) of sodium t-butoxide were put in a round-bottomed flask, and 155 ml of toluene was added thereto to dissolve them. Then, 0.115 g (0.2 mmol) of Pd(dba)$_2$ and 0.101 g (0.5 mmol) of tri-tertiary-butylphosphine were sequentially added thereto, and the mixture was refluxed and agitated under a nitrogen atmosphere for 4 hours. When the reaction was complete, the resultant was extracted with toluene and distilled water, an organic layer obtained therefrom was dried with magnesium sulfate and filtered, and the filtered solution was concentrated under a reduced pressure. Then, a product obtained therefrom was purified with n-hexane/dichloromethane (8:2 of a volume ratio) through silica gel column chromatography, obtaining 14 g (a yield of 94%) of a target compound A-138.

LC-Mass (a theoretical value: 743.26 g/mol, a measured value: M+=743.29 g/mol)

Example ad-3

Synthesis of Compound A-147

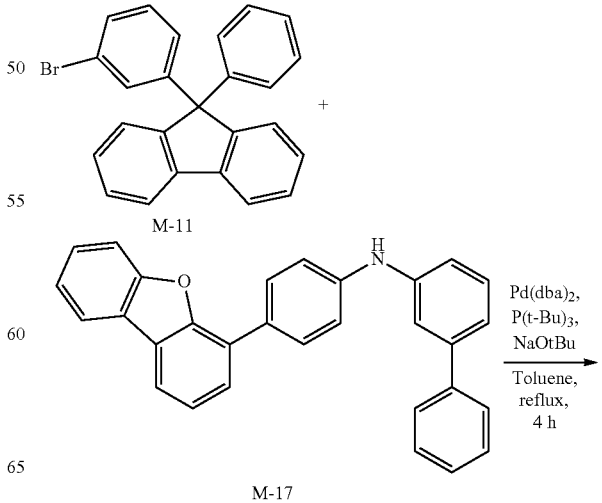

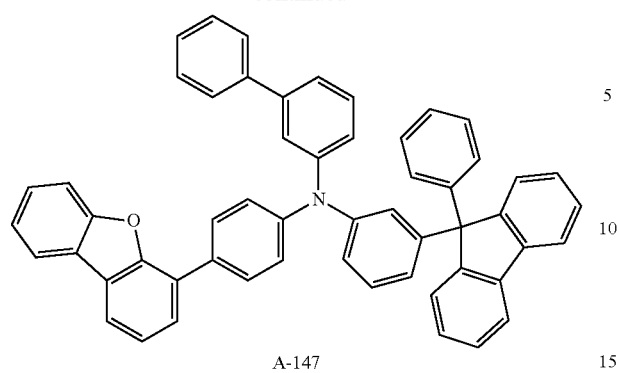

A-147

7.95 g (20 mmol) of the intermediate M-11, 8.22 g (20 mmol) of the intermediate M-17, and 2.9 g (30 mmol) of sodium t-butoxide were put in a round-bottomed flask, and 155 ml of toluene was added thereto to dissolve them. Then, 0.115 g (0.2 mmol) of Pd(dba)$_2$ and 0.101 g (0.5 mmol) of tri-tertiary-butylphosphine were sequentially added thereto, and the mixture was refluxed and agitated under a nitrogen atmosphere for 4 hours. When the reaction was complete, the resultant was extracted with toluene and distilled water, an organic layer obtained after the extraction was dried with magnesium sulfate and filtered, and the filtered solution was concentrated under a reduced pressure. Then, a product obtained therefrom was purified with n-hexane/dichloromethane (8:2 of a volume ratio) through silica gel column chromatography, obtaining 13.2 g (a yield of 91%) of a target compound A-147.

LC-Mass (a theoretical value: 727.29 g/mol, a measured value: M+=727.34 g/mol)

Example ad-4

Synthesis of Compound A-50

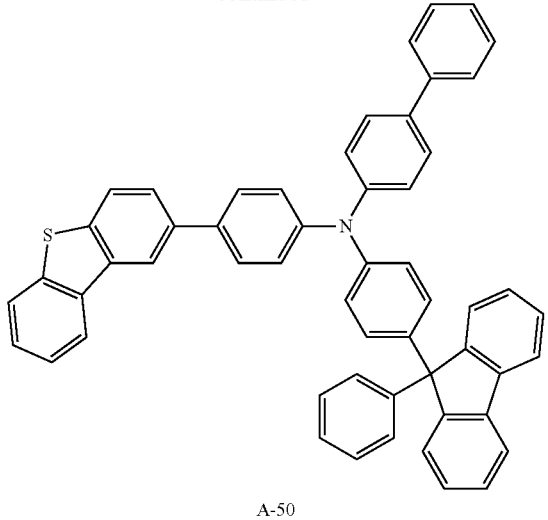

A-50

7.95 g (20 mmol) of the intermediate M-9, 8.6 g (20 mmol) of the intermediate M-18, and 2.9 g (30 mmol) of sodium t-butoxide were put in a round-bottomed flask, and 155 ml of toluene was added thereto to dissolve them. Then, 0.115 g (0.2 mmol) of Pd(dba)$_2$ and 0.101 g (0.5 mmol) of tri-tertiary-butylphosphine were sequentially added thereto, and the mixture was refluxed and agitated for 4 hours under a nitrogen atmosphere. When the reaction was complete, the resultant was extracted with toluene and distilled water, an organic layer obtained after the extraction was dried with magnesium sulfate and filtered, and the filtered solution was concentrated under a reduced pressure. Then, a product obtained therefrom was purified with n-hexane/dichloromethane (8:2 of a volume ratio) through silica gel column chromatography, obtaining 13.7 g (a yield of 92%) of a target compound A-50.

LC-Mass (a theoretical value: 743.26 g/mol, a measured value: M+=743.18 g/mol)

Example ad-5

Synthesis of Compound A-47

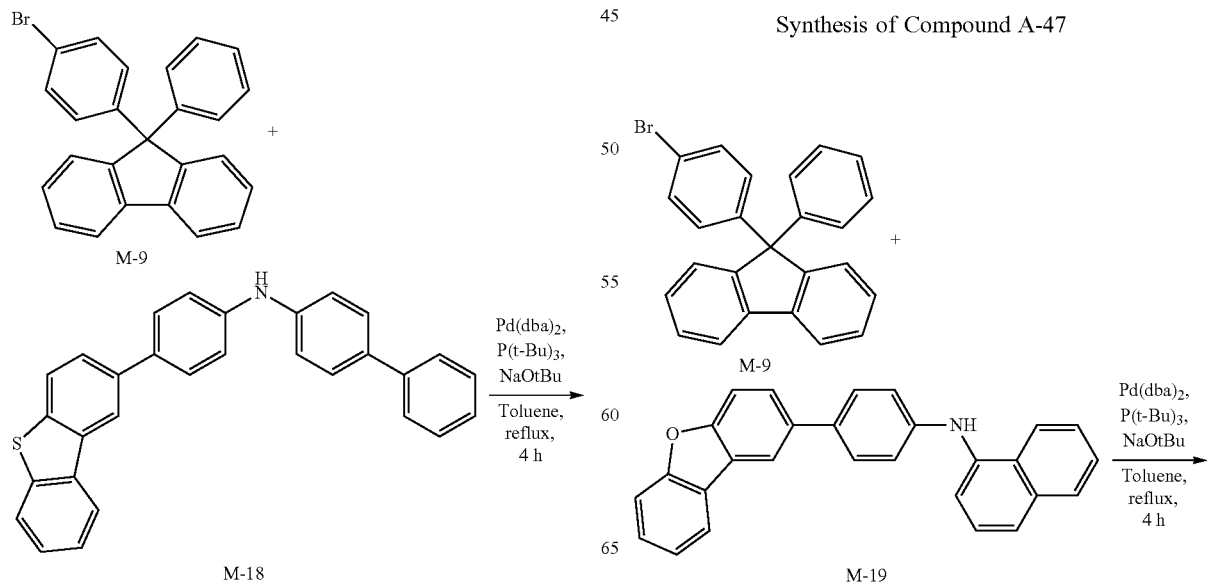

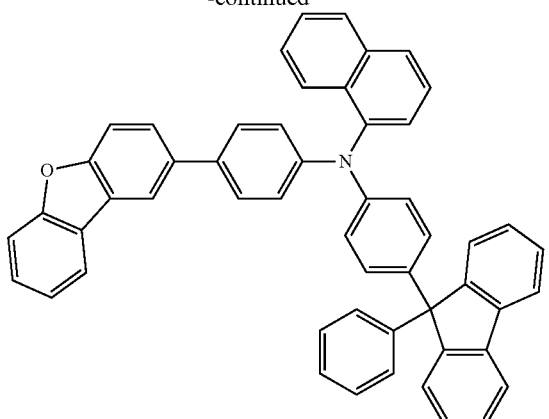

A-47

C-37

7.95 g (20 mmol) of the intermediate M-9, 7.7 g (20 mmol) of the intermediate M-19, and 2.9 g (30 mmol) of sodium t-butoxide were put in a round-bottomed flask, and 155 ml of toluene was added thereto to dissolve them. Then, 0.115 g (0.2 mmol) of Pd(dba)$_2$ and 0.101 g (0.5 mmol) of tri-tertiary-butylphosphine were sequentially added thereto, and the mixture was refluxed and agitated for 4 hours under a nitrogen atmosphere. When the reaction was complete, the resultant was extracted with toluene and distilled water, an organic layer obtained after the extraction was dried with magnesium sulfate and filtered, and the filtered solution was concentrated under a reduced pressure. Then, a product obtained therefrom was purified with n-hexane/dichloromethane (8:2 of a volume ratio) through silica gel column chromatography, obtaining 13.3 g (a yield of 95%) of a target compound A-47.

LC-Mass (a theoretical value: 701.27 g/mol, a measured value: M+=701.15 g/mol)

Example ad-6

Synthesis of Compound C-37

7.95 g (20 mmol) of the intermediate M-11, 9.7 g (20 mmol) of the intermediate M-20, and 2.9 g (30 mmol) of sodium t-butoxide were put in a round-bottomed flask, and 155 ml of toluene was added thereto to dissolve them. Then, 0.115 g (0.2 mmol) of Pd(dba)$_2$ and 0.101 g (0.5 mmol) of tri-tertiary-butylphosphine were sequentially added thereto, and the mixture was refluxed and agitated under a nitrogen atmosphere for 4 hours. When the reaction was complete, the resultant was extracted with toluene and distilled water, an organic layer obtained therefrom was dried with magnesium sulfate and filtered, and the filtered solution was concentrated under a reduced pressure. Then, a product obtained therefrom was purified with n-hexane/dichloromethane (8:2 of a volume ratio) through silica gel column chromatography, obtaining 14.6 g (a yield: 91%) of a target compound C-37.

LC-Mass (a theoretical value: 802.23 g/mol, a measured value: M+=803 g/mol)

Example ad-7

Synthesis of Compound A-173

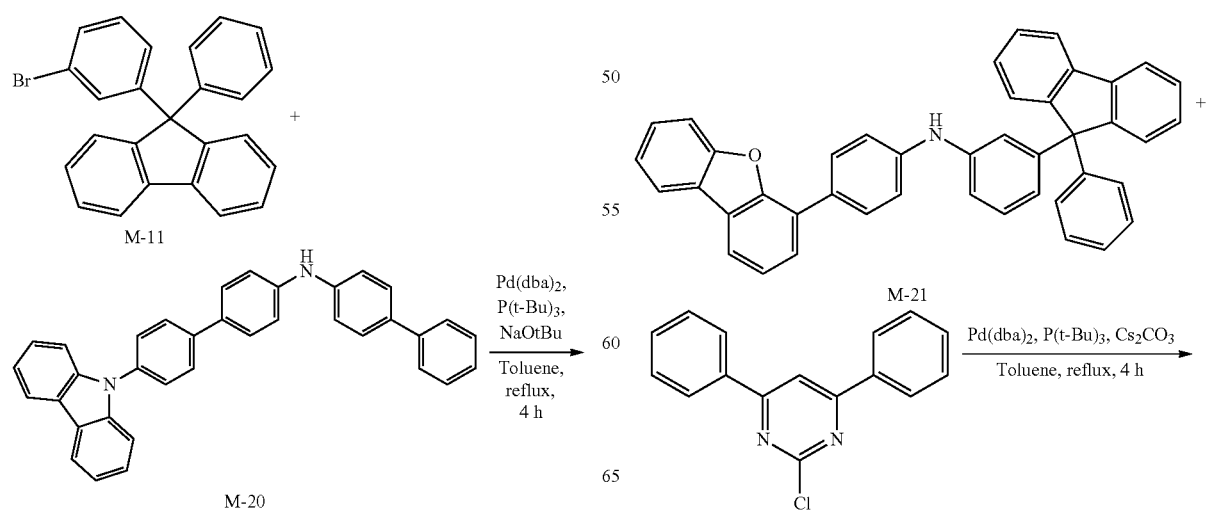

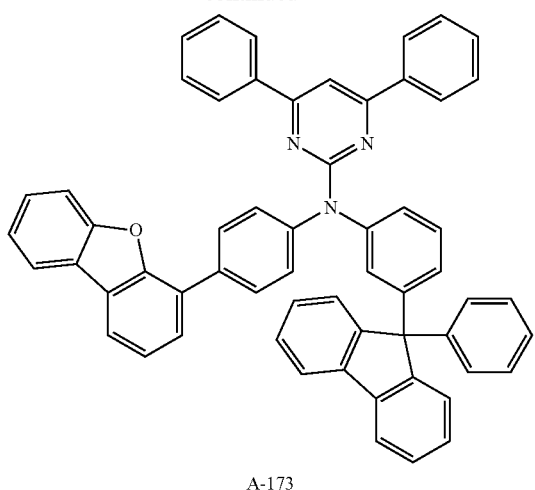

A-173

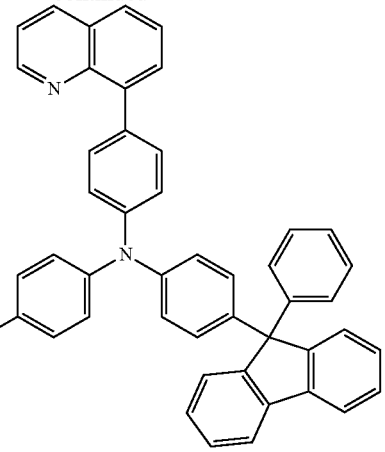

A-40

11.5 g (20 mmol) of the intermediate M-21, 5.3 g (20 mmol) of the intermediate 2-chloro-4,6-diphenylpyrimidine, and 9.8 g (30 mmol) of cesium carbonate were put in a round-bottomed flask, and 155 ml of toluene was added thereto to dissolve them. Then, 0.115 g (0.2 mmol) of Pd(dba)$_2$ and 0.101 g (0.5 mmol) of tri-tertiary-butylphosphine were sequentially added thereto, and the mixture was refluxed and agitated under a nitrogen atmosphere for 4 hours. When the reaction was complete, the resultant was extracted with toluene and distilled water, an organic layer obtained therefrom was dried with magnesium sulfate and filtered, and the filtered solution was concentrated under a reduced pressure. Then, a product obtained therefrom was purified with n-hexane/dichloromethane (8:2 of a volume ratio) through silica gel column chromatography, obtaining 14.5 g (a yield of 90%) of a target compound A-173.

LC-Mass (a theoretical value: 805.31 g/mol, a measured value: M+=805.23 g/mol)

Example ad-8

Synthesis of Compound A-40

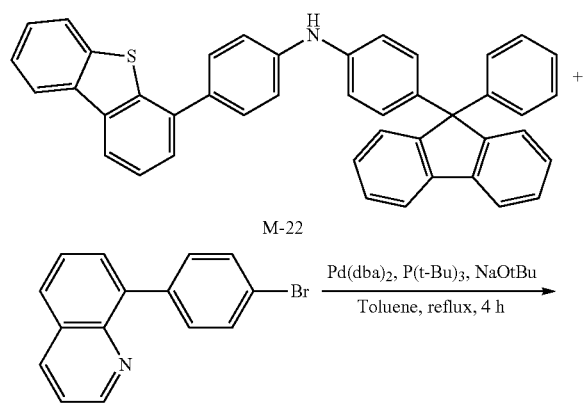

11.8 g (20 mmol) of the intermediate M-22, 5.7 g (20 mmol) of 8-(4-bromophenyl)quinoline, and 2.9 g (30 mmol) of sodium t-butoxide were put in a round-bottomed flask, and 155 ml of toluene was added thereto to dissolve them. Then, 0.115 g (0.2 mmol) of Pd(dba)$_2$ and 0.101 g (0.5 mmol) of tri-tertiary-butylphosphine were sequentially added thereto, and the mixture was refluxed and agitated under a nitrogen atmosphere for 4 hours. When the reaction was complete, the resultant was extracted with toluene and distilled water, an organic layer obtained after the extraction was dried with magnesium sulfate and filtered, and the filtered solution was concentrated under a reduced pressure. Then, a product was purified with n-hexane/dichloromethane (8:2 of a volume ratio) through silica gel column chromatography, obtaining 14.5 g (a yield of 91%) of a target compound A-40.

LC-Mass (a theoretical value: 794.28 g/mol, a measured value: M+=794.35 g/mol)

(Analysis of Prepared Compound and Measurement of Characteristics)

1. Analysis of Fluorescent Characteristics

The fluorescent characteristics of Examples 1 to 4 were measured by dissolving each compound in THF and measuring its PL (photoluminescence) wavelength with HITACHI F-4500. The PL wavelength measurement result of the compound A-137 of Example 2 was provided in FIG. 3.

2. Analysis of Electrochemical Characteristics

Energy level of each material was calculated in a Gaussian 09 method by using a supercomputer GAIA (IBM power 6), and the result is provided in the following Table 1.

TABLE 1

| Test | Compound | HOMO (eV) | LUMO (eV) | T1 (eV) | S1 (eV) |
|---|---|---|---|---|---|
| Example 1 | A-5 | −4.84 | −1.12 | 2.70 | 3.30 |
| Example 2 | A-137 | −4.88 | −1.12 | 2.70 | 3.33 |
| Example 3 | B-1 | −4.84 | −1.17 | 2.65 | 3.24 |
| Example 4 | B-13 | −4.84 | −1.15 | 2.65 | 3.25 |
| Comparative Example | HT-1 | −4.70 | −0.91 | 2.64 | 3.33 |
| | HT-2 | −4.74 | −0.87 | 2.77 | 3.46 |

As shown in Table 1, the synthesized compounds of Examples 1 to 4 showed a HOMO energy level of greater than or equal to 0.1 eV compared with the compound of Comparative Example and thus, may have an influence on device efficiency when used to form a hole transport layer for an organic optoelectric device.

Manufacture of Organic Light Emitting Diode

Example 5

Manufacture of Blue Organic Light Emitting Diode

A glass substrate coated with ITO (indium tin oxide) to be 1500 Å thick was ultrasonic wave-washed with a distilled water. Subsequently, the glass substrate was ultrasonic wave-washed with a solvent such as isopropyl alcohol, acetone, methanol, and the like, moved to a plasma cleaner, cleaned by using oxygen plasma for 10 minutes, and then, moved to a vacuum depositor. This obtained ITO transparent electrode was used as an anode, and 4,4'-bis[N4-[4-{N,N-bis(3-methylphenyl)amino}-phenyl]-N-phenylamino]biphenyl [DNTPD] was vacuum-deposited on the ITO substrate to form 600 Å-thick hole injection layer. Then, HT-1 was vacuum-deposited thereon to form a 250 Å-thick auxiliary hole transport layer. The compound prepared in Example 1 was vacuum-deposited to form a 50 Å-thick auxiliary hole transport layer on the hole transport layer. On the auxiliary hole transport layer, a 250 Å-thick emission layer was formed by vacuum-depositing 9,10-di-(2-naphthyl)anthracene (ADN) as a host doped with 3 wt % of 2,5,8,11-tetra(tert-butyl)perylene (TBPe) as a dopant.

Subsequently, Alq3 was vacuum-deposited on the emission layer to form a 250 Å-thick electron transport layer. LiF 10 Å and Al 1000 Å were sequentially vacuum-deposited on the electron transport layer to form a cathode, manufacturing an organic light emitting diode.

The organic light emitting diode had a five-layered organic thin film structure and specifically, a structure of Al 1000 Å/LiF 10 Å/Alq3 250 Å/EML[ADN:TBPe=97:3] 250 Å/auxiliary hole transport layer 50 Å/HT-1 250 Å/DNTPD 600 Å/ITO 1500 Å.

Example 6

An organic light emitting diode was manufactured according to the same method as Example 5 except for using Example 2 instead of Example 1.

Example 7

An organic light emitting diode was manufactured according to the same method as Example 5 except for using Example 3 instead of Example 1.

Example 8

An organic light emitting diode was manufactured according to the same method as Example 5 except for using Example 4 instead of Example 1.

Example ad-9

An organic light emitting diode was manufactured according to the same method as Example 5 except for using Example ad-3 instead of Example 1.

Example ad-10

An organic light emitting diode was manufactured according to the same method as Example 5 except for using Example ad-6 instead of Example 1.

Comparative Example 1

An organic light emitting diode was manufactured according to the same method as Example 5 except for using HT-1 instead of the compound A-5 of Example 1.

Comparative Example 2

An organic light emitting diode was manufactured according to the same method as Example 5 except for using HT-2 instead of the compound A-5 of Example 1.

The structures of the DNTPD, HT-1, HT-2, Alq3, ADN, and TBPe used for manufacturing the organic light emitting diode were as follows.

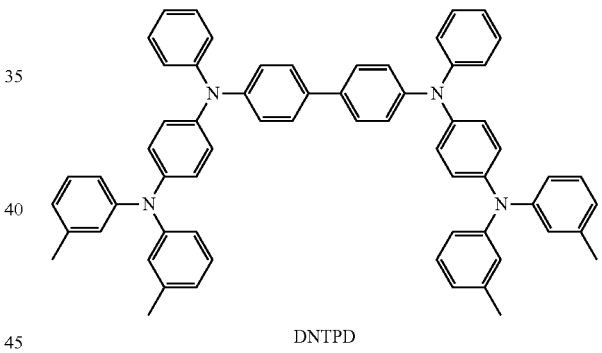

DNTPD

HT-1

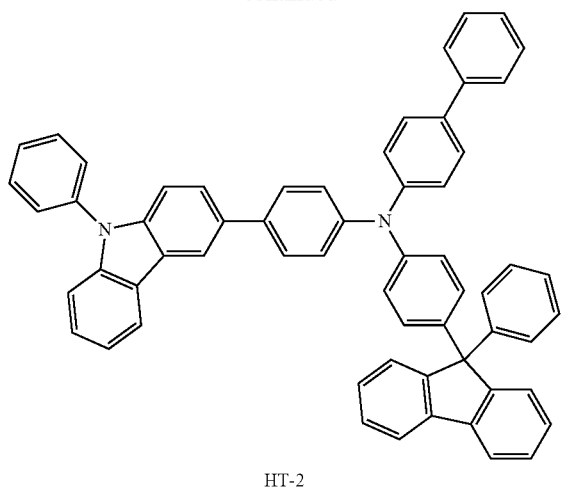

HT-2

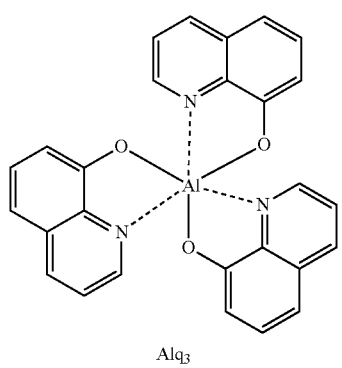

Alq₃

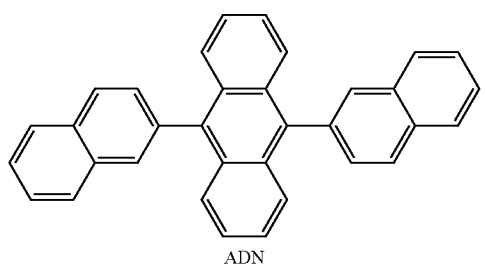

ADN

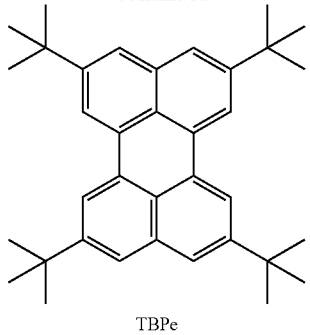

TBPe (Performance Measurement of Blue Organic Light Emitting Diode)

Current density and luminance changes depending on a voltage, luminous efficiency and life-span of each organic light emitting diode according to Examples 5 to 8, Examples ad-9 and ad-10 and Comparative Examples 1 to 2 were measured.

Specific measurement methods were as follows, and the results were provided in Table 2.

(1) Measurement of Current Density Change Depending on Voltage Change

The obtained organic light emitting diodes were measured for current value flowing in the unit device while increasing the voltage from 0 V to 10 V using a current-voltage meter (Keithley 2400), the measured current value was divided by area to provide the results.

(2) Measurement of Luminance Change Depending on Voltage Change

Luminance was measured by using a luminance meter (Minolta Cs-1000 A), while the voltage of the organic light emitting diodes was increased from 0 V to 10 V.

(3) Measurement of Luminous Efficiency

Current efficiency (cd/A) at the same current density (10 mA/cm$^2$) were calculated by using the luminance, current density, and voltages (V) from the items (1) and (2).

(4) Life-Span

Life-spans of the organic light emitting diodes of Examples 5 to 8 and Comparative Examples 1 and 2 were measured as a time when their luminance decreased down to ½ relative to the initial luminance after emitting light with 1,000 nit as the initial luminance (cd/m$^2$) and measuring their luminance decrease depending on time with a Polanonix life-span measurement system.

TABLE 2

| Devices | HTL | Auxiliary HTL | Voltage (V) | Light emitting color (EL color) | Efficiency (cd/A) | Half-life life-span (h) at 1000 cd/m$^2$ |
|---|---|---|---|---|---|---|
| Example 5 | HT-1 | A-5 | 6.3 | Blue | 6.6 | 1,360 |
| Example 6 | HT-1 | A-137 | 6.3 | Blue | 6.5 | 1,390 |
| Example 7 | HT-1 | B-1 | 6.3 | Blue | 6.9 | 1,370 |
| Example 8 | HT-1 | B-13 | 6.4 | Blue | 6.7 | 1,400 |
| Example ad-9 | HT-1 | A-147 | 6.5 | Blue | 6.6 | 1,380 |
| Example ad-10 | HT-1 | C-37 | 6.2 | Blue | 6.5 | 1,360 |
| Comparative Example 1 | HT-1 | HT-1 | 6.4 | Blue | 5.8 | 1,310 |
| Comparative Example 2 | HT-1 | HT-2 | 6.4 | Blue | 6.0 | 1,120 |

Current density: 10 mA/cm$^2$

As shown in Table 2, Examples 5 to 8 and Examples ad-9 and ad-10 showed largely improved luminous efficiency and the same or further improved life-span compared with Comparative Examples 1 and 2. Particularly, Examples 5 to 8 and Examples ad-9 and ad-10 showed at least greater than or equal to 13% improved efficiency compared with Comparative Example 1 using no auxiliary HTL and at least greater than or equal to 20% increased half-life life-span compared with Comparative Example 2 using HT-2 as the auxiliary HTL.

Example ad-11

Manufacture of Green Organic Light Emitting Diode

A glass substrate coated with ITO (indium tin oxide) to be 1500 Å thick was ultrasonic wave-washed with a distilled water. Subsequently, the glass substrate was ultrasonic wave-washed with a solvent such as isopropyl alcohol, acetone, methanol, and the like, moved to a plasma cleaner, cleaned by using oxygen plasma for 10 minutes, and then, moved to a vacuum depositor. This obtained ITO transparent electrode was used as an anode, and HT-1 was vacuum-deposited on the ITO substrate to form 700 Å-thick hole injection and transport layer. Then, the compound of Example 1 was vacuum-deposited thereon to form a 100 Å-thick auxiliary hole transport layer. On the auxiliary hole transport layer, a 300 Å-thick emission layer was formed by vacuum-depositing (4,4'-N,N'-dicarbazole)biphenyl [CBP] as a host doped with 5 wt % of tris(2-phenylpyridine)iridium (III) [Ir(ppy)$_3$].

Subsequently, biphenoxy-bis(8-hydroxyquinoline)aluminum [Balq] was vacuum-deposited on the emission layer to form a 50 Å-thick hole blocking layer. On the hole blocking layer, tris(8-hydroxyquinoline)aluminum [Alq$_3$] was vacuum-deposited to form a 250 Å-thick electron transport layer and on the electron transport layer, LiF 10 Å and Al 1000 Å was vacuum-deposited to form a cathode, manufacturing an organic light emitting diode.

The organic light emitting diode had a five-layered organic thin film structure and specifically, a structure of Al 1000 Å/LiF 10 Å/Alq3 250 Å/Balq 50 Å/EML[CBP:Ir(ppy)$_3$=95:5] 300 Å/auxiliary HTL 100 Å/HT-1 700 Å/ITO 1500 Å.

Example ad-12

An organic light emitting diode was manufactured according to the same method as Example ad-11 except for using Example 2 instead of Example 1.

Example ad-13

An organic light emitting diode was manufactured according to the same method as Example ad-11 except for using Example 3 instead of Example 1.

Example ad-14

An organic light emitting diode was manufactured according to the same method as Example ad-11 except for using Example ad-1 instead of Example 1.

Example ad-15

An organic light emitting diode was manufactured according to the same method as Example ad-11 except for using Example ad-2 instead of Example 1.

Example ad-16

An organic light emitting diode was manufactured according to the same method as Example ad-11 except for using Example ad-3 instead of Example 1.

Example ad-17

An organic light emitting diode was manufactured according to the same method as Example ad-11 except for using Example ad-4 instead of Example 1.

Comparative Example 3

An organic light emitting diode was manufactured according to the same method as Example ad-11 except for using N,N'-di(1-naphthyl)-N,N'-diphenylbenzidine [NPB] instead of HT-1, and using N,N'-di(1-naphthyl)-N,N'-diphenylbenzidine[NPB] instead of Example 1.

Comparative Example 4

An organic light emitting diode was manufactured according to the same method as Example ad-11 except for using N,N'-di(1-naphthyl)-N,N'-diphenylbenzidine [NPB] instead of HT-1, and using tris (4,4',4"-(9-carbazolyl))-triphenylamine [TCTA] instead of Example 1.

Comparative Example 5

An organic light emitting diode was manufactured according to the same method as Example ad-11 except for using HT-1 instead of Example 1.

The structures of the HT-1 and Alq3 used for manufacturing the organic light emitting diode were the same as above, and the structures of NPB, TCTA, CBP, Balq, Ir(ppy)$_3$ were as follows.

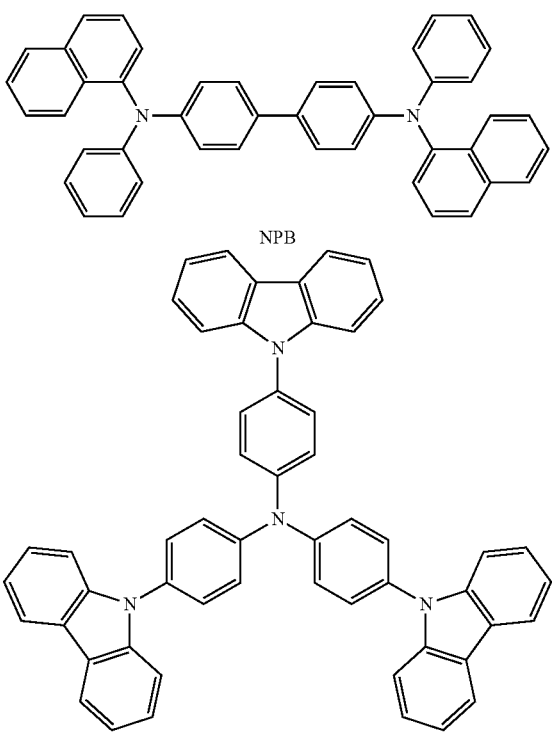

NPB

TCTA

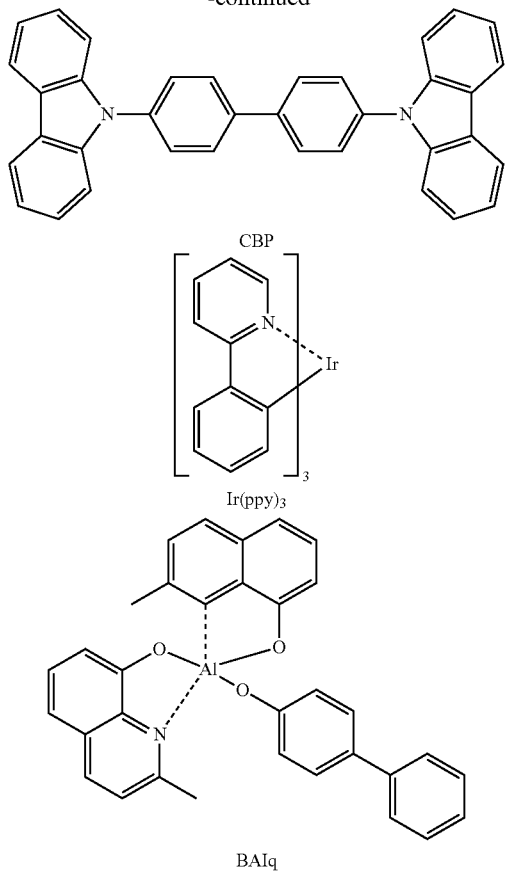

CBP

Ir(ppy)₃

BAlq (Performance Measurement of Green Organic Light Emitting Diode)

Current density and luminance changes depending on a voltage, luminous efficiency and life-span of each organic light emitting diode according to Examples ad-11 to ad-17 and Comparative Examples 3 to 5 were measured.

Specific measurement methods for Current density and luminance changes depending on a voltage and luminous efficiency were the same as in the methods for the blue organic light emitting diode, a measurement method of life-span were as follow, and the results were provided in Table 3.

Life-Span

Life-spans of the organic light emitting diodes of Examples ad-11 to ad-17 and Comparative Examples 3 to 5 were measured as a time when their luminance decreased down to ½ relative to the initial luminance after emitting light with 3,000 nit as the initial luminance (cd/m$^2$) and measuring their luminance decrease depending on time with a Polanonix life-span measurement system.

TABLE 3

| Devices | HTL | Auxiliary HTL | Driving voltage (V) | Luminous efficiency (cd/A) | EL peak (nm) | Half-life life-span (h) @3000 nit |
|---|---|---|---|---|---|---|
| Example ad-11 | HT-1 | A-5 | 6.8 | 48.2 | 516 | 280 |
| Example ad-12 | HT-1 | A-137 | 6.9 | 47.3 | 516 | 270 |
| Example ad-13 | HT-1 | B-1 | 7.0 | 48.0 | 516 | 260 |
| Example ad-14 | HT-1 | A-6 | 7.0 | 49.0 | 516 | 300 |
| Example ad-15 | HT-1 | A-138 | 7.1 | 48.1 | 516 | 280 |
| Example ad-16 | HT-1 | A-147 | 7.1 | 47.5 | 516 | 250 |
| Example ad-17 | HT-1 | A-50 | 6.6 | 46.2 | 516 | 240 |
| Comparative Example 3 | NPB | NPB | 8.2 | 25.8 | 516 | 175 |
| Comparative Example 4 | NPB | TCTA | 7.1 | 45.0 | 516 | 181 |
| Comparative Example 5 | HT-1 | HT-1 | 7.2 | 37.8 | 516 | 220 |

As shown in Table 3, Examples ad-11 to ad-17 showed improved characteristics in terms of luminous efficiency, driving voltage and life-span compared with Comparative Examples 3 to 5. Particularly, Examples ad-11 to ad-17 showed at least greater than or equal to 70% increased efficiency compared with Comparative Example 3 using no auxiliary HTL and at least greater than or equal to 20% increased efficiency compared with Comparative Example 5. Examples ad-11 to ad-17 showed high efficiency and at least greater than or equal to 30% increased half-life life-span compared with Comparative Example 4 using TCTA as the auxiliary HTL.

Example ad-18

Manufacture of Red Organic Light Emitting Diode

A glass substrate coated with ITO (indium tin oxide) to be 1500 Å thick was ultrasonic wave-washed with a distilled water. Subsequently, the glass substrate was ultrasonic wave-washed with a solvent such as isopropyl alcohol, acetone, methanol, and the like, moved to a plasma cleaner, cleaned by using oxygen plasma for 10 minutes, and then, moved to a vacuum depositor. This obtained ITO transparent electrode was used as an anode, and 4,4'-bis[N-[4-{N,N-bis(3-methylphenyl)amino}-phenyl]N-phenylamino]biphenyl [DNTPD] was vacuum-deposited on the ITO substrate to form 600 Å-thick hole injection layer. Then, HT-1 was vacuum-deposited thereon to form a 200 Å-thick hole transport layer. Then, the compound of Example 1 was vacuum-deposited on the hole transport layer to form a 100 Å-thick auxiliary hole transport layer. On the auxiliary hole transport layer, a 300 Å-thick emission layer was formed by vacuum-depositing (4,4'-N,N'-dicarbazole)biphenyl[CBP] as a host doped with 5 wt % of bis(2-phenylquinoline) (acetylacetonate)iridium(III) [Ir (pq)$_2$acac].

Subsequently, biphenoxy-bis(8-hydroxyquinoline)aluminum [Balq] was vacuum-deposited on the emission layer to form a 50 Å-thick hole blocking layer. On the hole blocking layer upper, tris (8-hydroxyquinoline)aluminum [Alq$_3$] was vacuum-deposited to form a 250 Å-thick electron transport layer and on the electron transport layer, LiF 10 Å and Al 1000 Å was vacuum-deposited to form a cathode, manufacturing an organic light emitting diode.

The organic light emitting diode had a six-layered organic thin film structure and specifically, a structure of Al 1000 Å/LiF 10 Å/Alq3 250 Å/Balq 50 Å/EML[CBP: Ir (pq)$_2$acac=95:5] 300 Å/auxiliary HTL 100 Å/HT-1 700 Å/DNTPD 600 Å/ITO 1500 Å.

Example ad-19

An organic light emitting diode was manufactured according to the same method as Example ad-18 except for using Example 2 instead of Example 1.

Example ad-20

An organic light emitting diode was manufactured according to the same method as Example ad-18 except for using Example 4 instead of Example 1.

Example ad-21

An organic light emitting diode was manufactured according to the same method as Example ad-18 except for using Example ad-1 instead of Example 1.

Example ad-22

An organic light emitting diode was manufactured according to the same method as Example ad-18 except for using Example ad-3 instead of Example 1.

Example ad-23

An organic light emitting diode was manufactured according to the same method as Example ad-18 except for using Example ad-5 instead of Example 1.

Comparative Example 6

An organic light emitting diode was manufactured according to the same method as Example ad-18 except for using N,N'-di(1-naphthyl)-N,N'-diphenylbenzidine [NPB] instead of HT-1, and using N,N'-di(1-naphthyl)-N,N'-diphenylbenzidine[NPB] instead of Example 1.

Comparative Example 7

An organic light emitting diode was manufactured according to the same method as Example ad-18 except for using N,N'-di(1-naphthyl)-N,N'-diphenylbenzidine [NPB] instead of HT-1, and using tris (4,4',4"-(9-carbazolyl))-triphenylamine [TCTA] instead of Example 1.

Comparative Example 8

An organic light emitting diode was manufactured according to the same method as Example ad-18 except for using HT-1 instead of Example 1.

The structures of the DNTPD, NPB, HT-1, TCTA, CBP, Balq and Alq3 used for manufacturing the organic light emitting diode were the same as above, and the structure of Ir(pq)$_2$acac was as follows.

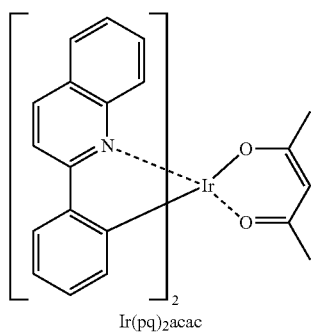

Ir(pq)$_2$acac (Performance Measurement of Red Organic Light Emitting Diode)

Current density and luminance changes depending on a voltage, luminous efficiency and life-span of each organic light emitting diode according to Examples ad-18 to ad-23 and Comparative Examples 6 to 8 were measured.

Specific measurement methods for Current density and luminance changes depending on a voltage and luminous efficiency were the same as in the methods for the blue organic light emitting diode, a measurement method of life-span were as follow, and the results were provided in Table 4.

Life-Span

T80 life-spans of the organic light emitting diodes of Examples ad-18 to ad-23 and Comparative Example 6 to 8 were measured as a time when their luminance decreased down to 80% relative to the initial luminance after emitting light with 1,000 nit as the initial luminance (cd/m$^2$) and measuring their luminance decrease depending on time with a Polanonix life-span measurement system.

TABLE 4

| Devices | HTL | Auxiliary HTL | Driving voltage (V) | Luminous efficiency (cd/A) | EL peak (nm) | T80 life-span (h) @1000 nit |
|---|---|---|---|---|---|---|
| Example ad-18 | HT-1 | A-5 | 8.1 | 17.9 | 600 | 890 |
| Example ad-19 | HT-1 | A-137 | 8.3 | 18.3 | 600 | 910 |
| Example ad-20 | HT-1 | B-13 | 8.4 | 18.5 | 600 | 870 |
| Example ad-21 | HT-1 | A-6 | 8.3 | 18.1 | 600 | 890 |
| Example ad-22 | HT-1 | A-147 | 8.4 | 18.9 | 600 | 880 |
| Example ad-23 | HT-1 | A-47 | 8.0 | 18.2 | 600 | 830 |
| Comparative Example 6 | NPB | NPB | 8.7 | 15.1 | 600 | 720 |
| Comparative Example 7 | NPB | TCTA | 9.1 | 17.3 | 600 | 650 |
| Comparative Example 8 | HT-1 | HT-1 | 8.4 | 16.6 | 600 | 800 |

As shown in Table 4, Examples ad-18 to ad-23 showed improved characteristics in terms of luminous efficiency, driving voltage and life-span compared with Comparative Examples 6 to 8. Particularly, Examples ad-18 to ad-23 showed at least greater than or equal to 19% increased efficiency compared with Comparative Example 6 using no auxiliary HTL and at least greater than or equal to 8% increased efficiency compared with Comparative Example 8. Examples ad-18 to ad-23 showed higher efficiency than Comparative Example 7 using TCTA as the auxiliary HTL and at least greater than or equal to 28% increased T80 life-span.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present invention in any way.

The invention claimed is:

1. A compound represented by Chemical Formula 1:

[Chemical Formula 1]

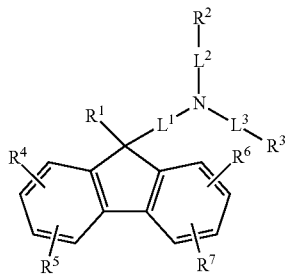

in Chemical Formula 1, $L^1$ to $L^3$ are independently a single bond or an unsubstituted phenylene group, $R^1$ is an unsubstituted phenyl group, $R^2$ is a substituted or unsubstituted group listed in Group I, and $R^3$ is a substituted or unsubstituted group listed in Group I-1:

[Group I]

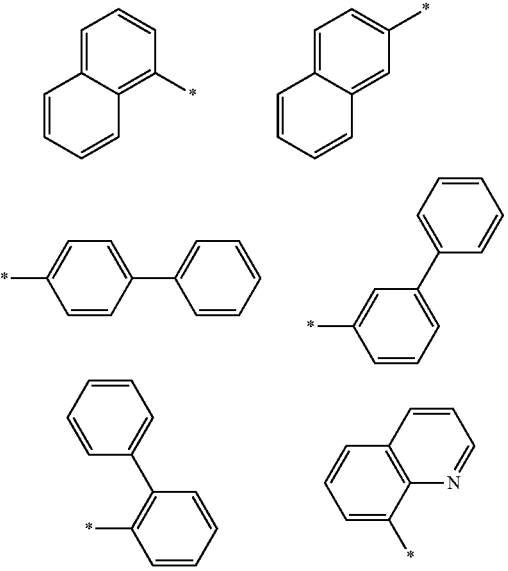

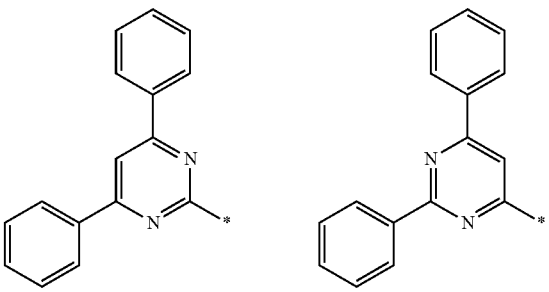

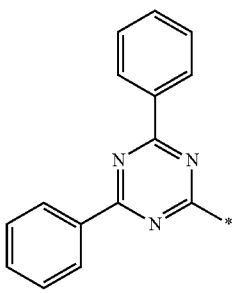

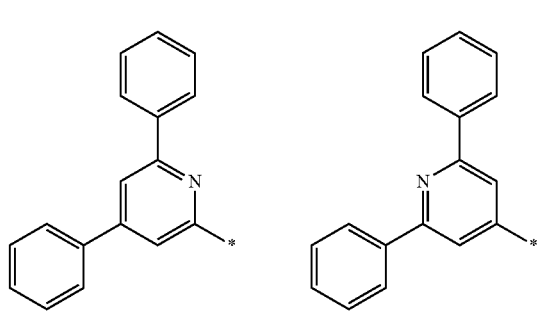

[Group I-1]

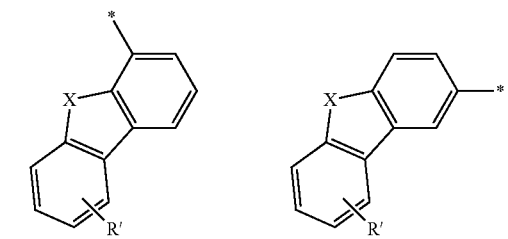

In Groups I and I-1,

X is O or S,

R' is hydrogen, a substituted or unsubstituted C1 to C30 alkyl group, or a substituted or unsubstituted C6 to C30 aryl group,

* is a linking point, and $R^4$ to $R^7$ are each hydrogen.

2. The compound of claim 1, wherein the Chemical Formula 1 is represented by Chemical Formula 4 or Chemical Formula 5:

[Chemical Formula 4]

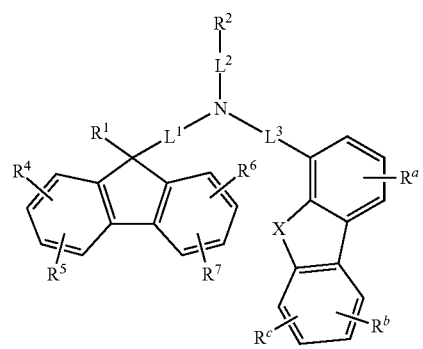

[Chemical Formula 5]

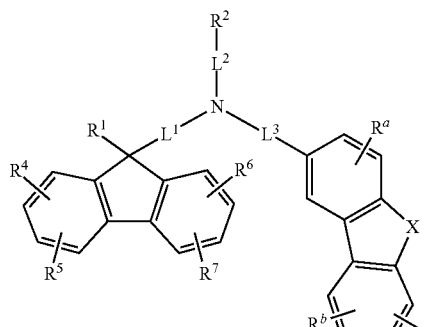

in Chemical Formulae 4 and 5,

X is O or S,

L¹ to L³ are defined the same as those of Chemical Formula 1,

R¹ is an unsubstituted phenyl group,

R² is defined the same as that of Chemical Formula 1,

R$^a$ to R$^c$ and are each independently hydrogen, deuterium, a substituted or unsubstituted C2 to C30 heterocyclic group, a substituted or unsubstituted C6 to C30 aryl group, or a combination thereof, and R⁴ to R⁷ are each hydrogen.

3. The compound of claim 1, wherein the compound represented by Chemical Formula 1 is selected from Chemical Formulae A-5, A-6, A-15 A-21, A-22, A-25, A-26, A-49, A-50, A-59, A-65, A-66, A-69, A-70, A-137, A-138, A-147, A-153, A-154, A-157, and A-158:

[A-5]

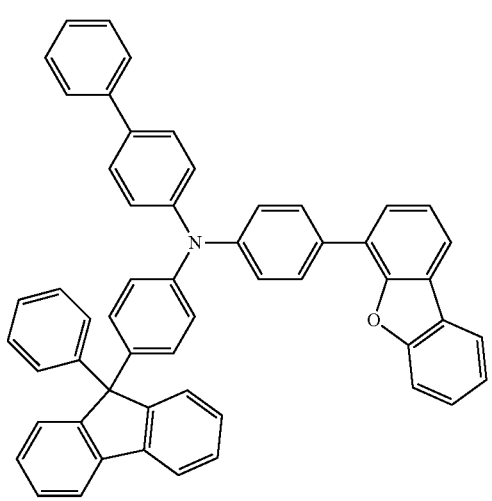

[A-6]

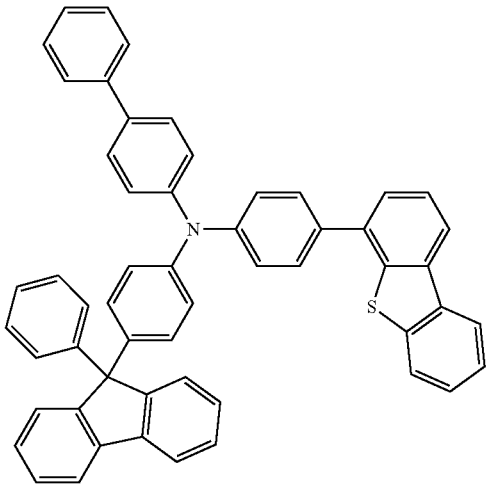

[A-15]

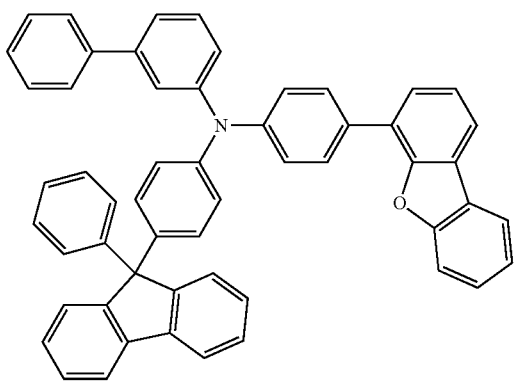

[A-21]

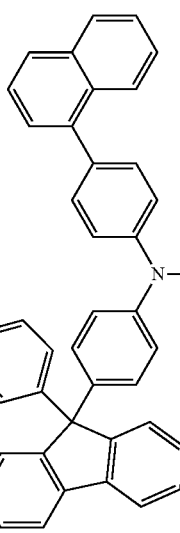

[A-22]
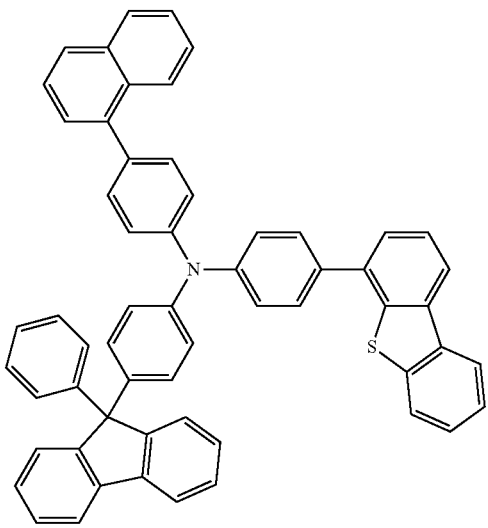
[A-25]
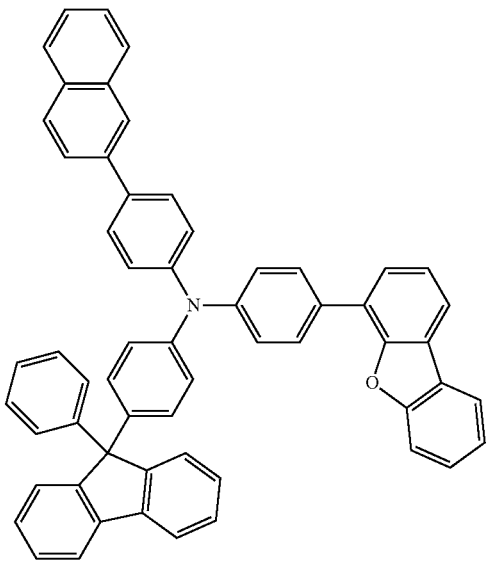
[A-26]
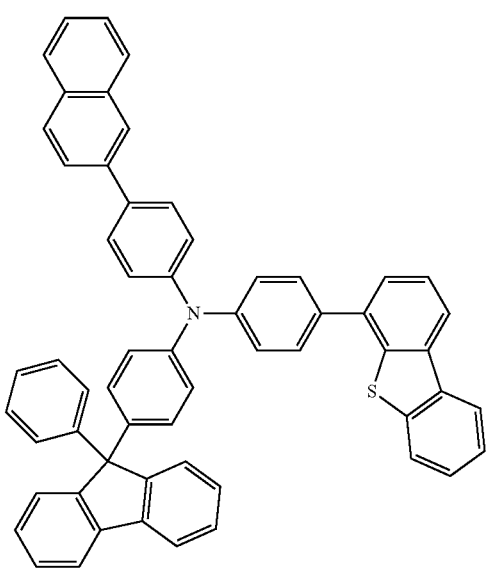
[A-49]
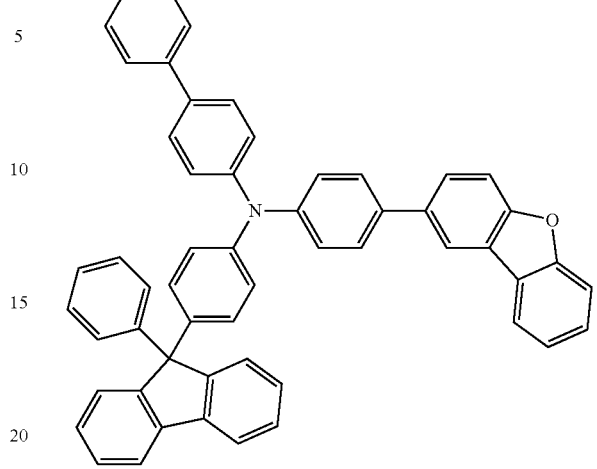
[A-50]
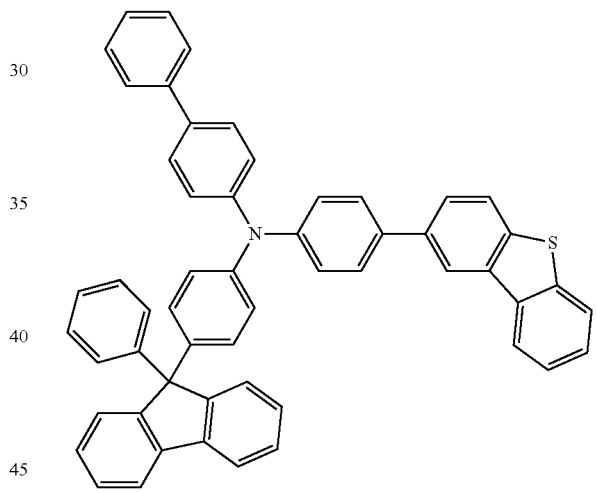
[A-59]
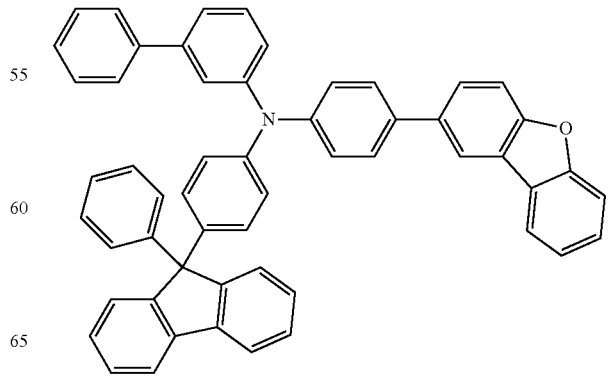

[A-65]
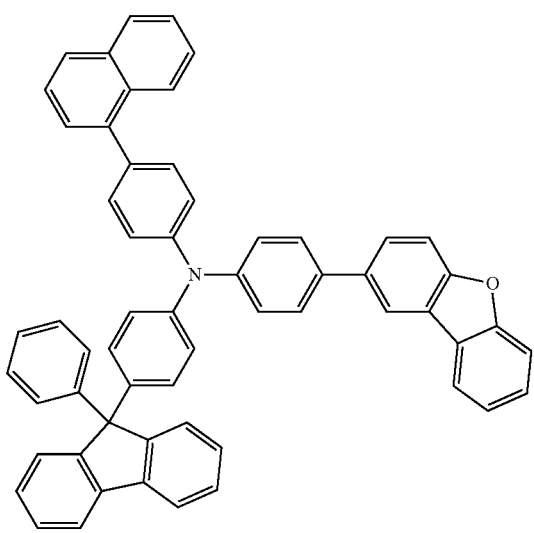
[A-66]
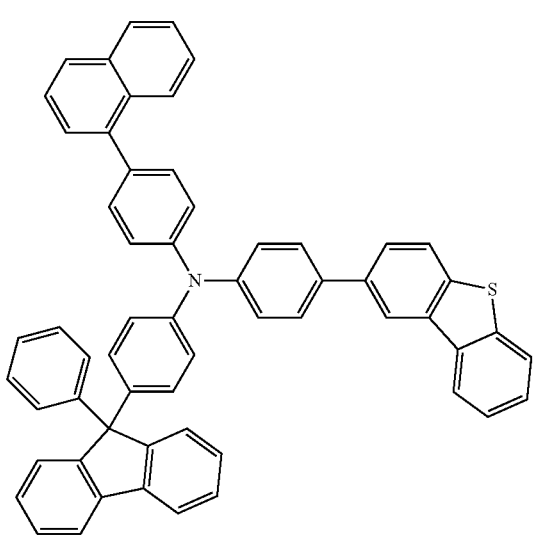
[A-69]
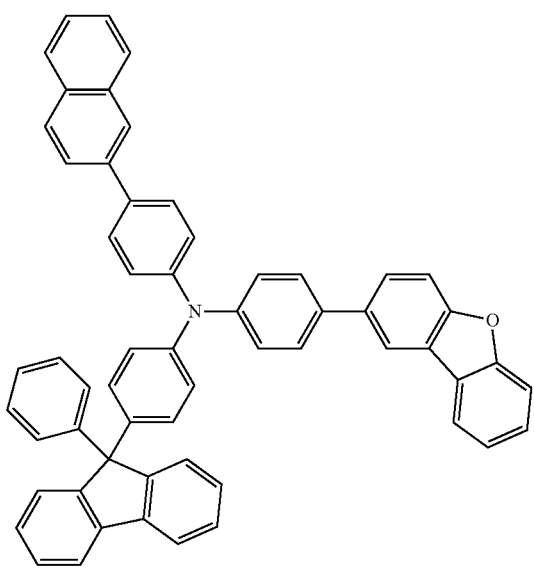
[A-70]
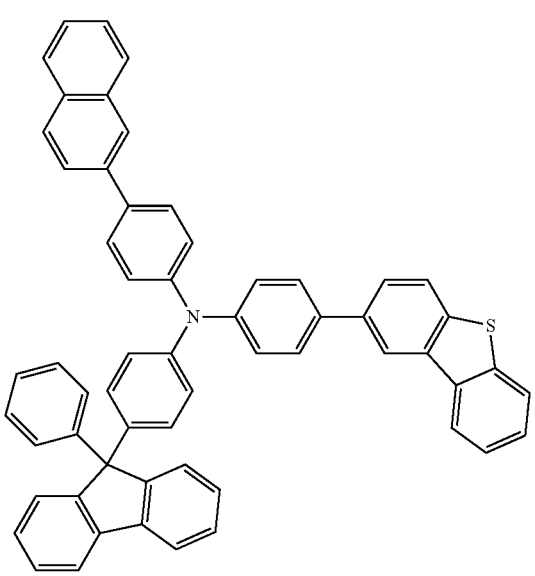
[A-137]
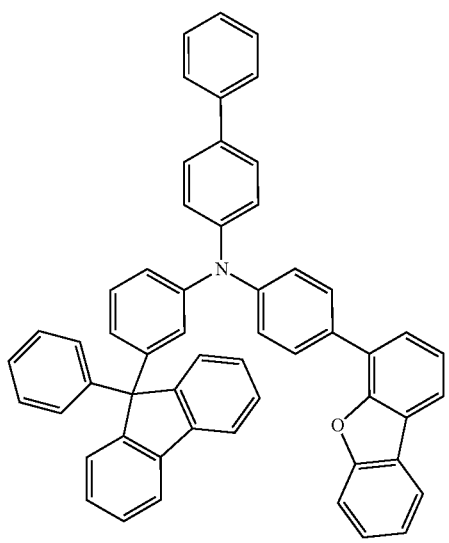

[A-138]
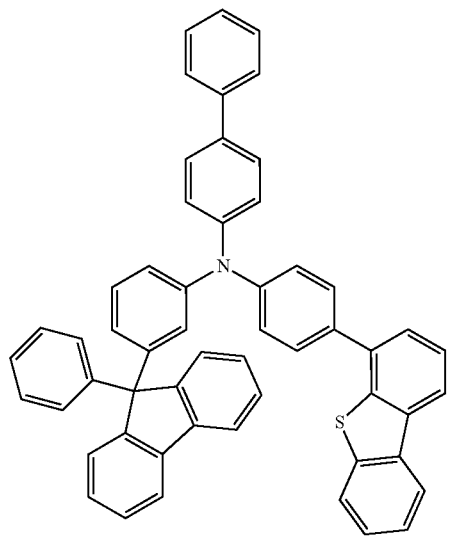
[A-147]
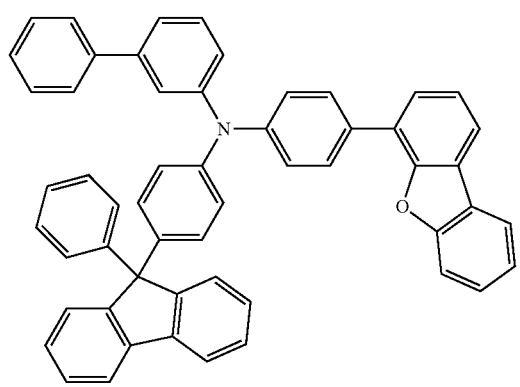
[A-153]
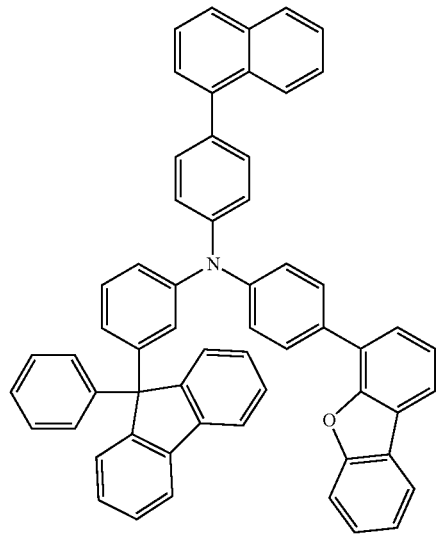
[A154]
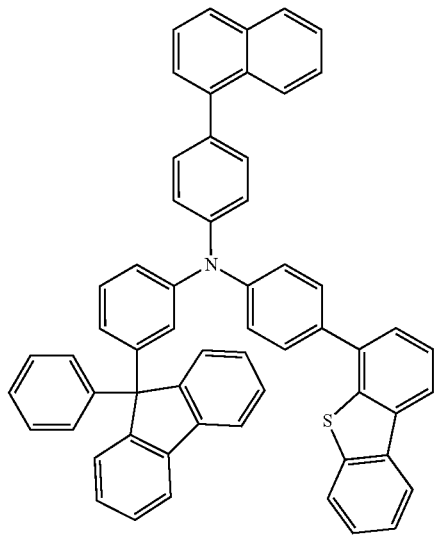
[A-157]
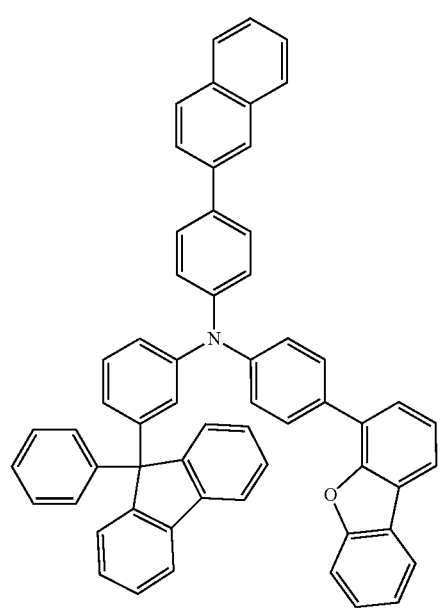

-continued

[A-158]

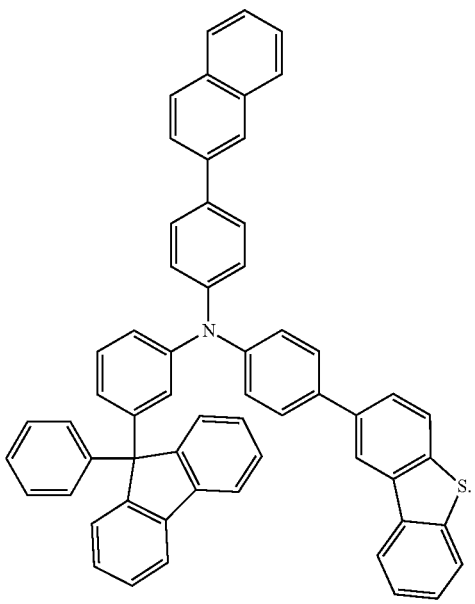

4. An organic optoelectric device including the compound as claimed in claim 1.

5. An organic optoelectric device, comprising:
an anode and a cathode facing each other, and
at least one organic layer between the anode and the cathode,
wherein:
the organic layer includes:
an emission layer, and
at least one auxiliary layer selected from a hole injection layer, a hole transport layer, an electron blocking layer, an electron transport layer, an electron injection layer, and a hole blocking layer, and
the auxiliary layer includes the compound of claim 1.

6. The organic optoelectric device of claim 5, wherein:
the auxiliary layer further includes an auxiliary hole transport layer that is adjacent to the emission layer, and
the auxiliary hole transport layer includes the compound.

7. The organic optoelectric device of claim 5, wherein the compound is a fluorescent material.

8. A display device comprising the organic optoelectric device of claim 5.

* * * * *